US012605373B2

(12) United States Patent
Min et al.

(10) Patent No.: US 12,605,373 B2
(45) Date of Patent: **\*Apr. 21, 2026**

(54) METHODS AND COMPOSITIONS OF INHIBITING DCN1-UBC12 INTERACTION

(71) Applicants: MEMORIAL SLOAN KETTERING CANCER CENTER, New York, NY (US); ST. JUDE CHILDREN'S RESEARCH HOSPITAL, INC., Memphis, TN (US)

(72) Inventors: Jaeki Min, Memphis, TN (US); Daniel C. Scott, Marion, AR (US); Deepak Bhasin, Cordova, TN (US); Brenda A. Schulman, Memphis, TN (US); Bhuvanesh Singh, Old Westbury, NY (US); Jared T. Hammill, Memphis, TN (US); R. Kiplin Guy, Memphis, TN (US)

(73) Assignees: Memorial Sloan Kettering Cancer Center, New York, NY (US); St. Jude Children's Research Hospital, Inc., Memphis, TN (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/596,521

(22) Filed: Mar. 5, 2024

(65) Prior Publication Data

US 2025/0120965 A1     Apr. 17, 2025

Related U.S. Application Data

(63) Continuation of application No. 17/470,678, filed on Sep. 9, 2021, now Pat. No. 9,963,954, which is a
(Continued)

(51) Int. Cl.

| | |
|---|---|
| *A61K 31/4545* | (2006.01) |
| *A61K 31/17* | (2006.01) |
| *A61K 31/437* | (2006.01) |
| *A61K 31/451* | (2006.01) |
| *A61K 31/4525* | (2006.01) |
| *A61K 31/454* | (2006.01) |
| *A61K 31/506* | (2006.01) |
| *A61P 15/16* | (2006.01) |
| *A61P 31/04* | (2006.01) |
| *A61P 31/12* | (2006.01) |
| *C07D 211/58* | (2006.01) |

(Continued)

(52) U.S. Cl.
CPC .......... *A61K 31/4545* (2013.01); *A61K 31/17* (2013.01); *A61K 31/437* (2013.01); *A61K 31/451* (2013.01); *A61K 31/4525* (2013.01); *A61K 31/454* (2013.01); *A61K 31/506* (2013.01); *A61P 15/16* (2018.01); *A61P 31/04* (2018.01); *A61P 31/12* (2018.01); *C07D 211/58* (2013.01); *C07D 401/04* (2013.01);

*C07D 401/06* (2013.01); *C07D 401/12* (2013.01); *C07D 405/06* (2013.01); *C07D 405/12* (2013.01); *C07D 409/14* (2013.01); *C07D 417/04* (2013.01); *C07D 417/06* (2013.01); *C07D 471/04* (2013.01)

(58) Field of Classification Search
CPC .. C07D 401/04; C07D 405/06; C07D 401/06; C07D 471/04; C07D 405/12; C07D 409/14; C07D 417/06; C07D 401/12; C07D 417/04; C07D 211/58; A61K 31/4545; A61K 31/451; A61K 31/454; A61K 31/17; A61K 31/506; A61K 31/4525; A61P 35/00
See application file for complete search history.

(56) References Cited

U.S. PATENT DOCUMENTS

| | | | |
|---|---|---|---|
| 7,115,634 | B2 | 10/2006 | Thurieau et al. |
| 2004/0006081 | A1 | 1/2004 | Burrows et al. |
| 2014/0057938 | A1 | 2/2014 | Dounay et al. |

FOREIGN PATENT DOCUMENTS

| | | |
|---|---|---|
| CN | 103189378 A | 7/2013 |
| CN | 107271687 A | 10/2017 |

(Continued)

OTHER PUBLICATIONS

Jae Wook Lee and Philip L. Fuchs. Reduction of Azides to Primary Amines in Substrates Bearing Labile Ester Functionality. Synthesis of a PEG-Solubilized, "Y"-Shaped Iminodiacetic Acid Reagent for Preparation of Folate-Tethered Drugs. 1999, Organic Lett., 1: 179-181 (Year: 1999).

(Continued)

*Primary Examiner* — Alicia L Otton
(74) *Attorney, Agent, or Firm* — Foley & Lardner LLP

(57)     ABSTRACT

In one aspect, the invention relates to substituted 1-phenyl-3-(piperidin-4-yl)urea analogs, derivatives thereof, and related compounds, which are useful as inhibitors of the DCN1-UBC12 interaction inhibitors of DCN1-mediated cullin-RING ligase activity, methods of making same, pharmaceutical compositions comprising same, methods of treating disorders using the disclosed compounds and compositions, methods of treating disorders associated with a DCN1-UBC12 interaction dysfunction, methods of treating disorders associated with a DCN1-mediated cullin-RING ligase activity dysfunction, methods of male contraception comprising the disclosed compounds and compositions, and kits comprising the disclosed compounds and compositions. This abstract is intended as a scanning tool for purposes of searching in the particular art and is not intended to be limiting of the present invention.

14 Claims, 30 Drawing Sheets

Related U.S. Application Data continuation of application No. 16/683,076, filed on Nov. 13, 2019, now Pat. No. 11,116,757, which is a continuation of application No. 15/760,560, filed as application No. PCT/US2016/052493 on Sep. 19, 2016, now Pat. No. 10,525,048.

(60) Provisional application No. 62/220,683, filed on Sep. 18, 2015.

(51) Int. Cl.

| | |
|---|---|
| *C07D 401/04* | (2006.01) |
| *C07D 401/06* | (2006.01) |
| *C07D 401/12* | (2006.01) |
| *C07D 405/06* | (2006.01) |
| *C07D 405/12* | (2006.01) |
| *C07D 409/14* | (2006.01) |
| *C07D 417/04* | (2006.01) |
| *C07D 417/06* | (2006.01) |
| *C07D 471/04* | (2006.01) |

(56) References Cited

FOREIGN PATENT DOCUMENTS

| | | |
|---|---|---|
| WO | WO-99/07672 | 2/1999 |
| WO | WO-01/44191 A1 | 6/2001 |
| WO | WO-02/24649 A1 | 3/2002 |
| WO | WO-03/007888 A2 | 1/2003 |
| WO | WO-03/070242 | 8/2003 |
| WO | WO-2004/009549 A2 | 1/2004 |
| WO | WO-2011/060396 | 5/2011 |
| WO | WO-2015/054555 A1 | 4/2015 |
| WO | WO-2017/049295 A1 | 3/2017 |
| WO | WO-2020/257790 | 12/2020 |

OTHER PUBLICATIONS

Aher, et al., "3D-QSAR studies of substituted 1-(3, 3-diphenylpropyl)-piperidinyl amides and ureas as CCR5 receptor antagonists," J. Mol. Model, vol. 13, pp. 519-529 (Feb. 16, 2007).

Archibald, et al., "Antihypertensive Ureidopiperidines," J. Med. Chem., vol. 23, pp. 857-861 (1980).

Burrows, et al., "Modulators of the human CCR5 receptor. Part 1: Discovery and initial SAR of 1-(3, 3-diphenylpropyl)-piperidinyl amides and ureas," Bioorg. & Med. Chem. Lett., vol. 15, pp. 25-28 (Nov. 6, 2004).

Carling et al., "1-(3-Cyanobenzylpiperidin-4-yl)-5-methyl-4-phenyl-1,3-dihydroimidazol-2-one: A Selective High-Affinity Antagonist for the Human Dopamine D4 Receptor with Excellent Selectivity over Ion Channels", Journal of Medicinal Chemistry, 42, pp. 2706-2715, Jul. 15, 1999.

CAS Registry No. 898183-92-1; STN Entry Date Aug. 3, 2006; Urea, N'-(4-chlorophenyl)-N-(3-methylbutyl)-N-[1-(1-methylethyl)-4-piperidinyl]-.

CAS Registry No. 898206-60-5; STN Entry Date Aug. 3, 2006; Urea, N'-(3,4-dichlorophenyl)-N-(2- methoxyethyl)-N-[1-(1-methylethyl)-4-piperidinyl]-.

CAS Registry No. 898206-72-9; STN Entry Date Aug. 3, 2006; Urea, N'-(3,4-dimethylphenyl)-N-(3- methylbutyl)-N-[1-(1-methylethyl)-4-piperidinyl]-.

CAS Registry No. 909663-27-0; STN Entry Date Oct. 5, 2006; Urea, N-(2-methoxyethyl)-N-[1-[2-(2-thienyl) ethyl]-4-piperidinyl]-N'-[3- (trifluoromethyl)phenyl]-.

CAS Registry No. 909663-30-5; STN Entry Date Oct. 5, 2006; Urea, N'-(3-fluorophenyl)-N-(2-methoxyethyl)-N-[1-[2-(2-thienyl)ethyl]-4-piperidinyl]-.

CAS Registry No. 909664-01-3; STN Entry Date Oct. 5, 2006; Urea, N'-(3-fluorophenyl)-N-(2-methoxyethyl)-N-[1-[2-(2-pyridinyl) ethyl]-4-piperidinyl]-.

CAS Registry No. 909665-71-0; STN Entry Date Oct. 5, 2006; Urea, N-[1-[2-(4-chlorophenyl) ethyl]-4-piperidinyl]-N-(2-methoxyethyl)-N'-[3-(trifluoromethyl)phenyl]-.

CAS Registry No. 909684-72-6; STN Entry Date Oct. 5, 2006; Urea, N-(2-methoxyethyl)-N-[1-(4- pyridinylmethyl)-4-piperidinyl]-N'-[3-(trifluoromethyl)phenyl]-.

CAS Registry No. 909684-75-9; STN Entry Date Oct. 5, 2006; Urea, N'-(3-fluorophenyl)-N-(2-methoxyethyl)-N-[1-(4-pyridinylmethyl)-4-piperidinyl]-.

CAS Registry No. 909689-50-5; STN Entry Date Oct. 5, 2006; Urea, N-[1-[2-(4- chlorophenyl)ethyl]-4-piperidinyl]-N'-(3-fluorophenyl)-N-(2-methoxyethyl)-.

CAS Registry No. 909689-68-5; STN Entry Date Oct. 5, 2006; Urea, N'-(3-fluorophenyl)-N-(2-methoxyethyl)-N-[1-(3-phenylpropyl)-4-piperidinyl]-.

CAS Registry No. 909695-29-0; STN Entry Date Oct. 5, 2006; Urea, N-(2-methoxyethyl)-N-[1-(3- phenylpropyl)-4-piperidinyl]-N'-[3-(trifluoromethyl)phenyl]-.

Devegowda et al., "Novel 6-N-arylcarboxamidopyrazolo[4,3-d]pyrimidin-7-one derivatives as potential anti-cancer agents", Bioorganic & Medicinal Chemistry Letters, 2010, vol. 20, pp. 1630-1633.

Duan, et al., "Discovery of novel pyridyl carboxamides as potent CCR5 antagonists and optimization of their pharmacokinetic profile in rats," Bioorg. Med. Chem. Lett., 21, pp. 6470-6475 (2011).

Examination Report in AU Application No. 2016324483, mailed on Aug. 26, 2020.

Examination Report on EP 16847549.9 DTD Mar. 11, 2021.

Extended European Search Report, App. No. 16847549.9 (Mar. 15, 2019).

Final Office Action on U.S. Appl. No. 16/683,076 DTD Apr. 15, 2021.

Foreign Action other than Search Report on AU DTD Sep. 30, 2022.

Foreign Action other than Search Report on CA DTD Oct. 21, 2022.

Foreign Action other than Search Report on CA DTD Aug. 28, 2023.

Foreign Action other than Search Report on EP DTD Jun. 30, 2023.

Foreign Action other than Search Report on IN DTD Sep. 26, 2023.

Foreign Search Report on EP DTD Jun. 13, 2023.

Hammill, J.T., et al., "Discovery of an Orally Bioavailable Inhibitor of Defective in Cullin Neddylation 1 (DCN1)-Mediated Cullin Neddylation," J. Med. Chem., 61:2694-2706 (2018) (13 pages).

Hammill, J.T., et al., "Piperidinyl Ureas Chemically Control Defective in Cullin Neddylation 1 (DCN1)-Mediated Cullin Neddylation," J. Med. Chem., 61:2680-2693 (2018) (14 pages).

International Search Report and Written Opinion on PCT PCT/US2020/038998 dated Oct. 5, 2020 (13 pages).

Ito et al., Cancer Science, 94(1), 3-8 (2003).

Kim et al., "Discovery of Novel Pyrazolo-Pyridone DCN1 Inhibitors Controlling Cullin Neddylation", J. Med. Chem., 2019, vol. 62, pp. 8429-8442.

Leonard, et al., "Comparative QSAR modeling of CCR5 receptor binding affinity of substituted 1-(3,3-diphenylpropyl)-piperidinyl amides and ureas," Bioorg. & Med. Chem. Lett., vol. 16, pp. 4467-4474 (Jun. 27, 2006).

Lolicato et al., Nature Chemical Biology, vol. 10, No. 8, Jun. 2014, pp. 457-462 Supplementary Information.

Mahobia, et al., "3D QSAR analysis of some piperidinyl amide and ureas as CCR5 antagonist," Journal of Pharmacy Research, vol. 5, Issue 9, pp. 4706-4709 (Sep. 2012).

Mouhibi, et al., "Using multiple linear regression and artificial neural network techniques for predicting CCR5 binding affinity of substituted 1-(3, 3-diphenylpropyl)-piperidinyl amides and ureas," Journal of Medicinal Chemistry, vol. 3, pp. 7-15 (Mar. 2013).

Non-Final Office Action on U.S. Appl. No. 15/760,560 DTD Oct. 15, 2018.

Non-Final Office Action on U.S. Appl. No. 16/683,076 DTD Oct. 16, 2020.

Non-Final Office Action on U.S. Appl. No. 17/470,678 DTD Apr. 13, 2023.

Notice of Allowance on U.S. Appl. No. 15/760,560 DTD Jul. 5, 2019.

Notice of Allowance on U.S. Appl. No. 15/760,560 DTD Oct. 11, 2019.

(56) References Cited

OTHER PUBLICATIONS

Notice of Allowance on U.S. Appl. No. 16/683,076 DTD May 4, 2021.

Notice of Allowance on U.S. Appl. No. 17/470,678 DTD Nov. 15, 2023.

Raffa et al., "Pyrazolo[3,4-d]pyrimidine Derivatives as COX-2 Selective Inhibitors: Synthesis and Molecular Modelling Studies", Arch. Pharm. Chem. Life Sci., 2009, vol. 342, pp. 321-326.

Restriction Requirement on U.S. Appl. No. 15/760,560 DTD Jul. 30, 2018.

Scott, D.C., et al., "Blocking an N-terminal acetylation-dependent protein interaction inhibits an E3 ligase," Nature Chem. Biol., doi: 10.1038/nchembio.2386 (2017) (12 pages).

Shahlaei, et al., "QSAR analysis of some 1-(3, 3-diphenylpropyl)-piperidinyl amides and ureas as CCR5 inhibitors using genetic algorithm-least square support vector machine," Med. Chem. Res., vol. 22, pp. 4384-4400 (Jan. 10, 2013).

Shin Kim, H., et al., "Discovery of Novel Pyrazolo-pyridone DCN1 Inhibitors Controlling Cullin Neddylation," J. Med. Chem., 62:8429-8442 (2019) (14 pages).

Shin Kim, H., et al., "Improvement of Oral Bioavailability of Pyrazolo-Pyridone Inhibitors of the Interaction of DCN1/2 and UBE2M," J. Med. Chem., 64:5850-5862 (2021) (13 pages).

STN Registry database entry for CAS RN 898206-78-5, entry date Aug. 3, 2006, Accessed Oct. 10, 2018.

STN Registry entry for CAS RN 1171707-20-2; entered STN Registry database Aug. 2, 2009.

Watson et al., "Development of CXCR3 antagonists. Part 2: Identification of 2-amino(4-piperidinyl)azoles as potent CXCR3 antagonists," Bioorganic & Medicinal Chemistry Letters, 2007, vol. 17, No. 24, pp. 6806-6810.

Yuan, et al., "Prediction of CCR5 receptor binding affinity of substituted 1-(3, 3-diphenylpropyl)-piperidinyl amides and ureas based on the heuristic method, support vector machine and projection pursuit regression," European Journal of Medicinal Chemistry, vol. 44, pp. 25-34 (2009).

Series 1

$IC_{50}$ = 8.5 µM (TR-FRET)
$EC_{50}$ = 3.4 µM (Pulse-Chase)
Cytotox. = >24 µM (wt Cells)

Compound B7

Series 2

$IC_{50}$ = 1.3 µM (TR-FRET)
$EC_{50}$ = 3.1 µM (Pulse-Chase)
Cytotox. = >24 µM (wt Cells)

Compound E1

Series 3

$IC_{50}$ = 1.9 µM (TR-FRET)
$EC_{50}$ = 0.7 µM (Pulse-Chase)
Cytotox. = >24 µM (wt Cells)

Compound F1

FIG. 7

5 Subpockets for Optimization

| | Cmpd B7 | Cmpd A7 | Cmpd A18 |
|---|---|---|---|
| TR-FRET IC$_{50}$ (µM) = | 8.5 | 0.08 | 0.03* |
| Pulse-Chase EC$_{50}$ (µM) = | 3.4 | 0.24 | 0.36 |
| Kd (µM) = | 1.9 | 0.14 | ND* |
| Microsomal Stability (hrs)= | 0.45 | 2.1 | 0.1 |

Reversible Inhibitor:          Covalent Inhibitor:

Cmpd A7                    Cmpd A18

Inactive Compounds:

Cmpd A280                    Cmpd A232

Cmpd A15 I-6
(10 uM on cells)

Cmpd A83 F-8
(3 uM on cells)

DMSO

Cmpd A232 L-4
(28 uM on cells)

Cmpd A15
TR-FRET: 50 nM
T(1/2) = 0.2 h

DMSO

Cmpd A3
TR-FRET: <50 nM

Cmpd A7
TR-FRET: 80 nM
T(1/2) = 2 h

Cmpd A7
T(1/2): 4–5 hr
Cmax: 1.5–3 µM
AUC: 7400–1500 hr*ng/mL

IV Dosing of Cmpd A7

- 1.5 mg/kg
- 1.0 mg/kg
- 0.5 mg/kg
- LLOQ

METHODS AND COMPOSITIONS OF INHIBITING DCN1-UBC12 INTERACTION

CROSS-REFERENCE TO RELATED APPLICATIONS

This application is a continuation of U.S. patent application Ser. No. 17/470,678, filed Sep. 9, 2021, which is a continuation of U.S. patent application Ser. No. 16/683,076, filed Nov. 13, 2019, now U.S. Pat. No. 11,116,757, which is a continuation of U.S. patent application Ser. No. 15/760, 560, filed Mar. 15, 2018, now U.S. Pat. No. 10,525,048, which is a National Stage Application of PCT/US2016/ 052493, filed Sep. 19, 2016, which claims the benefit of and priority to U.S. Provisional Application No. 62/220,683, filed Sep. 18, 2015, each of which is incorporated herein by reference in its entirety.

STATEMENT REGARDING FEDERALLY SPONSORED RESEARCH

This invention was made with government support under grant numbers GM113310 and CA008748 awarded by the National Institutes of Health. The government has certain rights in the invention.

BACKGROUND

Ubiquitin-like protein (UBL) modification pathways have emerged as important targets for drug discovery based on their vast roles in regulation, and on clinical and preclinical successes of proteasome inhibitors (e.g. bortezomib or carfelzomib), E3 inhibitors, and the NEDD8 E1 inhibitor (MLN4924) (e.g., see Ciechanover, A. *Bioorg Med Chem* 2013, 21:3400; and Bassermann, F.; Eichner, R.; Pagano, M. *Biochim Biophys Acta* 2014 1843(1):150-62). These chemical inhibitors of UBL pathways have also proven to be essential probes for dissecting multifactorial regulatory networks that were opaque to genetic approaches.

Currently, the FDA approved drugs that target the ubiquitin-proteasome system (UPS), bortezomib and carfilzomib, completely block proteasome activity (see Petroski, M. D.; and Deshaies, R. J. Nat. Rev. Mol. Cell Biol. 2005, 6:9; da Silva, S. R, et al. J. Med. Chem. 2013, 56:2165; Hideshima, T., et al. Cancer Res. 2001, 61:3071; Shi, D.; and Grossman, S. R. Cancer Biol. Ther. 2010, 10:737). Clinically, this leads to toxicity; 50% of the patient population taking either proteasome inhibitor exhibit grade 3 hematologic adverse events (thrombocytopenia and neutropenia) and nearly 15% suffer grade 4 adverse events (potentially life-threatening) (see Jagannath, S., et al. Clin Lymphoma Myeloma Leuk 2012, 12:310; Siegel, D. S., et al., Blood 2012, 120:2817; Curran, M. P.; and McKeage, K. Drugs 2009, 69:859). However, there are no currently available therapeutic agents that specifically target components of the UBL system such as the DCN1-UBC12 interaction.

The function of DCN1 is to bind the acetylated N-terminus of UBC12 (an E2 enzyme for the UBL NEDD8) and the "Cullin (or CUL)" family of proteins to act as a co-E3 promoting NEDD8 modification (neddylation) of the CULs (see Kurz, T., et al. Mol. Cell 2008, 29:23; Scott, D. C., et al. Mol. Cell 2010, 39:784; Kim, A. Y. et. al. J. Biol. Chem. 2008, 283:33211; and Scott, D. C., et al. Science 2011, 334:674). DCN1 is part of a dynamic signaling system that regulates ligation of both NEDD8 and ubiquitin (UB), which are among more than a dozen human UBLs that dynamically post-translationally modify and regulate the functions of thousands of different eukaryotic proteins. It is believed that inhibition of the DCN1-UBC12 interaction could regulate CRL activity without completely blocking neddylation and provide efficacious compounds with less severe off-target effects and toxicity relative to existing drugs that target the UPS system (see Sun, Y. Neoplasia 2006, 8:645; Petroski, M. D.; and Deshaies, R. J. Nat Rev Mol Cell Biol 2005, 6:9; Nakayama, K. I.; and Nakayama, K. Nat Rev Cancer 2006, 6:369).

Despite advances in small molecule regulation of UBL modification pathways, there is still a scarcity of compounds that are potent, efficacious, and selective inhibitors of Cullin neddylation and also effective in the treatment of aberrant DCN1 expression associated with squamous cell carcinomas and other cancers and diseases in which the dysregulation of DCN1-dependent neddylation is involved. These needs and other needs are satisfied by the present invention.

SUMMARY

In accordance with the purpose(s) of the invention, as embodied and broadly described herein, the invention, in one aspect, relates to compounds useful as inhibitors of the DCN1-UBC12 interaction, inhibitors of DCN1-mediated cullin-RING ligase activity, methods of making same, pharmaceutical compositions comprising same, methods of treating disorders using the disclosed compounds and compositions, methods of treating disorders associated with a DCN1-UBC12 interaction dysfunction, methods of treating disorders associated with a DCN1-mediated cullin-RING ligase activity dysfunction, methods of male contraception comprising the disclosed compounds and compositions, and kits comprising the disclosed compounds and compositions.

Disclosed are compounds having a structure represented by a formula:

each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and $R^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$; R$^3$ is C1-C8 alkyl; C1-C8 alkoxyalkyl; —(C1-C3 alkyl)-(C3-C8 cycloalkyl); or —(C1-C3 alkyl)-Ar$^1$; Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Also disclosed are compounds having a structure represented by a formula:

each of R$^{1a}$, R$^{1b}$, and R$^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of R$^{1a}$, R$^{1b}$, and R$^{1c}$ is not hydrogen; or R$^{1a}$ and R$^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and R$^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; R$^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Also disclosed are pharmaceutical compositions comprising a therapeutically effective amount of a disclosed compound, or a pharmaceutically acceptable salt thereof, and a pharmaceutically acceptable carrier.

Also disclosed are methods for the treatment of a disorder of uncontrolled cellular proliferation, comprising the step of administering to a mammal a therapeutically effective amount of a compound inhibiting DCN1-UBC12 interaction, wherein the compound is a disclosed compound.

Also disclosed are methods for the treatment of a neurodegenerative disorder, comprising the step of administering to a mammal a therapeutically effective amount of a compound inhibiting DCN1-UBC12 interaction, wherein the compound is a disclosed compound.

Also disclosed are methods for the treatment of a viral or bacterial infection, comprising the step of administering to a mammal a therapeutically effective amount of a compound inhibiting DCN1-UBC12 interaction, wherein the compound is a disclosed compound.

Also disclosed are methods for male contraception, comprising the step of administering to a mammal a therapeutically effective amount of a compound inhibiting DCN1-UBC12 interaction, wherein the compound is a disclosed compound.

Also disclosed are methods for inhibiting in at least one cell DCN1-mediated cullin-RING ligase activity, comprising the step of contacting the at least one cell with an effective amount of at least one compound of that is an inhibitor of DCN1-UBC12 interaction, wherein the compound is a disclosed compound.

Also disclosed are kits comprising at least one disclosed compound, or a pharmaceutically acceptable salt thereof; and one or more of: (a) at least one agent known to increase cell proliferation; (b) at least one agent known to increase activity of the ubiquitin-proteosome system; (c) at least one agent known to decrease activity of the ubiquitin-proteosome system; (d) at least one agent known to treat a disorder associated with DCN1-UBC12 interaction; or (e) at least one agent known to treat a disease of uncontrolled cellular proliferation; or (f) instructions for treating a disease of uncontrolled cellular proliferation.

Also disclosed are kits comprising at least one disclosed compound, or a pharmaceutically acceptable salt thereof; and one or more of: (a) at least one agent known to increase activity of the ubiquitin-proteosome system; (b) at least one agent known to decrease activity of the ubiquitin-proteosome system; (c) at least one agent known to treat a disorder associated with DCN1-UBC12 interaction; (d) at least one agent known to treat a neurodegenerative disease; or (e) instructions for treating a neurodegenerative disease.

Also disclosed are kits comprising at least one disclosed compound, or a pharmaceutically acceptable salt thereof; and one or more of: (a) at least one agent known to increase activity of the ubiquitin-proteosome system; (b) at least one agent known to decrease activity of the ubiquitin-proteosome system; (c) at least one agent known to treat a disorder associated with DCN1-UBC12 interaction; (d) at least one agent known to treat a viral or bacterial infection; or (e) instructions for treating a viral or bacterial infection.

Also disclosed are kits comprising at least one disclosed compound, or a pharmaceutically acceptable salt thereof; and one or more of: (a) at least one agent known to increase activity of the ubiquitin-proteosome system; (b) at least one agent known to decrease activity of the ubiquitin-proteosome system; (c) at least one agent known to treat a disorder associated with DCN1-UBC12 interaction; (d) at least one agent known to be used as a male contraceptive; or (e) instructions for effecting male contraception.

Also disclosed are uses of a disclosed compound, a disclosed product of making, or a pharmaceutically acceptable salt thereof, in the manufacture of a medicament for the treatment of a disorder associated with a DCN1-UBC12 interaction dysfunction.

Also disclosed are uses of a disclosed compound, a disclosed product of making, or a pharmaceutically acceptable salt thereof, in the manufacture of a medicament for the treatment of a disorder associated with a DCN1-mediated cullin-RING ligase activity dysfunction.

Also disclosed are uses of a disclosed compound, a disclosed product of making, or a pharmaceutically acceptable salt thereof, in the manufacture of a medicament for the male contraception.

Also disclosed are methods for the manufacture of a medicament to inhibit the DCN1-UBC12 interaction interaction in a mammal comprising combining at least one disclosed compound or at least one disclosed product with a pharmaceutically acceptable carrier or diluent.

Also disclosed are methods for the manufacture of a medicament to inhibit DCN1-mediated cullin-RING ligase activity in a mammal comprising combining at least one disclosed compound or at least one disclosed product with a pharmaceutically acceptable carrier or diluent.

Also disclosed are methods for the manufacture of a medicament for male contraception in a mammal comprising combining at least one disclosed compound or at least one disclosed product with a pharmaceutically acceptable carrier or diluent.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 3A shows a schematic representation of the TR-FRET assay for DCN1 binding to UBC12$^{NAc}$. FIG. 3B shows a representative dose response curve of unlabeled UBC12$^{NAc}$ peptide. In the assay, desired inhibitors will exhibit a low FRET signal.

6

Figure 7:
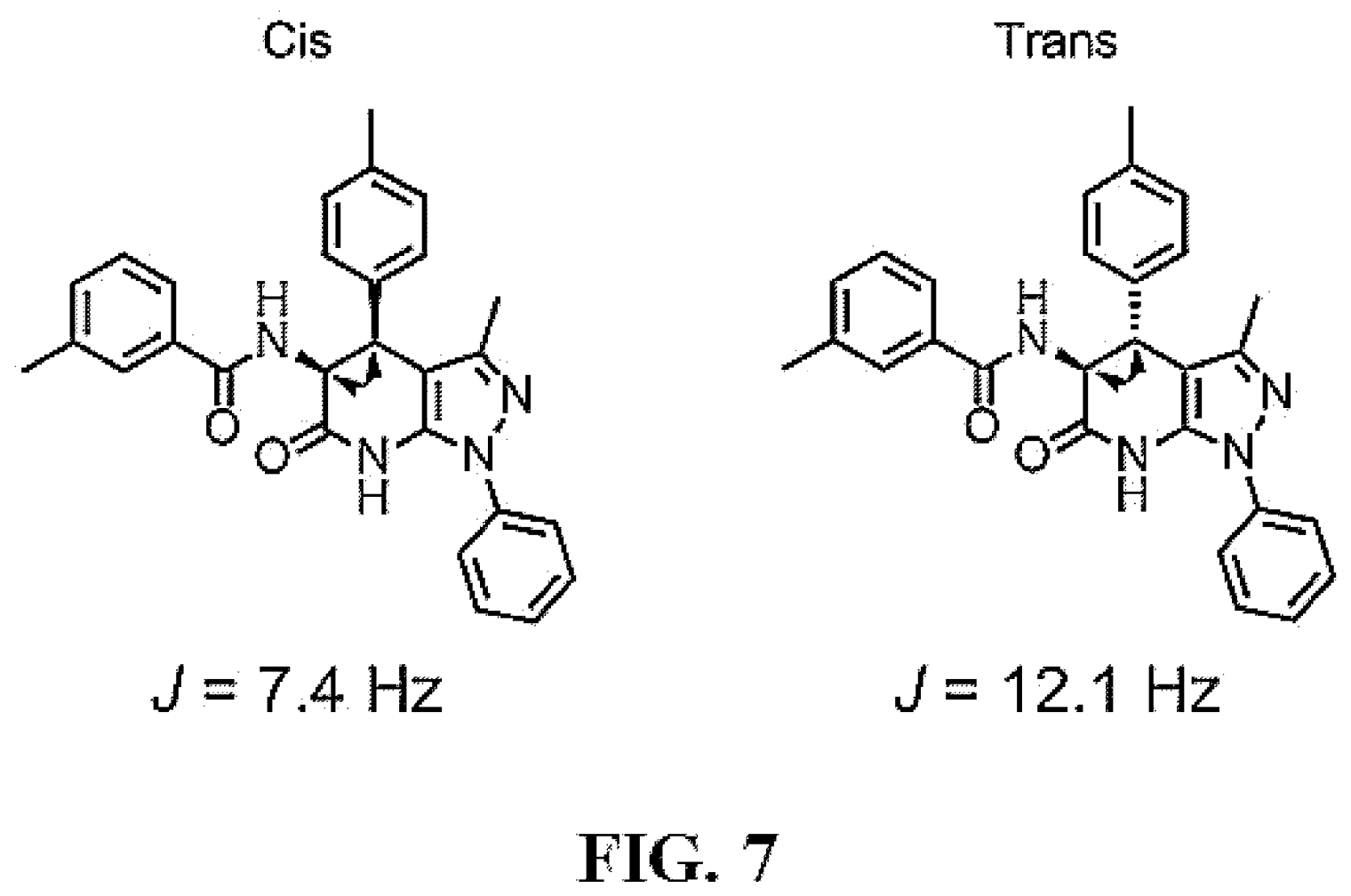

FIG. 7 shows representative images illustrating the stereogenic centers of the cis and trans diastereomers as assigned by 1H NMR coupling constant analysis.

Figure 8:
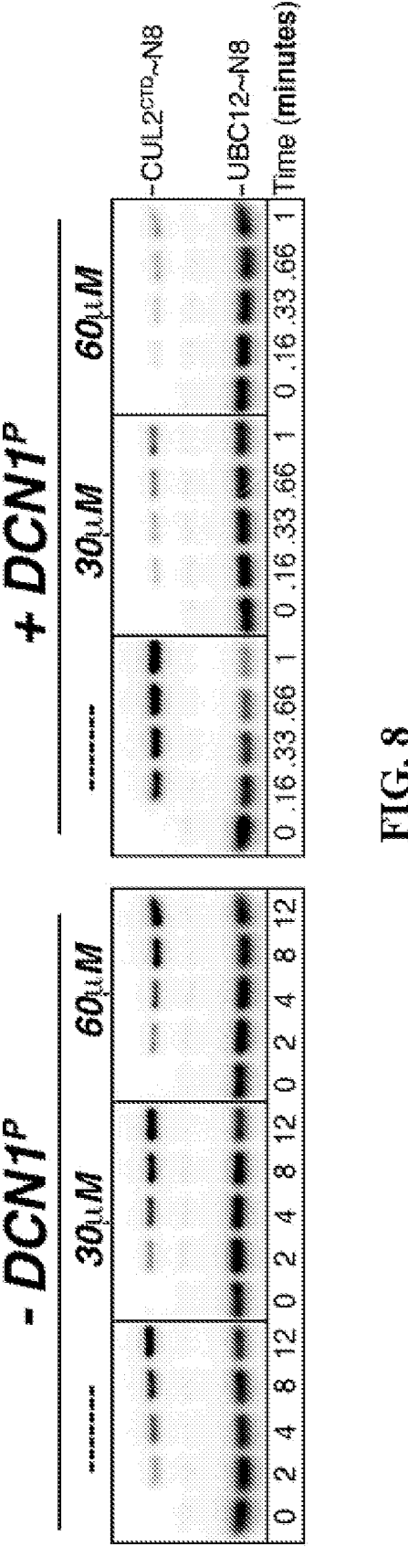

FIG. 8 shows representative data illustrating the biochemical validation and characterization of B7. Specifically, the dependence on presence of DCN1 for inhibition of neddylation by compound B7 is shown.

Figure 9A:
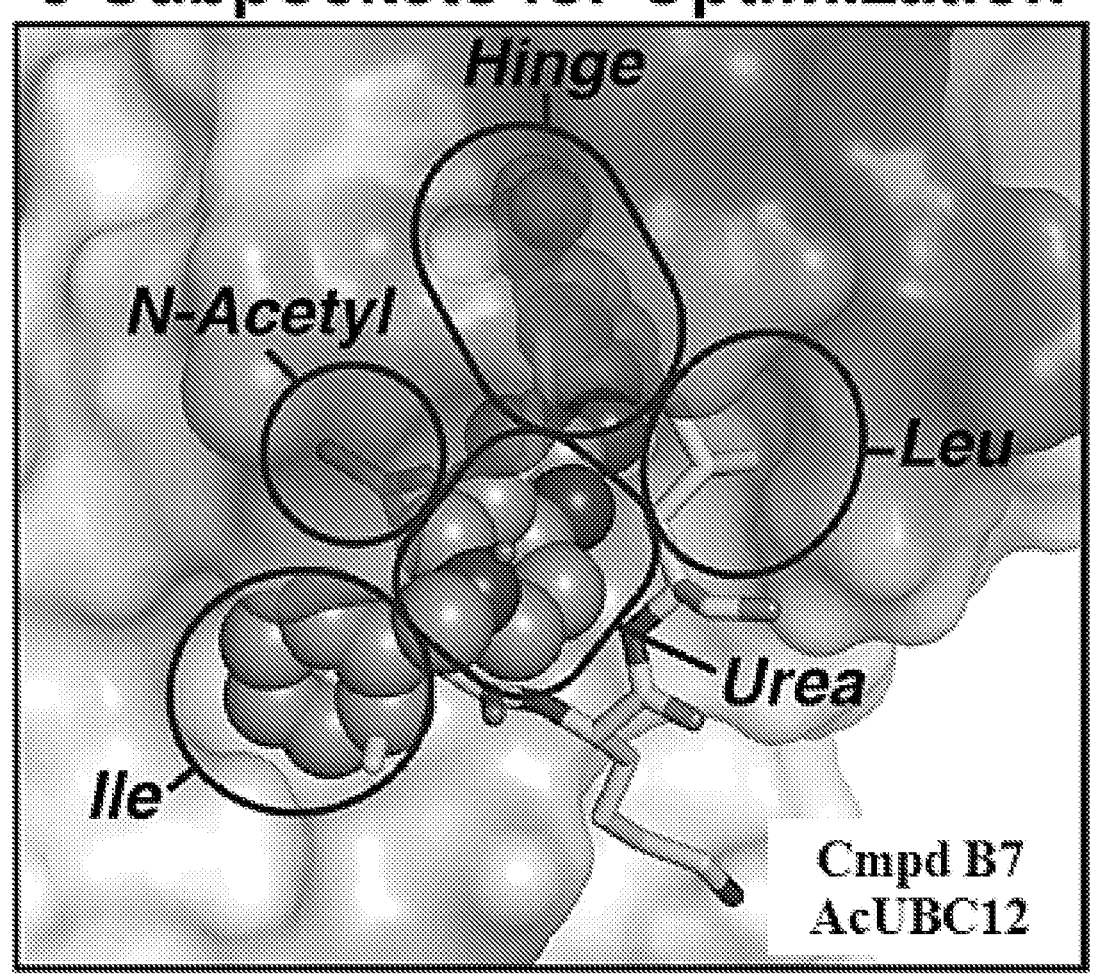
Figure 9B:
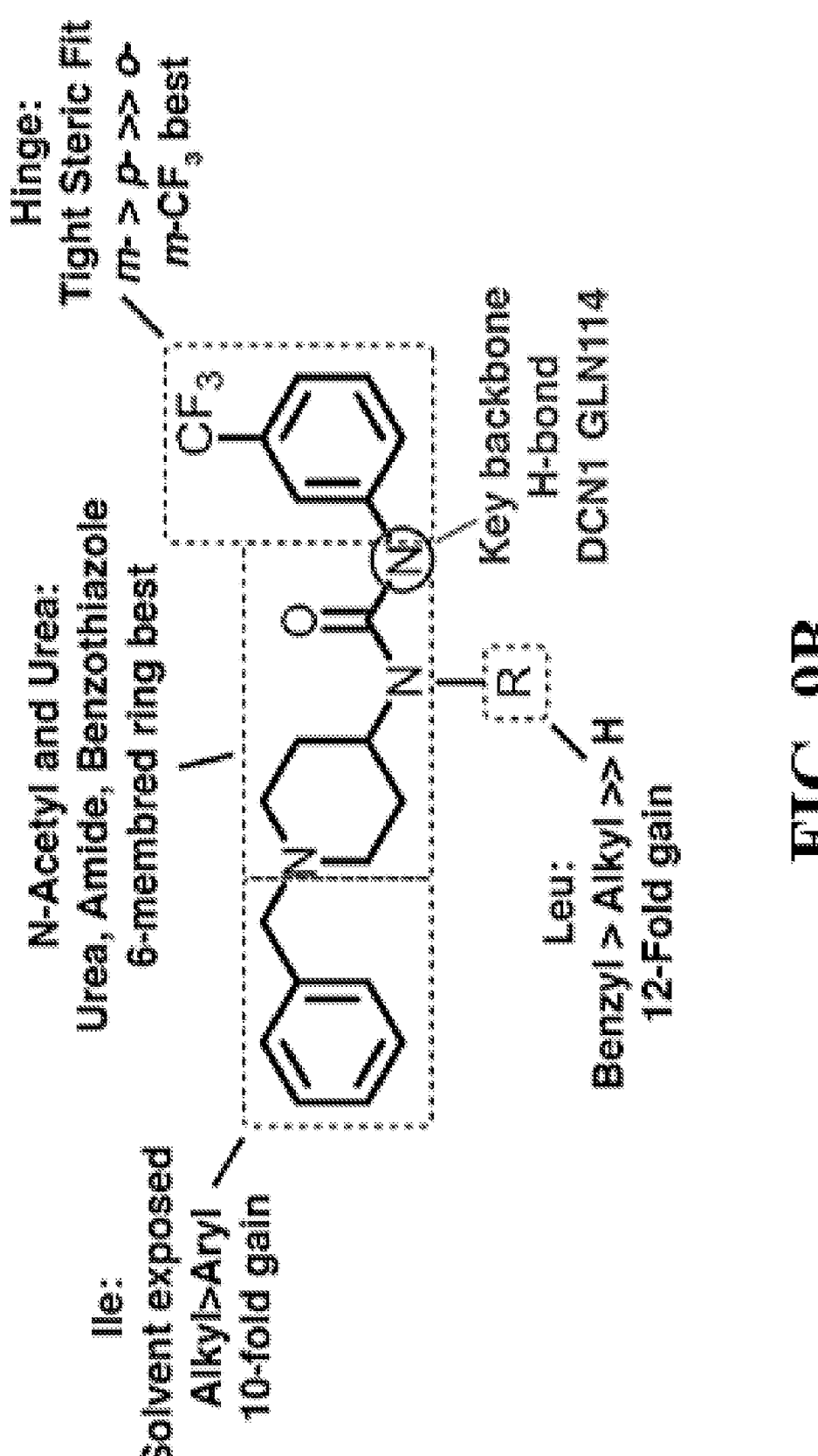

FIG. 9A and FIG. 9B show representative images pertaining to the development of a structure activity relationship (SAR) of the series represented by B7 (the 329 series). Specifically, FIG. 9A shows an overlay of B7 and the crystal structure of the targeted site (in the DCN1-UBC12$^{NAc}$ pocket) for binding of the disclosed inhibitors. FIG. 9B shows regions of the 329 series that were targeted for optimization.

Figure 10:
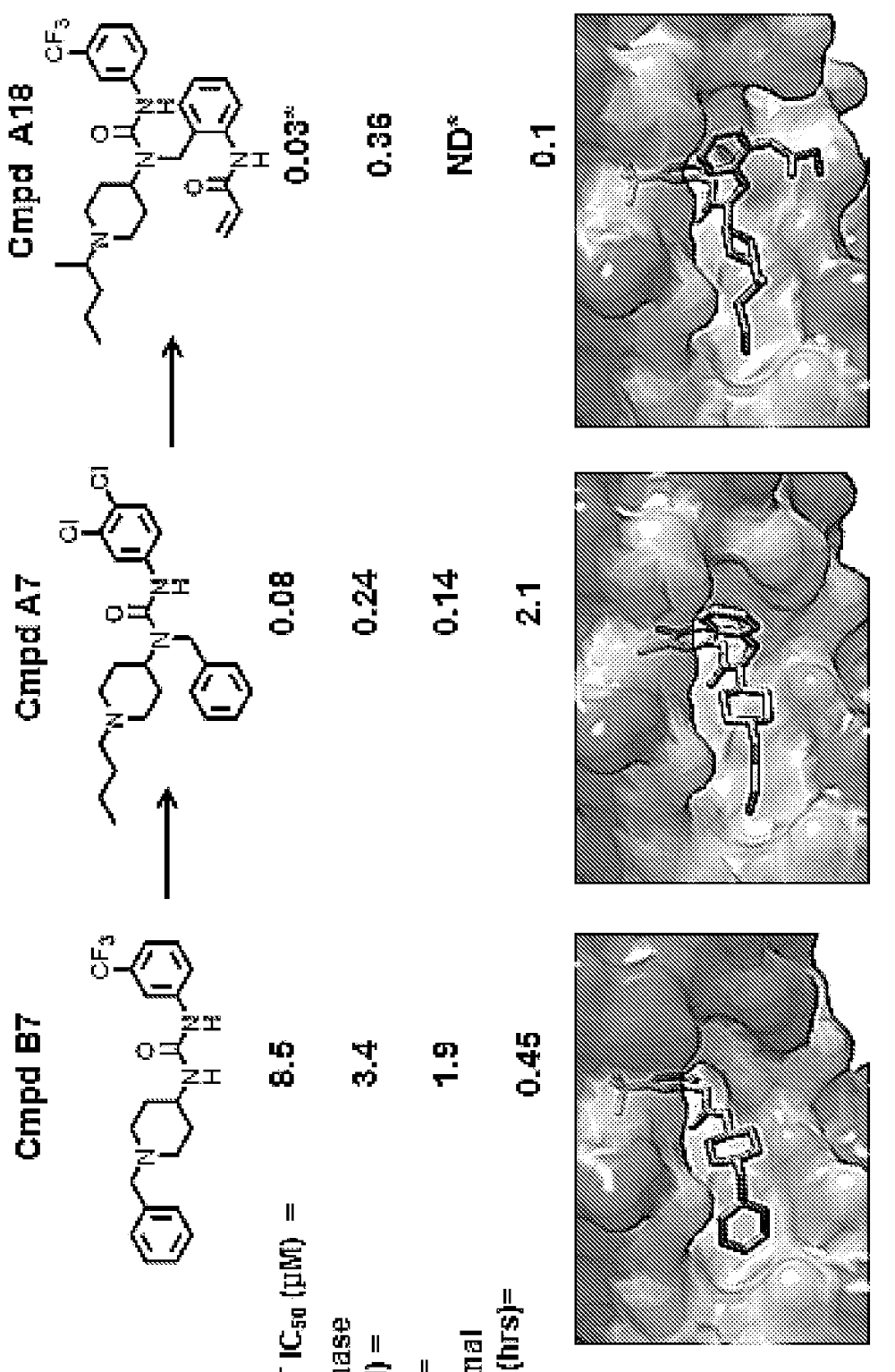

FIG. 10 shows a summary of the potency gains for series 1, represented by compound B7.

Figure 11A:
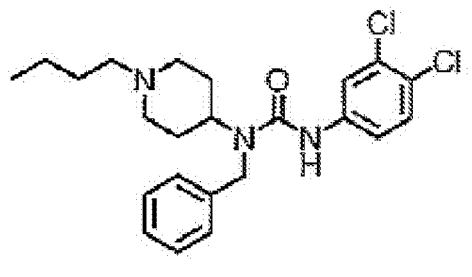
Figure 11A:
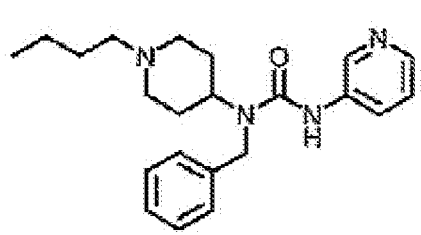
Figure 11B:
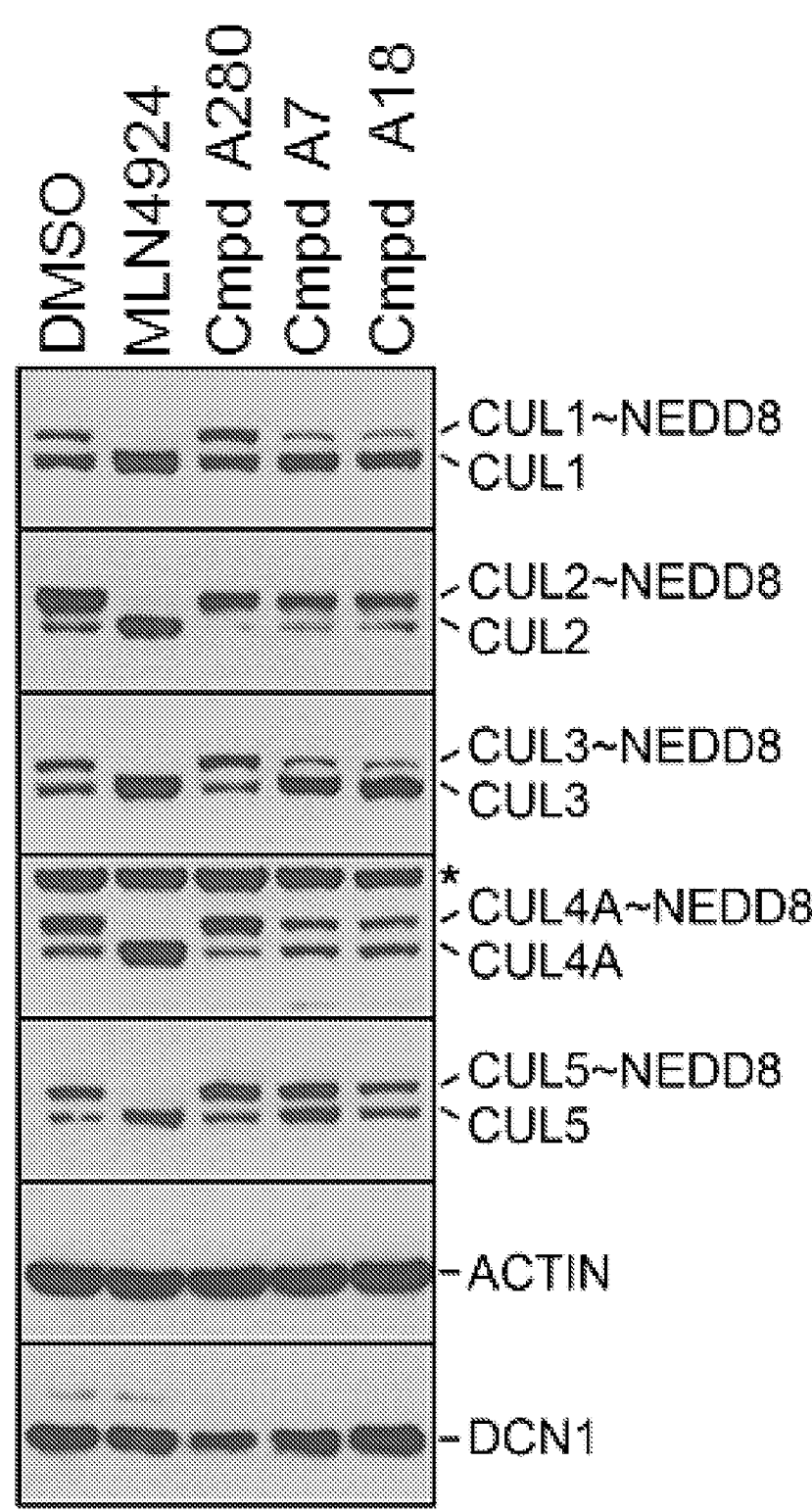

FIG. 11A and FIG. 11B show representative data illustrating that cmpd A7 and cmpd A18, but not cmpd A280 reduce the levels of neddylated Cullins with the most pronounced effects on the levels of neddylated CUL1 and CUL3 in HCC95 cancer cells.

Figure 12B:
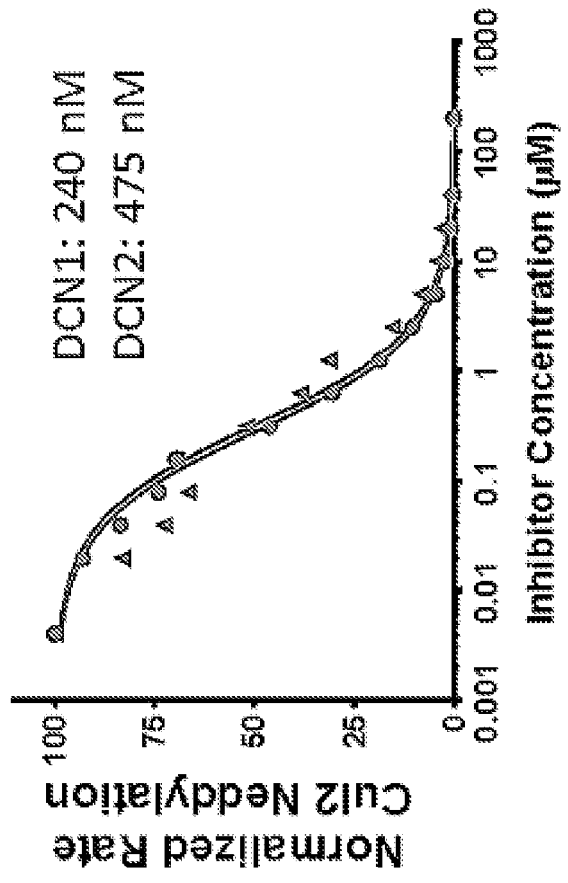
Figure 12A:
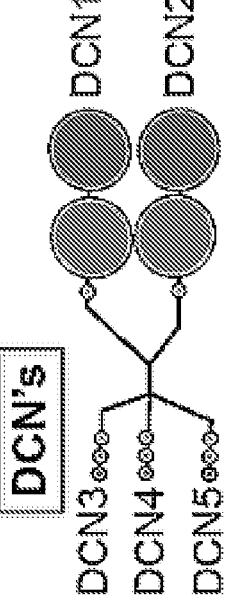

FIG. 12A and FIG. 12B show representative data illustrating that A7 selectively inhibits DCN1 and DCN2 over DCN3, DCN4, and DCN5.

Figure 13B:
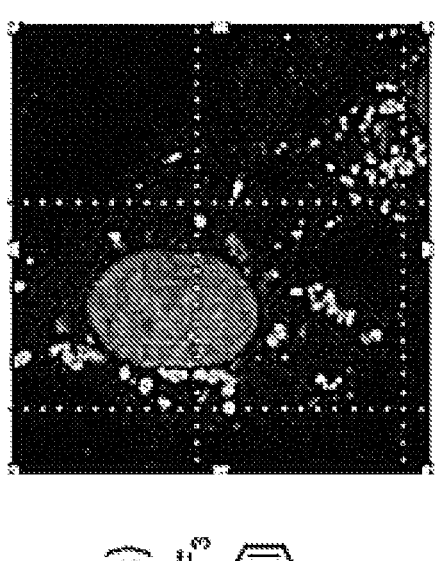
Figure 13B:
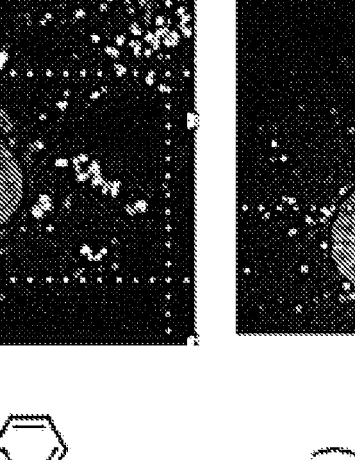
Figure 13B:
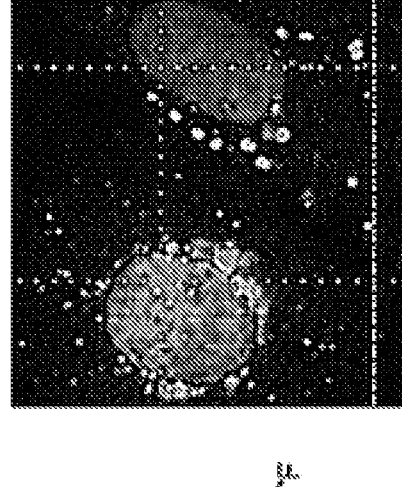
Figure 13B:
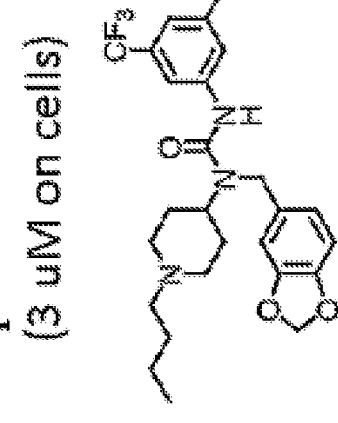
Figure 13A:
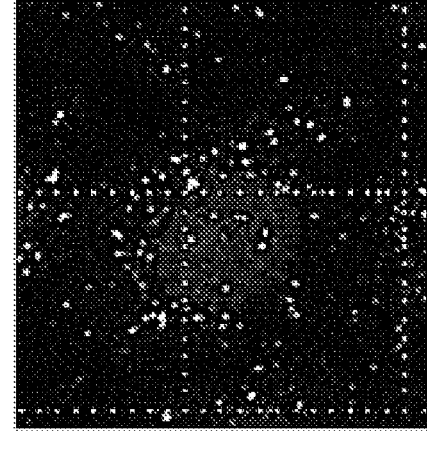
Figure 13C:
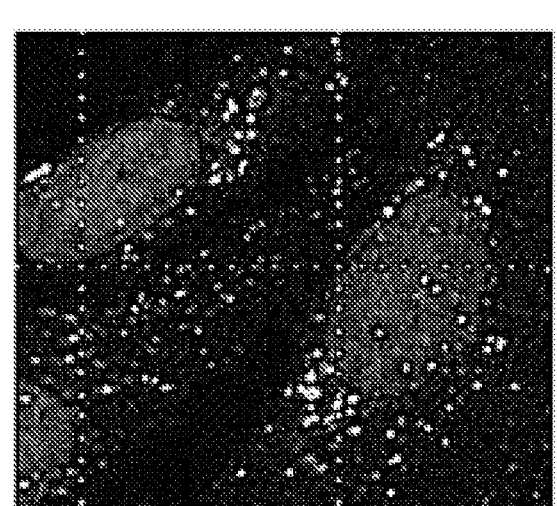
Figure 14B:
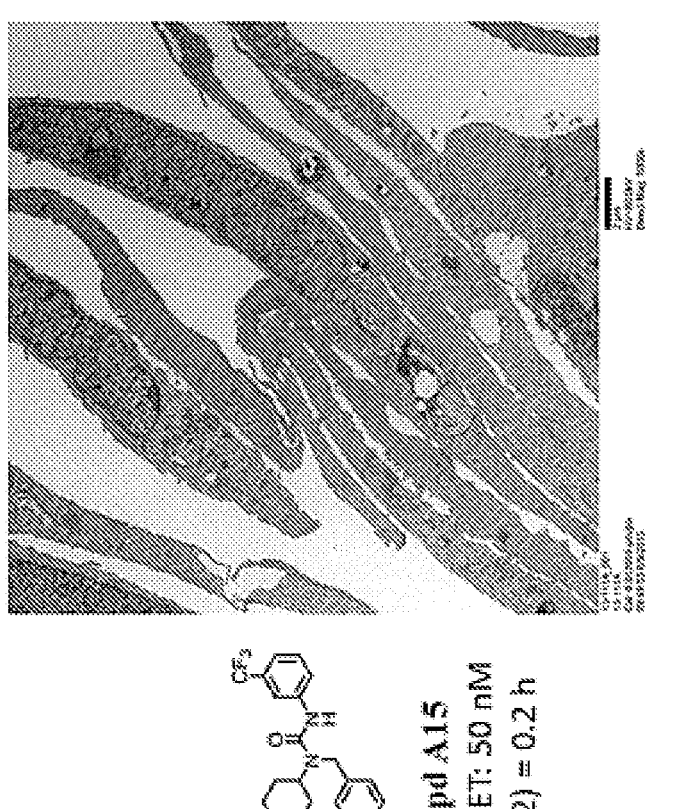
Figure 14A:
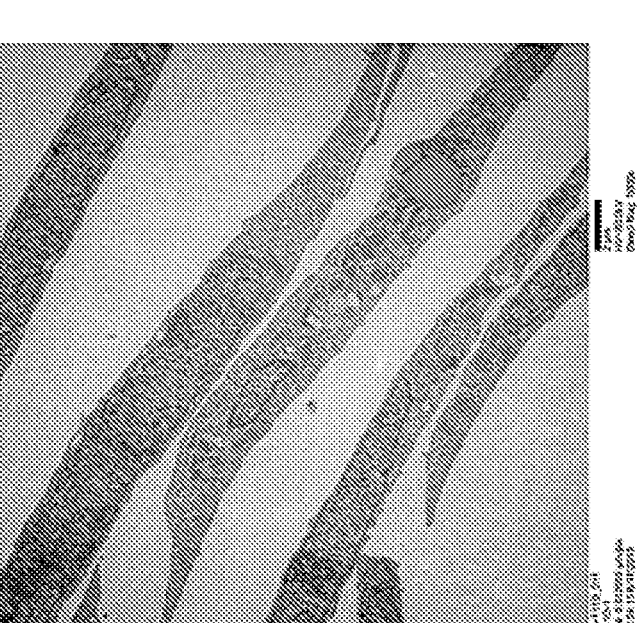
Figure 14D:
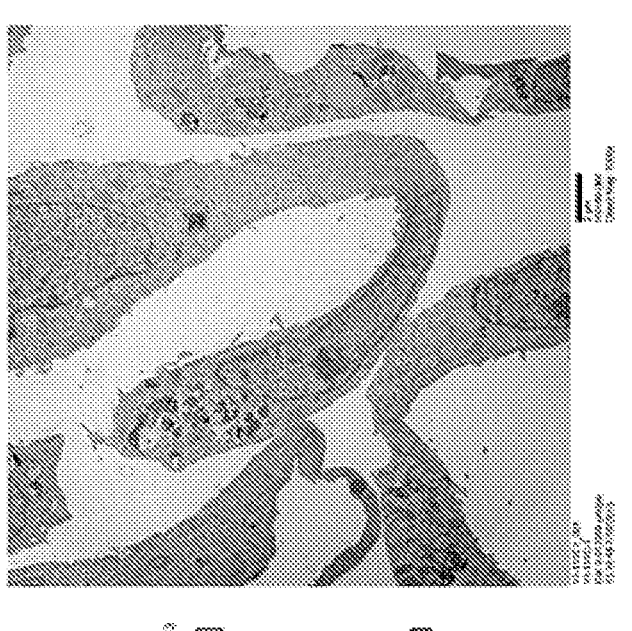
Figure 14D:
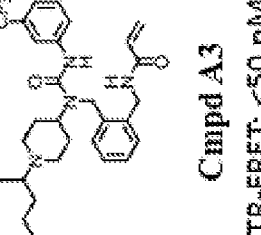
Figure 14C:
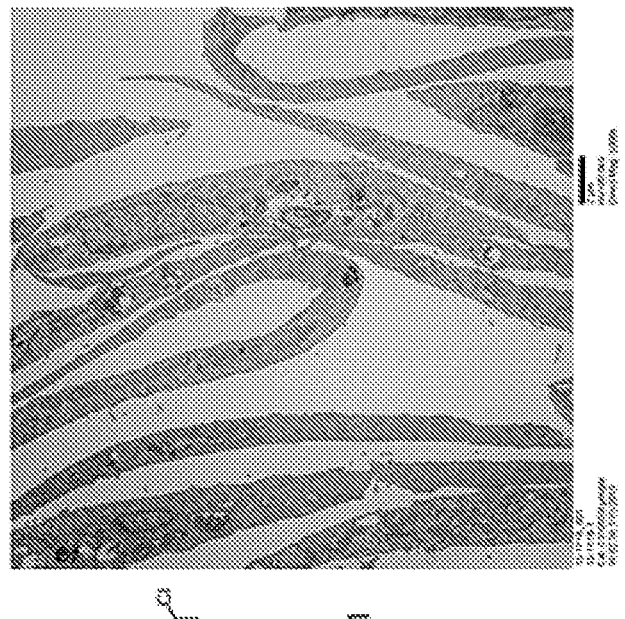

FIG. 13A-C show representative images illustrating that compounds A15 (10 μM on cells) and A83 (3 μM on cells) affect endosome maturation. Specifically, images demonstrate the accumulation of large LAMP1 positive vesicles when treated with either compounds A15 (top) or A83 (bottom) (13B), but not when treated with DMSO (13A) or the negative control (13C).

FIG. 14A-D show representative electron microscopy images of compound treated U-2 OS cells, demonstrating the presence of large vacuolar structures. Specifically, images of DMSO (14A) and compounds A15 (14B), A7 (14C), and A3 (14D) are shown.

Figure 15:
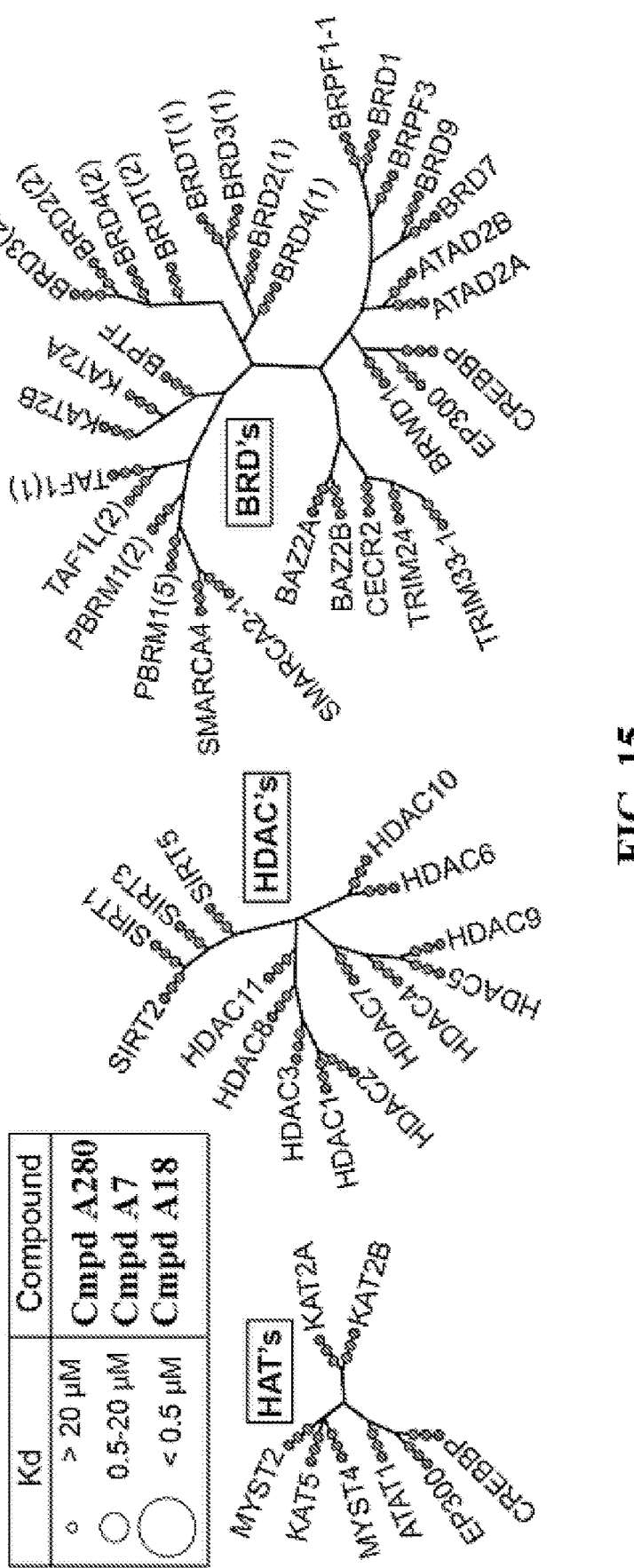

FIG. 15 shows representative data illustrating the off-target selectivity of compounds A7, A18, and A280.

Figure 16B:
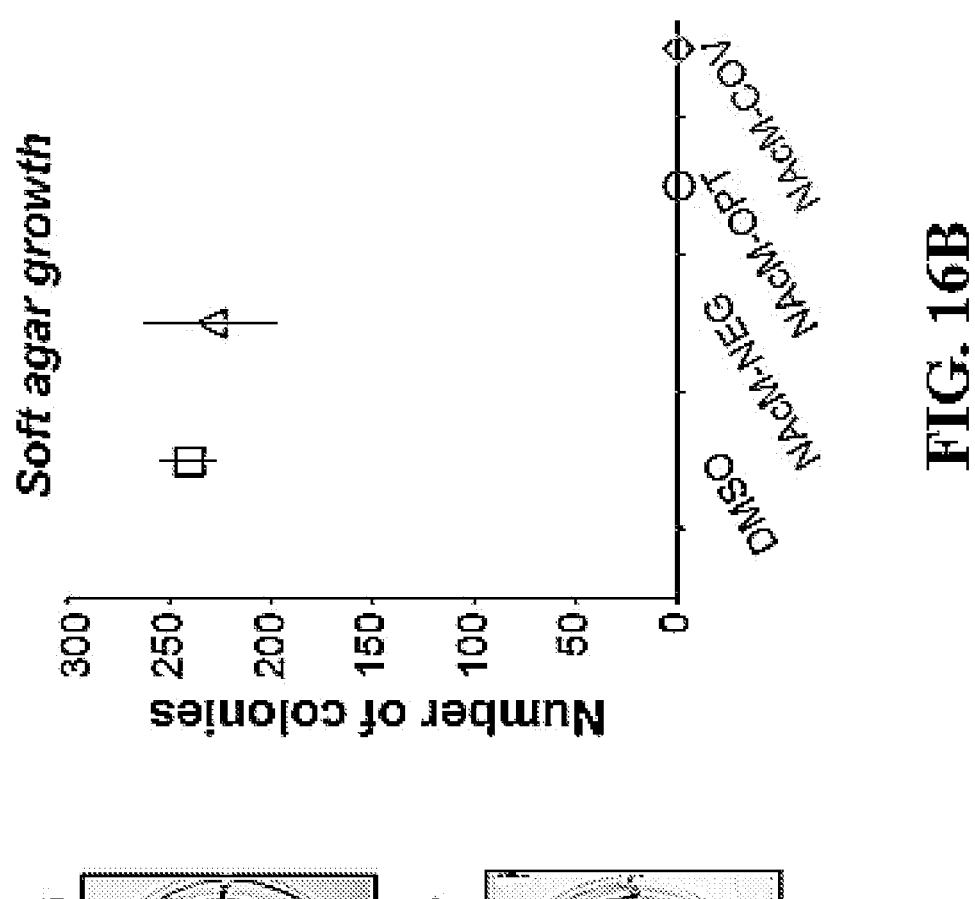
Figure 16A:
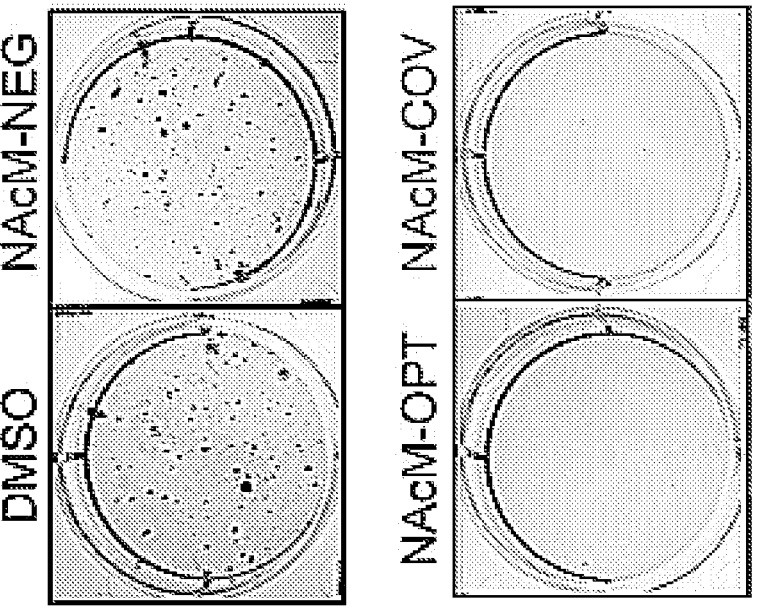
Figures 17A, 17B:
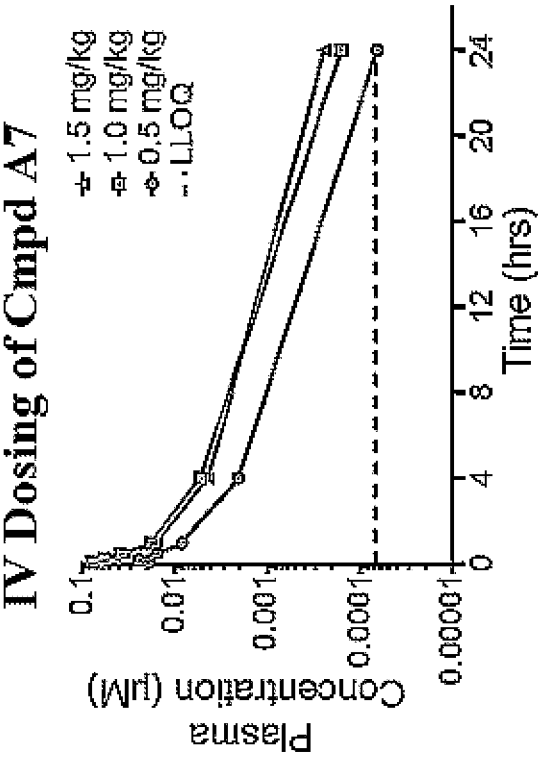
Figures 17C, 17D:
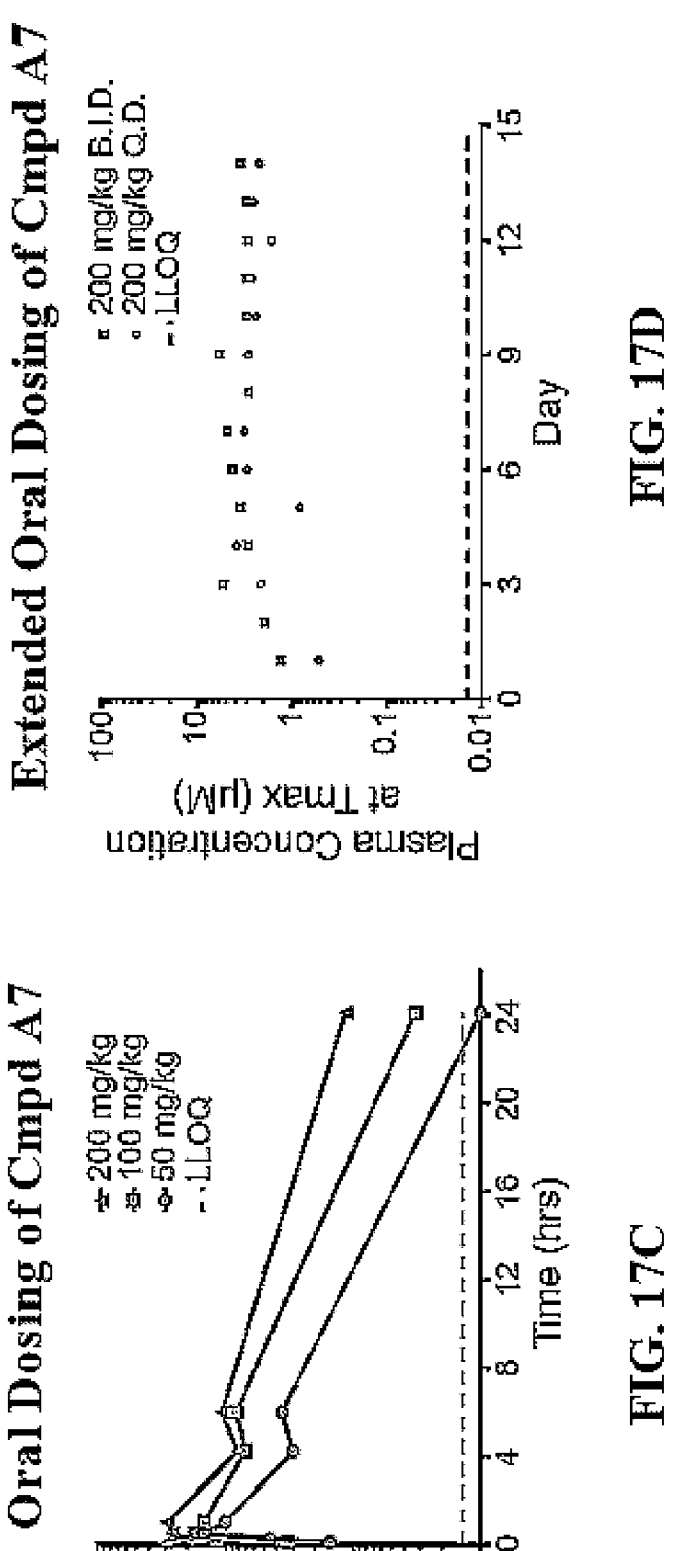

FIG. 16A and FIG. 16B show representative data indicating that cmpd A7 mediated reductions in CUL neddylation prevents anchorage independent growth of a DCN1 amplified carcinoma cell line. Specifically, FIG. 16A shows representative wells from soft agar growth assay showing that 10 μM Cmpd A7 and Cmpd A18, but not Cmpd A280, inhibit the anchorage independent growth of HCC95 cells. FIG. 16B shows the quantification of results from FIG. 16A.

FIG. 17A-D show representative data illustrating the in vivo plasma pharmacokinetic properties of compound A7 (17A) and intravenous dosing (17B), oral dosing (17C), and extended oral dosing (17D) of compound A7.

Figure 18:
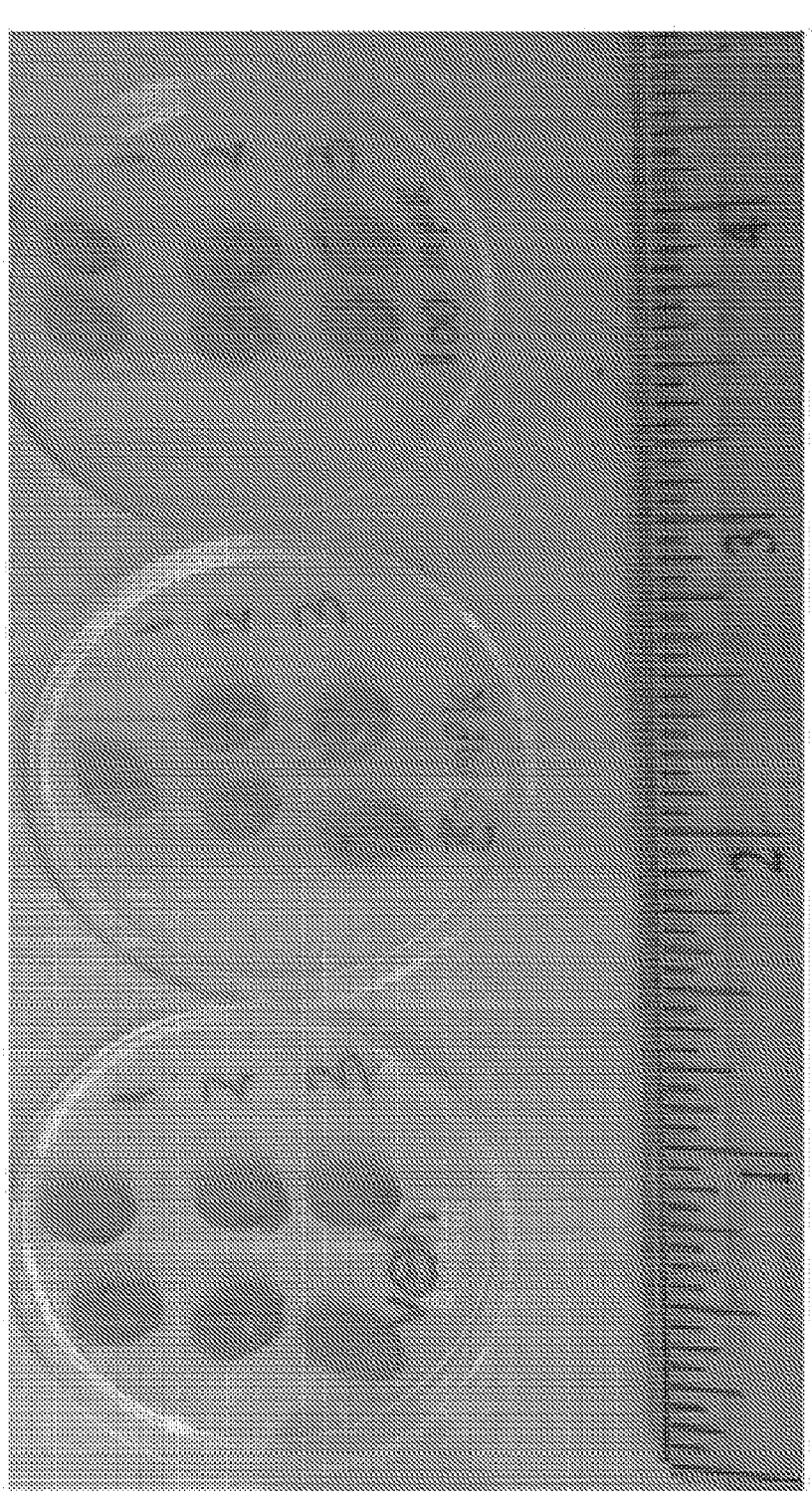

FIG. 18 shows a representative image of the spermatogenesis study groups.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

7
DESCRIPTION

The present invention can be understood more readily by reference to the following detailed description of the invention and the Examples included therein.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders, e.g., a neurodegenerative disease or disease of uncontrolled cellular proliferation, associated with DCN1-UBC12 interaction prior to the administering step. In some aspects of the disclosed method, the subject has been diagnosed with a need for inhibition of DCN1-mediated cullin-RING ligase activity prior to the administering step. In some aspects of the disclosed method, the subject has been diagnosed with a disorder of uncontrolled cellular proliferation, e.g., a cancer, prior to the administering step. In some aspects of the disclosed method, the subject has been diagnosed with a neurodegenerative disorder prior to the administering step. In some aspects of the disclosed method, the subject has been identified with a disorder treatable by inhibiting the DCN1-UBC12 interaction prior to the administering step. In some aspects of the disclosed method, the subject has been identified with a disorder treatable by inhibiting DCN1-mediated cullin-RING ligase activity prior to the administering step. In some aspects of the disclosed method, the subject has been identified with a bacterial or viral infection prior to the administering step. In some aspects of the disclosed method, the subject has been identified with a need for male contraception. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibiting the DCN1-UBC12 interaction" means having been subjected to a physical examination by a person of skill, for example, a physician, and found to have a condition that can be diagnosed or treated by a compound or composition that can inhibit the DCN1-UBC12 interaction. As a further example, "diagnosed with a need for inhibiting the DCN1-UBC12 interaction" refers to having been subjected to a physical examination by a person of skill, for example, a physician, and found to have a condition characterized by a DCN1-UBC12 interaction dysfunction. Such a diagnosis can be in reference to a disorder, such as a neurodegenerative disease, and the like, as discussed herein. For example, the term "diagnosed with a need for treatment of a disorder of uncontrolled cellular proliferation" refers to having been subjected to a physical examination by a person of skill, for example, a physician, and found to have a condition of uncontrolled cellular proliferation, e.g., a cancer, that can be treated by various therapeutic agents or methods, including, but not limited to, the disclosed compounds and/or products of the disclosed methods of making. For example, "diagnosed with a need for treatment of one or more disorders of uncontrolled cellular proliferation associated with a DCN1-UBC12 interaction dysfunction" means having been subjected to a physical examination by a person of skill, for example, a physician, and found to have one or more disorders of uncontrolled cellular proliferation, e.g., a cancer, associated with a DCN1-UBC12 interaction dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a DCN1-UBC12 interaction dysfunction) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target protein(s) (e.g., the DCN1-UBC12 proteins), or other biological entity together in such a manner that the compound can affect the activity of the target, either directly; e.g., by interacting with the target protein(s) itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "IC$_{50}$," is intended to refer to the concentration of a substance (e.g., a compound or a drug) that is required for 50% inhibition of a biological process, or component of a process, including a protein, subunit, organelle, ribonucleoprotein, etc. For example, IC$_{50}$ refers to the half maximal (50%) inhibitory concentration (IC) of a substance as determined in a suitable assay. For example, an IC$_{50}$ for inhibiting DCN1-UBC12 interaction can be determined in an in vitro assay system.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group", as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula (CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as OA$^1$-OA$^2$ or OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and hetero-cycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, het-eroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not lim-ited to, cycloheptynyl, cyclooctynyl, cyclononynyl, and the like. The term "heterocycloalkynyl" is a type of cycloalk-enyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the 71 clouds contain $(4n+2)$ π electrons. A further discussion of aromaticity is found in Morrison and Boyd, Organic Chem-istry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, het-eroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are repre-sented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH2.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or het-eroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalky-nyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalky-nyl, aryl, or heteroaryl group described herein and "a" is an integer of from 1 to 500. Examples of polyether groups include polyethylene oxide, polypropylene oxide, and poly-butylene oxide.

The terms "halo," "halogen" or "halide," as used herein can be used interchangeably and refer to F, Cl, Br, or I.

The terms "pseudohalide," "pseudohalogen" or "pseudo-halo," as used herein can be used interchangeably and refer to functional groups that behave substantially similar to halides. Such functional groups include, by way of example, cyano, thiocyanato, azido, trifluoromethyl, trifluo-romethoxy, perfluoroalkyl, and perfluoroalkoxy groups.

The term "heteroalkyl," as used herein refers to an alkyl group containing at least one heteroatom. Suitable heteroa-toms include, but are not limited to, O, N, Si, P and S, the nitrogen, phosphorous and sulfur atoms are optionally oxi-dized, and the nitrogen heteroatom is optionally quaternized. Heteroalkyls can be substituted as defined above for alkyl groups.

The term "heteroaryl," as used herein refers to an aro-matic group that has at least one heteroatom incorporated within the ring of the aromatic group. Examples of heteroa-toms include, but are not limited to, nitrogen, oxygen, sulfur, and phosphorus, where N-oxides, sulfur oxides, and diox-
ides are permissible heteroatom substitutions. The het-
eroaryl group can be substituted or unsubstituted. The het-
eroaryl group can be substituted with one or more groups
including, but not limited to, alkyl, cycloalkyl, alkoxy,
amino, ether, halide, hydroxy, nitro, silyl, sulfo-oxo, or thiol
as described herein. Heteroaryl groups can be monocyclic,
or alternatively fused ring systems. Heteroaryl groups
include, but are not limited to, furyl, imidazolyl, pyrimidi-
nyl, tetrazolyl, thienyl, pyridinyl, pyrrolyl, N-methylpyrro-
lyl, quinolinyl, isoquinolinyl, pyrazolyl, triazolyl, thiazolyl,
oxazolyl, isoxazolyl, oxadiazolyl, thiadiazolyl, isothiazolyl,
pyridazinyl, pyrazinyl, benzofuranyl, benzodioxolyl, benzo-
thiophenyl, indolyl, indazolyl, benzimidazolyl, imida-
zopyridinyl, pyrazolopyridinyl, pyrazolopyrimidinyl, 1,2-
oxazol-4-yl, 1,2-oxazol-5-yl, 1,3-oxazolyl, 1,2,4-oxadiazol-
5-yl, 1,2,3-triazolyl, 1,3-thiazol-4-yl, pyridinyl, and
pyrimidin-5-yl.

The terms "heterocycle" or "heterocyclyl," as used herein
can be used interchangeably and refer to single and multi-
cyclic aromatic or non-aromatic ring systems in which at
least one of the ring members is other than carbon. Thus, the
term is inclusive of, but not limited to, "heterocycloalkyl,"
"heteroaryl," "bicyclic heterocycle" and "polycyclic hetero-
cycle." Heterocycle includes pyridine, pyrimidine, furan,
thiophene, pyrrole, isoxazole, isothiazole, pyrazole, oxazole,
thiazole, imidazole, oxazole, including, 1,2,3-oxadiazole,
1,2,5-oxadiazole and 1,3,4-oxadiazole, thiadiazole, includ-
ing, 1,2,3-thiadiazole, 1,2,5-thiadiazole, and 1,3,4-thiadiaz-
ole, triazole, including, 1,2,3-triazole, 1,3,4-triazole, tetra-
zole, including 1,2,3,4-tetrazole and 1,2,4,5-tetrazole,
pyridine, pyridazine, pyrimidine, pyrazine, triazine, includ-
ing 1,2,4-triazine and 1,3,5-triazine, tetrazine, including
1,2,4,5-tetrazine, pyrrolidine, piperidine, piperazine, mor-
pholine, azetidine, tetrahydropyran, tetrahydrofuran,
dioxane, and the like.

The term "bicyclic heterocycle" or "bicyclic heterocy-
clyl," as used herein refers to a ring system in which at least
one of the ring members is other than carbon. Bicyclic
heterocyclyl encompasses ring systems an aromatic ring is
fused with another aromatic ring, or an aromatic ring is
fused with a non-aromatic ring. Bicyclic heterocyclyl
encompasses ring systems a benzene ring is fused to a 5- or
a 6-membered ring containing 1, 2 or 3 ring heteroatoms or
a pyridine ring is fused to a 5- or a 6-membered ring
containing 1, 2 or 3 ring heteroatoms. Bicyclic heterocyclic
groups include, but are not limited to, indolyl, indazolyl,
pyrazolo[1,5-a]pyridinyl, benzofuranyl, quinolinyl, quinox-
alinyl, 1,3-benzodioxolyl, 2,3-dihydro-1,4-benzodioxinyl,
3,4-dihydro-2H-chromenyl, 1H-pyrazolo[4,3-c]pyridin-3-
yl; 1H-pyrrolo[3,2-b]pyridin-3-yl; and 1H-pyrazolo[3,2-b]
pyridin-3-yl.

The term "heterocycloalkyl" as used herein refers to an
aliphatic, partially unsaturated or fully saturated, 3- to
14-membered ring system, including single rings of 3 to 8
atoms and bi- and tricyclic ring systems. The heterocycloal-
kyl ring-systems include one to four heteroatoms indepen-
dently selected from oxygen, nitrogen, and sulfur, a nitrogen
and sulfur heteroatom optionally can be oxidized and a
nitrogen heteroatom optionally can be substituted. Repre-
sentative heterocycloalkyl groups include, but are not lim-
ited to, pyrrolidinyl, pyrazolinyl, pyrazolidinyl, imidazoli-
nyl, imidazolidinyl, piperidinyl, piperazinyl, oxazolidinyl,
isoxazolidinyl, morpholinyl, thiazolidinyl, isothiazolidinyl,
and tetrahydrofuryl.

The term "hydroxyl" as used herein is represented by the
formula —OH.

The term "ketone" as used herein is represented by the
formula $A^1C(O)A^2$, where $A^1$ and $A^2$ can be, independently,
an alkyl, cycloalkyl, alkenyl, cycloalkenyl, alkynyl,
cycloalkynyl, aryl, or heteroaryl group as described herein.

The term "azide" as used herein is represented by the
formula $—N_3$.

The term "nitro" as used herein is represented by the
formula $—NO_2$.

The term "nitrile" as used herein is represented by the
formula —CN.

The term "silyl" as used herein is represented by the
formula $—SiA^1A^2A^3$, where $A^1$, $A^2$, and $A^3$ can be, inde-
pendently, hydrogen or an alkyl, cycloalkyl, alkoxy, alkenyl,
cycloalkenyl, alkynyl, cycloalkynyl, aryl, or heteroaryl
group as described herein.

The term "sulfo-oxo" as used herein is represented by the
formulas $—S(O)A^1$, $—S(O)_2A^1$, $—OS(O)_2A^1$, or $—OS(O)_2OA^1$, where $A^1$ can be hydrogen or an alkyl, cycloalkyl,
alkenyl, cycloalkenyl, alkynyl, cycloalkynyl, aryl, or het-
eroaryl group as described herein. Throughout this specifi-
cation "S(O)" is a short hand notation for S=O. The term
"sulfonyl" is used herein to refer to the sulfo-oxo group
represented by the formula $—S(O)_2A^1$, where $A^1$ can be
hydrogen or an alkyl, cycloalkyl, alkenyl, cycloalkenyl,
alkynyl, cycloalkynyl, aryl, or heteroaryl group as described
herein. The term "sulfone" as used herein is represented by
the formula $A^1S(O)_2A^2$, where $A^1$ and $A^2$ can be, indepen-
dently, an alkyl, cycloalkyl, alkenyl, cycloalkenyl, alkynyl,
cycloalkynyl, aryl, or heteroaryl group as described herein.
The term "sulfoxide" as used herein is represented by the
formula $A^1S(O)A^2$, where $A^1$ and $A^2$ can be, independently,
an alkyl, cycloalkyl, alkenyl, cycloalkenyl, alkynyl,
cycloalkynyl, aryl, or heteroaryl group as described herein.

The term "thiol" as used herein is represented by the
formula —SH.

"$R^1$," "$R^2$," "$R^3$," "$R''$," where n is an integer, as used
herein can, independently, possess one or more of the groups
listed above. For example, if $R^1$ is a straight chain alkyl
group, one of the hydrogen atoms of the alkyl group can
optionally be substituted with a hydroxyl group, an alkoxy
group, an alkyl group, a halide, and the like. Depending
upon the groups that are selected, a first group can be
incorporated within second group or, alternatively, the first
group can be pendant (i.e., attached) to the second group.
For example, with the phrase "an alkyl group comprising an
amino group," the amino group can be incorporated within
the backbone of the alkyl group. Alternatively, the amino
group can be attached to the backbone of the alkyl group.
The nature of the group(s) that is (are) selected will deter-
mine if the first group is embedded or attached to the second
group.

As described herein, compounds of the invention may
contain "optionally substituted" moieties. In general, the
term "substituted," whether preceded by the term "option-
ally" or not, means that one or more hydrogens of the
designated moiety are replaced with a suitable substituent.
Unless otherwise indicated, an "optionally substituted"
group may have a suitable substituent at each substitutable
position of the group, and when more than one position in
any given structure may be substituted with more than one
substituent selected from a specified group, the substituent
may be either the same or different at every position.
Combinations of substituents envisioned by this invention
are preferably those that result in the formation of stable or
chemically feasible compounds. In is also contemplated that,
in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH (OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$ N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O) N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$ NR$^\circ$$_2$; —(CH$_2$)$_{0-4}$S(O)R$^\circ$; —N(R$^\circ$)S(O)$_2$NR$^\circ$$_2$; —N(R$^\circ$)S (O)$_2$R$^\circ$; —N(OR$^\circ$)R$^\circ$; —C(NH)NR$^\circ$$_2$; —P(O)$_2$R$^\circ$; —P(O) R$^\circ$$_2$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, each R$^\circ$ may be substituted as defined below and is independently hydrogen, C$_1$-6 aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$ C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or disubstituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thiohaloal-kyl, alkoxy, substituted alkoxy, haloalkyl, haloalkoxy, aryl, substituted aryl, heteroaryl, heterocyclic, or substituted het-erocyclic radicals, the terms are defined elsewhere herein. A few non-limiting examples of organic radicals that include heteroatoms include alkoxy radicals, trifluoromethoxy radi-cals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inor-ganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharma-ceutically acceptable cation for anionic inorganic radicals such as a sulfate, phosphate, or like anionic inorganic radical. Inorganic radicals do not comprise metalloids ele-ments such as boron, aluminum, gallium, germanium, arse-nic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enan-tiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically accept-able salts thereof. Mixtures of stereoisomers, as well as isolated specific stereoisomers, are also included. During the course of the synthetic procedures used to prepare such compounds, or in using racemization or epimerization pro-cedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configu-ration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are iden-tical except that they are non-superimposable mirror images of one another. A specific stereoisomer can also be referred to as an enantiomer, and a mixture of such isomers is often called an enantiomeric mixture. A 50:50 mixture of enan-tiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which are added together prior to crystallization. In certain instances, the two or more molecules may owe their stability through non-covalent interaction. One or more components of this molecular complex provide a stable framework in the crystalline lattice. In certain instances, the guest molecules are incorporated in the crystalline lattice as anhydrates or solvates, see e.g., "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

keto form          enol form

-continued amide form          imidic acid form

Likewise, amides with an N-hydrogen can exist in an equilibrium of the amide form and the imidic acid form. As another example, pyrazoles can exist in two tautomeric forms, $N^1$-unsubstituted, 3-$R^3$ and $N^1$-unsubstituted, 5-$R^3$ as shown below.

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

which is understood to be equivalent to a formula:

n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of DCN1-mediated cullin-RING ligase activity.

In a further aspect, the present invention relates to compounds that inhibit the DCN1-UBC12 interaction. In various aspects, the present invention relates to compounds that exhibit inhibition of the DCN1-UBC12 interaction in a TR-FRET assay comprising a labeled DCN1 protein or peptide and a labeled UBC12 protein or peptide. A list of potential targets of the disclosed compounds is shown in Table 1 below.

TABLE 1

| Human DCN family members | Other names |
| --- | --- |
| DCN1 | DCUN1D1, DCNL1, SCCRO, DCN1-like protein 1 |
| DCN2 | DCUN1D2, DCNL2, DCN1-like protein 2 |
| DCN3 | DCUN1D3, DCNL3, DCN1-like protein 3 |
| DCN4 | DCUN1D4, DCNL4, DCN1-like protein 4 |
| DCN5 | DCUN1D5, DCNL5, DCN1-like protein 5 |

| Human NEDD8 E2 family members | Other names |
| --- | --- |
| UBC12 UBE2F (binds same pocket in DCN-family members as UBC12) | UBE2M |

In one aspect, the compounds of the invention are useful in the treatment of disorders of uncontrolled cellular proliferation, e.g., a cancer. In a further aspect, the compounds of the invention are useful in the treatment of a squamous cell cancer. In a still further aspect, the compounds of the invention are useful in the treatment of a cancer associated with a DCN1-UBC12 interaction dysfunction. In a yet further aspect, the compounds of the invention are useful in the treatment of a cancer associated with a DCN1-mediated cullin-RING ligase activity dysfunction.

In one aspect, the compounds of the invention are useful in the treatment of a neurodegenerative disorder. In a further aspect, the compounds of the invention are useful in the treatment of a neurodegenerative disorder associated with a DCN1-UBC12 interaction dysfunction. In a yet further aspect, the compounds of the invention are useful in the treatment of a neurodegenerative disorder associated with a DCN1-mediated cullin-RING ligase activity dysfunction.

In one aspect, the compounds of the invention are useful in the treatment of a viral or bacterial infection.

In one aspect, the compounds of the invention are useful for male contraception.

In various aspects, a compound can be present as a racemate. For example, a compound can be selected from:

27

28

29
-continued

30
-continued

31

32

33

-continued

34

-continued

In various aspects, a compound can be present as a cis diastereomer. For example, a compound can be selected from:

35

36

37

-continued

38

-continued

39

-continued

40

-continued

, and

In a further aspect, a compound can be selected from:

41

42

43

44

45
-continued

46
-continued

In various aspects, a compound can be present as a trans diastereomer. For example, a compound can be selected from:

47

48

49

50

51
-continued

52
-continued

53
-continued

54
-continued

In a further aspect, a compound can be selected from:

55
-continued

56
-continued

57

58

-continued

-continued

In various aspects, the cis diastereomer may be preferred.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

Disclosed are compounds having a structure represented by a formula:

each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and R$^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$; R$^3$ is C$_1$-C$_8$ alkyl; C1-C8 alkoxyalkyl; —(C1-C3 alkyl)-(C3-C8 cycloalkyl); or —(C1-C3 alkyl)-Ar$^1$; Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Also disclosed are compounds having a structure represented by a formula:

each of R$^{1a}$, R$^{1b}$, and R$^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of R$^{1a}$, R$^{1b}$, and R$^{1c}$ is not hydrogen; or R$^{1a}$ and R$^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and R$^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; R$^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

In a further aspect, a compound has a structure represented by the formula:

each of R$^{1a}$ and R$^{1c}$ are independently selected from halogen, —SF$_5$, —NO$_2$, —CH$_3$, —CH$_2$F, —CHF$_2$, —CF$_3$, —OCF$_3$, —NHCH$_3$, and —N(CH$_3$)$_2$.

In a further aspect, a compound has a structure represented by the formula:

each of R$^{1a}$ and R$^{1b}$ are independently halogen, —SF$_5$, —NO$_2$, —CH$_3$, —CH$_2$F, —CHF$_2$, —CF$_3$, —OCF$_3$, —NHCH$_3$, or —N(CH$_3$)$_2$.

In a further aspect, a compound has a structure selected from the formula:

-continued

In a further aspect, a compound has a structure represented by the formula:

each of $R^{10a}$, $R^{10b}$, $R^{10c}$, $R^{10d}$, and $R^{10e}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —C(O) CH=CH$_2$, and —(CH$_2$)C(O)CH=CH$_2$; that no more than one of $R^{10a}$, $R^{10b}$, $R^{10c}$, $R^{10d}$, and $R^{10e}$ is —C(O)CH=CH$_2$ or —(CH$_2$)C(O)CH=CH$_2$; and at least two of $R^{10a}$, $R^{10b}$, $R^{10c}$, $R^{10d}$, and $R^{10e}$ is hydrogen.

In a further aspect, a compound has a structure represented by the formula:

each of $R^{10a}$, $R^{10b}$, $R^{10c}$, $R^{10d}$, and $R^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; and at least one of $R^{10a}$, $R^{10b}$, $R^{10c}$, $R^{10d}$, and $R^{10e}$ is hydrogen.

In a further aspect, a compound has a structure represented by the formula:

each of $R^{10a}$, $R^{10b}$, $R^{10c}$, $R^{10d}$, and $R^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; and at least one of $R^{10a}$, $R^{10b}$, $R^{10c}$, $R^{10d}$, and $R^{10e}$ is hydrogen.

In a further aspect, a compound has a structure represented by the formula:

each of $R^{10a}$, $R^{10b}$, $R^{10c}$, $R^{10d}$, and $R^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; and at least one of $R^{10a}$, $R^{10b}$, $R^{10c}$, $R^{10d}$, and $R^{10e}$ is hydrogen.

In a further aspect, a compound has a structure represented by the formula:

each of $R^{10a}$, $R^{10b}$, $R^{10c}$, $R^{10d}$, and $R^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; and at least one of $R^{10a}$, $R^{10b}$, $R^{10c}$, $R^{10d}$, and $R^{10e}$ is hydrogen.

In a further aspect, a compound has a structure selected from the formula:

In a further aspect, a compound has a structure represented by the formula:

In a further aspect, a compound has a structure represented by the formula:

Disclosed are compounds having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and wherein $R^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$; wherein $R^3$ is C$_1$-C$_8$ alkyl; C1-C8 alkoxyalkyl; —(C1-C3 alkyl)-(C3-C8 cycloalkyl); or —(C1-C3 alkyl)-Ar$^1$; wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Disclosed are compounds having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Disclosed are compounds having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$; wherein $R^3$ is C$_1$-C$_8$ alkyl; C1-C8 alkoxyalkyl; —(C1-C3 alkyl)-(C3-C8 cycloalkyl); or —(C1-C3 alkyl)-Ar$^1$; wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Disclosed are compounds having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$; or a pharmaceutically acceptable salt thereof.

Disclosed are compounds having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and wherein $R^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$; wherein $R^3$ is C1-C8 alkyl; C1-C8 alkoxyalkyl; —(C1-C3 alkyl)-(C3-C8 cycloalkyl); or —(C1-C3 alkyl)-Ar$^1$; wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$)NHC(O)CH=CH$_2$; or a pharmaceutically acceptable salt thereof.

Disclosed are compounds having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$)NHC(O)CH=CH$_2$; or a pharmaceutically acceptable salt thereof.

Disclosed are compounds having a structure represented by a formula:

Disclosed are compounds having a structure represented by a formula:

a. $R^{1a}$, $R^{1b}$, and $R^{1c}$ Groups

In one aspect, each of Ria, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of Ria, $R^{1b}$, and $R^{1c}$ is not hydrogen; or $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$.

In a further aspect, each of $R^{1a}$, $R^{1b}$, and $R^{1c}$ is independently hydrogen, halogen, —SF$_5$, —CH$_3$, —CF$_3$, or —OCF$_3$, provided that at least one of Ria, $R^{1b}$, and $R^{1c}$ is not hydrogen.

In various aspects, $R^{1c}$ is hydrogen; and each of $R^{1a}$ and $R^{1b}$ is independently halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl. In a further aspect, $R^{1c}$ is hydrogen; and each of $R^{1a}$ and $R^{1b}$ is independently halogen, —SF$_5$, —CH$_3$, —CF$_3$, or —OCF$_3$.

In various aspects, $R^{1b}$ is hydrogen; and each of $R^{1a}$ and $R^{1c}$ is independently halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl. In a further aspect, $R^{1b}$ is hydrogen; and each of $R^{1a}$ and $R^{1c}$ is independently halogen, —SF$_5$, —CH$_3$, —CF$_3$, or —OCF$_3$.

In various aspects, each of $R^{1b}$ and $R^{1c}$ is hydrogen; and $R^{1a}$ is halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl. In a further aspect, each of $R^{1b}$ and $R^{1c}$ is hydrogen; and $R^{1a}$ is independently halogen, —SF$_5$, —CH$_3$, —CF$_3$, or —OCF$_3$.

In various aspects, each of $R^{1a}$ and $R^{1c}$ is hydrogen; and $R^{1b}$ is halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl. In a further aspect, each of $R^{1a}$ and $R^{1c}$ is hydrogen; and $R^{1b}$ is independently halogen, —SF$_5$, —CH$_3$, —CF$_3$, or —OCF$_3$.

b. $R^2$ Groups

In one aspect, $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and $R^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$.

In a further aspect, $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and $R^2$ is unsubstituted. In a still further aspect, $R^2$ is —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, or —(C1-C3)-(bicyclic); and $R^2$ is unsubstituted.

In one aspect, $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl).

In a further aspect, $R^2$ is C3-C6 alkyl, —(C1-C6)-CF$_3$, or —(C1-C6)-C≡CH. In a still further aspect, $R^2$ is —SO$_2$—(C1-C6 alkyl). In a yet further aspect, $R^2$ is —(CH$_2$)-cyclopropyl.

In a further aspect, $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl). In a still further aspect, $R^2$ is C3-C6 alkyl, —(CH$_2$)-cyclopropyl, —(CH$_2$)-cyclobutyl, —(CH$_2$)-cyclopentyl, or —(CH$_2$)-cyclohexyl. In a yet further aspect, $R^2$ is C3-C6 alkyl, —(CH$_2$)-cyclopropyl, —(CH$_2$)-cyclopentyl, or —(CH$_2$)-cyclohexyl. In an even further aspect, $R^2$ is C3-C6 alkyl or —(CH$_2$)-cyclopropyl.

In a further aspect, $R^2$ is C3-C6 alkyl. In a still further aspect, $R^2$ has a structure represented by a formula:

-continued

In a yet further aspect, $R^2$ has a structure represented by a formula:

In a further aspect, $R^2$ is —(C1-C3 alkyl)-(bicycloalkyl); and the —(C1-C3 alkyl)-(bicycloalkyl) group has 3 to 8 carbon atoms in each ring structure. In a still further aspect, $R^2$ is —(C1-C3 alkyl)-(bicycloalkyl); and the —(C1-C3 alkyl)-(bicycloalkyl) group has two fused ring systems collectively composed of 7-12 carbon atoms. In a yet further aspect, $R^2$ is —(C1-C3 alkyl)-(bicycloalkenyl); and the —(C1-C3 alkyl)-(bicycloalkenyl) group has 3 to 8 carbon atoms in each ring structure. In an even further aspect, $R^2$ is —(C1-C3 alkyl)-(bicycloalkenyl); and the —(C1-C3 alkyl)-(bicycloalkenyl) group has two fused ring systems collectively composed of 7-12 carbon atoms. In a still further aspect, $R^2$ is —(C1-C3 alkyl)-(1R,4S)-bicyclo[2.2.1]hept-2-ene. In a yet further aspect, $R^2$ is —(CH$_2$)-(1R,4S)-bicyclo[2.2.1]hept-2-ene.

c. $R^3$ Groups

In one aspect, $R^3$ is $C_1$-$C_8$ alkyl; C1-C8 alkoxyalkyl; —(C1-C3 alkyl)-(C3-C8 cycloalkyl); or —(C1-C3 alkyl)-Ar$^1$.

In a further aspect, $R^3$ is a group having a structure represented by a formula:

In a further aspect, $R^3$ is a group having a structure represented by a formula:

In a further aspect, $R^3$ is —CH$_2$—Ar$^1$.

d. $R^{10a}$, $R^{10b}$, $R^{10c}$, $R^{10d}$, and $R^{10e}$ Groups

In one aspect, each of $R^{10a}$, $R^{10b}$, $R^{10c}$, $R^{10d}$, and $R^{10e}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —C(O)CH=CH$_2$, and —(CH$_2$)C(O)CH=CH$_2$; provided that no more than one of R$^{10a}$, R$^{10b}$, R$^{10c}$, R$^{10d}$, and R$^{10e}$ is —C(O)CH=CH$_2$ or —(CH$_2$)C(O)CH=CH$_2$; and provided at least two of R$^{10a}$, R$^{10b}$, R$^{10c}$, R$^{10d}$, and R$^{10e}$ are hydrogen. In a further aspect, each of R$^{10a}$, R$^{10b}$, R$^{10c}$, R$^{10d}$ and R$^{10e}$ is hydrogen.

In a further aspect, each of R$^{10a}$, R$^{10b}$, R$^{10c}$, R$^{10d}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least one of R$^{10a}$, R$^{10b}$, R$^{10c}$, R$^{10d}$, and R$^{10e}$ is hydrogen. In a still further aspect, each of R$^{10a}$, R$^{10b}$, R$^{10c}$, R$^{10d}$, and R$^{10e}$ is independently hydrogen, halogen, —SF$_5$, —CH$_3$, —CF$_3$, or —OCF$_3$; provided that at least one of R$^{10a}$, R$^{10b}$, R$^{10c}$, R$^{10d}$, and R$^{10e}$ is hydrogen. In a yet further aspect, each of R$^{10a}$, R$^{10b}$, R$^{10c}$, R$^{10d}$, and R$^{10e}$ is independently hydrogen, halogen, —SF$_5$, and —CF$_3$; provided that at least one of R$^{10a}$, R$^{10b}$, R$^{10c}$, R$^{10d}$, and R$^{10e}$ is hydrogen.

In a further aspect, each of R$^{10a}$, R$^{10b}$, R$^{10c}$, R$^{10d}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least two of R$^{10a}$, R$^{10b}$, R$^{10c}$, R$^{10d}$, and R$^{10e}$ are hydrogen. In a still further aspect, each of R$^{10a}$, R$^{10b}$, R$^{10c}$, R$^{10d}$, and R$^{10e}$ is independently hydrogen, halogen, —SF$_5$, —CH$_3$, —CF$_3$, or —OCF$_3$; provided that at least two of R$^{10a}$, R$^{10b}$, R$^{10c}$, R$^{10d}$, and R$^{10e}$ are hydrogen. In a yet further aspect, each of R$^{10a}$, R$^{10b}$, R$^{10c}$, R$^{10d}$, and R$^{10e}$ is independently hydrogen, halogen, —SF$_5$, and —CF$_3$; provided that at least two of R$^{10a}$, R$^{10b}$, R$^{10c}$, R$^{10d}$, and R$^{10c}$ are hydrogen.

In a further aspect, each of R$^{10a}$, R$^{10b}$, R$^{10c}$, R$^{10d}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least three of R$^{10a}$, R$^{10b}$, R$^{10c}$, R$^{10d}$, and R$^{10e}$ are hydrogen. In a still further aspect, each of R$^{10a}$, R$^{10b}$, R$^{10c}$, R$^{10d}$, and R$^{10e}$ is independently hydrogen, halogen, —SF$_5$, —CH$_3$, —CF$_3$, or —OCF$_3$; provided that at least three of R$^{10a}$, R$^{10b}$, R$^{10c}$, R$^{10d}$, and R$^{10e}$ are hydrogen. In a yet further aspect, each of R$^{10a}$, R$^{10b}$, R$^{10c}$, R$^{10d}$, and R$^{10e}$ is independently hydrogen, halogen, —SF$_5$, and —CF$_3$; provided that at least three of R$^{10a}$, R$^{10b}$, R$^{10c}$, R$^{10d}$, and R$^{10e}$ are hydrogen.

In a further aspect, each of R$^{10a}$, R$^{10b}$, R$^{10c}$, R$^{10d}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least four of R$^{10a}$, R$^{10b}$, R$^{10c}$, R$^{10d}$, and R$^{10e}$ are hydrogen. In a still further aspect, each of R$^{10a}$, R$^{10b}$, R$^{10c}$, R$^{10d}$, and R$^{10e}$ is independently hydrogen, halogen, —SF$_5$, —CH$_3$, —CF$_3$, or —OCF$_3$; provided that at least four of R$^{10a}$, R$^{10b}$, R$^{10c}$, R$^{10d}$, and R$^{10e}$ are hydrogen. In a yet further aspect, each of R$^{10a}$, R$^{10b}$, R$^{10c}$, R$^{10d}$, and R$^{10e}$ is independently hydrogen, halogen, —SF$_5$, and —CF$_3$; provided that at least four of R$^{10a}$, R$^{10b}$, R$^{10c}$, R$^{10d}$, and R$^{10e}$ are hydrogen.

In a further aspect one of R$^{10a}$, R$^{10b}$, R$^{10c}$, R$^{10d}$, and R$^{10e}$ is —NHC(O)CH=CH$_2$ and —(CH$_2$)NHC(O)CH=CH$_2$; and each of the remaining of R$^{10a}$, R$^{10b}$, R$^{10c}$, R$^{10d}$, and R$^{10e}$ is hydrogen. In a still further aspect one of R$^{10a}$, R$^{10b}$, R$^{10c}$, R$^{10d}$, and R$^{10e}$ is —NHC(O)CH=CH$_2$; and each of the remaining of R$^{10a}$, R$^{10b}$, R$^{10c}$, R$^{10d}$, and R$^{10e}$ is hydrogen. In a further aspect one of R$^{10a}$, R$^{10b}$, R$^{10c}$, R$^{10d}$, and R$^{10e}$ is —(CH$_2$)NHC(O)CH=CH$_2$; and each of the remaining of R$^{10a}$, R$^{10b}$, R$^{10c}$, R$^{10d}$, and R$^{10e}$ is hydrogen.

In one aspect, each of R$^{10a}$, R$^{10b}$, R$^{10c}$, and R$^{10d}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least one of R$^{10a}$, R$^{10b}$, R$^{10c}$, and R$^{10d}$ is hydrogen. In a still further aspect, each of R$^{10a}$, R$^{10b}$, R$^{10c}$, and R$^{10d}$ is independently hydrogen, halogen, —SF$_5$, —CH$_3$, —CF$_3$, or —OCF$_3$; provided that at least one of R$^{10a}$, R$^{10b}$, R$^{10c}$, and R$^{10d}$ is hydrogen. In a yet further aspect, each of R$^{10a}$, R$^{10b}$, R$^{10c}$, and R$^{10d}$ is independently hydrogen, halogen, —SF$_5$, and —CF$_3$; provided that at least one of R$^{10a}$, R$^{10b}$, R$^{10c}$, and R$^{10d}$ is hydrogen. In an even further aspect, each of R$^{10a}$, R$^{10b}$, R$^{10c}$, and R$^{10d}$ is hydrogen.

In a further aspect, each of R$^{10a}$, R$^{10b}$, R$^{10c}$, and R$^{10d}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least two of R$^{10a}$, R$^{10b}$, R$^{10c}$, and R$^{10d}$ are hydrogen. In a still further aspect, each of R$^{10a}$, R$^{10b}$, R$^{10c}$, and R$^{10d}$ is independently hydrogen, halogen, —SF$_5$, —CH$_3$, —CF$_3$, or —OCF$_3$; provided that at least two of R$^{10a}$, R$^{10b}$, R$^{10c}$, and R$^{10d}$ are hydrogen. In a yet further aspect, each of R$^{10a}$, R$^{10b}$, R$^{10c}$, and R$^{10d}$ is independently hydrogen, halogen, —SF$_5$, and —CF$_3$; provided that at least two of R$^{10a}$, R$^{10b}$, R$^{10c}$, and R$^{10d}$ are hydrogen.

In a further aspect, each of R$^{10a}$, R$^{10b}$, R$^{10c}$, and R$^{10d}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least three Of R$^{10a}$, R$^{10b}$, R$^{10c}$, and R$^{10d}$ are hydrogen. In a still further aspect, each of R$^{10a}$, R$^{10b}$, R$^{10c}$, and R$^{10d}$ is independently hydrogen, halogen, —SF$_5$, —CH$_3$, —CF$_3$, or —OCF$_3$; provided that at least three of R$^{10a}$, R$^{10b}$, R$^{10c}$, R$^{10d}$, and R$^{10e}$ are hydrogen. In a yet further aspect, each of R$^{10a}$, R$^{10b}$, R$^{10c}$, and R$^{10d}$ is independently hydrogen, halogen, —SF$_5$, and —CF$_3$; provided that at least three of R$^{10a}$, R$^{10b}$, R$^{10c}$, and R$^{10d}$ are hydrogen.

In one aspect, each Of R$^{10a}$, R$^{10b}$, R$^{10c}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least one of R$^{10a}$, R$^{10b}$, R$^{10c}$, and R$^{10e}$ is hydrogen. In a still further aspect, each of R$^{10a}$, R$^{10b}$, R$^{10c}$, and R$^{10e}$ is independently hydrogen, halogen, —SF$_5$, —CH$_3$, —CF$_3$, or —OCF$_3$; provided that at least one of R$^{10a}$, R$^{10b}$, R$^{10c}$, and R$^{10e}$ is hydrogen. In a yet further aspect, each of R$^{10a}$, R$^{10b}$, R$^{10c}$, and R$^{10e}$ is independently hydrogen, halogen, —SF$_5$, and —CF$_3$; provided that at least one of R$^{10a}$, R$^{10b}$, R$^{10c}$, and R$^{10e}$ is hydrogen. In an even further aspect, each of R$^{10a}$, R$^{10b}$, R$^{10c}$, and R$^{10d}$ is hydrogen.

In a further aspect, each of R$^{10a}$, R$^{10b}$, R$^{1c}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least two of R$^{10a}$, R$^{10b}$, R$^{10c}$, and R$^{10e}$ are hydrogen. In a still further aspect, each of R$^{10a}$, R$^{10b}$, R$^{10c}$, and R$^{10e}$ is independently hydrogen, halogen, —SF$_5$, —CH$_3$, —CF$_3$, or —OCF$_3$; provided that at least two of R$^{10a}$, R$^{10b}$, R$^{10c}$, and R$^{10e}$ are hydrogen. In a yet further aspect, each of R$^{10a}$, R$^{10b}$, R$^{10c}$, and R$^{10e}$ is independently hydrogen, halogen, —SF$_5$, and —CF$_3$; provided that at least two of R$^{10a}$, R$^{10b}$, R$^{10c}$, and R$^{10e}$ are hydrogen.

In a further aspect, each of R$^{10a}$, R$^{10b}$, R$^{1c}$, and R$^{10e}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least three Of R$^{10a}$, R$^{10b}$, R$^{10c}$, and R$^{10e}$ are hydrogen. In a still further aspect, each of R$^{10a}$, R$^{10b}$, R$^{10c}$, and R$^{10e}$ is independently hydrogen, halogen, —SF$_5$, —CH$_3$, —CF$_3$, or —OCF$_3$; provided that at least three of R$^{10a}$, R$^{10b}$, R$^{10c}$, R$^{10d}$, and R$^{10e}$ are hydrogen. In a yet further aspect, each of R$^{10a}$, R$^{10b}$, R$^{10c}$, and R$^{10e}$ is independently hydrogen, halogen, —SF$_5$, and —CF$_3$; provided that at least three of R$^{10a}$, R$^{10b}$, R$^{10c}$, and R$^{10e}$ are hydrogen.

e. R$^{20a}$, R$^{20b}$, R$^{20c}$, and R$^{21d}$ Groups

In one aspect, each of R$^{20a}$, R$^{20b}$, R$^{20c}$, and R$^{20d}$ is independently selected from hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH=CH$_2$, and —(CH$_2$) NHC(O)CH=CH$_2$, provided that at least one of R$^{20a}$, R$^{20b}$, R$^{20c}$, and R$^{20d}$ is hydrogen. In a further aspect, each of R$^{20a}$, R$^{20b}$, R$^{20c}$, and R$^{20d}$ is hydrogen.

In one aspect, each of R$^{20a}$, R$^{20b}$, R$^{20c}$, and R$^{20d}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least one of R$^{20a}$, R$^{20b}$, R$^{20c}$, and R$^{20d}$ is hydrogen. In a still further aspect, each of R$^{20a}$, R$^{20b}$, R$^{20c}$, and R$^{20d}$ is independently hydrogen, halogen, —SF$_5$, —CH$_3$, —CF$_3$, or —OCF$_3$; provided that at least one of R$^{20a}$, R$^{20b}$, R$^{20c}$, and R$^{20d}$ is hydrogen. In a yet further aspect, each of R$^{20a}$, R$^{20b}$, R$^{20c}$, and R$^{20d}$ is independently hydrogen, halogen, —SF$_5$, and —CF$_3$; provided that at least one of R$^{20a}$, R$^{20b}$, R$^{20c}$, and R$^{20d}$ is hydrogen.

In a further aspect, each of R$^{20a}$, R$^{20b}$, R$^{20c}$, and R$^{20d}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least two of R$^{20a}$, R$^{20b}$, R$^{20c}$, and R$^{20d}$ are hydrogen. In a still further aspect, each of R$^{20a}$, R$^{20b}$, R$^{20c}$, and R$^{20d}$ is independently hydrogen, halogen, —SF$_5$, —CH$_3$, —CF$_3$, or —OCF$_3$; provided that at least two of R$^{20a}$, R$^{20b}$, R$^{20c}$, and R$^{20d}$ are hydrogen. In a yet further aspect, each of R$^{20a}$, R$^{20b}$, R$^{20c}$, and R$^{20d}$ is independently hydrogen, halogen, —SF$_5$, and —CF$_3$; provided that at least two of R$^{20a}$, R$^{20b}$, R$^{20c}$, and R$^{20d}$ are hydrogen.

In a further aspect, each of R$^{20a}$, R$^{20b}$, R$^{20c}$, and R$^{20d}$ is independently hydrogen, halogen, —SF$_5$, —NO$_2$, —CH$_3$, —CH$_2$F, —CHF$_2$, —CF$_3$, —OCF$_3$, —NHCH$_3$, or —N(CH$_3$)$_2$; provided that at least three of R$^{20a}$, R$^{20b}$, R$^{20c}$, and R$^{20d}$ are hydrogen. In a still further aspect, each of R$^{20a}$, R$^{20b}$, R$^{20c}$, and R$^{20d}$ is independently hydrogen, halogen, —SF$_5$, —CH$_3$, —CF$_3$, or —OCF$_3$; provided that at least three of R$^{20a}$, R$^{20b}$, R$^{20c}$, R$^{20d}$, and R$^{10e}$ are hydrogen. In a yet further aspect, each of R$^{20a}$, R$^{20b}$, R$^{20c}$, and R$^{20d}$ is independently hydrogen, halogen, —SF$_5$, and —CF$_3$; provided that at least three of R$^{20a}$, R$^{20b}$, R$^{20c}$, and R$^{20d}$ are hydrogen.

In a further aspect one of R$^{20a}$, R$^{20b}$, R$^{20c}$, and R$^{20d}$ is —NHC(O)CH=CH$_2$ and —(CH$_2$)NHC(O)CH=CH$_2$; and each of the remaining of R$^{20a}$, R$^{20b}$, R$^{20c}$, and R$^{20d}$ is hydrogen. In a still further aspect one of R$^{20a}$, R$^{20b}$, R$^{20c}$, and R$^{10d}$ is —NHC(O)CH=CH$_2$; and each of the remaining of R$^{20a}$, R$^{20b}$, R$^{20c}$, and R$^{20d}$ is hydrogen. In a further aspect one of R$^{20a}$, R$^{20b}$, R$^{20c}$ and R$^{20d}$ is —(CH$_2$)NHC(O)CH=CH$_2$; and each of the remaining of R$^{20a}$, R$^{20b}$, R$^{20c}$, and R$^{20d}$ is hydrogen.

f. Ar$^1$ Groups

In one aspect, Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$) NHC(O)CH=CH$_2$. In a further aspect, Ar$^1$ is unsubstituted.

In a further aspect, Ar$^1$ is substituted with 0 or 1 group that is —NHC(O)CH=CH$_2$ or —(CH$_2$)NHC(O)CH=CH$_2$. In a further aspect, Ar$^1$ is substituted with 0 or 1 group that is —NHC(O)CH$_2$Cl or —NHSO$_2$CH=CH$_2$.

In a further aspect, Ar$^1$ is phenyl independently substituted with 0, 1, 2, or 3 groups selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$) NHC(O)CH=CH$_2$. In a still further aspect, Ar$^1$ is phenyl independently substituted with 0, 1, 2, or 3 groups selected from halogen, —SF$_5$, —NO$_2$, —CH$_3$, —CH$_2$F, —CHF$_2$, —CF$_3$, —OCF$_3$, —NHCH$_3$, and —N(CH$_3$)$_2$. In a yet further aspect, Ar$^1$ is phenyl independently substituted with 0, 1, 2, or 3 groups selected from halogen, —SF$_5$, —CH$_3$, —CF$_3$, and —OCF$_3$. In an even further aspect, Ar$^1$ is phenyl independently substituted with 0, 1, 2, or 3 groups selected from halogen, —SF$_5$, and —CF$_3$.

In a further aspect, Ar$^1$ is phenyl monosubstituted with a group selected from hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$)NHC(O)CH=CH$_2$. In a still further aspect, Ar$^1$ is phenyl monosubstituted with a group selected —NHC(O)CH$_2$Cl, —NHSO$_2$CH=CH$_2$, —NHC(O)CH=CH$_2$, and —(CH$_2$)NHC(O)CH=CH$_2$. In a yet further aspect, Ar$^1$ is phenyl monosubstituted with —NHC(O)CH=CH$_2$. In an even further aspect, Ar$^1$ is phenyl monosubstituted with —(CH$_2$)NHC(O)CH=CH$_2$. In a still further aspect, Ar$^1$ is phenyl monosubstituted with —NHC(O)CH$_2$Cl. In yet a further aspect, Ar$^1$ is phenyl monosubstituted with —NHSO$_2$CH=CH$_2$.

In a further aspect, Ar$^1$ is unsubstituted phenyl.

In a further aspect, Ar$^1$ is pyridinyl independently substituted with 0, 1, 2, or 3 groups selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$) NHC(O)CH=CH$_2$, provided that no more than one group is —NHC(O)CH=CH$_2$ or —(CH$_2$)NHC(O)CH=CH$_2$. In a still further aspect, Ar$^1$ is pyridinyl independently substituted with 0, 1, 2, or 3 groups selected from halogen, —SF$_5$, —NO$_2$, —CH$_3$, —CH$_2$F, —CHF$_2$, —CF$_3$, —OCF$_3$, —NHCH$_3$, and —N(CH$_3$)$_2$. In a yet further aspect, Ar$^1$ is pyridinyl independently substituted with 0, 1, 2, or 3 groups selected from halogen, —SF$_5$, —CH$_3$, —CF$_3$, and —OCF$_3$. In an even further aspect, Ar$^1$ is pyridinyl independently substituted with 0, 1, 2, or 3 groups selected from halogen, —SF$_5$, and —CF$_3$.

In a further aspect, Ar$^1$ is pyridinyl monosubstituted with a group selected from hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$)NHC(O)CH=CH$_2$. In a still furher aspect, Ar$^1$ is pyridinyl monosubstituted with a group selected —NHC(O)CH$_2$Cl, —NHSO$_2$CH=CH$_2$, —NHC(O)CH=CH$_2$, and —(CH$_2$)NHC(O)CH=CH$_2$. In a yet further aspect, Ar$^1$ is pyridinyl monosubstituted with —NHC(O)CH=CH$_2$. In an even further aspect, Ar$^1$ is pyridinyl monosubstituted with —(CH$_2$)NHC(O) CH=CH$_2$. In a still further aspect, Ar$^1$ is pyridinyl monosubstituted with —NHC(O)CH$_2$Cl. In yet a further aspect, Ar$^1$ is pyridinyl monosubstituted with —NHSO$_2$CH=CH$_2$.

In a further aspect, Ar$^1$ is unsubstituted pyridinyl.

In a further aspect, pyridinyl is a group having a structure represented by a formula:

each of $R^{20a}$, $R^{20b}$, $R^{20c}$, and $R^{20d}$ is independently selected from hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$)NHC(O)CH=CH$_2$, provided that at least one of $R^{20a}$, $R^{20b}$, $R^{20c}$, and $R^{20d}$ is hydrogen.

In a further aspect, pyridinyl is a group having a structure represented by a formula:

each of $R^{20a}$, $R^{20b}$, $R^{20c}$, and $R^{20d}$ is independently selected from hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$)NHC(O)CH=CH$_2$, provided that at least three of $R^{20a}$, $R^{20b}$, $R^{20c}$, and $R^{20d}$ are hydrogen.

In a further aspect, Ar$^1$ is phenyl, pyridinyl, furanyl, thiophenyl, pyrrolyl, benzofuranyl, 2,3-dihydrobenzofuranyl, 1,3-dihydroisobenzofuranyl, or benzo[d][1,3]dioxolyl. In a still further aspect, Ar$^1$ is phenyl, pyridinyl, furanyl, thiophenyl, pyrrolyl, benzofuranyl, 2,3-dihydrobenzofuranyl, 1,3-dihydroisobenzofuranyl, or benzo[d][1,3]dioxolyl, and Ar$^1$ is unsubstituted.

In a further aspect, Ar$^1$ is phenyl, pyridinyl, furanyl, or benzo[d][1,3]dioxolyl. In a still further aspect, Ar$^1$ is phenyl, pyridinyl, furanyl, or benzo[d][1,3]dioxolyl, and Ar$^1$ is unsubstituted.

2. Example Compounds

In one aspect, a compound is selected from:

-continued

79

80

81

-continued

82

-continued

83

84

85

86

In one aspect, a compound is selected from:

87

88

89

-continued

90

-continued

91

92

93
-continued

94
-continued

95

96

97

In one aspect, a compound is selected from:

98

101

102

103

-continued

104

In one aspect, a compound is selected from:

105

-continued

106

-continued

107

-continued

108

-continued

109

110

In one aspect, a compound is selected from:

111

112

113

-continued

114

-continued

115

116

117

118

119

120

121

122

123

-continued

In one aspect, a compound is selected from:

124

-continued

125

-continued

126

-continued

127

128

129

130

131

132

133

-continued

134

-continued

135

136

137

138

139

140

141
-continued

142
-continued

143

-continued

144

-continued

145

-continued

146

-continued

147

-continued

148

-continued

149

150

151

152

153

154

155

-continued

156

-continued

157

158

159

160

161

-continued

162

-continued

163

164

165

166

167
-continued

168
-continued

169

170

171

172

173

174

US 12,605,373 B2

175

-continued

176

-continued

177

-continued

178

-continued

179

180

181

182

183

184

185

-continued

186

-continued

187

-continued

188

-continued

189

190

191

-continued

192

-continued

193

194

195

-continued

196

-continued

197

198

199

200

201

202

203

204

205

206

207

208

209

-continued

210

-continued

211

212

213

-continued

214

-continued

215

216

217

218

219

220

221

222

223

-continued

224

-continued

225

226

227

228

229

230

231

-continued

232

-continued

233
-continued

234
-continued

In a further aspect, a compound is selected from:

235

236

237

-continued

238

-continued

239

240

241

242

243

244

245

246

247
-continued

248
-continued

249

250

251

252

253

-continued

254

-continued

255

-continued

256

-continued

257

-continued

258

-continued

259
-continued

260
-continued

261

262

263

264

265

-continued

266

-continued

267

268

269

270

271

272

273

274

275

276

277

278

279

280

281

282

283
-continued

284
-continued

285

286

287

-continued

288

-continued

289

290

291

292

293

-continued

294

-continued

295

296

297

298

, and

299

In one aspect, a compound is selected from:

300

301

-continued

302

-continued

303

304

305

306

307

308

309

310

311

-continued

312

-continued

313
-continued

314
-continued

315

316

317

-continued

318

-continued

319

320

321

322

323
-continued

324
-continued

325
-continued

326
-continued

327

328

329

330

331

332

333

334

335

336

337

338

339

340

341

342

343

344

345

-continued

346

-continued

347

348

349
-continued

350
-continued

351

352

353

354

355

356

357

-continued

358

-continued

359

360

361

362

363

364

365

366

367

368

369

370

371

372

373

374

375

376

377

-continued

378

-continued

379

380

381

382

383

-continued

384

-continued

385

-continued

386

-continued

387

-continued

388

-continued

389

390

In one aspect, a compound is:

In one aspect, a compound is:

In one aspect, a compound is:

391

In one aspect, a compound is:

or

In one aspect, a compound is:

392

, or

.

In one aspect, a compound is:

or

.

393

In one aspect, a compound is:

394 or

In one aspect, a compound is:

, or

395

In one aspect, a compound is:

396

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Methods of Making the Compounds

In one aspect, the invention relates to methods of making compounds useful as inhibitors of the DCN1-UBC12 interaction, which can be useful in the treatment of disorders of uncontrolled cellular proliferation, e.g., a cancer, and other diseases in which a DCN1-UBC12 interaction dysfunction involved. In one aspect, the invention relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the invention might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, substituted 1-phenyl-3-(piperidin-4-yl)urea analogs can be prepared as shown below.

Scheme 1A.

1.1

1.3

1.5

PG: protecting group

Compounds are represented in generic form, with substituents as noted in compound descriptions elsewhere herein. A more specific example is set forth below.

SCHEME 1B.

1.1

1.7

1.8

DIPEA, CH₂Cl₂

-continued 1.9

In one aspect, the synthesis of 1-phenyl-3-(piperidin-4-yl)urea analogs can begin with tert-butyl piperidin-4-ylcarbamate. Tert-butyl piperidin-4-ylcarbamates are commercially available or readily prepared by one skilled in the art. Thus, compounds of type 1.9, and similar compounds, can be prepared according to reaction Scheme 1B above. Compounds of type 1.7 can be prepared by reductive amination of an appropriate amine, e.g., 1.1 as shown above. The reductive amination is carried out in the presence of an appropriate aldehyde, e.g., 1.6 as shown above, an appropriate reducing agent, e.g., sodium triacetoxyborohydride, and an appropriate acid, e.g., acetic acid, in an appropriate solvent, e.g., dichloromethane. Compounds of type 1.9 can be prepared by deprotection of an appropriate amine, e.g., 1.7 as shown above, followed by a coupling reaction. The coupling reaction is carried out in the presence of an appropriate isocyanate, e.g., 1.8 as shown above, and an appropriate coupling agent, e.g., N,N-diisopropylethylamine, in an appropriate solvent, e.g., dichloromethane. As can be appreciated by one skilled in the art, the above reaction provides an example of a generalized approach compounds similar in structure to the specific reactants above (compounds similar to compounds of type 1.1, 1.2, 1.3, and 1.4), can be substituted in the reaction to provide substituted 1-phenyl-3-(piperidin-4-yl)urea analogs similar to Formula 1.5.

2. Route II

In one aspect, substituted 1-phenyl-3-(piperidin-4-yl)urea analogs can be prepared as shown below.

SCHEME 2A.

2.1

3.1

-continued

-continued 3.2

3.3

PG: Protecting group

SCHEME 2C.

2.1

Compounds are represented in generic form, with substituents as noted in compound descriptions elsewhere herein. A more specific example is set forth below.

SCHEME 2B.

2.1

3.4

3.6

3.7

3.4

3.6

3.7

In one aspect, the synthesis of 1-phenyl-3-(piperidin-4-yl)urea analogs can begin with tert-butyl 4-oxopiperidine-1-carboxylate. Tert-butyl 4-oxopiperidine-1-carboxylates are commercially available or readily prepared by one skilled in the art. Thus, compounds of type 3.7, and similar compounds, can be prepared according to reaction Scheme 2B above. Compounds of type 3.4 can be prepared by reductive amination of an appropriate ketone, e.g., 2.1 as shown above. The reductive amination is carried out in the presence of an appropriate amine, e.g., 2.9 as shown above, an appropriate reducing agent, e.g., sodium triacetoxyboro-hydride, and an appropriate acid, e.g., acetic acid, in an appropriate solvent, e.g., dichloromethane. Compounds of type 3.6 can be prepared by a coupling reaction of an appropriate amine, e.g., 3.4 as shown above. The coupling reaction is carried out in the presence of an appropriate isocyanate, e.g., 3.5 as shown above, and an appropriate coupling agent, e.g., N,N-diisopropylethylamine, in an appropriate solvent, e.g., dichloromethane. Compounds of type 3.7 can be prepared by deprotection of an appropriate amine, e.g., 1.6 as shown above, followed by reductive amination. The reductive amination is carried out in the presence of an appropriate amine, e.g., 2.9 as shown above, an appropriate reducing agent, e.g., sodium triacetoxyborohydride, and an appropriate acid, e.g., acetic acid, in an appropriate solvent, e.g., dichloromethane. Alternatively, the reductive amination is carried out in the presence of an appropriate catalyst, e.g., $(Bu)_2SnCl_2$, and an appropriate reducing agent, e.g., $C_6H_5SiH_3$, in an appropriate solvent, e.g., THF. As can be appreciated by one skilled in the art, the above reaction provides an example of a generalized approach compounds similar in structure to the specific reactants above (compounds similar to compounds of type 1.2, 1.4, 2.1, 2.4, 3.1, and 3.2), can be substituted in the reaction to provide substituted 1-phenyl-3-(piperidin-4-yl) urea analogs similar to Formula 3.3.

3. Route III

In one aspect, substituted 1-phenyl-3-(piperidin-4-yl)urea analogs can be prepared as shown below.

SCHEME 3A.

4.1

4.2

3.3

Compounds are represented in generic form, with substituents as noted in compound descriptions elsewhere herein. A more specific example is set forth below.

SCHEME 3B.

4.3

4.4

4.5

In one aspect, the synthesis of 1-phenyl-3-(piperidin-4-yl)urea analogs can begin with piperidinone 4.1. Piperidinones are commercially available or readily prepared by one skilled in the art. Thus, compounds of type 4.5, and similar compounds, can be prepared according to reaction Scheme 3B above. Compounds of type 4.4 can be prepared by reductive amination of an appropriate ketone, e.g., 2.1 as shown above. The reductive amination is carried out in the presence of an appropriate amine, e.g., 2.9 as shown above, an appropriate reducing agent, e.g., sodium triacetoxyborohydride, and an appropriate acid, e.g., acetic acid, in an appropriate solvent, e.g., dichloromethane. Compounds of type 4.5 can be prepared by a coupling reaction of an appropriate amine, e.g., 4.4 as shown above. The coupling reaction is carried out in the presence of an appropriate isocyanate, e.g., 3.5 as shown above, and an appropriate coupling agent, e.g., N,N-diisopropylethylamine, in an appropriate solvent, e.g., dichloromethane. As can be appreciated by one skilled in the art, the above reaction provides an example of a generalized approach compounds similar in structure to the specific reactants above (compounds similar to compounds of type 1.4, 2.4, 4.1, and 4.2), can be substituted in the reaction to provide substituted 1-phenyl-3-(piperidin-4-yl)urea analogs similar to Formula 3.3.

4. Route IV

In one aspect, substituted 1-phenyl-3-(piperidin-4-yl)urea analogs can be prepared as shown below.

SCHEME 4A.

4.2

5.1

3.3

Compounds are represented in generic form, with substituents as noted in compound descriptions elsewhere herein. A more specific example is set forth below.

SCHEME 4B.

4.4

5.2
DIPEA, CDI
CH₂Cl₂

4.5

In one aspect, the synthesis of 1-phenyl-3-(piperidin-4-yl)urea analogs can begin with piperidine 4.2. Thus, compounds of type 4.5, and similar compounds, can be prepared according to reaction Scheme 4B above. Compounds of type 4.5 can be prepared by acetylation of an appropriate amine, e.g., 4.4 as shown above. The acetylation is carried out in the presence of an appropriate amine, e.g., 5.2 as shown above, an appropriate coupling agent, e.g., 1,1'-carbonyldiimidazole (CDI), an appropriate base, e.g, N,N-diisopropylethylamine, in an appropriate solvent, e.g., dichloromethane. As can be appreciated by one skilled in the art, the above reaction provides an example of a generalized approach compounds similar in structure to the specific reactants above (compounds similar to compounds of type 4.2 and 5.1), can be substituted in the reaction to provide substituted 1-phenyl-3-(piperidin-4-yl)urea analogs similar to Formula 3.3.

D. Pharmaceutical Compositions

In one aspect, the invention relates to pharmaceutical compositions comprising the disclosed compounds. That is, a pharmaceutical composition can be provided comprising an effective amount of at least one disclosed compound, or a pharmaceutically acceptable salt thereof, or at least one product of a disclosed method, or a pharmaceutically acceptable salt thereof. In various aspects, the compound of the pharmaceutical composition is a solvate or polymorph of a disclosed compound or product of a disclosed method of making.

In one aspect, the invention relates to pharmaceutical compositions comprising a compound selected from a compound in Table 2, 3, 4, 5, 6, or 7. That is, a pharmaceutical composition can be provided comprising an effective amount of at least one a compound selected from a compound in Table 2, 3, 4, 5, 6, or 7, or a pharmaceutically acceptable salt thereof, or at least one product of a disclosed method, or a pharmaceutically acceptable salt thereof. In various aspects, the compound of the pharmaceutical composition is a solvate or polymorph of a compound selected from a compound in Table 2, 3, 4, 5, 6, or 7 or product of a disclosed method of making.

In one aspect, disclosed are pharmaceutical compositions comprising a therapeutically effective amount of a compound selected from:

405

406

407

408

, and

35 or a pharmaceutically acceptable salt thereof, and a pharmaceutically acceptable carrier.

In a further aspect, the effective amount of the pharmaceutical composition is a therapeutically effective amount. In a still further aspect, the effective amount of the pharmaceutical composition is a prophylactically effective amount.

In a further aspect, the pharmaceutical composition comprises a disclosed compound. In a yet further aspect, the pharmaceutical composition comprises a product of a disclosed method of making.

In a further aspect, the pharmaceutical composition exhibits inhibition of the DCN1-UBC12 interaction with an $IC_{50}$ of less than about 50,000 nM. In a still further aspect, the pharmaceutical composition exhibits inhibition of the DCN1-UBC12 interaction with an $IC_{50}$ of less than about 30,000 nM. In a yet further aspect, the pharmaceutical composition exhibits inhibition of the DCN1-UBC12 interaction with an $IC_{50}$ of less than about 20,000 nM. In an even further aspect, the pharmaceutical composition exhibits inhibition of the DCN1-UBC12 interaction with an $IC_{50}$ of less than about 10,000 nM. In a still further aspect, the pharmaceutical composition exhibits inhibition of the DCN1-UBC12 interaction with an $IC_{50}$ of less than about 5,000 nM. In a yet further aspect, the pharmaceutical composition exhibits inhibition of the DCN1-UBC12 interaction with an $IC_{50}$ of less than about 2,500 nM. In an even further aspect the pharmaceutical composition exhibits inhibition of the DCN1-UBC12 interaction with an $IC_{50}$ of less than about 1,000 nM. In a further aspect, the pharmaceutical composition exhibits inhibition of the DCN1-UBC12 interaction with an $IC_{50}$ of less than about 500 nM. In a still further aspect, the pharmaceutical composition exhibits inhibition of the DCN1-UBC12 interaction with an $IC_{50}$ of less than about 250 nM. In a yet further aspect, the pharmaceutical composition inhibition of the DCN1-UBC12 interaction with an $IC_{50}$ of less than about 100 nM.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder. In a further aspect, the pharmaceutical composition is used to treat a neurological and/or psychiatric disorder. In a yet further aspect, the disorder is associated with a DCN1-UBC12 interaction dysfunction. In an even further aspect, the disorder is associated with a DCN1-mediated cullin-RING ligase activity dysfunction.

In a further aspect, the pharmaceutical composition is used to treat a disorder of uncontrolled cellular proliferation. In an even further aspect, the disorder of uncontrolled cellular proliferation associated with the DCN1-UBC12 interaction. In a yet further aspect, the disorder of uncontrolled cellular proliferation associated with the DCN1-mediated cullin-RING ligase pathway. In a still further aspect, the pharmaceutical composition is used to treat a cancer.

In various aspects, the pharmaceutical composition is used to treat a squamous cell carcinoma. In a further aspect, the pharmaceutical composition is used to treat a metastatic squamous cell carcinoma. In a still further aspect, the pharmaceutical composition is used to treat a non-small cell lung carcinoma.

In a further aspect, the pharmaceutical composition is used to treat a uterine carcinosarcoma. In a still further aspect, the pharmaceutical composition is used to treat an embryonal rhabdomyosarcoma, glioblastoma, medulloblastoma, or osteosarcoma. In a yet further aspect, the pharmaceutical composition is used to treat an adrenocortical tumor. In an even further aspect, the pharmaceutical composition is used to treat a solid tumor.

In various aspects, the pharmaceutical composition is used to treat a hematological malignancy. In a further aspect, the pharmaceutical composition is used to treat a leukemia, lymphoma, or myeloma. In a still further aspect, the pharmaceutical composition is used to treat multiple lymphoma or B-cell non-Hodgkin's lymphoma. In a yet further aspect, the pharmaceutical composition is used to treat multiple myeloma. In an even further aspect, the pharmaceutical composition is used to treat acute myeloid leukemia.

In a further aspect, the pharmaceutical composition is used to treat a cancer of lung, cervix, ovary, uterus, esophagus, prostate, or head and neck. In a still further aspect, the pharmaceutical composition is used to treat a cancer of lung, cervix, esophagus, uterus, or prostate.

In a further aspect, the pharmaceutical composition is used to treat a lung cancer. In a still further aspect, the lung cancer is a non-small cell lung cancer. In a yet further aspect, the pharmaceutical composition is used to treat a squamous cell carcinoma, adenocarcinoma, or large cell-undifferentiated carcinoma.

In various aspects, the pharmaceutical composition is used to treat a neurodegenerative disorder.

In various aspects, the pharmaceutical composition is used to treat a bacterial or viral infection.

In various aspects, the pharmaceutical composition is used for male contraception.

In a further aspect, the disorder is associated with the DCN1-UBC12 interaction. In a still further aspect, the disorder is associated with the DCN1-mediated cullin-RING ligase pathway.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition of the DCN1-UBC12 interaction with an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibition of the DCN1-UBC12 interaction with an $IC_{50}$ of less than about (e.g., treatment of one or more disorders associated with a inhibition of the DCN1-UBC12 interaction with an $IC_{50}$ of less than about dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

Diseases and disorders involving uncontrolled cellular proliferation or cell overproliferation that can be treated or prevented include but are not limited to cancers, premalignant conditions (e.g., hyperplasia, metaplasia, and dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne. Malignancies and related disorders that can be treated, prevented, managed, ameliorated, particularly metastatic cancer, by administration of a compound of the invention that inhibits ceramidase function as discussed below (for a review of such disorders, see Fishman et al., 1985, Medicine, 2d Ed., J. B. Lippincott Co., Philadelphia).

In one aspect, cancers and related disorders that can be treated or prevented by methods and compositions disclosed herein include, but are not limited, to the following: a squamous cell carcinoma, a metastatic squamous cell carcinoma, a non-small cell lung carcinoma, a uterine carcinosarcoma, an embryonal rhabdomyosarcoma, a glioblastoma, a medulloblastoma, an osteosarcoma, or an adrenocortical tumor.

In a further aspect, cancers and related disorders that can be treated or prevented by methods and compositions disclosed herein include a cancer of the lung, cervix, ovary, uterus, esophagus, prostate, or head and neck.

In a further aspect, cancers and related disorders that can be treated or prevented by methods and compositions disclosed herein include a cancer of the lung, such as a non-small cell lung cancer, including, but not limited to a squamous cell carcinoma, adenocarcinoma, or large cell-undifferentiated carcinoma.

In a further aspect, cancers and related disorders that can be treated or prevented by methods and compositions disclosed herein include a hematological malignancy such as a leukemia, a lymphoma, a myeloma, a multiple lymphoma, a B-cell non-Hodgkin's lymphoma, or an acute myeloid leukemia.

In a further aspect, the disclosed compounds and/or compositions can be useful for the treatment of a cancer, including, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia vera, Lymphoma, Hodgkin's disease, non-Hodgkin's disease, multiple myeloma, Waldenstrom's macroglobulinemia, heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. For a review of such disorders, see Fishman et al., 1985, Medicine, 2d Ed., J.B. Lippincott Co., Philadelphia).

In a further aspect, cancers and related disorders that can be treated or prevented by methods and compositions disclosed herein include, but are not limited, to the following: leukemia, including, but not limited to, acute leukemia, acute lymphocytic leukemia; acute myelocytic leukemia, including, but not limited to, myeloblastic, promyelocytic, myelomonocytic, monocytic, erythroleukemia and myelodysplastic syndrome; chronic leukemia, including, but not limited to, chronic myelocytic (granulocytic) leukemia, chronic lymphocytic leukemia, hairy cell leukemia; polycythemia vera; lymphomas, including, but not limited to, Hodgkin's lymphoma, non-Hodgkin's lymphoma; myeloma, including, but not limited, to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumor, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer, including, but not limited to, papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers, including, but not limited to, Cushing's disease, prolactin-secreting tumor, acromegaly, and diabetes insipius; eye cancer, including, but not limited to, ocular melanoma such as iris melanoma, choroidal melanoma, and cilliary body melanoma, and retinoblastoma; vaginal cancer, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancer, including, but not limited to, squamous cell carcinoma, and adenocarcinoma; uterine cancer, including, but not limited to, endometrial carcinoma and uterine sarcoma; ovarian cancers, including, but not limited to, ovarian epithelial carcinoma, borderline tumor, germ cell tumor, and stromal tumor; esophageal cancer, including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancer, including, but not limited to, adenocarcinoma, fungating (polypoid), ulcerating, superficial spreading, diffusely spreading, malignant lymphom, liposarcoma, fibrosarcoma, and carcinosarcoma; colon cancer; rectal cancer; liver cancer, including, but not limited to, hepatocellular carcinoma and hepatoblastoma, gallbladder cancer, including, but not limited to, adenocarcinoma; cholangiocarcinoma, including, but not limited to, pappillary, nodular, and diffuse; lung cancer, including, but not limited to, non-small cell lung cancer, squamous cell carcinoma (epidermoid carcinoma), adenocarcinoma, large-cell carcinoma and small-cell lung cancer; testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); prostate cancer, including, but not limited to, adenocarcinoma, leiomyosarcoma, and rhabdomyosarcoma; penal cancers; oral cancer, including, but not limited to, squamous cell carcinoma; basal cancers; salivary gland cancer, including, but not limited to, adenocarcinoma, mucoepidermoid carcinoma, and adenoidcystic carcinoma; pharynx cancer, including, but not limited to, squamous cell cancer, and verrucous; skin cancer, including, but not limited to, basal cell carcinoma, squamous cell carcinoma and melanoma, superficial spreading melanoma, nodular melanoma, lentigo malignant melanoma, and acral lentiginous melanoma; kidney cancer, including, but not limited to, renal cell cancer, adenocarcinoma, hypernephroma, fibrosarcoma, and transitional cell cancer (renal pelvis and/or uterer); Wilms' tumor; bladder cancer, including, but not limited to, transitional cell carcinoma, squamous cell cancer, adenocarcinoma, carcinosarcoma. In addition, cancer includes myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A, Inc., United States of America).

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In various aspects, the methods and compositions disclosed herein can be used to treat a neurodegenerative disorder.

In various aspects, the methods and compositions disclosed herein can be used to treat a bacterial or viral infection.

In various aspects, the methods and compositions disclosed herein can be used for male contraception.

1. Treatment Methods

The compounds disclosed herein are useful for treating, preventing, ameliorating, controlling or reducing the risk of a variety of disorders in a patient or subject that would benefit from inhibition of the DCN1-UBC12 interaction. In one aspect, a treatment can include DCN1-UBC12 interaction to an extent effective to inhibit the NEDD8/CUL pathway. Thus, a disorder can be associated with the NEDD8/CUL pathway. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided are methods for the treatment of one or more disorders, for which inhibition of the DCN1-UBC12 interaction is predicted to be beneficial, in a subject comprising the step of administering to the subject at least one disclosed compound; at least one disclosed pharmaceutical composition; and/or at least one disclosed product in a dosage and amount effective to treat the disorder in the subject.

Also provided are methods for the treatment of one or more disorders, for which inhibition of DCN1-mediated cullin-RING ligase activity is predicted to be beneficial, in a subject comprising the step of administering to the subject at least one disclosed compound; at least one disclosed pharmaceutical composition; and/or at least one disclosed product in a dosage and amount effective to treat the disorder in the subject.

The invention is directed at the use of described chemical compositions to treat diseases or disorders in patients (preferably human) inhibition of the DCN1-UBC12 interaction or intervention in an DCN1-UBC12 interaction dysfunction would be predicted to have a therapeutic effect, e.g., a cancer or a neurodegenerative disorder, by administering one or more disclosed compounds or products.

In one aspect, provided is a method for treating or preventing a bacterial or viral infection, comprising: administering to a subject at least one disclosed compound; at least one disclosed pharmaceutical composition; and/or at least one disclosed product in a dosage and amount effective to treat the disorder in the subject.

Also provided is a method for the treatment of a disorder in a mammal comprising the step of administering to the mammal at least one disclosed compound, composition, or medicament.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of an inhibitor of the DCN1-UBC12 interaction for improving treatment outcomes in the context of cancer therapy. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy, e.g., surgical intervention, chemotherapeutic therapy, or radiotherapy for cancer treatment. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer can be provided within 1, 2, 3, or 4 weeks before or after administration of the compound. As a still further example, cancer therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

Thus, in one aspect, the invention relates to methods for inhibiting the DCN1-UBC12 interaction in at least one cell, comprising the step of contacting the at least one cell with at least one compound of the invention, in an amount effective to inhibit the DCN1-UBC12 interaction in the at least one cell. In a further aspect, the cell is mammalian, for example human. In a further aspect, the cell has been isolated from a subject prior to the contacting step. In a further aspect, contacting is via administration to a subject.

a. Treating a Disorder of Uncontrolled Cellular Proliferation

In various aspects, the invention relates to a method for the treatment of a disorder of uncontrolled cellular proliferation, comprising the step of administering to a mammal a therapeutically effective amount of a compound inhibiting DCN1-mediated cullin-RING ligase activity. In a further aspect, the invention relates to a method for the treatment of a disorder of uncontrolled cellular proliferation, comprising the step of administering to a mammal a therapeutically effective amount of a compound inhibiting the DCN1-UBC12 interaction. In a further aspect, the compound used in the treatment of the disorder of uncontrolled cellular proliferation is at least one disclosed compound, or a pharmaceutically acceptable salt thereof, or an effective amount of at least one product of a disclosed method of making, or a pharmaceutically acceptable salt thereof. In a still further aspect, the compound used in the treatment of the disorder of uncontrolled cellular proliferation is at least one compound, or a pharmaceutically acceptable salt thereof, selected from Table 2, 3, 4, 5, 6, or 7.

Thus, in one aspect, disclosed are methods method for treating a disorder of uncontrolled cellular proliferation, the method comprising the step of administering to a mammal a therapeutically effective amount of a compound having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); and wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$) NHC(O)CH=CH$_2$, or a pharmaceutically acceptable salt thereof.

In one aspect, disclosed are methods for treating a disorder of uncontrolled cellular proliferation, the method comprising the step of administering to a mammal a therapeutically effective amount of a compound having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); and wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH=CH$_2$, —NHC(O)CH=CH$_2$, and —(CH$_2$) NHC(O)CH=CH$_2$, or a pharmaceutically acceptable salt thereof.

In one aspect, disclosed are methods for treating a disorder of uncontrolled cellular proliferation, the method comprising the step of administering to a mammal a therapeutically effective amount of a compound selected from:

421

422

423

-continued

424

-continued or a pharmaceutically acceptable salt thereof.

In a further aspect, the compound is administered to a mammal, and the mammal is a human. In a still further aspect, the mammal has been diagnosed with a need for treatment of the disorder of uncontrolled cellular proliferation prior to the administering step. In a yet further aspect, the method for the treatment of a disorder of uncontrolled cellular proliferation further comprises the step of identifying a mammal in need of treatment of the disorder of uncontrolled cellular proliferation.

In a further aspect, the disorder of uncontrolled cellular proliferation is a cancer. In a still further aspect, the cancer is a squamous cell carcinoma. In a yet further aspect, the squamous cell carcinoma is a metastatic squamous cell carcinoma. In an even further aspect, the squamous cell carcinoma is a non-small cell lung carcinoma.

In a further aspect, the cancer is a uterine carcinosarcoma. In a still further aspect, the cancer is an embryonal rhabdomyosarcoma, a glioblastoma, a medulloblastoma, or an osteosarcoma. In yet a further aspect, the cancer is an adrenocortical tumor.

In a further aspect, the cancer is a solid tumor.

In a further aspect, the cancer is a hematological malignancy. In a still further aspect, the hematological malignancy is a leukemia, a lymphoma, or a myeloma. In yet a further aspect, the lymphoma is multiple lymphoma or B-cell non-Hodgkin's lymphoma. In an even further aspect, the myeloma is multiple myeloma. In a still further aspect, the leukemia is acute myeloid leukemia.

In a further aspect, the cancer is a cancer of lung, cervix, ovary, uterus, esophagus, prostate, or head and neck. In a still further aspect, the cancer is a cancer of lung, cervix, esophagus, uterus, or prostate.

In a further aspect, the method for the treatment of a disorder of uncontrolled cellular proliferation is a treatment for lung cancer. In a still further aspect, the lung cancer is a non-small cell lung cancer. In a yet further aspect, the non-small cell lung cancer is a squamous cell carcinoma, adenocarcinoma, or large cell-undifferentiated carcinoma.

b. Treating a Neurodegenerative Disorder

In various aspects, the invention relates to a method for the treatment of a neurodegenerative disorder, comprising the step of administering to a mammal a therapeutically effective amount of a compound inhibiting DCN1-mediated cullin-RING ligase activity. In various aspects, the invention relates to a method for the treatment of a neurodegenerative disorder, comprising the step of administering to a mammal a therapeutically effective amount of a compound inhibiting the DCN1-UBC12 interaction. In a further aspect, the compound used in the treatment of the neurodegenerative disorder is at least one disclosed compound, or a pharmaceutically acceptable salt thereof, or an effective amount of at least one product of a disclosed method of making, or a pharmaceutically acceptable salt thereof. In a still further aspect, the compound used in the treatment of the neurodegenerative disorder is at least one compound, or a pharmaceutically acceptable salt thereof, selected from Table 2, 3, 4, 5, 6, or 7. In a further aspect, the compound is administered to a mammal, and the mammal is a human. In a still further aspect, the mammal has been diagnosed with a need for treatment of the neurodegenerative disorder prior to the administering step. Examples of neurodegenerative disorders include, but are not limited to, Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease.

Thus, in one aspect, disclosed are methods for treating a neurodegenerative disorder, the method comprising the step of administering to a mammal a therapeutically effective amount of a compound having a structure represented by a formula:

wherein each of $R^{1a}$, $R^{1b}$, and $R^{1c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C6)-CF$_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —SO$_2$—(C1-C6 alkyl); and wherein $R^2$ is substituted with 0, 1, 2, or 3 groups independently selected from halogen, —OH, —SCF$_3$, —SF$_5$, —NO$_2$, —CH$_3$, —CH$_2$F, —CHF$_2$, —CF$_3$, —OCF$_3$, —NHCH$_3$, and —N(CH$_3$)$_2$; wherein $R^3$ is C$_1$-C$_8$ alkyl; C1-C8 alkoxyalkyl; —(C1-C3 alkyl)-(C3-C8 cycloalkyl); or —(C1-C3 alkyl)-Ar$^1$; and wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$, or a pharmaceutically acceptable salt thereof.

In one aspect, disclosed are methods for treating a neurodegenerative disorder, the method comprising the step of administering to a mammal a therapeutically effective amount of a compound having a structure represented by a formula:

wherein each of $R^{1a}$, $R^{1b}$, and $R^{10c}$ is independently hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —(CH$_2$)-phenyl, —(CH$_2$)-pyridinyl, —(CH$_2$)-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —SCF$_3$, —SF$_5$, —NO$_2$, —CH$_3$, —CH$_2$F, —CHF$_2$, —CF$_3$, —OCF$_3$, —NHCH$_3$, or —N(CH$_3$)$_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); and wherein Ar$^1$ is aryl or heteroaryl substituted with 0, 1, 2, or 3 groups independently selected from halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH$_2$Cl, —NHSO$_2$CH═CH$_2$, —NHC(O)CH═CH$_2$, and —(CH$_2$)NHC(O)CH═CH$_2$, or a pharmaceutically acceptable salt thereof.

In one aspect, disclosed are methods for treating a neurodegenerative disorder, the method comprising the step of administering to a mammal a therapeutically effective amount of a compound selected from:

427

428

429

430

55 or a pharmaceutically acceptable salt thereof.

c. Treating a Viral or Bacterial Infection

In various aspects, the invention relates to a method for the treatment of a viral or bacterial infection, comprising the step of administering to a mammal a therapeutically effective amount of a compound inhibiting DCN1-mediated cullin-RING ligase activity. In various aspects, the invention relates to a method for the treatment of a viral or bacterial infection, comprising the step of administering to a mammal a therapeutically effective amount of a compound inhibiting the DCN1-UBC12 interaction. In a further aspect, the compound used in the treatment of a viral or bacterial infection is at least one disclosed compound, or a pharmaceutically acceptable salt thereof, or an effective amount of at least one product of a disclosed method of making, or a pharmaceutically acceptable salt thereof. In a still further aspect, the compound used in the treatment of a viral or bacterial infection is at least one compound, or a pharmaceutically acceptable salt thereof, selected from Table 2, 3, 4, 5, 6, or 7. In a further aspect, the compound is administered to a mammal, and the mammal is a human. In a still further aspect, the mammal has been diagnosed with a need for treatment of a viral or bacterial infection prior to the administering step. Examples of viral infections include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, and viral pneumonia. Examples of bacterial infections include, but are not limited to, *M. tuberculosis*, *M bovis*, *M. bovis* strain BCG, BCG substrains, *M. avium*, *M. intracellulare*, *M. africanum*, *M. kansasii*, *M. marinum*, *M. ulcerans*, *M. avium* subspecies paratuberculosis, *Nocardia asteroides*, other *Nocardia* species, *Legionella pneumophila*, other *Legionella* species, *Salmonella typhi*, other *Salmonella* species, *Shigella* species, *Yersinia pestis*, *Pasteurella haemolytica*, *Pasteurella multocida*, other *Pasteurella* species, *Actinobacillus pleuropneumoniae*, *Listeria monocytogenes*, *Listeria ivanovii*, *Brucella abortus*, other *Brucella* species, *Cowdria ruminantium*, *Chlamydia pneumoniae*, *Chlamydia trachomatis*, *Chlamydia psittaci*, *Coxiella burnetti*, other Rickettsial species, *Ehrlichia* species, *Staphylococcus aureus*, *Staphylococcus epidermidis*, *Streptococcus pneumoniae*, *Streptococcus pyogenes*, *Streptococcus agalactiae*, *Bacillus anthracis*, *Escherichia coli*, *Vibrio cholerae*, *Campylobacter* species, *Neisseria meningitidis*, *Neiserria gonorrhea*, *Pseudomonas aeruginosa*, other *Pseudomonas* species, *Haemophilus influenzae*, *Haemophilus ducreyi*, other Hemophilus species, *Clostridium tetani*, other *Clostridium* species, *Yersinia enterolitica*, and other *Yersinia* species.

Thus, in one aspect, disclosed are methods for treating a viral or bacterial infection, the method comprising the step of administering to a mammal a therapeutically effective amount of a compound having a structure represented by a formula:

wherein each of $R^{1a}$, $R^{1b}$, and $R^{1c}$ is independently hydrogen, halogen, $-SF_5$, $-NO_2$, $-CH_3$, $-CH_2F$, $-CHF_2$, $-CF_3$, $-OCF_3$, $-NHCH_3$, $-N(CH_3)_2$, $-(CH_2)$-phenyl, $-(CH_2)$-pyridinyl, $-(CH_2)$-pyrimidinyl, $-O$-phenyl, $-O$-pyridinyl, or $-O$-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, $-OH$, $-SCF_3$, $-SF_5$, $-NO_2$, $-CH_3$, $-CH_2F$, $-CHF_2$, $-CF_3$, $-OCF_3$, $-NHCH_3$, or $-N(CH_3)_2$; wherein $R^2$ is C3-C6 alkyl, $-(C1-C6)-CF_3$, $-(C1-C6)-C\equiv CH$, $-(C1-C3 \text{ alkyl})$-cyclopropyl, $-(C1-C3 \text{ alkyl})$-cyclobutyl, $-(C1-C3 \text{ alkyl})$-cyclopentyl, $-(C1-C3 \text{ alkyl})$-cyclohexyl, $-(C1-C3 \text{ alkyl})$-(bicycloalkyl), $-(C1-C3 \text{ alkyl})$-(bicycloalkenyl), $-(C1-C3)$-aryl, $-(C1-C3)$-heteroaryl, $-(C1-C3)$-(bicyclic), or $-SO_2-(C1-C6 \text{ alkyl})$; and wherein $R^2$ is substituted with 0, 1, 2, or 3 groups independently selected from halogen, $-OH$, $-SCF_3$, $-SF_5$, $-NO_2$, $-CH_3$, $-CH_2F$, $-CHF_2$, $-CF_3$, $-OCF_3$, $-NHCH_3$, and $-N(CH_3)_2$; wherein $R^3$ is C1-C8 alkyl; C1-C8 alkoxyalkyl; $-(C1-C3 \text{ alkyl})$-(C3-C8 cycloalkyl); or $-(C1-C3 \text{ alkyl})-Ar^1$; and wherein $Ar^1$ is aryl or heteroaryl substituted with 0, 1, 2, or 3 groups independently selected from halogen, $-SF_5$, $-NO_2$, $-CH_3$, $-CH_2F$, $-CHF_2$, $-CF_3$, $-OCF_3$, $-NHCH_3$, $-N(CH_3)_2$, $-NHC(O)CH_2Cl$, $-NHSO_2CH=CH_2$, $-NHC(O)CH=CH_2$, and $-(CH_2)NHC(O)CH=CH_2$, or a pharmaceutically acceptable salt thereof.

In one aspect, disclosed are methods for treating a viral or bacterial infection, the method comprising the step of administering to a mammal a therapeutically effective amount of a compound having a structure represented by a formula:

wherein each of $R^{1a}$, $R^{1b}$, and $R^{1c}$ is independently hydrogen, halogen, $-SF_5$, $-NO_2$, $-CH_3$, $-CH_2F$, $-CHF_2$, $-CF_3$, $-OCF_3$, $-NHCH_3$, $-N(CH_3)_2$, $-(CH_2)$-phenyl, $-(CH_2)$-pyridinyl, $-(CH_2)$-pyrimidinyl, $-O$-phenyl, $-O$-pyridinyl, or $-O$-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, $-OH$, $-SCF_3$, $-SF_5$, $-NO_2$, $-CH_3$, $-CH_2F$, $-CHF_2$, $-CF_3$, $-OCF_3$, $-NHCH_3$, or $-N(CH_3)_2$; wherein $R^2$ is C3-C6 alkyl, $-(C1-C3 \text{ alkyl})$-cyclopropyl, $-(C1-C3 \text{ alkyl})$-cyclobutyl, $-(C1-C3 \text{ alkyl})$-cyclopentyl, $-(C1-C3 \text{ alkyl})$-cyclohexyl, $-(C1-C3 \text{ alkyl})$-(bicycloalkyl), or $-(C1-C3 \text{ alkyl})$-(bicycloalkenyl); and wherein $Ar^1$ is aryl or heteroaryl substituted with 0, 1, 2, or 3 groups independently selected from halogen, $-SF_5$, $-NO_2$, $-CH_3$, $-CH_2F$, $-CHF_2$, $-CF_3$, $-OCF_3$, $-NHCH_3$, $-N(CH_3)_2$, $-NHC(O)CH_2Cl$, $-NHSO_2CH=CH_2$, $-NHC(O)CH=CH_2$, and $-(CH_2)NHC(O)CH=CH_2$, or a pharmaceutically acceptable salt thereof.

In one aspect, disclosed are methods for treating a viral or bacterial infection, the method comprising the step of administering to a mammal a therapeutically effective amount of a compound selected from:

433

434

435
-continued

436
-continued

-continued or a pharmaceutically acceptable salt thereof.

d. Male Contraception

In various aspects, the invention relates to a method for male contraception, comprising the step of administering to a mammal a therapeutically effective amount of a compound inhibiting DCN1-mediated cullin-RING ligase activity. In various aspects, the invention relates to a method for male contraception, comprising the step of administering to a mammal a therapeutically effective amount of a compound inhibiting the DCN1-UBC12 interaction. In a further aspect, the compound used for male contraception is at least one disclosed compound, or a pharmaceutically acceptable salt thereof, or an effective amount of at least one product of a disclosed method of making, or a pharmaceutically acceptable salt thereof. In a still further aspect, the compound used for male contraception is at least one compound, or a pharmaceutically acceptable salt thereof, selected from Table 2, 3, 4, 5, 6, or 7. In a further aspect, the compound is administered to a mammal, and the mammal is a human.

Thus, in one aspect, disclosed are contraceptive methods comprising the step of administering to a male mammal a prophylactically effective amount of a compound having a structure represented by a formula:

wherein each of $R^{1a}$, $R^{1b}$, and $R^{1c}$ is independently hydrogen, halogen, —$SF_5$, —$NO_2$, —$CH_3$, —$CH_2F$, —$CHF_2$, —$CF_3$, —$OCF_3$, —$NHCH_3$, —$N(CH_3)_2$, —$(CH_2)$-phenyl, —$(CH_2)$-pyridinyl, —$(CH_2)$-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —$SCF_3$, —$SF_5$, —$NO_2$, —$CH_3$, —$CH_2F$, —$CHF_2$, —$CF_3$, —$OCF_3$, —$NHCH_3$, or —$N(CH_3)_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); and wherein $Ar^1$ is aryl or heteroaryl substituted with 0, 1, 2, or 3 groups independently selected from halogen, —$SF_5$, —$NO_2$, —$CH_3$, —$CH_2F$, —$CHF_2$, —$CF_3$, —$OCF_3$, —$NHCH_3$, —$N(CH_3)_2$, —$NHC(O)CH_2Cl$, —$NHSO_2CH$=$CH_2$, —$NHC(O)CH$=$CH_2$, and —$(CH_2)NHC(O)CH$=$CH_2$, or a pharmaceutically acceptable salt thereof.

In one aspect, disclosed are contraceptive methods comprising the step of administering to a male mammal a prophylactically effective amount of a compound having a structure represented by a formula:

wherein each of $R^{1a}$, $R^{1b}$, and $R^{1c}$ is independently hydrogen, halogen, —$SF_5$, —$NO_2$, —$CH_3$, —$CH_2F$, —$CHF_2$, —$CF_3$, —$OCF_3$, —$NHCH_3$, —$N(CH_3)_2$, —$(CH_2)$-phenyl, —$(CH_2)$-pyridinyl, —$(CH_2)$-pyrimidinyl, —O-phenyl, —O-pyridinyl, or —O-pyrimidinyl, provided that at least one of $R^{1a}$, $R^{1b}$, and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and wherein $R^{1c}$ is hydrogen, halogen, —OH, —$SCF_3$, —$SF_5$, —$NO_2$, —$CH_3$, —$CH_2F$, —$CHF_2$, —$CF_3$, —$OCF_3$, —$NHCH_3$, or —$N(CH_3)_2$; wherein $R^2$ is C3-C6 alkyl, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), or —(C1-C3 alkyl)-(bicycloalkenyl); and wherein $Ar^1$ is aryl or heteroaryl substituted with 0, 1, 2, or 3 groups independently selected from halogen, —$SF_5$, —$NO_2$, —$CH_3$, —$CH_2F$, —$CHF_2$, —$CF_3$, —$OCF_3$, —$NHCH_3$, —$N(CH_3)_2$, —$NHC(O)CH_2Cl$, —$NHSO_2CH$=$CH_2$, —$NHC(O)CH$=$CH_2$, and —$(CH_2)NHC(O)CH$=$CH_2$, or a pharmaceutically acceptable salt thereof.

In one aspect, disclosed are contraceptive method comprising the step of administering to a male mammal a prophylactically effective amount of a compound selected from:

439

440

-continued

-continued or a pharmaceutically acceptable salt thereof.

e. Inhibiting in at Least One Cell DCN1-Mediated Cullin-Ring Ligase Activity

In one aspect, the invention relates to a method for inhibiting in at least one cell DCN1-mediated cullin-RING ligase activity, comprising the step of contacting the at least one cell with an effective amount of at least one compound of that is an inhibitor of DCN1-UBC12 interaction. In a further aspect, the compound contacting the at least one cell is at least one disclosed compound, or a pharmaceutically acceptable salt thereof, or an effective amount of at least one product of a disclosed method of making, or a pharmaceutically acceptable salt thereof. In a still further aspect, the compound contacting the at least one cell is at least one compound, or a pharmaceutically acceptable salt thereof, selected from Table 2, 3, 4, 5, 6, or 7. In a further aspect, the compound contacts a cell, and the cell is a mammalian cell. In a still further aspect, the mammalian cell is a human cell.

In various aspects, the cell of the method has been isolated from a mammal prior to the contacting step. In a further aspect, the contacting is via administration of the compound to a mammal.

2. Determining a Therapeutically Effective Amount

Toxicity and therapeutic efficacy of the disclosed compounds can be determined by standard pharmaceutical procedures in cell cultures or experimental animals, e. g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices can be desirable. While compounds that exhibit toxic side effects can be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds lies preferably within a range of circulating concentrations that include the $ED_{50}$ with little or no toxicity. Dosages can vary within this range depending upon the dosage form employed and the route of administration utilized. For any compound used in disclosed herein, the therapeutically effective dose can be estimated initially from cell culture assays. A dose can be formulated in animal models to achieve a circulating plasma concentration range that includes the $IC_{50}$ as determined in cell culture experiments. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a compound of a compound disclosed herein can be from about 0.1 mg to about 1000 mg per day, e.g., from about 0.1 to about 500 mg/kg/day, 0.1 to about 250 mg/kg/day, or 0.1 to about 100 mg/kg/day, per kg of body weight, given as a single dose, a single once-a-day dose, or as divided doses throughout a selected time period.

The anti-cancer activity of the disclosed therapies can be determined by using various experimental animal models of such as the SCID mouse model or nude mice with human tumor grafts known in the art and described in Yamanaka, 2001, Microbiol Immunol 2001; 45 (7): 507-14.

The disclosed protocols and compositions can be tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed.

A lower level of proliferation or survival of the contacted cells can indicate that the therapy can be effective to treat a selected disorder in a subject. Alternatively, instead of culturing cells from a patient, protocols can be screened using cells of a tumor or malignant cell line. Many assays known in the art can be used to assess such survival and/or growth; for example, cell proliferation can be assayed by measuring $^3$H-thymidine incorporation, by direct cell count, by detecting changes in transcriptional activity of known genes such as proto-oncogenes or cell cycle markers; cell viability can be assessed by trypan blue staining, while differentiation can be assessed visually based on changes in morphology, etc.

Compounds for use in therapy can be tested in suitable animal model systems prior to testing in humans, including but not limited to in rats, mice, chicken, cows, monkeys, rabbits, etc. The principle animal models for cancer known in the art and widely used include mice, such as described in Hann et al., 2001, Curr Opin Cell Biol 2001, 13 (6): 778-84, which is incorporated herein by reference in its entirety.

Further, any assays known to those skilled in the art can be used to evaluate the prophylactic and/or therapeutic utility of the combinatorial therapies disclosed herein for treatment, prophylaxis, management or amelioration of one or more symptoms associated with the disease or disorder as described hereinabove.

3. Co-Therapeutic Methods

In one aspect, other cancer treatments can be used in combination with the administration of one or more compounds disclosed herein. Such treatments include the use of one or more molecules, or compounds for the treatment of cancer (i. e., cancer therapeutics). Some examples include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, preferably the methods of the present invention increase patient compliance, improve therapy and/or reduce unwanted or adverse effects.

In one aspect, the methods of the invention includes the administration of one or more angiogenesis inhibitors such as but not limited to: angiostatin (plasminogen fragment); antiangiogenic antithrombin III; angiozyme; ABT-627; Bay 12-9566; benefin; bevacizumab; BMS-275291; cartilage-derived inhibitor (CDI); CAI; CD59 complement fragment; CEP-7055; Col 3; combretastatin A-4; endostatin (collagen XVIII fragment); fibronectin fragment; Gro-beta; halofuginone; heparinases; heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); marimastat; metalloproteinase inhibitors (TIMPs); 2-methoxyestradiol; MMI 270 (CGS 27023A); MoAb IMC-1C11; neovastat; NM-3; panzem; PI-88; placenta ribonuclease inhibitor; plasminogen activator inhibitor; platelet factor-4 (PF4); prinomastat; prolactin 16 kD fragment; proliferin-related protein (PRP); PTK 787/ZK 222594; retinoids; solimastat; squalamine; SS3304; SU5416; SU6668; SU11248; tetrahydrocortisol-S; tetrathiomolybdate; thalidomide; thrombospondin-1 (TSP-1); TNP-470; transforming growth factor-beta (TGF-b); vasculostatin; vasostatin (calreticulin fragment); ZD6126; ZD 6474; farnesyl transferase inhibitors (FTI); and bisphosphonates.

Additional examples of anti-cancer agents that can be used in the various aspects disclosed herein, including pharmaceutical compositions and dosage forms disclosed herein, include, but are not limited to: acivicin; aclarubicin;

acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL- PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators;

nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stemcell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In a further aspect, the treatment methods disclosed herein includes the administration of one or more immunotherapeutic agents, such as antibodies and immunomodulators, which include, but are not limited to, HERCEPTINS, RITUXANS, OVAREX™, PANOREX@, BEC2, IMC-C225, VITAMIN, CAMPATH@ I/H, Smart MI95, LYMPHOCIDE™, Smart I D10, and ONCOLYM™, rituximab, gemtuzumab, or trastuzumab.

In a still further aspect, the treatment methods disclosed herein includes administering one or more anti-angiogenic agents, which include, but are not limited to, angiostatin, thalidomide, kringle 5, endostatin, other Serpins, antithrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51: 2077), a 14-amino acid peptide corresponding to a fragment of collagen I (Tolma et al., 1993, J. Cell Biol. 122: 497), a 19 amino acid peptide corresponding to a fragment of Thrombospondin I (Tolsma et al., 1993, J Cell Biol. 122: 497), a 20-amino acid peptide corresponding to a fragment of SPARC (Sage et al., 1995, J: Cell. Biochem. 57: 1329-), or any fragments, family members, or derivatives thereof, including pharmaceutically acceptable derivatives thereof.

In one aspect, the treatment methods disclosed herein can comprise the use of radiation.

In a further aspect, the treatment methods further comprises the administration of one or more cytokines, which includes, but is not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In a further aspect, the treatment method comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e. g., dexamethasone, retinoids, betamethasone, cortisol, cortisone, prednisone, dehydrotestosterone, glucocorticoids, mineralocorticoids, estrogen, testosterone, progestins), antigestagens (e. g., mifepristone, onapristone), antiandrogens (e. g., cyproterone acetate), and the like.

In a further aspect, the disclosure also relates to kits comprising at least one disclosed compound and one or more other therapeutically active compounds, which are usually applied in the treatment of the above mentioned conditions. For example, the disclosed kits can comprise therapeutically effective amounts of one or more disclosed compound and one or anti-cancer agents. The kits can be co-packaged, co-formulated, and/or co-delivered with the anti-cancer agents. For example, a drug manufacturer, a drug reseller, a physician, or a pharmacist can provide a disclosed kit for delivery to a patient.

4. Prophylactic Treatment

In a further aspect, the disclosed compounds, compositions, and methods can be used prophylactically, i.e., to prevent progression to a neoplastic or malignant state, including but not limited to those disorders listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

5. Manufacture of a Medicament

Also provided is a method for the manufacture of a medicament for treatment of a disorder in a subject (e.g., a mammal), comprising a therapeutically effective amount of a compound inhibiting DCN1-mediated cullin-RING ligase activity. In a further aspect, the invention relates to a method for the manufacture of a medicament for treatment of a disorder in a subject (e.g., a mammal), comprising a therapeutically effective amount of a compound inhibiting the DCN1-UBC12 interaction. In a further aspect, the compound used in the manufacture of the medicament is at least one disclosed compound, or a pharmaceutically acceptable salt thereof, or an effective amount of at least one product of a disclosed method of making, or a pharmaceutically acceptable salt thereof. In a still further aspect, the compound used in the manufacture of a medicament is at least one compound, or a pharmaceutically acceptable salt thereof, selected from Table 2, 3, 4, 5, 6, or 7.

6. Use of Compounds

Also provided are uses of compounds inhibiting DCN1-mediated cullin-RING ligase activity. In a further aspect, the invention relates to uses of compounds inhibiting the DCN1-UBC12 interaction. In a further aspect, the compound used for inhibiting DCN1-mediated cullin-RING ligase activity or inhibiting the DCN1-UBC12 interaction is at least one disclosed compound, or a pharmaceutically acceptable salt thereof, or an effective amount of at least one product of a disclosed method of making, or a pharmaceutically acceptable salt thereof. In a still further aspect, the compound used for inhibiting DCN1-mediated cullin-RING ligase activity or inhibiting the DCN1-UBC12 interaction is at least one compound, or a pharmaceutically acceptable salt thereof, selected from Table 2, 3, 4, 5, 6, or 7.

In various aspects, the use relates to the treatment of a disorder in a subject, e.g., a mammal, including a human. The uses of the invention pertain to treatments of disorders such as a disorder of uncontrolled cellular proliferation, e.g., a cancer, or a neurodegenerative disorder.

In a further aspect, the use relates to the treatment of a viral or bacterial infection in a subject, e.g., a mammal, including a human.

In a further aspect, the use relates to contraception in a male subject, e.g., a mammal, including a human.

7. Kits

In one aspect, the invention relates to a kit comprising at least one disclosed compound, or a pharmaceutically acceptable salt thereof; and one or more of: (a) at least one agent known to increase cell proliferation; (b) at least one agent known to increase activity of the ubiquitin-proteosome system; (c) at least one agent known to decrease activity of the ubiquitin-proteosome system; (d) at least one agent known to treat a disorder associated with DCN1-UBC12 interaction; or (e) at least one agent known to treat a disease of uncontrolled cellular proliferation; or (f) instructions for treating a disease of uncontrolled cellular proliferation.

In one aspect, the invention relates to a kit comprising at least one disclosed compound, or a pharmaceutically acceptable salt thereof; and one or more of: (a) at least one agent known to increase activity of the ubiquitin-proteosome system; (b) at least one agent known to decrease activity of the ubiquitin-proteosome system; (c) at least one agent known to treat a disorder associated with DCN1-UBC12 interaction; (d) at least one agent known to treat a neurodegenerative disease; or (e) instructions for treating a neurodegenerative disease.

In one aspect, the invention relates to a kit comprising at least one disclosed compound, or a pharmaceutically acceptable salt thereof; and one or more of: (a) at least one agent known to increase activity of the ubiquitin-proteosome system; (b) at least one agent known to decrease activity of the ubiquitin-proteosome system; (c) at least one agent known to treat a disorder associated with DCN1-UBC12 interaction; (d) at least one agent known to treat a viral or bacterial infection; or (e) instructions for treating a viral or bacterial infection.

In one aspect, the invention relates to a kit comprising at least one disclosed compound, or a pharmaceutically acceptable salt thereof; and one or more of: (a) at least one agent known to increase activity of the ubiquitin-proteosome system; (b) at least one agent known to decrease activity of the ubiquitin-proteosome system; (c) at least one agent known to treat a disorder associated with DCN1-UBC12 interaction; (d) at least one agent known to be used as a male contraceptive; or (e) instructions for effecting male contraception.

In a further aspect, the at least one compound and the at least one agent are co-formulated. In a still further aspect, the at least one compound and the at least one agent are co-packaged.

In a further aspect, the at least one agent is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a still further aspect, the chemotherapeutic agent is selected from one or more of the group consisting of an alkylating-like agent, an antimetabolite agent, an antineoplastic antibiotic agent, a mitotic inhibitor agent, an mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating-like agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, sirolimus, and temsirolimus, or a pharmaceutically acceptable salt, hydrate, solvate, or polymorph thereof.

In a further aspect, the kit further comprises instructions to provide the compound in connection with surgery. In a still further aspect, the kit further comprises instructions to provide the compound in connection with surgery, wherein the instructions provide that surgery is performed prior to the administering of at least one compound. In a yet further aspect, the kit further comprises instructions to provide the compound in connection with surgery, wherein the instructions provide that surgery is performed after the administering of at least one compound. In an even further aspect, the kit further comprises instructions to provide the compound in connection with surgery, wherein the instructions provide that surgery is performed after the administering of at least one compound, and wherein the instructions provide that the administering of at least one compound is to effect presurgical debulking of a tumor. In a still further aspect, the kit further comprises instructions to provide the compound in connection with surgery, wherein the instructions provide that surgery is performed after the administering of at least one compound, and wherein the instructions provide that surgery is performed at about the same time as the administering of at least one compound.

In a further aspect, the kit further comprises instructions to provide the compound in connection with radiotherapy. In a still further aspect, the kit further comprises instructions to provide the compound in connection with radiotherapy, wherein the instructions provide that radiotherapy is performed prior to the administering of at least one compound. In a yet further aspect, the kit further comprises instructions to provide the compound in connection with radiotherapy, wherein the instructions provide that radiotherapy is performed after the step of the administering of at least one compound. In an even further aspect, the kit further comprises instructions to provide the compound in connection with radiotherapy, wherein the instructions provide that radiotherapy is performed at about the same time as the step of the administering of at least one compound.

In a further aspect, the kit further comprises a plurality of dosage forms, the plurality comprising one or more doses; wherein each dose comprises a therapeutically effective amount of the compound and the at least one agent. In a still further aspect, the kit further comprises a plurality of dosage forms, the plurality comprising one or more doses; wherein each dose comprises a therapeutically effective amount of the compound and the at least one agent, and wherein each dose of the compound and the at least one agent are co-formulated. In a yet further aspect, the kit further comprises a plurality of dosage forms, the plurality comprising one or more doses; wherein each dose comprises a therapeutically effective amount of the compound and the at least one agent, and wherein each dose of the compound and the at least one agent are co-packaged.

In a further aspect, the kit further comprises a plurality of dosage forms, the plurality comprising one or more doses; wherein each dose comprises a therapeutically effective amount of the compound and the at least one agent, and wherein the dosage forms are formulated for oral administration and/or intravenous administration. In a still further aspect, the kit further comprises a plurality of dosage forms, the plurality comprising one or more doses; wherein each dose comprises a therapeutically effective amount of the compound and the at least one agent, and wherein the dosage forms are formulated for oral administration. In a yet further aspect, the kit further comprises a plurality of dosage forms, the plurality comprising one or more doses; wherein each dose comprises a therapeutically effective amount of the compound and the at least one agent, and wherein the dosage forms are formulated for intravenous administration.

In a further aspect, the kit further comprises a plurality of dosage forms, the plurality comprising one or more doses; wherein each dose comprises a therapeutically effective amount of the compound and the at least one agent; and wherein the dosage form for the compound is formulated for oral administration and the dosage form for the at least one agent is formulated for intravenous administration. In a still further aspect, the kit further comprises a plurality of dosage forms, the plurality comprising one or more doses; wherein each dose comprises a therapeutically effective amount of the compound and the at least one agent; and wherein the dosage form for the compound is formulated for intravenous administration and the dosage form for the at least one agent is formulated for oral administration.

In a further aspect, the instructions for treating a disorder of uncontrolled cellular proliferation provide instructions for treating a cancer.

In various aspects, the cancer is a squamous cell carcinoma. In a further aspect, the squamous cell carcinoma is a metastatic squamous cell carcinoma. In a still further aspect, the squamous cell carcinoma is a non-small cell lung carcinoma.

In a further aspect, the cancer is a uterine carcinosarcoma. In a still further aspect, the cancer is an embryonal rhabdomyosarcoma, glioblastoma, medulloblastoma, or osteosarcoma. In a yet further aspect, the cancer is an adrenocortical tumor. In an even further aspect, the cancer is a solid tumor.

In various aspects, the cancer is a hematological malignancy. In a further aspect, the hematological malignancy is a leukemia, lymphoma, or myeloma. In a still further aspect, the lymphoma is multiple lymphoma or B-cell non-Hodgkin's lymphoma. In a yet further aspect, the myeloma is multiple myeloma. In an even further aspect, the leukemia is acute myeloid leukemia.

In a further aspect, the cancer is a cancer of lung, cervix, ovary, uterus, esophagus, prostate, or head and neck. In a still further aspect, the cancer is a cancer of lung, cervix, esophagus, uterus, or prostate.

In a further aspect, the cancer is lung cancer. In a still further aspect, the lung cancer is a non-small cell lung cancer. In a yet further aspect, the non-small cell lung cancer is a squamous cell carcinoma, adenocarcinoma, or large cell-undifferentiated carcinoma.

8. Subjects

The compounds, compositions, and methods disclosed herein can be useful for the treatment or prevention of one or more disorders associated with a need to inhibit the DCN1-UBC12 interaction or inhibiting DCN1-mediated cullin-RING ligase activity, as discussed hereinabove. In general, a subject can be any age, including a fetus. A subject to which a compound or compositions disclosed herein can be administered can be an animal, including but not limited to a mammal, such as a non-primate mammal (e.g., cows, pigs, sheep, goats, horses, chickens, dogs, rats, etc.) and a primate (e.g., a monkey such as a acynomolgous monkey and a human). A subject can also be a laboratory animal (e.g., a mouse, rabbit, guinea pig, fruit fly, etc.).

In one aspect, a subject can be diagnosed with one or more disorders as discussed herein elsewhere. In a specific aspect, a subject can be diagnosed with one or more disorders as discussed herein elsewhere before the step of administering to the subject a therapeutically effective amount of one more compounds disclosed herein.

In a further aspect, a subject can be a subject in need of treatment for disorder of uncontrolled cellular proliferation, e.g., cancer. In a still further aspect, a subject can have cancer or a related disorder, as discussed hereinbefore. In one aspect, a subject can be treated prophylactically with a compound or composition disclosed herein, as discussed herein elsewhere.

One or more compounds or compositions disclosed herein can be utilized for the prevention of a variety of cancers, e.g, in individuals who are predisposed as a result of familial history or in individuals with an enhanced risk to cancer due to environmental factors.

The methods and compositions of the invention can be used in patients who are treatment naive, in patients who have previously received or are currently receiving treatment with other pharmaceutical agents or combinations, including but not limited to anti-cancer agents. Other subjects can include patients that have metastasis or no metastasis.

The methods and compositions of the invention are useful not only in untreated patients but are also useful in the treatment of patients partially or completely un-responsive to other treatments. In various aspects, the disclosure provides methods and compositions useful for the treatment of diseases or disorders in patients that have been shown to be or can be refractory or non-responsive to therapies comprising the administration of other agents.

In one aspect, subjects that can be treated with the compositions disclosed herein include those subjects displaying the presence of one or more characteristics of a transformed phenotype, or of a malignant phenotype, displayed in vivo or displayed in vitro by a cell sample from a subject, can indicate the desirability of prophylactic/therapeutic administration of a compound or composition disclosed herein. As mentioned hereinabove, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 Dalton cell surface protein, etc.

In a further aspect, a subject that exhibits one or more of the following predisposing factors for malignancy can be treated by administration of an effective amount of a compound disclosed herein.

F. Examples

The following examples are put forth so as to provide those of ordinary skill in the art with a complete disclosure and description of how the compounds, and/or methods disclosed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. General Chemistry Methods

All moisture sensitive reactions were performed using syringe-septum techniques under an atmosphere of either dry $N_2$ or dry argon unless otherwise noted. All glassware was dried in an oven at 140° C. for a minimum of 6 hr or flame-dried under an atmosphere of dry nitrogen prior to use. Reactions carried out at −78° C. employed a $CO_2(s)$/acetone bath. Dry methylene chloride, tetrahydrofuran, diethylether, toluene, dimethylformamide, and acetonitrile were dried using an aluminum oxide column. All degassed solvents were prepared using the freeze/pump/thaw method (×3). Methanol, acetonitrile, and N,N-dimethylformamide were stored over molecular sieves (3 Å). Deuterated chloroform was stored over anhydrous potassium carbonate. Reactions were monitored by TLC analysis (pre-coated silica gel 60 $F_{254}$ plates, 250 m layer thickness) and visualized by using UV lamp (254 nm) or by staining with either Vaughn's reagent (4.8 g of $(NH_4)_6Mo_7O_{24} \cdot 4H_2O$ and 0.2 g of $Ce(SO_4)_2$ in 100 mL of a 3.5 N $H_2SO_4$) or a potassium permanganate solution (1.5 g of $KMnO_4$ and 1.5 g of $K_2CO_3$ in 100 mL of a 0.1% NaOH solution). Flash column chromatography was performed using a Biotage Isolera one and Biotage KP-SIL SNAP cartridges. Microwave reactions were performed on a Biotage Initiator microwave reactor. Unless otherwise indicated, all NMR data were collected at room temperature in $CDCl_3$ or $(CD_3)_2SO$ on a 400 or 600 MHz Bruker instrument. Chemical shifts (δ) are reported in parts per million (ppm) with internal $CHCl_3$ (δ 7.26 ppm for $^1H$ and 77.00 ppm for $^{13}C$), or internal trimethylsilane (TMS) (δ 0.00 ppm for $^1H$ and 0.0 ppm for $^{13}C$), as the reference. $^1H$ NMR data are reported as follows: chemical shift, multiplicity (s=singlet, bs=broad singlet, d=doublet, t=triplet, q=quartet, p=pentet, sext=sextet, sep=septet, m=multiplet, dd=doublet of doublets, dt=doublet of triplets, td=triplet of doublets, qd=quartet of doublets), coupling constant(s) (J) in Hertz (Hz), and integration. The purity of all final compounds was assessed using LC/MS/UV/ELSD using a Waters Acquity UPLC with the purity being assigned as the average determined by UV/Vis and ELSD.

2. Synthetic Methods a. General Synthetic Routes I (i)

455
-continued 456
b. General Synthetic Routes II
Method 1

(ii)

(iii)

(a) R¹—CHO, NaBH(OAc)₃, AcOH, CH₂Cl₂; (b) TFA, CH₂Cl₂; (c) R²-isocyanate, DIPEA, CH₂Cl₂; (d) K₂CO₃, R³—I, CH₃CN; (e) R⁴—NH₂, NaBH(OAc)₃, AcOH, CH₂Cl₂; (f) R⁵-isocyanate, DIPEA, CH₂Cl₂; (g) R⁴—NH₂, NaBH(OAc)₃, AcOH, CH₂Cl₂; (h) R⁶-isocyanate, DIPEA, CH₂Cl₂; (i) TFA, CH₂Cl₂; (j) R⁷—CHO, NaBH(OAc)₃, AcOH, CH₂Cl₂.

Method 2

-continued $R^2CHO$
$(Bu)_2SnCl_2$,
$C_6H_5SiH_3$, THF

CDI, THF

Method 3

Benzyl amine $NaBH(OAc)_3$,
$AcOH$, $CH_2Cl_2$

CDI, THF

-continued

TFA, $CH_2Cl_2$;

then $R^2CHO$,
$(Bu)_2SnCl_2$,
$C_6H_5SiH_3$, THF c. Preparation of Compounds Nos. A137, A155, A172, A179, A183, A186, A238, A263, A276, A282, A292, A306, B7, B20, and B59.

Synthesis of Tert-butyl (1-Benzylpiperidin-4-yl)carbamate

To a stirred solution of Boc-4-aminopiperidine (5.00 g, 25.0 mmol, 1 equiv) and benzaldehyde (2.54 mL, 25.0 mmol, 1 equiv) in dry $CH_2Cl_2$ (60 mL) was added acetic acid (1.72 mL, 25.0 mmol, 1.2 equiv). The resulting cloudy mixture was stirred at room temperature for 1 hr and sodium triacetoxyborohydride (10.6 g, 50.0 mmol, 2 equiv) was added portion-wise. The resulting heterogeneous mixture was stirred at room temperature overnight (ca. 16 hr), quenched with a saturated aqueous solution of $NaHCO_3$, the organic layer was separated, and the remaining aqueous layer was extracted with EtOAc (×2). The combined organic layers were dried ($MgSO_4$), filtered, and concentrated under reduced pressure. The crude mixture was purified by chromatography on $SiO_2$ ($MeOH/CH_2Cl_2$, 1:20 to 1:9) to give 5.63 g (78% yield) of the desired product as a colorless oil.

Synthesis of 1-Benzylpiperidin-4-amine

To a stirred solution of crude tert-butyl (1-benzylpiperidin-4-yl)carbamate (1.00 g, 3.44 mmol, 1 equiv) in CH$_2$Cl$_2$ (20 mL) at 0° C. was slowly added trifluoroacetic acid (1.32 mL, 17.2 mmol, 5 equiv). The reaction mixture was slowly warmed to room temperature, stirred at room temperature overnight (ca. 16 hr), and concentrated under reduced pressure. The crude reaction mixture was directly carried onto the next reaction without purification.

Synthesis of 1-(1-Benzylpiperidin-4-yl)-3-(3-(trifluoromethyl)phenyl)urea (Compound No. B7)

To a stirred solution of 1-benzylpiperidin-4-amine (0.250 g, 1.314 mmol, 1.2 equiv) in CH$_2$Cl$_2$ (6 mL) was added 1-isocyanato-3-(trifluoromethyl)benzene (1.53 mL, 1.10 mmol, 1 equiv) and N,N-diisopropylethylamine (0.286 mL, 1.64 mmol, 1.5 equiv). The resulting mixture was stirred at room temperature overnight (ca. 16 hr), concentrated under reduced pressure, and the crude mixture was purified by chromatography on SiO$_2$ (MeOH/CH$_2$Cl$_2$, 2:100 to 2:8) to give 0.300 g (92% yield) of the desired product as a white solid. $^1$H NMR (400 MHz, DMSO-d$_6$) δ 8.71 (s, 1H), 7.96 (d, J=2.2 Hz, 1H), 7.50-7.38 (m, 2H), 7.35-7.27 (m, 4H), 7.27-7.19 (m, 2H), 6.24 (d, J=7.6 Hz, 1H), 3.56-3.40 (m, 3H), 2.71 (d, J=11.4 Hz, 2H), 2.07 (t, J=11.0 Hz, 2H), 1.80 (dd, J=16.0, 4.0 Hz, 2H), 1.41 (qd, J=16.0, 4.0 Hz, 2H). $^{13}$C NMR (101 MHz, DMSO) δ 154.3, 141.3, 138.6, 129.7, 129.4 (q, J=30.3 Hz, 1C), 128.8, 128.1, 126.9, 124.3 (q, J=273.3 Hz, 1C), 121.0, 117.1 (q, J=4.0 Hz, 1C), 113.4 (q, J=4.0 Hz, 1C), 62.2, 51.7, 46.3, 32.0. m/z (APCI-pos) M+1=378.5. HRMS (ESI+) m/z calcd for C$_{20}$H$_{23}$F$_3$N$_3$O [M+H]$^+$ 378.1793, found 378.1790.

Synthesis of 1-(1-(2-methylbenzyl)piperidin-4-yl)-3-(3-(trifluoromethyl)phenyl)urea (Compound No. A137)

Prepared as described above from 1-isocyanato-3-(trifluoromethyl)benzene and 1-(2-methylbenzyl)piperidin-4-amine. $^1$H NMR (400 MHz, DMSO-d6) δ 8.72 (s, 1H), 7.97 (s, 1H), 7.46-7.41 (m, 2H), 7.22-7.19 (m, 2H), 7.75-7.12 (m, 3H), 6.24 (d, J=7.6 Hz, 1H), 3.51-3.47 (m, 1H), 3.40 (bs, 2H), 3.33 (bs, 1H), 2.70 (d, J=12.0 Hz, 2H), 2.31 (s, 3H), 2.09 (t, J=10.9 Hz, 2H), 1.79 (d, J=12.0 Hz, 2H), 1.38 (q, J=12.0 Hz, 2H). $^{13}$C NMR (101 MHz, DMSO) δ 154.3, 141.3, 136.9, 136.6, 130.0, 129.7, 129.4, 129.4 (q, J=31.3 Hz, 1C), 126.8, 125.3, 124.2 (q, J=272.7 Hz, 1C), 121.0, 117.1 (q, J=4.0 Hz, 1C), 113.4 (q, J=4.0 Hz, 1C), 60.2, 51.9, 46.4, 32.1, 18.8. m/z (APCI-pos) M+1=392.4. HRMS (ESI+) m/z calcd for C$_{21}$H$_{25}$F$_3$N$_3$O [M+H]$^+$ 392.1978, found 392.1948.

Synthesis of 1-(1-(2-chlorobenzyl)piperidin-4-yl)-3-(3-(trifluoromethyl)phenyl)urea (Compound No. A292)

Prepared as described above from 1-isocyanato-3-(trifluoromethyl)benzene and 1-(2-chlorobenzyl)piperidin-4-amine. $^1$H NMR (400 MHz, DMSO-d6) δ 8.73 (s, 1H), 7.97 (s, 1H), 7.50-7.40 (m, 4H), 7.35-7.28 (m, 2H), 7.22-7.20 (m, 1H), 6.26 (d, J=4.0 1H), 3.55 (s, 2 hr) 3.54-3.48 (m, 1H), 2.74 (d, J=8.1 Hz, 2H), 2.18 (t, J=10.0 Hz, 2H), 1.81 (d, J=12.1 Hz, 1H) 1.43 (q, J=12.1 Hz, 2H). $^{13}$C NMR (101 MHz, DMSO) δ 154.3, 141.3, 136.0, 133.2, 130.7, 129.7, 129.4 (q, J=31.3 Hz, 1C), 129.2, 128.5, 127.0, 124.3 (q, J=273.7 Hz, 1C), 121.0, 117.1 (q, J=4.0 Hz, 1C), 113.5 (q, J=4.0 Hz, 1C) 58.7, 51.8, 46.2, 32.0. m/z (APCI-pos) M+1=413.32. HRMS (ESI+) m/z calcd for C$_{20}$H$_{22}$ClF$_3$N$_3$O [M+H]$^+$ 412.1404, found 412.1400.

Synthesis of 1-(1-(2-fluorobenzyl)piperidin-4-yl)-3-(3-(trifluoromethyl)phenyl)urea (Compound No. A238)

Prepared as described above from 1-isocyanato-3-(trifluoromethyl)benzene and 1-(2-fluorobenzyl)piperidin-4-amine. $^1$H NMR (400 MHz, DMSO-d$_6$) δ 8.71 (s, 1H), 7.96 (s, 1H), 7.48-7.38 (m, 3H), 7.31 (qd, J=7.6, 2.7 Hz, 1 hr), 7.24-7.11 (m, 3H), 6.24 (d, J=7.6 Hz, 1H), 3.51 (s, 2H), 3.51-3.46 (m, 1 hr) 2.72 (d, J=11.5 Hz, 2H), 2.11 (t, J=10.8 Hz, 2H), 1.79 (d, J=10.8 Hz, 2H), 1.41 (qd, 10.8, 3.3 Hz, 2H). $^{13}$C NMR (101 MHz, DMSO) δ 162.0, 159.5, 154.3, 141.3, 131.5, 131.4, 129.7, 129.4 (q, J=31.3 Hz, 1C), 129.0, 128.9, 125.0, 124.8, 124.3 (q, J=273.7 Hz, 1C), 124.2, 124.1, 121.0, 117.2 (q, J=4.0 Hz, 1C), 115.2, 115.0, 113.4 (q, J=4.0 Hz, 1C), 54.7, 51.5, 46.1, 32.0. m/z (APCI-pos) M+1=396.4. HRMS (ESI+) m/z calcd for C$_{20}$H$_{22}$F$_4$N$_3$O [M+H]$^+$ 396.1699, found 396.1697.

Synthesis of 1-(1-(3-methylbenzyl)piperidin-4-yl)-3-(3-(trifluoromethyl)phenyl)urea (Compound No. A155)

461

Prepared as described above from 1-isocyanato-3-(trifluoromethyl)benzene and 1-(3-methylbenzyl)piperidin-4-amine. $^1$H NMR (400 MHz, DMSO-d$_6$) δ 8.75 (s, 1H), 7.97 (s, 1H), 7.50-7.37 (m, 2H), 7.22-7.18 (m, 2H), 7.11-7.05 (m, 3H), 6.27 (d, J=7.6 Hz, 1H), 3.53-3.42 (m, 3H), 2.71 (bs, 2H), 2.29 (s, 3H), 2.19-1.94 (m, 2H), 1.80 (d, J=10.8 Hz, 2H) 1.41 (q, J=11.1 Hz, 2H). $^{13}$C NMR (101 MHz, DMSO) δ 154.3, 141.3, 137.2, 129.7, 129.5, 129.4 (q, J=31.3 Hz, 1C), 128.0, 127.6, 126.0, 124.3 (q, J=272.7 Hz, 1C), 121.0, 117.2 (q, J=4.0 Hz, 1C), 113.4 (q, J=4.0 Hz, 1C), 62.1, 51.7, 46.2, 39.2, 31.9, 21.0. m/z (APCI-pos) M+1=392.4. HRMS (ESI+) m/z calcd for C$_{21}$H$_{25}$F$_3$N$_3$O [M+H]$^+$ 392.1949, found 392.1945.

Synthesis of 1-(1-(3-chlorobenzyl)piperidin-4-yl)-3-(3-(trifluoromethyl)phenyl)urea (Compound No. A192)

Prepared as described above from 1-isocyanato-3-(trifluoromethyl)benzene and 1-(3-chlorobenzyl)piperidin-4-amine. $^1$H NMR (400 MHz, DMSO-d6) δ 8.73 (s, 1H), 7.97 (s, 1H), 7.46-7.41 (m, 2H), 7.37-7.25 (m, 3H), 7.26 (d (J=8.0 Hz, 1 hr), 7.20 (d, J=8.0 Hz), 6.25 (d, J=7.6 Hz, 1H), 3.51-3.45 (m, 3H), 2.70 (d, J=11.2 Hz, 2H), 2.12-2.07 (m, 2H), 1.87-1.72 (m, 2H), 1.50-1.29 (m, 2H). $^{13}$C NMR (101 MHz, DMSO) δ 154.3, 141.3, 132.9, 130.0, 129.7, 129.4 (q, J=31.3 Hz, 1C), 128.3, 127.3, 126.9, 124.3 (q, J=273.7 Hz, 1C), 121.0, 117.2 (q, J=4.0 Hz, 1C), 113.4 (q, J=4.0 Hz, 1C), 61.3, 51.7, 46.2, 32.0. m/z (APCI-pos) M+1=412.4. HRMS (ESI+) m/z calcd for C$_{20}$H$_{22}$ClF$_3$N$_3$O [M+H]$^+$ 412.1403, found 412.1399.

Synthesis of 1-(1-(3-fluorobenzyl)piperidin-4-yl)-3-(3-(trifluoromethyl)phenyl)urea (Compound No. A183)

Prepared as described above from 1-isocyanato-3-(trifluoromethyl)benzene and 1-(3-fluorobenzyl)piperidin-4-amine. $^1$H NMR (400 MHz, DMSO-d$_6$) δ 8.73 (s, 1H), 7.97 (s, 1H), 7.46-7.42 (m, 2H), 7.35 (q, J=8.0 Hz, 1H), 7.22-7.19 (m, 2H), 7.17-7.01 (m, 3H), 6.26 (d, J=7.7 Hz, 1H), 3.48 (bs, 3H), 2.78-2.62 (m, 2H), 2.08 (t, J=10.8 Hz, 2H), 1.80 (dd, J=12.3, 4.8 Hz, 2H), 1.42 (q, J=10.5 Hz, 2H). $^{13}$C NMR (101 MHz, DMSO) δ 161.3 (d, J=243.4 Hz, 1C), 154.3, 141.3, 134.7, 130.6, 129.7, 129.4 (q, J=31.3 Hz, 1C), 124.3 (q, J=273.7 Hz, 1C), 121.0, 117.2 (q, J=4.0 Hz, 1C), 115.0, 114.8, 113.4 (q, J=4.0 Hz, 1 C), 61.1, 51.6, 46.2, 31.9. m/z (APCI-pos) M+1=396.4. HRMS (ESI+) m/z calcd for C$_{20}$H$_{22}$F$_4$N$_3$O [M+H]$^+$ 396.1699, found 396.1696.

Synthesis of 1-(1-(4-methylbenzyl)piperidin-4-yl)-3-(3-(trifluoromethyl)phenyl)urea (Compound No. A179)

Prepared as described above from 1-isocyanato-3-(trifluoromethyl)benzene and 1-(4-methylbenzyl)piperidin-4-amine. $^1$H NMR (400 MHz, DMSO-d6) δ 8.86 (s, 1H), 7.96 (s, 1H), 7.45 (s, 1H), 7.44 (q, J=8.0 Hz, 1H), 7.24-7.13 (m, 5H), 6.40 (bs, 1H), 3.60-3.42 (m, 3H), 2.78 (bs, 3H), 2.29 (s, 3H), 2.08 (s, 2H), 1.84 (bs, 2H), 1.46 (bs, 2H). $^{13}$C NMR (101 MHz, DMSO) δ 154.4, 141.3, 129.7, 129.4 (q, J=31.3 Hz, 1C), 128.9, 124.3 (q, J=273.7 Hz, 1C), 121.0, 117.2 (q, J=4.0 Hz, 1C), 113.4 (q, J=4.0 Hz, 1C), 62.1, 51.3, 30.7, 20.7. m/z (APCI-pos) M+1=392.4. HRMS (ESI+) m/z calcd for C$_{21}$H$_{25}$F$_3$N$_3$O [M+H]$^+$ 392.1950, found 392.1942.

Synthesis of 1-(1-(4-chlorobenzyl)piperidin-4-yl)-3-(3-(trifluoromethyl)phenyl)urea (Compound No. A186)

Prepared as described above from 1-isocyanato-3-(trifluoromethyl)benzene and 1-(4-chlorobenzyl)piperidin-4-amine. $^1$H NMR (400 MHz, DMSO-d$_6$) δ 8.78 (s, 1H), 7.98 (s, 1H), 7.52-7.28 (m, 6H), 7.21 (dd, J=6.6, 2.3 Hz, 1H), 6.30 (d, J=8.0 Hz, 1H), 3.51-3.40 (m, 3H), 2.77-2.65 (m, 2H), 2.20-1.97 (m, 2H), 1.88-1.74 (m, 2H), 1.42 (q, J=10.8 Hz, 2H). $^{13}$C NMR (101 MHz, DMSO) δ 154.3, 141.3, 130.6, 129.7, 129.4 (q, J=31.3 Hz, 1C), 128.1, 124.3 (q, J=273.7 Hz, 1C), 121.0, 117.2 (q, J=4.0 Hz, 1C), 113.4 (q, J=4.0 Hz, 1 C), 61.1, 51.6, 46.2, 32.1. m/z (APCI-pos) M+1=412.4. HRMS (ESI+) m/z calcd for C$_{20}$H$_{22}$ClF$_3$N$_3$O [M+H]$^+$ 412.1403, found 412.1403.

Synthesis of 1-(1-(4-fluorobenzyl)piperidin-4-yl)-3-(3-(trifluoromethyl)phenyl)urea ((Compound No. A172)

Prepared as described above from 1-isocyanato-3-(trifluoromethyl)benzene and 1-(4-fluorobenzyl)piperidin-4-amine. 1H NMR (400 MHz, DMSO-d6) δ 8.75 (s, 1H), 7.97 (s, 1H), 7.49-7.38 (m, 2H), 7.33 (t, J=7.0 Hz, 2H), 7.26-7.18 (m, 1H), 7.14 (t, J=8.6 Hz, 2H), 6.28 (d, J=6.5 Hz, 1H), 3.58-3.38 (m, 3H), 2.70 (bs, 2H), 2.19-1.97 (m, 2H), 1.89-1.74 (m, 2H), 1.40 (q, J=11.0 Hz, 2H). $^{13}$C NMR (101 MHz, DMSO) δ 161.2 (d, J=243.4 Hz, 1C), 154.3, 141.3, 134.7, 130.6, 129.7, 129.4 (q, J=31.3 Hz, 1C), 124.3 (q, J=273.7 Hz, 1C), 121.0, 117.2 (q, J=4.0 Hz, 1C), 115.0, 114.8, 113.4 (q, J=4.0 Hz, 1C), 61.1, 51.6, 46.2, 31.9. m/z (APCI-pos) M+1=396.4. HRMS (ESI+) m/z calcd for $C_{20}H_{22}F_4N_3O$ [M+H]$^+$ 396.1699, found 396.1700.

Synthesis of 1-(1-benzoylpiperidin-4-yl)-3-(3-(trifluoromethyl)phenyl)urea (Compound No. A306)

Prepared as described above from 1-isocyanato-3-(trifluoromethyl)benzene and 1-(4-fluorobenzyl)piperidine. $^1$H NMR (500 MHz, DMSO-d$_6$) δ 8.76 (s, 1H), 7.97 (s, 1H), 7.51-7.41 (m, 5H), 7.41-7.35 (m, 2H), 7.22 (d, J=7.4 Hz, 1H), 6.33 (d, J=7.6 Hz, 1H), 4.31 (bs, 1H), 3.76 (tdt, J=10.9, 7.9, 4.1 Hz, 1H), 3.53 (s, 1H), 3.15 (s, 1H), 3.03 (s, 1H), 1.91 (s, 1H), 1.81 (s, 1H), 1.37 (bs, 2H). $^{13}$C NMR (126 MHz, DMSO) δ 169.0, 154.3, 141.2, 136.2, 129.7, 129.4 (q, J=30.2 Hz, 1C), 129.4, 128.4, 126.7, 117.3 (q, J=4.0 Hz, 1C), 1163.5 (q, J=4.0 Hz, 1C), 46.4, 45.9, 32.3, 31.6. m/z (APCI-pos) M+1=3952.4. HRMS (ESI+) m/z calcd for $C_{20}H_{21}F_4N_3O$ [M+H]$^+$ 392.1586, found 392.1583.

Synthesis of 1-(1-benzylpiperidin-4-yl)-3-phenylurea (Compound No. B20)

Prepared as described above from isocyanatobenzene and 1-benzylpiperidine. $^1$H NMR (400 MHz, DMSO-d6) δ 8.34 (s, 1H), 7.39-7.23 (m, 6H), 7.23-7.16 (m, 2H), 6.87 (td, J=7.3, 1.2 Hz, 1H), 6.12 (d, J=7.6 Hz, 1H), 3.47 (bs, 3H), 2.70 (bs, 2H), 2.19-1.97 (m, 2H), 1.81-1.78 (m, 2H), 1.49-1.25 (m, 2H). $^{13}$C NMR (101 MHz, DMSO) δ 154.5, 140.4, 128.8, 128.6, 128.1, 126.9, 120.9, 117.5, 62.1, 51.7, 46.0, 32.1. m/z (APCI-pos) M+1=310.3. HRMS (ESI+) m/z calcd for $C_{19}H_{24}N_3O$ [M+H]$^+$ 310.1919, found 310.1915.

Synthesis of 1-(3-(1H-pyrrol-1-yl)phenyl)-3-(1-benzylpiperidin-4-yl)urea (Compound No. A282)

Prepared as described above from 1-(3-isocyanatophenyl)-1H-pyrrole and 1-benzylpiperidine. $^1$H NMR (400 MHz, DMSO-d6) δ 8.52 (s, 1H), 7.67 (s, 1H), 7.37-7.19 (m, 9H), 7.18-7.09 (m, 1H), 7.07-7.04 (m, 1H), 6.25 (t, J=2.2 Hz, 2H), 6.24-6.18 (m, 1 hr), 3.48 (d, J=19.4 Hz, 3H), 2.70 (bs, 2H), 2.07 (t, J=11.3 Hz, 2H), 1.81 (d, J=11.3 Hz), 1.41 (q, J=11.3 Hz, 2H). $^{13}$C NMR (101 MHz, DMSO) δ 154.4, 141.7, 140.3, 138.6, 129.8, 128.7, 128.2, 126.8, 118.9, 114.5, 112.3, 110.3, 108.7, 62.2, 51.7, 46.2, 40.15, 32.1. m/z (APCI-pos) M+1=375.40. HRMS (ESI+) m/z calcd for $C_{23}H_{27}N_4O$ [M+H]$^+$ 375.2178, found 375.2181.

Synthesis of 1-(1-benzylpiperidin-4-yl)-3-(3-(1-methyl-1H-pyrazol-5-yl)phenyl)urea (Compound No. A263)

Prepared as described above from 5-(3-isocyanatophenyl)-1-methyl-1H-pyrazole and 1-benzylpiperidine. $^1$H NMR (500 MHz, DMSO-d$_6$) δ 8.54 (s, 1H), 7.60 (s, 1H), 7.45 (d, J=1.8 Hz, 1H), 7.39-7.20 (m, 7H), 7.03 (dt, J=7.3, 1.4 Hz, 1H), 6.34 (d, J=1.8 Hz, 1H), 6.30-6.18 (m, 1H), 3.83 (s, 3H), 3.48 (s, 2H), 2.73 (s, 2H), 2.22-1.91 (m, 2H), 1.91-1.73 (m, 2H), 1.41 (q, J=11.4 Hz, 2H). $^{13}$C NMR (126 MHz, DMSO) δ 155.0, 143.3, 141.3, 139.0, 138.3, 131.0, 129.6, 129.3, 128.7, 127.4, 121.5, 117.9, 117.8, 106.0, 62.6, 52.2, 46.6, 40.6, 40.5, 40.4, 40.3, 40.3, 40.2, 40.1, 40.0, 39.9, 39.8, 39.7, 39.5, 38.0, 32.5. m/z (APCI-pos) M+1=390.4. HRMS (ESI+) m/z calcd for $C_{23}H_{28}N_5O$ [M+H]$^+$ 390.2294, found 390.2292.

Synthesis of 1-(1-benzylpiperidin-4-yl)-3-(3-(morpholinomethyl)phenyl)urea (Compound No. A276)

Prepared as described above from 4-(3-isocyanatobenzyl)morpholine and 1-benzylpiperidine. $^1$H NMR (500 MHz, DMSO-d$_6$) δ 8.41 (s, 1H), 7.33 (s, 5H), 7.25 (dd, J=8.1, 2.0 Hz, 1H), 7.14 (t, J=7.8 Hz, 1H), 6.81 (d, J=7.5 Hz, 1H), 6.16 (bs, 1H), 3.56 (t, J=4.6 Hz, 4H), 3.54-3.42 (m, 6H), 3.38 (bs, 2 hr), 3.33 (bs, 2 hr), 2.74 (bs, 2H), 2.33 (s, 4H), 1.81 (bs, 2H), 1.41 (s, 2H). $^{13}$C NMR (126 MHz, DMSO) δ 154.5, 140.4, 138.2, 128.9, 128.4, 128.2, 127.0, 121.6, 117.9, 116.2, 66.2, 62.6, 53.2, 51.6, 39.0, 32.0. m/z (APCI-pos) M+1=409.4. HRMS (ESI+) m/z calcd for $C_{24}H_{33}N_4O_2$ [M+H]$^+$ 409.2603, found 409.2596.

<table>
<tr><td>465</td><td>466</td></tr>
</table>

465

Synthesis of 1-(1-benzylpiperidin-4-yl)-3-(3-chloro-4-methylphenyl)urea (Compound No. B59)

466

Synthesis of N-Benzyl-1-(pentan-2-yl)piperidin-4-amine

Prepared as described above from 2-chloro-4-isocyanato-1-methylbenzene and 1-benzylpiperidine. $^1$H NMR (400 MHz, DMSO-d$_6$) δ 8.44 (s, 1H), 7.63 (d, J=2.1 Hz, 1H), 7.34-7.24 (m, 5H), 7.16 (d, J=8.3 Hz, 1H), 7.06 (dd, J=8.3, 2.2 Hz, 1H), 6.15 (d, J=7.5 Hz, 1H), 3.45 (s, 3H), 2.69 (bs, 2H), 2.22 (s, 3H), 2.06 (bs, 2H), 1.87-1.71 (m, 1H), 1.38 (q, J=11.2 Hz, 2H). $^{13}$C NMR (101 MHz, DMSO) δ 154.1, 139.7, 138.6, 133.0, 131.0, 128.8, 128.2, 127.2, 126.9, 117.4, 116.2, 62.2, 51.7, 46.2, 32.1, 18.7. m/z (APCI-pos) M+1=358.4. HRMS (ESI+) m/z calcd for C$_{20}$H$_{25}$N$_3$O [M+H]$^+$ 358.1686, found 358.1681.

d. Preparation of Compound Nos. A15, A21, A30, A34, A37, A43, A58, A65, A68, A76, A77, A79, A85, A88, A90, A92, A93, A96, A97, A102, A106, A117, A130, A146, A147, A149, A150, A167, A170, A171, A180, A184, A248, A264, A289, A293, A294, AND A298

Synthesis of 1-(pentan-2-yl)piperidin-4-one

To a stirred solution of 4-Piperidone hydrochloride (7.50 g, 55.3 mmol, 1 equiv) in CH$_3$CN (100 mL) and K$_2$CO$_3$ (38.2 g, 277 mmol, 5 equiv) and 2-bromopentane (8.20 mL, 66.4 mmol, 1.2 equiv) were added sequentially. The mixture was stirred at 80° C. overnight (ca. 16 hr), cooled to room temperature, filtered, diluted with EtOAc, washed with brine, dried (MgSO$_4$), filtered, and concentrated under reduced pressure. The crude mixture was purified by chromatography on SiO$_2$ (MeOH/CH$_2$Cl$_2$, 2% to 12%) to give 3.5 g (37%) of the desired product as a pale yellow oil.

To a stirred solution of 1-(pentan-2-yl)piperidin-4-one (2.00 g, 11.8 mmol, 1 equiv) and benzylamine (1.29 ml, 11.8 mmol, 1.2 equiv) in CH$_2$Cl$_2$ (50 mL) was added acetic acid (0.812 mL, 14.2 mmol, 1.2 equiv). The resulting cloudy mixture was stirred at room temperature for 1 hr and sodium triacetoxyborohydride (3.51 g, 16.5 mmol, 1.4 equiv) was added portion-wise over 10 min. The resulting heterogeneous mixture was stirred at room temperature overnight (ca. 16 hr), quenched with a saturated aqueous solution of NaHCO$_3$, extracted with EtOAc (×2), dried (MgSO$_4$), filtered, and concentrated under reduced pressure to give 3.10 g (101% yield) of the desired product as a yellow oil. The crude reaction mixture was directly carried onto the next reaction without further purification.

Synthesis of 1-Benzyl-1-(1-(pentan-2-yl)piperidin-4-yl)-3-(3-(trifluoromethyl)phenyl)urea (Compound No. A15)

To a stirred solution of crude N-benzyl-1-(pentan-2-yl)piperidin-4-amine (3.00 g, 11.5 mmol, 1.1 equiv) in CH$_2$Cl$_2$ (50 mL) was added 3-(trifluoromethyl)phenyl isocyanate (1.44 mL, 10.5 mmol, 1 equiv) and DIPEA (2.74 mL, 15.7 mmol, 1.5 equiv). The resulting mixture was stirred at room temperature overnight (ca. 16 hr) and concentrated under reduced pressure. The crude product was purified by chromatography on SiO$_2$ (MeOH/CH$_2$Cl$_2$, 2:100 to 12:100) to give 4.2 g (90% yield) of the desired product as a white solid.

Synthesis of 1-propyl-1-(1-propylpiperidin-4-yl)-3-(3-(trifluoromethyl)phenyl)urea (Compound No. A167)

Prepared as described above from 3-(trifluoromethyl) phenyl isocyanate and N,1-dipropylpiperidin-4-amine. $^1$H NMR (400 MHz, Chloroform-d) δ 7.68 (s, 1H), 7.48 (t, J=7.6 Hz, 1H), 7.30 (q, J=8.2 Hz, 1H), 7.24-7.14 (m, 1H), 6.57 (s, 1H), 4.25 (s, 1H), 3.20-3.09 (m, 4H), 2.59-2.39 (m, 2H), 2.39-2.16 (m, 2H), 2.16-1.92 (m, 2H), 1.71 (bs, 2H), 1.64-1.54 (m, 4H), 0.95-0.82 (m, 6H). $^{13}$C NMR (101 MHz, Chloroform-d) δ 154.7, 139.7, 131.60, 131.3 (q, J=32.3 Hz, 1C), 129.2, 124.0 (q, J=273.7 Hz, 1C), 123.0, 119.5 (q, J=4.0 Hz, 1C), 116.6 (q, J=4.0 Hz, 1C), 59.7, 52.8, 51.5, 44.4, 28.6, 24.0, 19.0, 11.6, 11.4. m/z (APCI-pos) M+1=372.4. HRMS (ESI+) m/z calcd for $C_{19}H_{29}F_3N_3O$ [M+H]$^+$ 372.2262, found 372.2265.

Synthesis of 1-butyl-1-(1-propylpiperidin-4-yl)-3-(3-(trifluoromethyl)phenyl)urea (Compound No. A96)

Prepared as described above from 3-(trifluoromethyl) phenyl isocyanate and N-butyl-1-propylpiperidin-4-amine. $^1$H NMR (500 MHz, Chloroform-d) δ 7.69 (s, 1H), 7.51 (s, 1H), 7.33 (s, 1H), 7.22 (s, 1H), 6.69-6.50 (m, 1H), 4.32 (bs, 1H), 3.17 (bs, 2H), 2.97 (s, 2H), 2.26 (bs, 2H), 1.96 (bs, 2H), 1.84-1.63 (m, 5H), 1.63-1.52 (m, 2H), 1.50-1.45 (m, 2H), 1.40-1.16 (m, 2H), 0.95 (s, 3H), 0.87 (2, 3H). $^{13}$C NMR (126 MHz, CDCl$_3$) δ 154.6, 139.8, 131.0 (q, J=32.3 Hz, 1C), 129.1, 123.0 (q, J=273.4 Hz, 1C), 122.9, 119.2 (q, J=4.0 Hz, 1 C), 116.5 (q, J=4.0 Hz, 1C), 60.6, 53.2, 53.0, 42.4, 32.8, 30.3, 20.3, 20.2, 13.8, 11.9. m/z (APCI-pos) M+1=386.4. HRMS (ESI+) m/z calcd for $C_{20}H_{31}F_3N_3O$ [M+H]$^+$ 386.2419, found 386.2417.

Synthesis of 1-Isobutyl-1-(1-propylpiperidin-4-yl)-3-(3-(trifluoromethyl)phenyl)urea (Compound No. A146)

Prepared as described above from 3-(trifluoromethyl) phenyl isocyanate and N-isobutyl-1-propylpiperidin-4-amine. $^1$H NMR (400 MHz, Chloroform-d) δ 7.65 (s, 1H), 7.48-7.44 (m, 1H), 7.32-7.25 (m, 1H), 7.21-7.16 (m, 1H), 6.66 (d, J=4.3 Hz, 1H), 4.09-4.00 (m, 1H), 3.03-2.97 (m, 4H), 2.38-2.24 (m, 2H), 2.08 (t, J=11.3 Hz, 2H), 1.93-1.80 (m, 3H), 1.72-1.67 (m, 2H), 1.52-1.45 (m, 2H), 0.91-0.88 (m, 6H), 0.86-0.81 (m, 3H). $^{13}$C NMR (101 MHz, CDCl$_3$) δ 155.4, 139.7, 131.0 (q, J=32.3 Hz, 1C), 129.1, 123.9 (q, J=273.7 Hz, 1C), 122.9, 119.3 (q, J=4.0 Hz, 1C), 116.4 (q, J=4.0 Hz, 1C), 60.1, 53.7, 53.1, 50.4, 28.7, 29.0, 20.4, 19.7, 11.8. m/z (APCI-pos) M+1=386.4. HRMS (ESI+) m/z calcd for $C_{20}H_{31}F_3N_3O$ [M+H]$^+$ 386.2419, found 386.2411.

Synthesis of 1-Isopentyl-1-(1-propylpiperidin-4-yl)-3-(3-(trifluoromethyl)phenyl)urea (Compound No. A130)

Prepared as described above from 3-(trifluoromethyl) phenyl isocyanate and N-isopentyl-1-propylpiperidin-4-amine. $^1$H NMR (500 MHz, Chloroform-d) δ 7.67 (s, 1H), 7.46 (d, J=8.2 Hz, 1H), 7.27 (t, J=8.2 Hz, 1H), 7.17 (d, J=7.8 Hz, 1H), 6.83 (s, 1H), 4.06 (t, J=10.8 Hz, 1H), 3.16 (t, J=7.8 Hz, 2H), 2.92 (d, J=11.6 Hz, 2H), 2.21 (t, J=7.8 Hz, 2H), 1.90 (t, J=11.6 Hz, 2H), 1.77-1.50 (m, 5H), 1.45 (p, J=7.6 Hz, 4H), 0.89 (d, J=6.8 Hz, 6H), 0.84 (t, J=7.4 Hz, 3H). $^{13}$C NMR (126 MHz, CDCl$_3$) δ 155.5, 139.8, 130.7 (q, J=32.7 Hz, 1C), 128.8, 123.8 (q, J=273.4 Hz, 1C), 120.6, 118.9 (q, J=4.0 Hz, 1C), 116.5 (q, J=4.0 Hz, 1C), 60.4, 53.0, 40.8, 39.3, 30.3, 26.5, 22.3, 20.1, 11.8. m/z (APCI-pos) M+1=400.5. HRMS (ESI+) m/z calcd for $C_{21}H_{33}F_3N_3O$ [M+H]$^+$, 400.2575 found 400.2576.

Synthesis of 1-(2-Methoxyethyl)-1-(1-propylpiperi-din-4-yl)-3-(3-(trifluoromethyl)phenyl)urea (Compound No. A248)

Prepared as described above from 3-(trifluoromethyl) phenyl isocyanate and N-(2-methoxyethyl)-1-propylpiperi-din-4-amine. $^1$H NMR (500 MHz, Chloroform-d) δ 8.78 (s, 1H), 7.68 (s, 1H), 7.37 (d, J=8.2 Hz, 1H), 7.27 (t, J=7.9 Hz, 1H), 7.13 (d, J=7.7 Hz, 1H), 4.18 (t, J=11.5 Hz, 1H), 3.52 (s, 2H), 3.48-3.32 (m, 5H), 2.95 (d, J=11.1 Hz, 2H), 2.34-2.16 (m, 2H), 2.01 (t, J=11.7 Hz, 2H), 1.70 (d, J=11.1 Hz, 2H), 1.63 (q, J=11.6 Hz, 2 hr), 1.45 (sext, J=7.4 Hz, 2H), 0.84 (t, J=7.4 Hz, 3H). $^{13}$C NMR (126 MHz, CDCl$_3$) δ 156.6, 140.7, 130.7 (q, J=31.5 Hz, 1C), 128.9, 123.9 (q, J=272.2 Hz, 1C), 121.6, 118.1 (q, J=3.8 Hz, 1C), 115.2 (q, J=3.8 Hz, 1C), 75.1, 60.3, 59.1, 52.9, 52.5, 43.1, 29.6, 20.0, 11.7. m/z (APCI-pos) M+1=384.4. HRMS (ESI+) m/z calcd for C$_{19}$H$_{29}$F$_3$N$_3$O$_2$[M+H]$^+$, 388.2211 found 388.2209.

Synthesis of 1-(Cyclohexylmethyl)-1-(1-propylpip-eridin-4-yl)-3-(3-(trifluoromethyl)phenyl)urea (Compound No. A92)

Prepared as described above from 3-(trifluoromethyl) phenyl isocyanate and N-(cyclohexylmethyl)-1-propylpip-eridin-4-amine. $^1$H NMR (500 MHz, Chloroform-d) δ 7.48 (s, 1H), 7.30 (d, J=8.2 Hz, 1H), 7.10 (t, J=7.9 Hz, 1H), 7.00 (d, J=7.7 Hz, 1H), 6.66 (s, 1H), 3.86-3.76 (m, 1H), 2.85 (d, J=7.5 Hz, 2H), 2.75 (d, J=11.6 Hz, 2H), 2.04 (dd, J=9.5, 6.3 Hz, 2H), 1.74 (t, J=11.2 Hz, 2H), 1.66-1.32 (m, 11H), 1.26 (sext, J=7.4 Hz, 2H), 1.07-0.83 (m, 3H), 0.73-0.65 (m, 5H). $^{13}$C NMR (126 MHz, CDCl$_3$) δ 155.4, 139.8, 130.8 (q, J=32.7 Hz, 1C), 128.9, 123.9 (q, J=273.4 Hz, 1C), 122.9, 119.0 (q, J=3.8 Hz, 1C), 116.4 (q, J=3.8 Hz, 1C), 60.4, 54.2, 53.1, 49.1, 38.5, 31.2, 30.4, 26.2, 25.9, 20.1, 11.8. m/z (APCI-pos) M+1=426.4 HRMS (ESI+) m/z calcd for C$_{23}$H$_{34}$F$_3$N$_3$O [M+H]$^+$ 426.2732, found 426.2729.

Synthesis of 1-(furan-2-ylmethyl)-1-(1-propylpiperi-din-4-yl)-3-(3-(trifluoromethyl)phenyl)urea (Compound No. A77)

Prepared as described above from 3-(trifluoromethyl) phenyl isocyanate and N-(furan-2-ylmethyl)-1-propylpiperi-din-4-amine. $^1$H NMR (400 MHz, Chloroform-d) δ 7.68 (s, 1H), 7.51-7.44 (m, 1H), 7.30 (q, J=8.2 Hz, 1H), 7.24-7.14 (m, 1H), 6.57 (s, 1H), 4.25 (s, 1H), 3.23-3.05 (m, 4H), 2.59-2.39 (m, 2H), 2.39-2.16 (m, 2H), 2.16-1.92 (m, 2H), 1.71 (bs, 2H), 1.63-1.50 (m, 5H), 0.95-0.80 (m, 6H). $^{13}$C NMR (101 MHz, CDCl$_3$) δ 155.5, 151.6, 142.6, 139.9, 131.2 (q, J=32.3 Hz, 1C), 129.2, 124.0 (q, J=273.7 Hz, 1C), 122.7, 119.4 (q, J=3.8 Hz, 1C), 116.4 (q, J=3.8 Hz, 1C), 110.9, 108.2, 60.4, 53.1, 52.7, 39.5, 29.6, 20.0, 11.9. m/z (APCI-pos) M+1=410.4 HRMS (ESI+) m/z calcd for C$_{21}$H$_{27}$F$_3$N$_3$O$_2$[M+H]$^+$ 410.2055, found 410.2052.

Synthesis of 1-benzyl-1-(1-propylpiperidin-4-yl)-3-(3-(trifluoromethyl)phenyl)urea (Compound No. A85)

Prepared as described above from 3-(trifluoromethyl) phenyl isocyanate and N-benzyl-1-propylpiperidin-4-amine. H NMR (500 MHz, DMSO-d$_6$) δ 10.03 (bs, 1H), 8.79 (s, 1H), 7.93 (s, 1H), 7.76 (dd, J=8.2, 2.0 Hz, 1H), 7.46 (t, J=8.0 Hz, 1H), 7.33 (t, J=7.5 Hz, 2H), 7.27 (d, J=7.5 Hz, 3H), 7.22 (t, J=7.2 Hz, 1H), 4.62 (s, 2H), 4.26 (s, 1H), 3.33 (s, 2H), 3.17 (s, 2H), 2.49 (bs, 2H), 1.89 (s, 2H), 1.66 (s, 2H), 1.52 (s, 2H), 0.85 (t, J=7.4 Hz, 3H). $^{13}$C NMR (126 MHz, DMSO) δ 155.1, 141.3, 139.9, 129.4, 129.0 (q, J=31.5 Hz, 1C), 128.3, 126.6, 126.3, 124.3 (q, J=273.4 Hz, 1C), 123.5, 118.1 (q, J=3.8 Hz, 1C), 116.0 (q, J=3.8 Hz, 1C), 58.5, 51.9, 45.1, 28.2, 18.7, 11.4. m/z (APCI-pos) M+1=420.5 HRMS (ESI+) m/z calcd for C$_{23}$H$_{29}$F$_3$N$_3$O [M+H]$^+$ 420.2262, found 420.2259.

Synthesis of 1-(1-propylpiperidin-4-yl)-1-(pyridin-3-ylmethyl)-3-(3-(trifluoromethyl)phenyl)urea (Compound No. A117)

Synthesis of 1-(benzo[d][1,3]dioxol-5-ylmethyl)-1-(1-propylpiperidin-4-yl)-3-(3-(trifluoromethyl)phenyl)urea (Compound No. A93)

Prepared as described above from 3-(trifluoromethyl)phenyl isocyanate and 1-propyl-N-(pyridin-3-ylmethyl)piperidin-4-amine. $^1$H NMR (500 MHz, Chloroform-d) δ 8.16 (s, 2H), 7.26 (s, 2H), 7.04 (d, J=8.2 Hz, 1H), 6.99-6.81 (m, 3H), 6.57 (s, 1H), 4.21 (s, 2H), 3.91-3.85 (m, 1H), 2.64 (d, J=11.4 Hz, 2H), 1.95 (t, J=10.0 Hz, 2H), 1.70 (t, J=11.6 Hz, 2H), 1.50-1.25 (m, 4H), 1.13 (sext, J=7.5 Hz, 2H), 0.52 (t, J=7.4 Hz, 3H). $^{13}$C NMR (126 MHz, CDCl$_3$) δ 155.3, 148.8, 147.9, 139.4, 134.1, 133.9, 130.9 (q, J=32.7 Hz, 1C), 129.1, 123.8 (q, J=273.4 Hz, 1C), 123.7, 123.3, 119.6 (q, J=3.8 Hz, 1C), 116.9 (q, J=3.8 Hz, 1C), 60.2, 53.5, 52.8, 43.6, 29.9, 19.9, 11.8. HRMS (ESI+) m/z calcd for C$_{22}$H$_{28}$F$_3$N$_4$O [M+H]$^+$ 421.2215, found 421.2214.

Prepared as described above from 3-(trifluoromethyl)phenyl isocyanate and N-(benzo[d][1,3]dioxol-5-ylmethyl)-1-propylpiperidin-4-amine. $^1$H NMR (400 MHz, Chloroform-d) δ 7.53 (s, 1H), 7.27-7.10 (m, 3H), 6.78-6.68 (m, 3H), 6.44 (s, 1H), 5.91 (s, 2H), 4.34 (s, 3H), 2.97 (d, J=15.0 Hz, 2H), 2.34-2.20 (m, 2H), 2.12-1.97 (m, 2H), 1.80-1.66 (m, 4H), 1.44 (sext, J=10.0 Hz, 2H), 0.82 (t, J=7.3 Hz, 3H). $^{13}$C NMR (101 MHz, CDCl$_3$) δ 155.5, 148.7, 147.4, 139.6, 131.2, 131.0 (q, J=31.5 Hz, 1C), 120.1, 123.9 (q, J=273.7 Hz, 1C), 122.6, 121.1, 119.4 (q, J=3.8 Hz, 1C), 119.1, 116.3 (q, J=3.8 Hz, 1C), 108.7, 106.6, 101.3, 60.4, 53.0, 52.5, 45.9, 29.8, 20.0, 11.8. m/z (APCI-pos) M+1=464.4 HRMS (ESI+) m/z calcd for C$_{24}$H$_{29}$F$_3$N$_3$O$_3$[M+H]$^+$, 464.2161 found 464.2159.

Synthesis of 1-(1-propylpiperidin-4-yl)-1-(pyridin-4-ylmethyl)-3-(3-(trifluoromethyl)phenyl)urea (Compound No. A147)

Synthesis of 1-(3-fluoro-5-(trifluoromethyl)benzyl)-1-(1-propylpiperidin-4-yl)-3-(3-(trifluoromethyl)phenyl)urea (Compound No. A68)

Prepared as described above from 3-(trifluoromethyl)phenyl isocyanate and 1-propyl-N-(pyridin-4-ylmethyl)piperidin-4-amine. $^1$H NMR (500 MHz, Chloroform-d) δ 8.39 (d, J=5.3 Hz, 2H), 7.53 (s, 1H), 7.31 (s, 2H), 7.19 (t, J=7.9 Hz, 1H), 7.15 (d, J=8.0 Hz, 1H), 7.07 (d, J=4.8 Hz, 2H), 4.45 (s, 2H), 4.15-4.07 (m, 1H), 2.85 (d, J=11.4 Hz, 2H), 2.17 (dd, J=9.3, 6.3 Hz, 2H), 1.87 (q, J=10.3, 8.8 Hz, 2H), 1.58 (s, 4H), 1.37 (sext, J=7.7 Hz, 2H), 0.79 (t, J=7.5 Hz, 3H). $^{13}$C NMR (126 MHz, CDCl$_3$) δ 155.3, 149.7, 148.1, 139.3, 130.9 (q, J=31.5 Hz, 1C), 128.9, 123.7 (q, J=273.4 Hz, 1C), 123.6, 121.1, 119.5 (q, J=3.8 Hz, 1C), 117.1 (q, J=3.8 Hz, 1C), 60.1, 53.4, 52.6, 44.7, 29.8, 19.9, 11.6. m/z (APCI-pos) M+1=421.5 HRMS (ESI+) m/z calcd for C$_{22}$H$_{28}$F$_3$N$_4$O [M+H]$^+$ 421.2215, found 421.2215.

Prepared as described above from 3-(trifluoromethyl)phenyl isocyanate and N-(3-fluoro-5-(trifluoromethyl)benzyl)-1-propylpiperidin-4-amine. $^1$H NMR (500 MHz, Chloroform-d) δ 7.58 (s, 1H), 7.39 (d, J=8.1 Hz, 1H), 7.34-7.30 (m, 2H), 7.26 (d, J=7.8 Hz, 1H), 7.22 (d, J=8.1 Hz, 1H), 7.17 (d, J=9.0 Hz, 1H), 6.79 (s, 1H), 4.56 (s, 2H), 4.18-4.04 (m, 1H), 2.94 (d, J=11.6 Hz, 2H), 2.25 (dd, J=9.2, 6.3 Hz, 2H), 1.99-1.90 (m, 2H), 1.69 (dd, J=7.9, 3.7 Hz, 4H), 1.45 (sext, J=7.6 Hz, 2H), 0.88 (t, J=7.4 Hz, 3H). $^{13}$C NMR (126 MHz, CDCl$_3$) δ 162.8 (d, J=250.7 Hz, 1C), 155.3, 142.9 (d, J=7.56 Hz, 1C), 139.1, 133.0 (qd, J=33.4, 8.2 Hz, 1C), 131.0 (q, J=32.3 Hz, 1C), 129.1, 123.8 (q, J=272.2 Hz, 1C), 123.0 (qd, J=273.4, 2.52 Hz, 1C), 119.9 (q, J=3.8 Hz, 1C), 118.6 (p, J=3.5 Hz, 1C), 117.2 (q, J=3.9 Hz, 1C), 116.70 (d, J=22.1 Hz, 1C). 60.4, 54.0, 52.8, 45.3, 30.2, 20.2, 11.8. m/z (APCI-pos) M+1=506.4 HRMS (ESI+) m/z calcd for $C_{24}H_{27}F_7N_3O$ [M+H]$^+$ 506.2042, found 506.2034.

Synthesis of 1-benzyl-1-(piperidin-4-yl)-3-(3-(trifluoromethyl)phenyl)urea (Compound No. A264)

Prepared as described above from 3-(trifluoromethyl)phenyl isocyanate and N-benzylpiperidin-4-amine. $^1$H NMR (500 MHz, Methanol-d$_4$) δ 7.96 (s, 1H), 7.74 (d, J=10.0 Hz, 1H), 7.61 (t, J=8.0 Hz, 1H), 7.58-7.50 (m, 4H), 7.49 (d, J=7.8 Hz, 1H), 7.45 (d, J=6.7 Hz, 1H), 4.88 (s, 2H), 4.58 (tt, J=11.9, 4.1 Hz, 1H), 3.65-3.58 (m, 2H), 3.26 (td, J=13.1, 3.1 Hz, 2H), 2.25 (qd, J=13.1, 4.2 Hz, 2H), 2.19-2.09 (m, 2H). $^{13}$C NMR (126 MHz, MeOD) δ 156.3, 140.2, 138.4, 130.5 (q, J=31.5 Hz, 1C), 129.0, 128.4, 127.0, 126.1, 124.2 (q, J=272.2 Hz, 1C), 124.1, 119.1 (q, J=3.8 Hz, 1C), 117.3 (p, J=3.8 Hz, 1C), 51.7, 46.2, 43.7, 26.8. m/z (APCI-pos) M+1=378.3. HRMS (ESI+) m/z calcd for $C_{20}H_{23}F_3N_3O$ [M+H]$^+$ 378.1793, found 378.1790.

Synthesis of 1-benzyl-1-(1-(pentan-2-yl)piperidin-4-yl)-3-(3-(trifluoromethyl)phenyl)urea (Compound No. A293)

Prepared as described above from 3-(trifluoromethyl)phenyl isocyanate and N-benzyl-1-(pentan-2-yl)piperidin-4-amine.

Smaller scale: $^1$H NMR (500 MHz, Chloroform-d) δ 7.56 (s, 1H), 7.41 (t, J=7.5 Hz, 2H), 7.37-7.32 (m, 3H), 7.28 (dd, J=13.9, 6.1 Hz, 2H), 7.25-7.13 (m, 2H), 6.39 (s, 1H), 4.56 (s, 2H), 4.56-4.40 (m, 1H), 3.01 (bs, 2H), 2.86-2.36 (m, 3H), 2.05-1.80 (m, 3H), 1.62 (s, 1H), 1.49-1.17 (m, 3H), 1.07 (bs, 3H), 0.92 (t, J=6.9 Hz, 3H). $^{13}$C NMR (126 MHz, CDCl$_3$) δ 155.5, 139.5, 137.2, 131.1 (q, J=32.7 Hz, 1C), 129.3, 129.1, 128.1, 126.1, 123.9 (q, J=272.2 Hz, 1C), 122.6, 119.5

(q, J=3.8 Hz, 1C), 116.4 (p, J=3.8 Hz, 1C), 59.8, 52.3, 49.3, 46.6, 46.2, 34.9, 29.7, 20.0, 14.1, 14.0.

From Large Scale: $^1$H NMR (500 MHz, Chloroform-d) δ 7.57 (s, 1H), 7.42-7.36 (m, 2H), 7.34-7.30 (m, 3H), 7.29-7.17 (m, 4H), 6.50 (s, 1H), 4.53 (s, 2H), 4.37 (tt, J=12.1, 4.2 Hz, 1H), 2.84-2.80 (m, 2H), 2.57 (sext, J=7.0 Hz, 1H), 2.42 (td, J=11.6, 2.5 Hz, 1H), 2.27 (td, J=11.6, 2.3 Hz, 1H), 1.83-1.76 (m, 2H), 1.69 (dqd, J=24.1, 12.0, 3.8 Hz, 2H), 1.47 (dq, J=12.5, 5.2 Hz, 1H), 1.41-1.13 (m, 3H), 0.95 (d, J=6.6 Hz, 3H), 0.89 (t, J=7.1 Hz, 3H). $^{13}$C NMR (126 MHz, CDCl$_3$) δ 155.4, 139.6, 137.5, 130.8 (q, J=31.5 Hz, 1C), 129.1, 129.0, 127.1, 126.0, 123.9 (q, J=273.4 Hz, 1C), 122.6, 119.2 (q, J=3.8 Hz, 1C), 116.3 (p, J=3.8 Hz, 1C), 58.8, 53.2, 49.5, 46.1, 46.0, 35.7, 30.6, 30.4, 20.1, 14.1, 14.0. m/z (APCI-pos) M+1=448.2. HRMS (ESI+) m/z calcd for $C_{25}H_{33}F_3N_3O$ [M+H]$^+$, 448.2575 found 448.2575.

Synthesis of 1-benzyl-3-(3-(trifluoromethyl)phenyl)-1-(1-(3,3,3-trifluoropropyl)piperidin-4-yl)urea (Compound No. A76)

Prepared as described above from 3-(trifluoromethyl)phenyl isocyanate and N-benzyl-1-(3,3,3-trifluoropropyl)piperidin-4-amine. $^1$H NMR (500 MHz, Chloroform-d) δ 7.55 (s, 1H), 7.42 (t, J=7.5 Hz, 2H), 7.37-7.31 (m, 3H), 7.31-7.24 (m, 1H), 7.24-7.18 (m, 2H), 6.40 (s, 1H), 4.51 (s, 2H), 4.45 (tt, J=12.2, 4.3 Hz, 1H), 2.94 (ddt, J=11.4, 4.2, 2.0 Hz, 2H), 2.67-2.54 (m, 2H), 2.35-2.21 (m, 2H), 2.16 (td, J=11.9, 2.5 Hz, 2H), 1.86-1.80 (m, 2H), 1.71 (qd, J=12.3, 4.0 Hz, 2H). $^{13}$C NMR (126 MHz, CDCl$_3$) δ 155.5, 139.5, 137.3, 131.1 (q, J=32.8 Hz, 1C), 129.3, 129.1, 128.0, 126.0, 122.7, 126.5 (q, J=277.2 Hz, 1C), 123.8 (q, J=273.4 Hz, 1C), 119.5 (q, J=3.8 Hz, 1C), 116.4 (p, J=3.8 Hz, 1C), 52.9, 52.5, 50.6 (q, J=3.8 Hz, 1C), 46.1, 32.0 (q, J=27.7 Hz, 1C), 29.9. m/z (APCI-pos) M+1=474.3. HRMS (ESI+) m/z calcd for $C_{23}H_{26}F_6N_3O$ [M+H]$^+$, 474.1980 found 474.1978.

Synthesis of 1-benzyl-1-(1-butyrylpiperidin-4-yl)-3-(3-(trifluoromethyl)phenyl)urea (Compound No. A88)

Prepared as described above from 3-(trifluoromethyl) phenyl isocyanate and 1-(4-(benzylamino)piperidin-1-yl) propan-1-one. ¹H NMR (500 MHz, Chloroform-d) δ 7.54 (s, 1H), 7.42 (t, J=7.6 Hz, 2H), 7.38-7.26 (m, 4H), 7.26-7.15 (m, 2H), 6.55 (s, 1H), 4.73 (ddt, J=13.6, 4.6, 2.6 Hz, 1H), 4.66 (tt, J=12.2, 4.1 Hz, 1H), 4.47 (s, 2H), 3.92 (ddt, J=14.1, 4.5, 2.8 Hz, 1H), 3.12 (td, J=12.9, 2.6 Hz, 1H), 2.66-2.51 (m, 1H), 2.27 (td, J=7.4, 3.9 Hz, 2H), 1.96-1.75 (m, 2H), 1.62 (sext, J=10.0 Hx, 2H), 1.53 (qt, J=12.4, 4.5 Hz, 2H), 0.94 (t, J=7.4 Hz, 3H). ¹³C NMR (126 MHz, CDCl₃) δ 171.3, 155.4, 139.4, 137.0, 131.0 (q, J=32.7 Hz, 1C), 129.3, 129.1, 128.1, 126.0, 123.8 (q, J=272.2 Hz, 1C), 122.8, 119.5 (q, J=3.8 Hz, 1C), 116.4 (p, J=3.8 Hz, 1C), 52.8, 46.2, 45.0, 41.1, 35.2, 30.7, 29.8, 18.7, 13.9. m/z (APCI-pos) M+1=448.2. HRMS (ESI+) m/z calcd for $C_{24}H_{29}F_3N_3O_2[M+H]^+$ 448.2212, found 448.2205.

Synthesis of 1-Benzyl-1-(1-(propylsulfonyl)piperidin-4-yl)-3-(3-(trifluoromethyl)phenyl)urea (Compound No. A79)

JTH-NB3-34

Prepared as described above from 3-(trifluoromethyl) phenyl isocyanate and. ¹H NMR (500 MHz, Chloroform-d) δ 7.56 (s, 1H), 7.42 (t, J=7.5 Hz, 2H), 7.32 (td, J=17.7, 16.3, 7.8 Hz, 4H), 7.24-7.19 (m, 3H), 6.51 (s, 1H), 4.56 (tt, J=12.3, 4.2 Hz, 1H), 4.49 (s, 2H), 3.96-3.77 (m, 2H), 2.93-2.75 (m, 4H), 1.90-1.84 (m, 2H), 1.81 (q, J=7.6 Hz, 2H), 1.73 (qd, J=12.3, 4.3 Hz, 3H), 1.04 (t, J=7.5 Hz, 3H). ¹³C NMR (126 MHz, CDCl₃) δ 155.4, 139.3, 136.8, 131.0 (q, J=32.8 Hz, 1C), 129.3, 129.1, 128.1, 125.9, 123.8 (q, J=272.2 Hz, 1C), 122.8, 119.6 (q, J=3.8 Hz, 1C), 116.5 (p, J=3.8 Hz, 1C), 52.1, 51.4, 46.3, 45.5, 30.0, 16.8, 13.0. m/z (APCI-pos) M+1=484.4. HRMS (ESI+) m/z calcd for $C_{23}H_{29}F_3N_3O_3S$ $[M+H]^+$ 484.1881, found 484.1880.

Synthesis of 1-Benzyl-1-(1-(butylsulfonyl)piperidin-4-yl)-3-(3-(trifluoromethyl)phenyl)urea (Compound No. A97)

Prepared as described above from 3-(trifluoromethyl) phenyl isocyanate and N-benzyl-1-(butylsulfonyl)piperidin-4-amine. ¹H NMR (500 MHz, Chloroform-d) δ 7.57 (s, 1H), 7.42 (t, J=7.4 Hz, 2H), 7.32 (td, J=17.4, 16.1, 8.1 Hz, 5H), 7.22 (d, J=7.9 Hz, 2H), 6.52 (s, 1H), 4.65-4.51 (m, 1H), 4.49 (s, 2H), 3.86 (dd, J=12.5, 3.5 Hz, 2H), 2.97-2.74 (m, 4H), 1.87 (dd, J=12.8, 3.5 Hz, 2H), 1.82-1.63 (m, 4H), 1.44 (sext, J=7.4 Hz, 2H), 0.94 (td, J=7.4, 1.9 Hz, 3H). ¹³C NMR (126 MHz, CDCl₃) δ 155.4, 139.3, 136.9, 131.0 (q, J=32.8 Hz, 1C), 129.3, 129.1, 128.1, 125.9, 123.8 (q, J=272.2 Hz, 1C), 122.8, 119.6 (q, J=3.8 Hz, 1C), 116.5 (p, J=3.8 Hz, 1C), 52.1, 49.5, 46.1, 45.6, 30.0, 25.0, 21.6, 13.5. m/z (APCI-pos) M+1=498.4. HRMS (ESI+) m/z calcd for $C_{24}H_{31}F_3N_3O_3S$ $[M+H]^+$ 498.2038, found 498.2036.

Synthesis of 1-Benzyl-1-(1-butylpiperidin-4-yl)-3-(3-(trifluoromethyl)phenyl)urea (Compound No. A37)

Prepared as described above from 3-(trifluoromethyl) phenyl isocyanate and N-benzyl-1-butylpiperidin-4-amine. H NMR (500 MHz, Chloroform-d) δ 7.60 (s, 1H), 7.37 (dd, J=8.5, 6.5 Hz, 2H), 7.34-7.26 (m, 3H), 7.25-7.21 (m, 2H), 7.20-7.17 (m, 1H), 6.67 (s, 1H), 4.51 (s, 2H), 4.38 (tt, J=10.6, 5.0 Hz, 1H), 2.96 (dt, J=12.4, 2.8 Hz, 2H), 2.35-2.21 (m, 2H), 1.99 (td, J=11.4, 3.4 Hz, 2H), 1.80-1.63 (m, 4H), 1.43 (ddd, J=15.4, 8.9, 6.1 Hz, 2H), 1.30 (sext, J=7.3 Hz, 2H), 0.90 (t, J=7.3 Hz, 3H). ¹³C NMR (126 MHz, CDCl₃) δ 155.4, 139.5, 137.5, 130.8 (q, J=31.5 Hz, 1C), 128.9, 128.8, 127.6, 125.9, 123.8 (q, J=272.2 Hz, 1C), 122.7, 119.1 (q, J=3.8 Hz, 1C), 116.4 (p, J=3.8 Hz, 1C), 58.1, 52.9, 52.8, 45.8, 29.9, 29.1, 20.6, 13.8. m/z (APCI-pos) M+1=434.4. HRMS (ESI+) m/z calcd for $C_{24}H_{31}F_3N_3O$ $[M+H]^+$ 434.2419, found 434.2418.

Synthesis of 1-benzyl-1-(1-pentylpiperidin-4-yl)-3-(3-(trifluoromethyl)phenyl)urea (Compound No. A43)

Prepared as described above from 3-(trifluoromethyl) phenyl isocyanate and N-benzyl-1-pentylpiperidin-4-amine. H NMR (500 MHz, Chloroform-d) δ 7.58 (s, 1H), 7.40 (dd, J=8.6, 6.6 Hz, 2H), 7.35-7.30 (m, 3H), 7.28 (t, J=7.9 Hz, 1H), 7.25-7.18 (m, 2H), 6.49 (s, 1H), 4.53 (s, 2H), 4.48 (tt, J=10.6, 5.0 Hz, 1H), 3.07 (d, J=11.3 Hz, 2H), 2.47-2.28 (m, 2H), 2.15 (td, J=11.4, 3.6 Hz, 2H), 1.90-1.78 (m, 4H), 1.54-1.46 (m, 2H), 1.38-1.20 (m, 4H), 0.89 (t, J=7.1 Hz, 3H). $^{13}$C NMR (126 MHz, CDCl$_3$) δ 155.5, 139.5, 137.3, 131.0 (q, J=32.8 Hz, 1C), 129.2, 129.0, 127.9, 126.0, 123.8 (q, J=273.4 Hz, 1C), 122.7, 119.4 (q, J=3.8 Hz, 1C), 116.4 (p, J=3.8 Hz, 1C), 58.3, 52.8, 52.4, 46.0, 29.6, 29.4, 26.2, 22.4, 13.9. m/z (APCI-pos) M+1=448.4. HRMS (ESI+) m/z calcd for C$_{25}$H$_{33}$F$_3$N$_3$O [M+H]$^+$ 448.2575, found 448.2572.

Synthesis of 1-Benzyl-1-(1-hexylpiperidin-4-yl)-3-(3-(trifluoromethyl)phenyl)urea (Compound No. A289)

Prepared as described above from 3-(trifluoromethyl) phenyl isocyanate and N-benzyl-1-hexylpiperidin-4-amine. $^1$H NMR (500 MHz, Chloroform-d) δ 7.57 (s, 1H), 7.40 (dd, J=8.5, 6.6 Hz, 2H), 7.35-7.30 (m, 3H), 7.28 (dd, J=9.0, 6.8 Hz, 1H), 7.23-7.19 (m, 2H), 6.46 (s, 1H), 4.53 (s, 2H), 4.50-4.40 (m, 1H), 3.04 (d, J=11.1 Hz, 2H), 2.47-2.31 (m, 2H), 2.21-2.07 (m, 2H), 1.85-7.78 (m, 4H), 1.48 (td, J=11.4, 9.5, 5.8 Hz, 2H), 1.35-1.20 (m, 8H), 0.93-0.84 (m, 4H). $^{13}$C NMR (126 MHz, CDCl$_3$) δ 155.5, 139.5, 137.4, 131.0 (q, J=32.8 Hz, 1C), 129.2, 129.0, 126.0, 123.9 (q, J=273.4 Hz, 1C), 122.7, 119.4 (q, J=3.8 Hz, 1C), 116.4 (p, J=3.8 Hz, 1C), 58.5, 53.0, 52.5, 46.0, 31.6, 29.6, 27.2, 26.7, 22.5, 14.0. m/z (APCI-pos) M+1=462.5 HRMS (ESI+) m/z calcd for C$_{26}$H$_{35}$F$_3$N$_3$O [M+H]$^+$ 462.2732, found 462.2730.

Synthesis of 1-Benzyl-1-(1-isopentylpiperidin-4-yl)-3-(3-(trifluoromethyl)phenyl)urea (Compound No. A90)

Prepared as described above from 3-(trifluoromethyl) phenyl isocyanate and N-benzyl-1-isopentylpiperidin-4- amine. H NMR (400 MHz, Chloroform-d) δ 7.55 (s, 1H), 7.43-7.37 (m, 2H), 7.36-7.28 (m, 3H), 7.28-7.24 (m, 1H), 7.23-7.16 (m, 2H), 6.41 (s, 1H), 4.52 (s, 2H), 4.51-4.40 (m, 1H), 3.05 (d, J=11.5 Hz, 2H), 2.49-2.26 (m, 2H), 2.20-2.07 (m, 2H), 1.82 (bs, 4H), 1.55 (sept, J=6.6 Hz, 1H), 1.46-1.29 (m, 2H), 0.88 (d, J=6.6, 6H). $^{13}$C NMR (101 MHz, CDCl$_3$) δ 155.5, 139.5, 137.3, 131.1 (q, J=32.3 Hz, 1C), 129.3, 129.1, 128.0, 126.1, 123.9 (q, J=273.7 Hz, 1C), 122.6, 119.4 (q, J=3.8 Hz, 1C), 116.4 (p, J=3.8 Hz, 1C), 56.7, 53.1, 52.5, 46.1, 35.7, 29.7, 26.7, 22.6. m/z (APCI-pos) M+1=448.36. HRMS (ESI+) m/z calcd for C$_{25}$H$_{33}$F$_3$N$_3$O [M+H]$^+$ 448.2576, found 448.2571.

Synthesis of 1-Benzyl-1-(1-(cyclopropylmethyl) piperidin-4-yl)-3-(3-(trifluoromethyl)phenyl)urea (Compound No. A30)

Prepared as described above from 3-(trifluoromethyl) phenyl isocyanate and N-benzyl-1-(cyclopropylmethyl)piperidin-4-amine. $^1$H NMR (400 MHz, Chloroform-d) δ 7.59 (s, 1H), 7.43-7.35 (m, 2H), 7.34-7.18 (m, 6H), 6.54 (s, 1H), 4.54 (s, 2H), 4.5-4.35 (m, 1H), 3.19 (d, J=9.4 Hz, 2H), 2.34-2.27 (m, 2H), 2.18 (t, J=9.4 Hz, 2H), 1.94-1.76 (m, 4H), 0.90-0.85 (m, 1H), 0.58-0.48 (m, 2H), 0.16-0.08 (m, 2H). $^{13}$C NMR (101 MHz, CDCl$_3$) δ 155.4, 139.5, 137.4, 131.0 (q, J=32.3 Hz, 1C), 129.2, 129.0, 127.8, 126.0, 123.8 (q, J=273.7 Hz, 1C), 122.7, 119.3 (q, J=3.8 Hz, 1C), 116.4 (p, J=3.8 Hz, 1C), 63.2, 52.8, 52.4, 46.0, 29.5, 8.0, 4.0. m/z (APCI-pos) M+1=432.4. HRMS (ESI+) m/z calcd for C$_{24}$H$_{29}$F$_3$N$_3$O [M+H]$^+$ 432.2262, found 432.2261.

Synthesis of 1-(1-Acryloylpiperidin-4-yl)-1-benzyl-3-(3-(trifluoromethyl)phenyl)urea (Compound No. A65)

Prepared as described above from 3-(trifluoromethyl) phenyl isocyanate and 1-(4-(benzylamino)piperidin-1-yl) prop-2-en-1-one. $^1$H NMR (500 MHz, Chloroform-d) δ 7.53 (s, 1H), 7.43 (t, J=7.5 Hz, 2H), 7 (m, 5H), 7.25-7.19 (m, 2H), 6.56 (dd, J=16.8, 10.6 Hz, 1H), 6.43 (s, 1H), 6.26 (dd, J=16.8, 1.9 Hz, 1H), 5.68 (dd, J=10.6, 1.9 Hz, 1H), 4.86-4.58 (m, 2H), 4.47 (s, 2H), 4.08 (d, J=13.7 Hz, 1H), 3.19 (t, J=13.0 Hz, 1H), 2.71 (t, J=12.7 Hz, 1H), 1.92 (t, J=15.6 Hz, 3H), 1.73-1.45 (m, 3H). $^{13}$C NMR (126 MHz, CDCl$_3$) δ 165.3, 155.4, 139.3, 136.81, 131.1 (q, J=32.8 Hz, 1C), 129.4, 129.2, 128.2, 128.0, 127.4, 126.0, 123.8 (q, J=273.4 Hz, 1C), 122.7, 119.6 (q, J=3.8 Hz, 1C), 116.4 (p, J=3.8 Hz, 1C), 52.6, 46.3, 45.3, 41.7, 30.8, 29.7. m/z (APCI-pos) M+1=432.4. HRMS (ESI+) m/z calcd for C$_{23}$H$_{25}$F$_3$N$_3$O$_2$ [M+H]$^+$ 432.1878, found 432.1884.

Synthesis of 1-Benzyl-1-(1-neopentylpiperidin-4-yl)-3-(3-(trifluoromethyl)phenyl)urea (Compound No. A102)

Prepared as described above from 3-(trifluoromethyl) phenyl isocyanate and N-benzyl-1-neopentylpiperidin-4-amine. $^1$H NMR (500 MHz, Chloroform-d) δ 7.53 (s, 1H), 7.42 (t, J=7.5 Hz, 2H), 7.38-7.32 (m, 3H), 7.31-7.24 (m, 2H), 7.21 (d, J=7.5 Hz, 2H), 6.33 (s, 1H), 4.53 (s, 2H), 4.45-4.26 (m, 1H), 2.85 (d, J=11.2 Hz, 2H), 2.46-2.29 (m, 2H), 2.05 (s, 2H), 1.74 (s, 4H), 0.84 (s, 9H). $^{13}$C NMR (126 MHz, CDCl$_3$) δ 155.5, 139.6, 137.5, 131.1 (q, J=31.5 Hz, 1C), 129.3, 129.1, 128.0, 126.2, 123.9 (q, J=272.2 Hz, 1C), 122.6, 119.4 (q, J=3.8 Hz, 1C), 116.3 (p, J=3.8 Hz, 1C), 69.6, 55.8, 52.9, 46.3, 33.1, 30.7, 27.7. m/z (APCI-pos) M+1=448.5. HRMS (ESI+) m/z calcd for C$_{25}$H$_{33}$F$_3$N$_3$O [M+H]$^+$ 448.2575, found 448.2571.

Synthesis of 1-Benzyl-1-(1-(3,3-dimethylbutyl)piperidin-4-yl)-3-(3-(trifluoromethyl)phenyl)urea (Compound No. A298)

Prepared as described above from 3-(trifluoromethyl) phenyl isocyanate and N-benzyl-1-(3,3-dimethylbutyl)piperidin-4-amine. $^1$H NMR (500 MHz, Chloroform-d) δ 7.57 (s, 1H), 7.40 (t, J=7.5 Hz, 2H), 7.36-7.30 (m, 3H), 7.30-7.25 (m, 1H), 7.21 (t, J=6.8 Hz, 2H), 6.48 (s, 1H), 4.52 (s, 2H), 4.49-4.40 (m, 1H), 3.03 (d, J=10.0 Hz, 2H), 2.40-2.29 (m, 2H), 2.08 (td, J=11.6, 2.9 Hz, 2H), 1.87-1.67 (m, 4H), 1.45-1.35 (m, 2H), 0.90 (s, 9H). $^{13}$C NMR (126 MHz, CDCl$_3$) δ 155.5, 139.5, 137.4, 131.0 (q, J=32.8 Hz, 1C), 129.2, 129.0, 127.9, 126.0, 123.8 (q, J=273.4 Hz, 1C), 122.7, 119.3 (q, J=3.8 Hz, 1C), 116.4 (p, J=3.8 Hz, 1C), 54.4, 53.2, 52.7, 46.0, 40.5, 29.9, 29.7, 29.4. m/z (APCI-pos) M+1=462.5. HRMS (ESI+) m/z calcd for C$_{26}$H$_{35}$F$_3$N$_3$O [M+H]$^+$ 462.2732, found 462.2731.

Synthesis of 1-Benzyl-1-(1-(cyclopentylmethyl) piperidin-4-yl)-3-(3-(trifluoromethyl)phenyl)urea (Compound No. A150)

Prepared as described above from 3-(trifluoromethyl) phenyl isocyanate and N-benzyl-1-(cyclopentylmethyl)piperidin-4-amine. $^1$H NMR (500 MHz, Chloroform-d) δ 7.60 (s, 1H), 7.43-7.36 (m, 2H), 7.34-7.29 (m, 3H), 7.28 (t, J=7.9 Hz, 1H), 7.24-7.19 (m, 2H), 6.61 (s, 1H), 4.61-4.42 (m, 3H), 3.47 (d, J=6.9 Hz, 1H), 3.22 (d, J=15.0 Hz, 2H), 2.52 (d, J=7.1 Hz, 2H), 2.34 (td, J=12.2, 2.7 Hz, 2H), 2.19-1.97 (m, 3H), 1.95 (s, 1H), 1.81 (ddd, J=19.2, 10.0, 5.0 Hz, 4H), 1.76-1.69 (m, 1H), 1.65-1.45 (m, 5H), 1.32-1.06 (m, 4H). $^{13}$C NMR (126 MHz, CDCl$_3$) δ 155.5, 139.5, 137.2, 131.0 (q, J=32.8 Hz, 1C), 129.2, 129.0, 127.9, 126.0, 123.8 (q, J=273.4 Hz, 1C), 122.7, 119.4 (q, J=3.8 Hz, 1C), 116.4 (p, J=3.8 Hz, 1C), 67.1, 63.3, 52.8, 51.7, 46.1, 42.0, 36.5, 31.6, 29.0, 28.4, 25.3, 25.0. m/z (APCI-pos) M+1=460.5. HRMS (ESI+) m/z calcd for C$_{26}$H$_{33}$F$_3$N$_3$O [M+H]$^+$ 460.2575, found 460.2573.

Synthesis of 1-Benzyl-1-(1-(cyclohexylmethyl)piperidin-4-yl)-3-(3-(trifluoromethyl)phenyl)urea (Compound No. A149)

Prepared as described above from 3-(trifluoromethyl) phenyl isocyanate and N-benzyl-1-(cyclohexylmethyl)piperidin-4-amine. $^1$H NMR (400 MHz, Chloroform-d) δ 7.55 (d, 1H), 7.41 (dd, J=8.1, 6.8 Hz, 2H), 7.36-7.31 (m, 3H), 7.29 (d, J=8.0 Hz, 1H), 7.21 (d, J=7.7 Hz, 2H), 6.36 (s, 1H), 4.53 (s, 4H), 4.50-4.38 (m, 1H), 2.97 (d, J=12.7 Hz, 2H), 2.25-2.00 (m, 4H), 1.89-1.58 (m, 10H), 1.54-1.37 (m, 1H), 1.30-1.10 (m, 4H), 0.97-0.73 (m, 3H). $^{13}$C NMR (101 MHz, CDCl$_3$) δ 155.5, 139.6, 137.4, 131.0 (q, J=32.3 Hz, 1C), 129.3, 129.1, 128.0, 126.1, 123.8 (q, J=273.7 Hz, 1C), 122.6, 119.4 (q, J=3.8 Hz, 1C), 116.4 (p, J=3.8 Hz, 1C), 65.3, 53.6, 52.8, 46.2, 35.2, 31.9, 29.8, 26.7, 26.1. m/z (APCI-pos) M+1=474.5. HRMS (ESI+) m/z calcd for C$_{27}$H$_{35}$F$_3$N$_3$O [M+H]$^+$ 474.2732, found 474.2725.

Synthesis of 1-Benzyl-1-(1-(thiazol-2-ylmethyl) piperidin-4-yl)-3-(3-(trifluoromethyl)phenyl)urea (Compound No. A106)

Prepared as described above from 3-(trifluoromethyl) phenyl isocyanate and N-benzyl-1-(thiazol-2-ylmethyl)pip-eridin-4-amine. $^1$H NMR (400 MHz, Chloroform-d) δ 7.68 (bs, 1H), 7.53 (bs, 1H), 7.40 (td, J=7.7, 1.8 Hz, 2H), 7.36-7.30 (m, 3H), 7.26 (s, 2H), 7.23-7.13 (m, 2H), 6.46 (s, 1H), 4.53 (s, 2H), 4.50-4.33 (m, 1H), 3.86 (s, 2H), 3.02 (d, J=11.2 Hz, 2H), 2.33 (q, J=11.2, 8.3 Hz, 2H), 1.81 (dd, J=8.4, 3.6 Hz, 4H). $^{13}$C NMR (101 MHz, CDCl$_3$) δ 155.4, 142.3, 139.5, 137.3, 131.0 (q, J=32.3 Hz, 1C), 129.3, 129.0, 128.0, 126.1, 123.8 (q, J=273.7 Hz, 1C), 122.6, 119.4 (q, J=3.8 Hz, 1C), 116.3 (p, J=3.8 Hz, 1C), 59.2, 53.1, 52.4, 46.1, 29.9. m/z (APCI-pos) M+1=475.3. HRMS (ESI+) m/z calcd for C$_{24}$H$_{26}$F$_3$N$_{40}$S [M+H]$^+$ 475.1779, found 475.1772.

Synthesis of 1-(1-((1H-imidazol-4-yl)methyl)piperi-din-4-yl)-1-benzyl-3-(3-(trifluoromethyl)phenyl)urea (Compound No. A184)

Prepared as described above from 3-(trifluoromethyl) phenyl isocyanate and 1-((1H-imidazol-4-yl)methyl)-N-benzylpiperidin-4-amine. $^1$H NMR (500 MHz, Chloroform-d) δ 7.54 (d, J=13.1 Hz, 2H), 7.40 (t, J=7.4 Hz, 2H), 7.32 (t, J=9.1 Hz, 3H), 7.26 (s, 1H), 7.20 (d, J=7.4 Hz, 2H), 6.90 (s, 1H), 6.41 (s, 1H), 4.50 (s, 2H), 4.42 (td, J=11.8, 5.9 Hz, 1H), 3.52 (s, 2H), 2.98 (d, J=11.3 Hz, 2H), 2.15 (td, J=11.9, 3.0 Hz, 2H), 1.86-1.67 (m, 4H). $^{13}$C NMR (126 MHz, CDCl$_3$) δ 155.5, 139.5, 137.3, 134.9, 131.1 (q, J=32.8 Hz, 1C), 129.3, 129.1, 128.0, 126.1, 123.9 (q, J=272.2 Hz, 1C), 122.7, 119.4 (q, J=3.8 Hz, 1C), 116.3 (p, J=3.8 Hz, 1C), 52.9, 52.8, 46.3, 38.9, 29.9. m/z (APCI-pos) M+1=458.4. HRMS (ESI+) m/z calcd for C$_{24}$H$_{27}$F$_3$N$_5$O [M+H]$^+$ 458.2167, found 458.2161.

Synthesis of 1-(1-((1H-pyrazol-3-yl)methyl)piperi-din-4-yl)-1-benzyl-3-(3-(trifluoromethyl)phenyl)urea (Compound No. A180)

Prepared as described above from 3-(trifluoromethyl) phenyl isocyanate and 1-((1H-pyrazol-3-yl)methyl)-N-ben-zylpiperidin-4-amine. $^1$H NMR (400 MHz, Chloroform-d) δ 7.53 (s, 1H), 7.48 (d, J=2.0 Hz, 1H), 7.40 (ddd, J=7.6, 6.2, 1.3 Hz, 2H), 7.36-7.30 (m, 3H), 7.26 (s, 1H), 7.20 (dt, J=9.0, 1.6 Hz, 2H), 6.39 (s, 1H), 6.20 (s, 1H), 4.53 (s, 2H), 4.50-4.41 (m, 1H), 3.60 (s, 2H), 3.07-2.90 (m, 2H), 2.25-2.10 (m, 3H), 1.88-1.68 (m, 4H). $^{13}$C NMR (101 MHz, CDCl$_3$) δ 155.5, 139.5, 137.3, 131.1 (q, J=32.3 Hz, 1C), 129.3, 129.1, 128.0, 126.1, 123.8 (q, J=273.7 Hz, 1C), 122.7, 119.5 (q, J=3.8 Hz, 1C), 116.4 (p, J=3.8 Hz, 1C), 54.2, 53.0, 52.7, 46.3, 30.9, 29.8 m/z (APCI-pos) M+1=458.4. HRMS (ESI+) m/z calcd for C$_{24}$H$_{27}$F$_3$N$_5$O [M+H]$^+$ 458.2167, found 458.2173.

Synthesis of 1-Benzyl-1-(1-benzylpiperidin-4-yl)-3-(3-(trifluoromethyl)phenyl)urea (Compound No. A294)

Prepared as described above from 3-(trifluoromethyl) phenyl isocyanate and N,1-dibenzylpiperidin-4-amine. $^1$H NMR (400 MHz, Chloroform-d) δ 7.79-7.68 (m, 1H), 7.53 (s, 1H), 7.47-7.37 (m, 2H), 7.37-7.11 (m, 10H), 6.33 (s, 1H), 4.53 (s, 2H), 4.50-4.40 (m, 1H), 3.50 (s, 2H), 3.03-2.84 (m, 2H), 2.23-2.07 (m, 2H), 1.77 (qt, J=11.9, 3.4 Hz, 4H). $^{13}$C NMR (101 MHz, CDCl$_3$) δ 155.5, 139.6, 138.4, 137.4, 131.1 (q, J=31.3 Hz, 1C), 129.5, 129.4, 129.1, 129.1, 128.2, 128.1, 127.05, 126.1, 123.9 (q, J=273.7 Hz, 1C), 122.6, 119.5 (q, J=3.8 Hz, 1C), 116.4 (p, J=3.8 Hz, 1C), 63.0, 53.0, 52.9, 46.2, 30.2. m/z (APCI-pos) M+1=468.4. HRMS (ESI+) m/z calcd for $C_{27}H_{29}F_3N_3O$ [M+H]$^+$ 468.2262, found 468.2259.

Synthesis of 1-(1-Benzylpiperidin-4-yl)-1-(pyridin-3-ylmethyl)-3-(3-(trifluoromethyl)phenyl)urea (Compound No. A170)

Prepared as described above from 3-(trifluoromethyl) phenyl isocyanate and N-benzyl-1-(pyridin-3-ylmethyl)piperidin-4-amine. $^1$H NMR (400 MHz, Chloroform-d) δ 8.54-8.40 (m, 2H), 7.63 (d, J=10.0 Hz, 1H), 7.58 (s, 1H), 7.44-7.35 (m, 2H), 7.33-7.27 (m, 3H), 7.26-7.17 (m, 4H), 6.63 (s, 1H), 4.52 (s, 2H), 4.44 (tt, J=10.7, 4.9 Hz, 1H), 3.48 (s, 2H), 2.90 (d, J=11.1 Hz, 2H), 2.12 (td, J=11.1, 10.6, 2.8 Hz, 2H), 1.80-1.66 (m, 4H). $^{13}$C NMR (101 MHz, CDCl$_3$) δ 155.4, 150.2, 148.5, 139.6, 137.4, 136.5, 133.6, 130.9 (q, J=32.3 Hz, 1C), 129.1, 128.9, 127.8, 126.0, 123.8 (q, J=273.7 Hz, 1C), 123.2, 122.7, 119.3 (q, J=3.8 Hz, 1C), 116.4 (p, J=3.8 Hz, 1C), 59.9, 52.8, 52.7, 46.0, 29.9. m/z (APCI-pos) M+1=469.41. HRMS (ESI+) m/z calcd for $C_{26}H_{28}F_3N_4O$ [M+H]$^+$ 469.2215, found 469.2215.

Synthesis of 1-Benzyl-1-(1-(4-fluorobenzyl)piperidin-4-yl)-3-(3-(trifluoromethyl)phenyl)urea (Compound No. A171)

Prepared as described above from 3-(trifluoromethyl) phenyl isocyanate and N-benzyl-1-(4-fluorobenzyl)piperidin-4-amine. $^1$H NMR (400 MHz, Chloroform-d) δ 7.59 (s, 1H), 7.47-7.39 (m, 2H), 7.39-7.32 (m, 3H), 7.32-7.21 (m, 6H), 7.04-6.97 (m, 2H), 6.45 (s, 1H), 4.55 (s, 2H), 4.47 (tt, J=11.9, 4.5 Hz, 1H), 3.47 (s, 2H), 3.00-2.89 (m, 2H), 2.19-2.07 (m, 2H), 1.88-1.67 (m, 4H). $^{13}$C NMR (101 MHz, CDCl$_3$) δ 161.9 (d, J=246.4 Hz, 1C), 155.4, 139.6, 137.4, 134.1, 131.0 (q, J=32.3 Hz, 1C), 130.5, 130.4, 129.2, 129.0, 127.9, 126.0, 123.9 (q, J=273.7 Hz, 1C), 122.6, 119.3 (q, J=3.8 Hz, 1C), 116.4 (p, J=3.8 Hz, 1C), 115.0, 114.8, 62.0, 52.9, 52.5, 46.1, 30.1. m/z (APCI-pos) M+1=486.3 HRMS (ESI+) m/z calcd for $C_{27}H_{28}F_4N_3O$ [M+H]$^+$ 486.2168, found 468.2171.

Synthesis of 1-(1-Benzylpiperidin-4-yl)-1-(3-chloro-5-ethoxy-4-hydroxybenzyl)-3-(3-(trifluoromethyl)phenyl)urea (Compound No. A34)

Prepared as described above from 3-(trifluoromethyl) phenyl isocyanate and 4-((4-(benzylamino)piperidin-1-yl) methyl)-2-chloro-6-ethoxyphenol. $^1$H NMR (400 MHz, Chloroform-d) δ 7.53 (s, 1H), 7.46-7.37 (m, 2H), 7.37-7.31 (m, 3H), 7.30-7.25 (m, 1H), 7.24-7.14 (m, 2H), 6.87 (d, J=1.8 Hz, 1H), 6.75 (bs, 1H), 6.34 (s, 1H), 4.52 (s, 2H), 4.49-4.39 (m, 1H), 4.11 (q, J=7.0 Hz, 2H), 3.39 (bs, 2H), 2.94 (d, J=10.7 Hz, 2H), 2.14 (d, J=17.1 Hz, 2H), 1.85-1.65 (m, 4H), 1.43 (t, J=6.9 Hz, 3H). $^{13}$C NMR (101 MHz, CDCl$_3$) δ 155.5, 146.6, 139.5, 137.3, 131.1 (q, J=32.3 Hz, 1C), 129.4, 129.1, 128.1, 126.1, 123.9 (q, J=273.7 Hz, 1C), 122.6, 119.4 (q, J=3.8 Hz, 1C), 119.1, 116.4 (p, J=3.8 Hz, 1C), 111.0, 65.0, 62.3, 52.9, 46.3, 29.9, 14.8. m/z (APCI-pos) M+1=562.4. HRMS (ESI+) m/z calcd for $C_{29}H_{32}ClF_3N_3O_3$ [M+H]$^+$ 562.2084, found 562.2091.

Synthesis of 1-(1-(Benzo[d][1,3]dioxol-5-ylmethyl) piperidin-4-yl)-1-benzyl-3-(3-(trifluoromethyl)phenyl)urea (Compound No. A58)

Prepared as described above from 3-(trifluoromethyl) phenyl isocyanate and 1-(benzo[d][1,3]dioxol-5-ylmethyl)-N-benzylpiperidin-4-amine. $^1$H NMR (500 MHz, Chloroform-d) δ 7.54 (s, 1H), 7.41 (t, J=7.5 Hz, 2H), 7.33 (d, J=7.6 Hz, 3H), 7.30-7.25 (m, 1H), 7.21 (d, J=7.9 Hz, 2H), 6.83 (s, 1H), 6.72 (s, 2H), 6.36 (s, 1H), 5.92 (s, 2H), 4.52 (s, 2H), 4.45 (tt, J=11.1, 4.2 Hz, 1H), 3.40 (s, 2H), 2.93 (d, J=11.3 Hz, 2H), 2.10 (t, J=10.0 Hz, 2H), 1.88-1.57 (m, 4H). $^{13}$C NMR (126 MHz, CDCl$_3$) δ 155.4, 147.6, 146.5, 139.6, 137.4, 132.2, 131.1 (q, J=32.7 Hz, 1C), 129.3, 129.1, 128.0, 126.1, 123.9 (q, J=273.4 Hz, 1C), 122.6, 122.1, 119.4 (q, J=3.8 Hz, 1C), 116.3 (p, J=3.8 Hz, 1C), 109.3, 107.8, 100.8, 62.6, 52.8, 46.2, 30.1. m/z (APCI-pos) M+1=512.4 HRMS (ESI+) m/z calcd for $C_{28}H_{29}F_3N_3O_3$[M+H]$^+$ 512.2161, found 512.2155.

Synthesis of 1-Benzyl-1-(1-((2,3-dihydrobenzo[b][1,4]dioxin-6-yl)methyl)piperidin-4-yl)-3-(3-(trifluoromethyl)phenyl)urea Prepared as described above from 3-(trifluoromethyl) phenyl isocyanate and N-benzyl-1-((2,3-dihydrobenzo[b][1,4]dioxin-6-yl)methyl)piperidin-4-amine. $^{1}$H NMR (400 MHz, Chloroform-d) δ 7.57 (s, 1H), 7.40-7.34 (m, 2H), 7.33-7.24 (m, 4H), 7.21 (d, J=7.7 Hz, 1H), 7.16 (d, J=8.1 Hz, 1H), 6.97-6.92 (m, 2H), 6.84 (d, J=12.0 Hz, 1H), 6.49 (s, 1H), 4.66-4.58 (m, 1H) 4.55 (s, 2H), 4.24 (s, 4H), 3.78 (bs, 2H), 3.48-3.10 (m, 2H), 2.59 (bs, 2H), 2.32 (s, 2H), 2.00-1.75 (m, 2H). $^{13}$C NMR (101 MHz, CDCl$_3$) δ 155.5, 143.6, 139.3, 136.9, 131.1 (q, J=32.3 Hz, 1C), 129.3, 129.1, 128.1, 126.1, 123.9 (q, J=273.7 Hz, 1C), 123.6, 122.7, 119.6 (q, J=3.8 Hz, 1C), 117.7, 116.5 (p, J=3.8 Hz, 1C), 64.3, 64.2, 60.8, 51.9, 50.8, 46.2, 27.5. m/z (APCI-pos) M+1=526.3 HRMS (ESI+) m/z calcd for C$_{29}$H$_{31}$F$_3$N$_3$O$_3$[M+H]$^{+}$ 526.2317, found 526.2312.

Synthesis of 1-(Benzo[d][1,3]dioxol-5-ylmethyl)-1-(1-butylpiperidin-4-yl)-3-(3-(trifluoromethyl)phenyl) urea Prepared as described above from 3-(trifluoromethyl) phenyl isocyanate and N-(benzo[d][1,3]dioxol-5-ylmethyl)-1-butylpiperidin-4-amine. $^{1}$H NMR (400 MHz, Chloroform-d) δ 7.53 (s, 1H), 7.22-7.18 (m, 2H), 7.15-7.10 (m, 1H), 6.77-6.65 (m, 3H), 6.53 (s, 1H), 5.88 (s, 2H), 4.33 (s, 2 hr), 4.33-4.19 (m, 1H), 2.97-2.83 (m, 2H), 2.29-2.16 (m, 2H), 1.95 (td, J=11.7, 3.2 Hz, 2H), 1.74-1.58 (m, 4H), 1.43-1.30 (m, 2H), 1.30-1.02 (m, 2H), 0.82 (t, J=7.3 Hz, 3H). $^{13}$C NMR (101 MHz, CDCl$_3$) δ 155.4, 148.5, 147.2, 139.6, 131.4, 130.9 (q, J=32.3 Hz, 1C), 129.0, 123.8 (q, J=272.7 Hz, 1C), 122.6, 119.2 (q, J=3.8 Hz, 1C), 119.1, 116.3 (p, J=3.8 Hz, 1C), 108.5, 106.5, 101.2, 58.2, 53.0, 52.8, 45.8, 30.0, 29.2, 20.6, 13.9. m/z (APCI-pos) M+1=478.5 HRMS (ESI+) m/z calcd for C$_{25}$H$_{31}$F$_3$N$_3$O$_3$ [M+H]$^{+}$ 478.2317 found 478.2316.

Synthesis of 1-(Benzo[d][1,3]dioxol-5-ylmethyl)-1-(1-(tert-butyl)piperidin-4-yl)-3-(3-(trifluoromethyl) phenyl)urea Prepared as described above from 3-(trifluoromethyl) phenyl isocyanate and N-(benzo[d][1,3]dioxol-5-ylmethyl)-1-(tert-butyl)piperidin-4-amine. $^{1}$H NMR (500 MHz, Chloroform-d) δ 7.64 (s, 1H), 7.33-7.25 (m, 2H), 7.25-7.19 (m, 1H), 6.85-6.75 (m, 3H), 6.62 (s, 1H), 5.97 (s, 2H), 4.45 (s, 2H), 4.39 (t, J=8.3 Hz, 1H), 3.17 (d, J=10.7 Hz, 2H), 2.34-2.22 (m, 2H), 1.91-1.68 (m, 4H), 1.12 (s, 9H). $^{13}$C NMR (126 MHz, CDCl$_3$) δ 155.5, 148.5, 147.2, 139.6, 131.3, 130.9 (q, J=31.5 Hz, 1C), 129.0, 123.9 (q, J=272.2 Hz, 1C), 122.6, 119.3 (q, J=3.8 Hz, 1C), 119.1, 116.3 (p, J=3.8 Hz, 1C), 108.6, 106.5, 101.2, 55.1, 52.7, 45.8, 45.6, 30.2, 25.8. m/z (APCI-pos) M+1=478.3. HRMS (ESI+) m/z calcd for C$_{25}$H$_{31}$F$_3$N$_3$O$_3$[M+H]$^{+}$ 478.2317, found 478.2323.

e. Preparation of Tert-butyl 4-(1-benzyl-3-(3-(trifluoromethyl)phenyl)ureido)piperidine-1-carboxylate

Synthesis of Tert-butyl 4-(Benzylamino)piperidine-1-carboxylate

To a stirred solution of 1-Boc-4-piperidone (0.200 g, 1.00 mmol, 1 equiv) and benzylamine (0.110 mL, 1.00 mmol, 1 equiv) in dry CH$_2$Cl$_2$ (4 mL) was added acetic acid (0.115 mL, 2.01 mmol, 2 equiv). The resulting cloudy mixture was stirred at room temperature for 1 hr and sodium triacetoxyborohydride (0.255 g, 1.21 mmol, 1.2 equiv) was added. The resulting heterogeneous mixture was stirred at room temperature overnight (ca. 16 hr), quenched with a saturated aqueous solution of NaHCO₃, extracted with EtOAc (×2), dried (MgSO₄), filtered, and concentrated under reduced pressure. The crude mixture was purified by chromatography on SiO₂ (MeOH/CH₂Cl₂, 2% to 15%) to give 0.295 g (100% yield) of the desired product as a colorless oil.

Synthesis of Tert-butyl 4-(1-benzyl-3-(3-(trifluoromethyl)phenyl)ureido)piperidine-1-carboxylate To a stirred solution of tert-butyl 4-(benzylamino)piperidine-1-carboxylate (0.280 g, 0.964 mmol, 1 equiv) in CH₂Cl₂ (5 mL) was added DIPEA (0.336 mL, 1.93 mmol, 2 equiv), after stirring for 5 min, 1-isocyanato-3-(trifluoromethyl)benzene (0.146 mL, 1.06 mmol, 1.1 equiv) was added. The reaction mixture was stirred at room temperature overnight (ca. 16 hr), diluted with EtOAc, washed with a saturated aqueous solution of NaHCO₃, brine, dried (MgSO₄), filtered, and concentrated under reduced pressure to give a pale yellow liquid. The crude mixture was purified by chromatography on SiO₂ (MeOH/CH₂Cl₂, 1% to 10%) to give 0.404 g (88% yield) of the desired product as a white solid.

f. Synthesis of 1-Benzyl-1-(piperidin-4-yl)-3-(3-(trifluoromethyl)phenyl)urea (Compound No. A261)

To a stirred solution of tert-butyl 4-(1-benzyl-3-(3-(trifluoromethyl)phenyl)ureido)piperidine-1-carboxylate (0.500 g, 1.05 mmol, 1 equiv) in CH₂Cl₂ (10 mL) at 0° C. was slowly added TFA (0.0481 mL, 6.28 mmol, 6 equiv). The reaction mixture was slowly warmed to room temperature, stirred at room temperature overnight (ca. 16 hr), and concentrated under reduced pressure. The crude mixture was suspended in H₂O (7 mL), neutralized with a 2 M aqueous NaOH solution (3 mL), extracted with CH₂Cl₂ (×3), dried (MgSO₄), filtered, and concentrated under reduced pressure to give 0.400 g (100% crude yield) as a white solid.

g. Synthesis of 1-Benzyl-1-(1-butylpiperidin-4-yl)-3-(3-(trifluoromethyl)phenyl)urea (Compound No. A21)

To a stirred solution of 1-benzyl-1-(piperidin-4-yl)-3-(3-(trifluoromethyl)phenyl)urea (0.100 g, 0.265 mmol, 1 equiv) and butyraldehyde (0.0240 ml, 0.265 mmol, 1 equiv) in dry CH₂Cl₂ (1.5 mL) was added acetic acid (0.0300 mL, 0.530 mmol, 2 equiv). The resulting cloudy mixture was stirred at room temperature for 1 hr and sodium triacetoxyborohydride (0.0840 g, 0.397 mmol, 1.5 equiv) was added. The resulting heterogeneous mixture was stirred at room temperature overnight (ca. 16 hr), quenched with a saturated aqueous solution of NaHCO₃, extracted with EtOAc (×2), dried (MgSO₄), filtered, and concentrated under reduced pressure. The crude mixture was purified by chromatography on SiO₂ (EtOAc/Hex, 1:1 to 1:0 then MeOH/CH₂Cl₂, 2% to 15%) to give 0.0840 g (73% yield) of the desired product as a white solid.

h. Preparation of 2-(1-(3-Methylbenzyl)piperidin-4-yl)benzo[d]thiazole

Synthesis of 2-(Piperidin-4-yl)benzo[d]thiazole

A solution of piperidine-4-carboxylic acid (0.150 g, 1.16 mmol, 1 equiv) in polyphosphoric acid (PPA) (2.0 mL) was heated to 160° C. and stirred until the acid was completely dissolved. To the stirring homogenous mixture was added 2-aminothiphenol (0.124 mL, 1.16 mmol, 1 equiv). The reaction mixture was stirred at 160° C. for 3 h, cooled to room temperature, neutralized with a 2 M aqueous solution of NaOH (20 mL), extracted with EtOAc, dried (MgSO₄), filtered, and concentrated under reduced pressure to give 0.285 g of a greenish solid. The crude mixture was purified by chromatography on SiO₂ (EtOAc/Hex, 1:10 to 2:1 to remove impurities/SM and then 20% MeOH/CH₂Cl₂ to elute the product). The column flush was then concentrated under reduced pressure to give 0.170 g (67%) of the desired product as a white solid.

Synthesis of 2-(1-(3-Methylbenzyl)piperidin-4-yl)benzo[d]thiazole

To a stirred solution of 2-(piperidin-4-yl)benzo[d]thiazole (0.055 g, 0.252 mmol, 1 equiv) and 3-methylbenzaldehyde (0.030 mL, 0.253 mmol, 1 equiv) in $CH_2Cl_2$ (2 mL) was added acetic acid (0.029 mL, 0.504 mmol, 2 equiv). The resulting cloudy mixture was stirred at room temperature for 1 hr and sodium triacetoxyborohydride (0.080 g, 0.378 mmol, 1.5 equiv) was added. The resulting cloudy mixture was stirred at room temperature overnight (ca. 16 hr), quenched with a saturated aqueous $NaHCO_3$ solution, extracted with EtOAc, dried ($MgSO_4$), filtered, and concentrated under reduced pressure to give 0.065 g (80% yield) of the desired product as a white solid.

i. Preparation of 1-(4-Methoxybenzoyl)-n-(3-(trifluoromethyl)phenyl)piperidine-4-carboxamide (Compound No. C1)

Synthesis of Tert-butyl 4-((3-(trifluoromethyl)phenyl)carbamoyl)piperidine-1-carboxylate To a stirred solution of 1-(tert-butoxycarbonyl)piperidine-4-carboxylic acid (0.229 g, 1.00 mmol, 1 equiv) in DMF (4 mL) was added DIPEA (0.523 mL, 3.00 mmol, 3 equiv), HBTU (0.455 g, 1.20 mmol, 1.2 equiv), and 3-(trifluoromethyl)aniline (0.150 mL, 1.20 mmol, 1.2 equiv). The reaction mixture was heated to 50° C. and stirred at this temperature overnight (ca. 16 hr). The following morning the reaction was diluted with EtOAc, washed with 0.1 N HCl, a saturated aqueous solution of $NaHCO_3$, brine, dried ($MgSO_4$), filtered, and concentrated under reduced pressure to give 0.5 g of impure red oil. The crude mixture was purified by chromatography on $SiO_2$ (EtOAc:hexane, 1:10 to 10:1) to give 0.372 g (100% yield) of the desired product as a white solid.

Synthesis of N-(3-(Trifluoromethyl)phenyl)piperidine-4-carboxamide

To a stirred solution of tert-butyl 4-((3-(trifluoromethyl)phenyl)carbamoyl)piperidine-1-carboxylate (0.350 g, 0.940 mmol, 1 equiv) in $CH_2Cl_2$ (4 mL) was added TFA (0.720 mL, 9.40 mmol, 10 equiv). The reaction mixture was stirred at room temperature for 3 h. The reaction mixture was diluted with EtOAc (50 mL), neutralized with a saturated aqueous solution of $NaHCO_3$, washed with brine, dried ($MgSO_4$), filtered, and concentrated under reduced pressure. The crude product was carried onto the next reaction without further characterization or purification.

Synthesis of 1-(4-Methoxybenzoyl)-n-(3-(trifluoromethyl)phenyl)piperidine-4-carboxamide (Compound No. C1)

To a stirred solution of crude N-(3-(trifluoromethyl)phenyl)piperidine-4-carboxamide (0.250 g, 0.918 mmol, 1 equiv) in $CH_2Cl_2$ (4 mL) was added DIPEA (0.240 mL, 1.38 mmol, 1.5 equiv), DMAP (0.022 g, 0.184 mmol, 0.2 equiv), and 4-methoxybenzoyl chloride (0.149 mL, 1.10 mmol, 1.2 equiv). The resulting solution was stirred at room temperature for 2 h, diluted with EtOAc, washed with 1 M aqueous HCl, a saturated aqueous solution of $NaHCO_3$, brine, dried ($MgSO_4$), filtered, and concentrated under reduced pressure. The crude mixture was purified by chromatography on $SiO_2$ (EtOAc/hex 1:10 to 10:1) to give 0.270 g (72% yield) of the desired product as a yellow solid.

j. Preparation of (5-isopropyl-1-(4-(thiophen-2-yl)pyrimidin-2-yl)-1H-pyrazol-4-yl)(4-propylpiperazin-1-yl)methanone (Compound No. E1)

Synthesis of 2-Chloro-4-phenylpyrimidine

To a stirred solution of 2,4-dichloropyrimidine (0.200 g, 1.34 mmol, 1 equiv) in mixture of toluene and DMF (1.8/0.2 ml) was added K$_2$CO$_3$ (0.557 g, 4.03 mmol, 1 equiv), and phenylboronic acid (0.196 g, 1.61 mmol, 1.2 equiv). The reaction mixture was irradiated in the microwave (185° C., 10 min), diluted with EtOAc, washed with brine, dried (MgSO$_4$), filtered, and concentrated under reduced pressure. The crude brown oil was purified by chromatography on SiO$_2$ (EtOAc/hex, 1:10 to 3:7) to give a 0.140 g (55% yield) of the desired product as a white solid.

Synthesis of 2-Chloro-4-(thiophen-2-yl)pyrimidine

To a stirred solution of thiophene (1.96 mL, 24.5 mmol, 2 equiv) in dry Et$_2$O (25 mL) at −40° C. was added drop-wise n-BuLi (1.7 M M in hexanes; 7.77 mL, 13.5 mmol, 1.1 equiv). The reaction mixture was warmed to 0° C., stirred for 15 minutes, and cooled to −40° C. A suspension of 2-chloropyrimidine (1.40 g, 12.2 mmol, 1 equiv) in dry Et$_2$O (30 ml) was added in 5 mL portions over 15 min. The resulting suspension was stirred for 30 min at −40° C., allowed to warm to 0° C., and stirred for 1 hr. The reaction was quenched at 0° C. with H$_2$O (0.33 ml, 1.5 equiv) in THE (3 ml) and a solution of DDQ (3.05 g, 13.5 mmol, 1.1 equiv) in THE (15 ml) was added. The resulting suspension was warmed to room temperature for 15 min, cooled to 0° C., diluted with hexanes (10 ml), and a 3M aqueous solution of NaOH (10 ml) was added. The suspension was stirred for 5 min at 0° C., diluted with H$_2$O, the organic layer was separated, dried (MgSO$_4$), and concentrated under reduced pressure. The crude mixture was purified by chromatography on SiO$_2$ (EtOAc:Hex, 1:10 to 1:1) to give 1.72 g (72% yield) of the desired product as an pale yellow solid.

Synthesis of Methyl (E)-2-((dimethylamino)methylene)-4-methyl-3-oxopentanoate

To a stirred solution of methyl 4-methyl-3-oxopentanoate (1.2 mL, 8.43 mmol, 1 equiv) in 1,2-dioxane (20 mL) was added N,N-Dimethylformamide dimethyl acetal (1.34 mL, 10.1 mmol, 1.2 equiv). The resulting mixture was stirred at 100° C. for 5 hr, cooled to room temperature, and concentrated under reduced pressure. The crude yellow oil was purified by chromatography on SiO$_2$ (EtOAc:Hex 1:10 to 3:1) to give 1.4 g (83% yield) as a yellow oil.

Synthesis of Methyl 5-isopropyl-1-(4-(thiophen-2-yl)pyrimidin-2-yl)-1H-pyrazole-4-carboxylate To a stirred solution of 2-chloro-4-(thiophen-2-yl)pyrimidine (0.700 g, 3.56 mmol, 1 equiv) in dry pyridine (12 mL) was added anhydrous hydrazine (CAUTION; 1.23 mL, 39.2 mmol, 11 equiv). The pale yellow homogenous reaction mixture was stirred at 90° C. for 1.5 h. The crude mixture was concentrated under reduced pressure and the residual solid was suspended in H$_2$O (4 mL), filtered, washed with cold MeOH and dried to give a pale yellow solid. The crude solid was suspended in dry ethanol (16 mL) and methyl (E)-2-((dimethylamino)methylene)-4-methyl-3-oxopentanoate (0.851 g, 4.27 mmol, 1.2 equiv) and acetic acid (0.410 mL, 7.12 mmol, 2 equiv) were added. The resulting mixture was stirred at 80° C. for 3 h, cooled to room temperature, diluted with EtOAc (200 mL), washed with 0.1 M HCl, a saturated aqueous solution of NaHCO$_3$, brine, dried (MgSO$_4$), and concentrated under reduced pressure to give 1.28 g (110% mass yield) of a yellow solid (ca. 90% pure by 1H NMR).

Synthesis of (5-isopropyl-1-(4-(thiophen-2-yl)pyrimidin-2-yl)-1H-pyrazol-4-yl)(4-propylpiperazin-1-yl)methanone (Compound No. E1)

To a stirred solution methyl 5-isopropyl-1-(4-(thiophen-2-yl)pyrimidin-2-yl)-1H-pyrazole-4-carboxylate (0.100 g, 0.305 mmol, 1 equiv) in dioxane (5 mL) was added a solution of lithium hydroxide (0.036 g, 1.52 mmol, 5 equiv) in water (1 mL). The reaction was stirred at room temperature overnight. The following morning TLC analysis revealed the presence of a large quantity of starting material therefore an addition solution of lithium hydroxide (0.109 g, 4.57 mmol, 15 equiv) in water (1.5 mL) was added. The reaction was stirred at room temperature for an additional 24 h, diluted with EtOAc, the desired acid was extracted into the water layer with a saturated aqueous solution of NaHCO$_3$, the organic layer was separated, the pH of the aqueous layer was adjusted to ca. 1 with concentrated HCl, the acidic aqueous layer was extracted with EtOAc, the organic layer was separated, and concentrated under reduced pressure to give the crude acid as a yellow oil.

The crude acid was diluted with DMF (1 mL), and 1-propylpiperazine (0.115 g, 0.396 mmol, 1.3 equiv), DIPEA (0.265 mL, 1.52 mmol, 5 equiv), and HBTU (0.139 g, 0.365 mmol, 1.2 equiv) were added sequentially. The mixture was heated to 50° C. and stirred at this temperature for 4 h. The reaction mixture was diluted with EtOAc, washed with a saturated aqueous solution of NaHCO$_3$, brine, dried (MgSO$_4$), filtered, and concentrated under reduced pressure. The crude residue was purified by chromatography on SiO$_2$ (CH$_2$Cl$_2$, MeOH 10:1 to 5:1) to give 0.043 g (33% yield) of the desired product.

k. Preparation of 3-methyl-N-(3-methyl-6-oxo-1-phenyl-4-(p-tolyl)-4,5,6,7-tetrahydro-1H-pyrazolo[3, 4-b]pyridin-5-yl)benzamide

Synthesis of (3-Methylbenzoyl)glycine

To a stirred solution of glycine (0.971 g, 12.9 mmol, 1 equiv) in a 10% aqueous NaOH solution (12 mL) was added benzoyl chloride (1.70 mL, 12.9 mmol, 1.0 equiv) dropwise. The reaction was stirred at room temperature for 30 min, cooled to 0° C., acidified to pHca. 2, extracted with EtOAc, dried (MgSO$_4$), filtered, and concentrated under reduced pressure to give 2.2 g (88% yield) of the desired product as a white solid.

Synthesis of (Z)-4-(4-Methylbenzylidene)-2-(m-tolyl)oxazol-5(4H)-one

To a mixture of 4-methylbenzaldehyde (0.610 mL, 5.18 mmol, 1 equiv), (3-methylbenzoyl)glycine (1.00 g, 5.18 mmol, 1 equiv), and tosyl chloride (0.987 g, 5.18 mmol, 1 equiv) was added DMF (0.399 mL, 5.18 mmol, 1 equiv).

The reaction mixture was heated using microwave irradiation (2.5 min at 80° C.). The reaction was diluted with an EtOH/H$_2$O (10:7.5 mL) and the suspension was stirred at room temperature for 5 min. The reaction mixture was filtered and the solid washed with H$_2$O to give 0.6 g (42% yield) as an impure white solid.

Synthesis of 3-Methyl-N-(3-methyl-6-oxo-1-phenyl-4-(p-tolyl)-4,5,6,7-tetrahydro-1H-pyrazolo[3,4-b] pyridin-5-yl)benzamide To a stirred solution of crude (Z)-4-(4-methylben-zylidene)-2-(m-tolyl)oxazol-5(4H)-one (0.200 g, 0.721 mmol, 1 equiv) and 3-methyl-1-phenyl-1H-pyrazol-5-amine (0.125 g, 0.721 mmol, 1 equiv) in NMP/acetic acid (2:1; 0.9 mL) was irradiated in the microwave (180° C., 5 min). The mixture was cooled to room temperature, diluted with EtOAc, washed with a saturated aqueous solution of NH$_4$Cl, a saturated aqueous solution of NaHCO$_3$, brine, dried (MgSO$_4$), filtered and concentrated under reduced pressure. The crude mixture was purified by chromatography on SiO$_2$ (EtOAc/hex; 1:10 to 2:1) to give two major fractions consisting of the cis and trans isomers. Each fraction was independently resubjected to chromatography on SiO$_2$ EtOAc/hex; 1:10 to 2:1) to give 15 mg of the cis isomer (5% yield) and 20 mg trans isomer (6% yield) as white solids.

3. Biology Methods a. TR-FRET Assay

Figure 1:
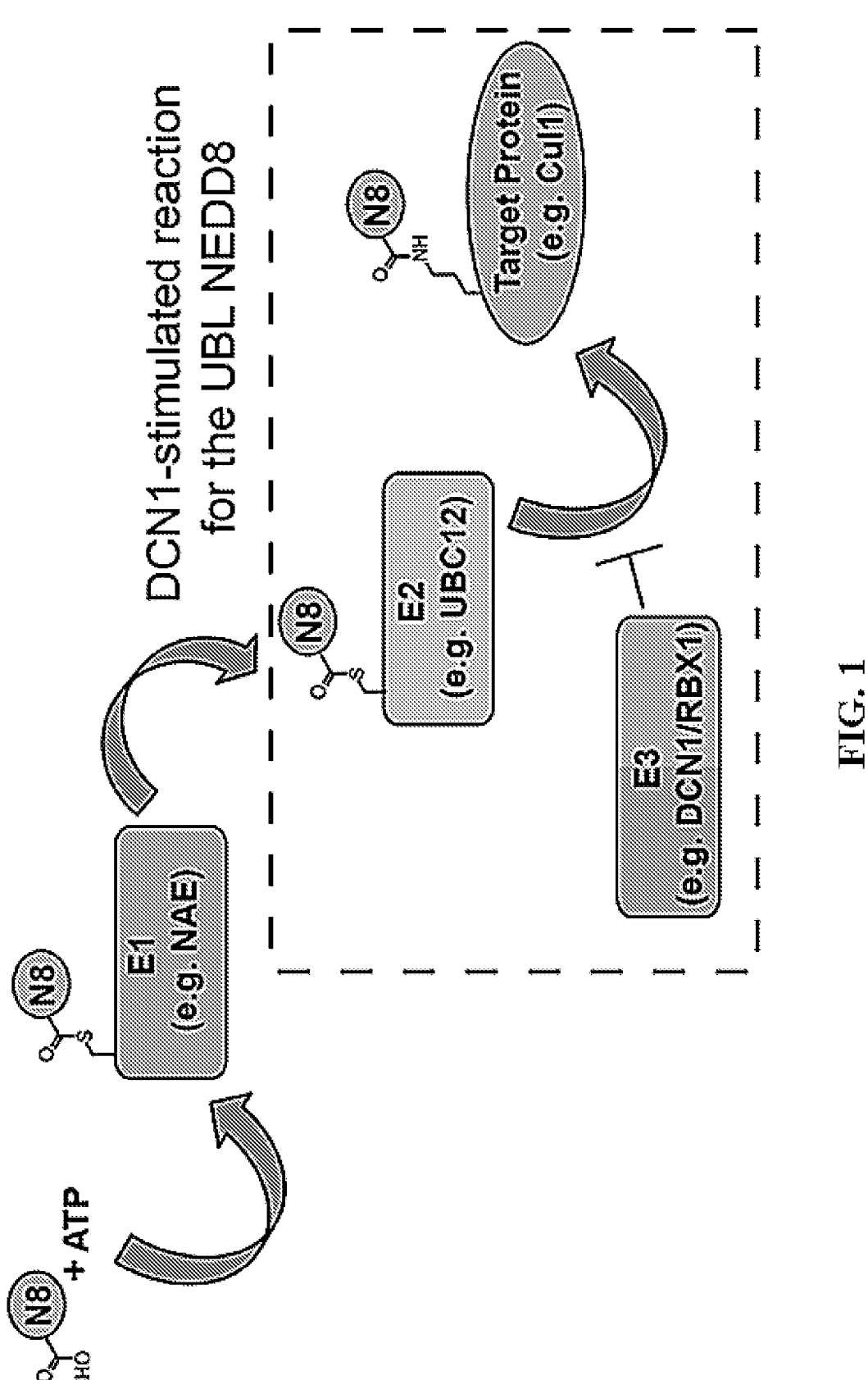
FIG. 1 shows a schematic representation of the general neddylation tri-enzyme cascade.
Figure 2:
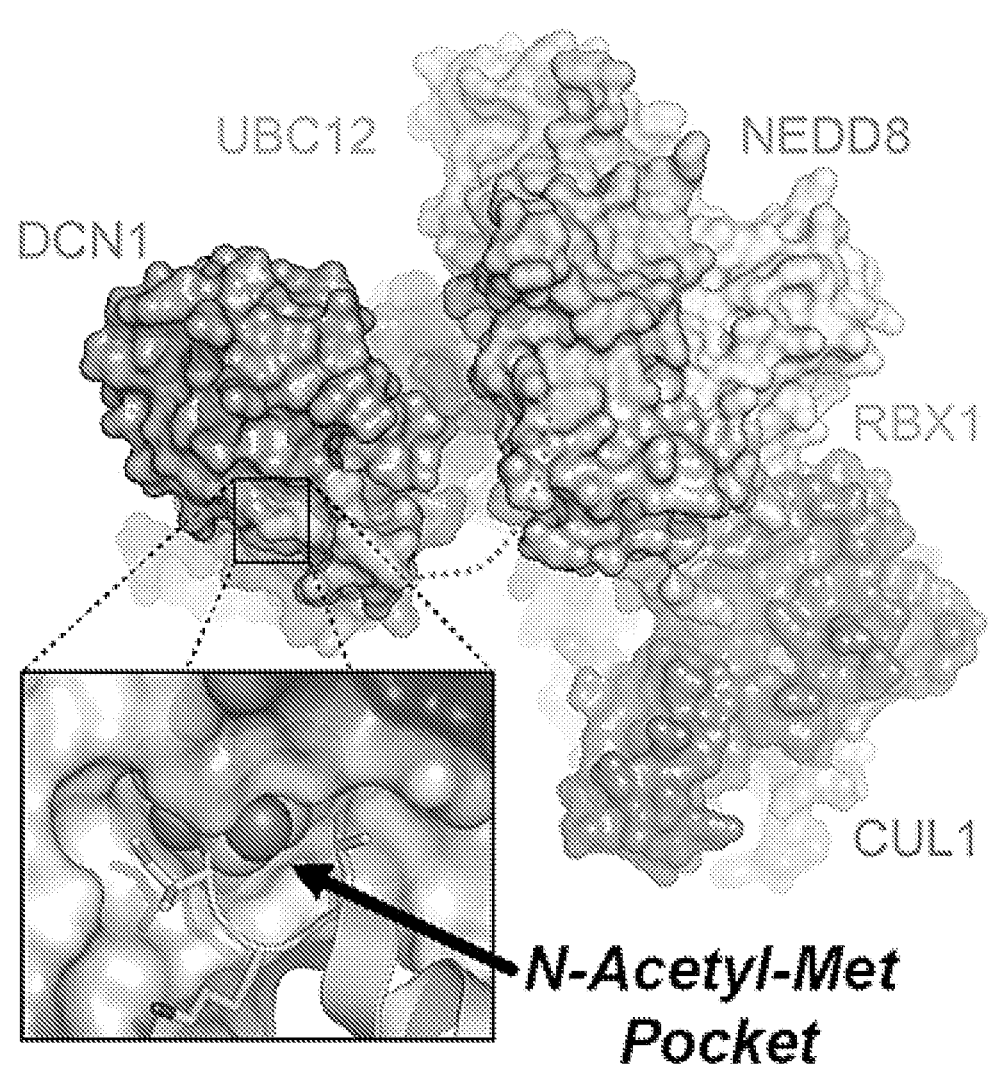
FIG. 2 shows a representative crystal structure of a trapped NEDD8 ligation complex illustrating the recognition of acetyl-UBC12 by DCN1 and its importance for selective NEDD8 modification of cullin-RING ligases.
Figure 3A:
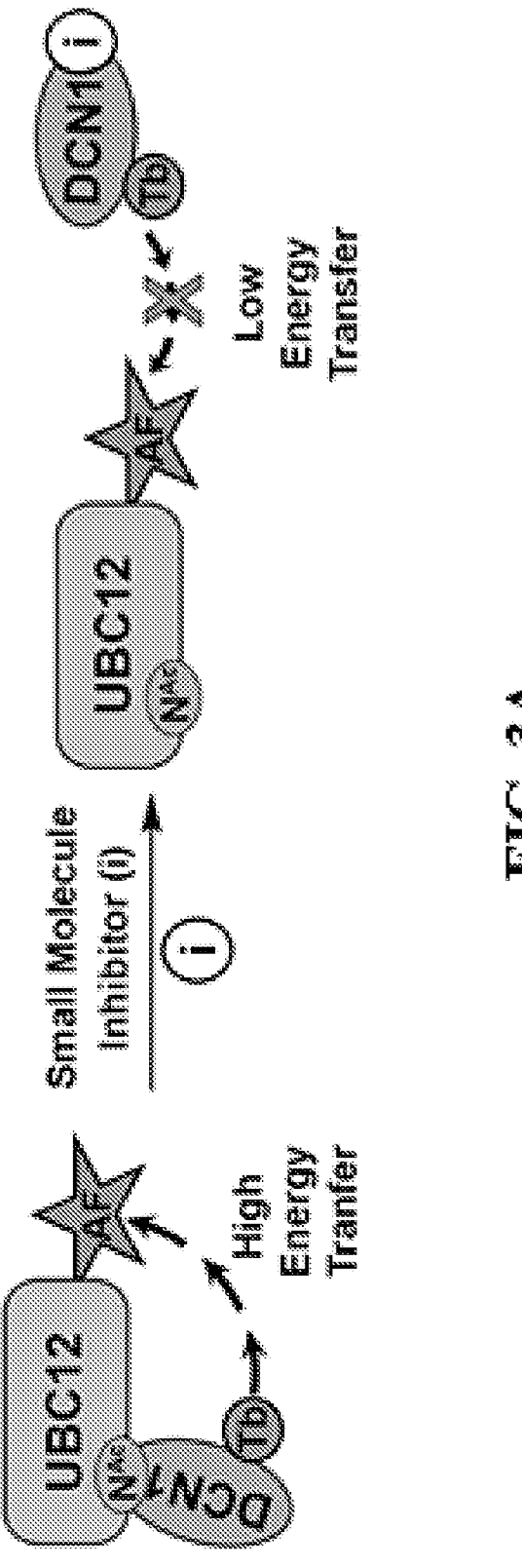
FIG. 3A and FIG. 3B show representative images pertaining to the development of a TR-FRET assay suitable for a high-throughput screen. Specifically.
Figure 3B:
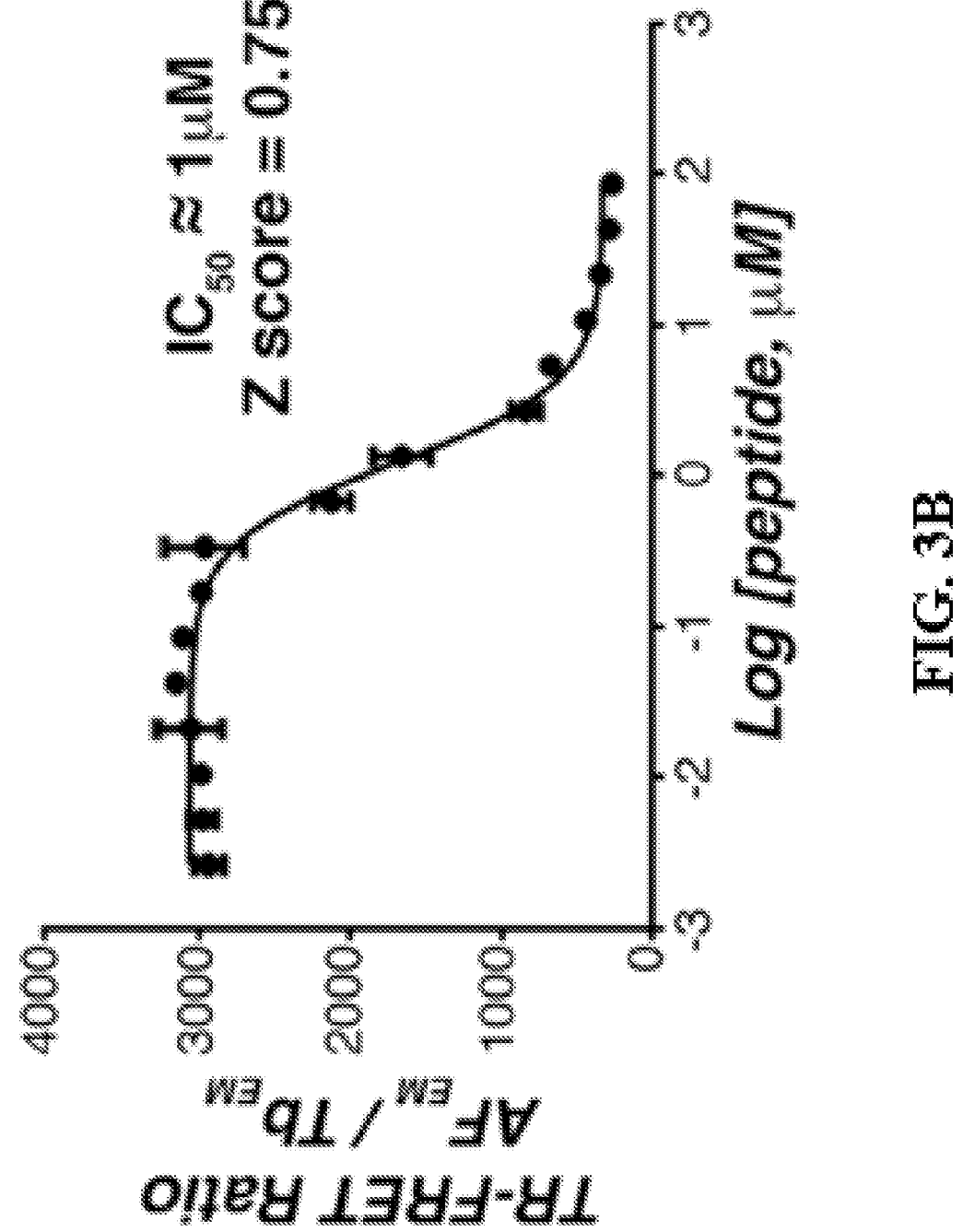

The TR-FRET assay is illustrated in FIG. 3A and FIG. 3B. The TR-FRET assay cocktail was prepared by mixing 50 nM Biotin-DCN1$^P$, 20 nM AlexaFluor488 UBC12 peptide, and 2.5 nM Tb-Streptavidin conjugate (Life Technologies) in 25 mM Hepes, 10 mM NaCl, 0.1% Triton X-100, 0.5 mM DTT, pH 7.5. 20 ul of the cocktail was aliquoted out into black 384-well plates (Corning8849BC) using the WellMate and incubated for about 1 hour. Compounds were introduced to the desired concentration using the Biomek and the samples were incubated at r.t. for 60 min. The TR-FRET signal was read by the Pherastar plate-reader.

IC$_{50}$ data were calculated as previously described (Stewart et al, Cell Rep. 2014 Nov. 6; 9(3):829-41. doi: 10.1016/j.celrep.2014.09.028. Epub 2014 Oct. 23). Briefly, concentration-response data were analyzed using a custom script written in the R language (R Core Team (2013). R: A language and environment for statistical computing. R Foundation for Statistical Computing, Vienna, Austria).

Briefly, compounds were modeled by the four-parameter log-logistic function ("Hill equation"):

$$y = y_0 + (y_{Fin} - y_0) / (1 + (EC_{50} / x)^{-Hill})$$

where y is activity, x=log concentration, $EC_{50}$ is the log concentration at half-maximal observed response, and $y_0$ and $y_{Fin}$ are the responses at zero and infinite concentrations, respectively.

The Hill parameters were estimated using the drm function in the R drc package (Ritz, C. & Streibig, J. C. (2005) Bioassay Analysis using R. J. Statist. Software, Vol 12, Issue 5) with modified arguments specifying parameter constraints and a custom-written function for estimating initial parameter values. To provide a robust estimate of model parameters, an outlier removal approach employing leave-one-out cross-validation was performed. Finally, the confidence intervals for model parameters were determined using a bootstrap approach. The best fit Hill parameters were used to define a base curve. The residuals from the model fit were sampled, with replacement, and added to the base curve at each observed concentration. The resulting dose-response curve was refit using the procedure described above to generate a new set of Hill parameters. This process was repeated 200 times to generate a distribution for each Hill parameter from which 95% confidence intervals could be obtained.

b. Pulse-Chase Assays

Figure 4A:
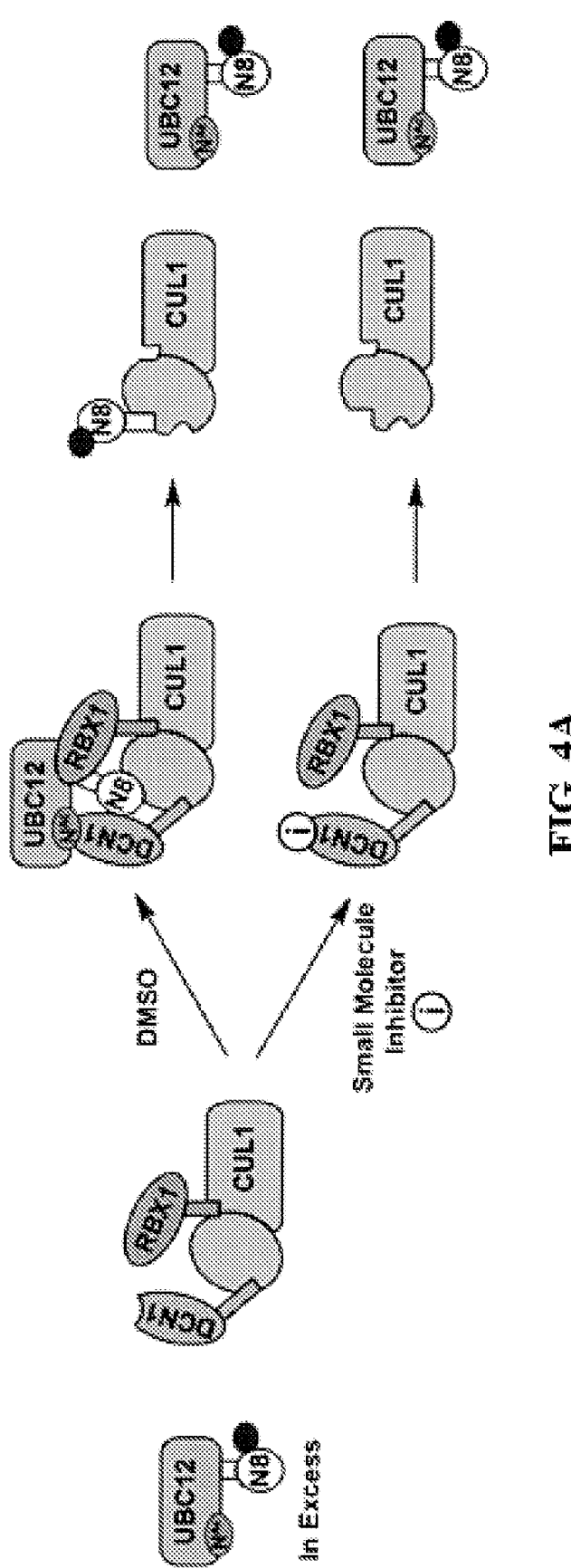
FIG. 4A and FIG. 4B show representative images pertaining to the Pulse-Chase assay monitoring neddylation with labeled NEDD8.
Figure 4B:
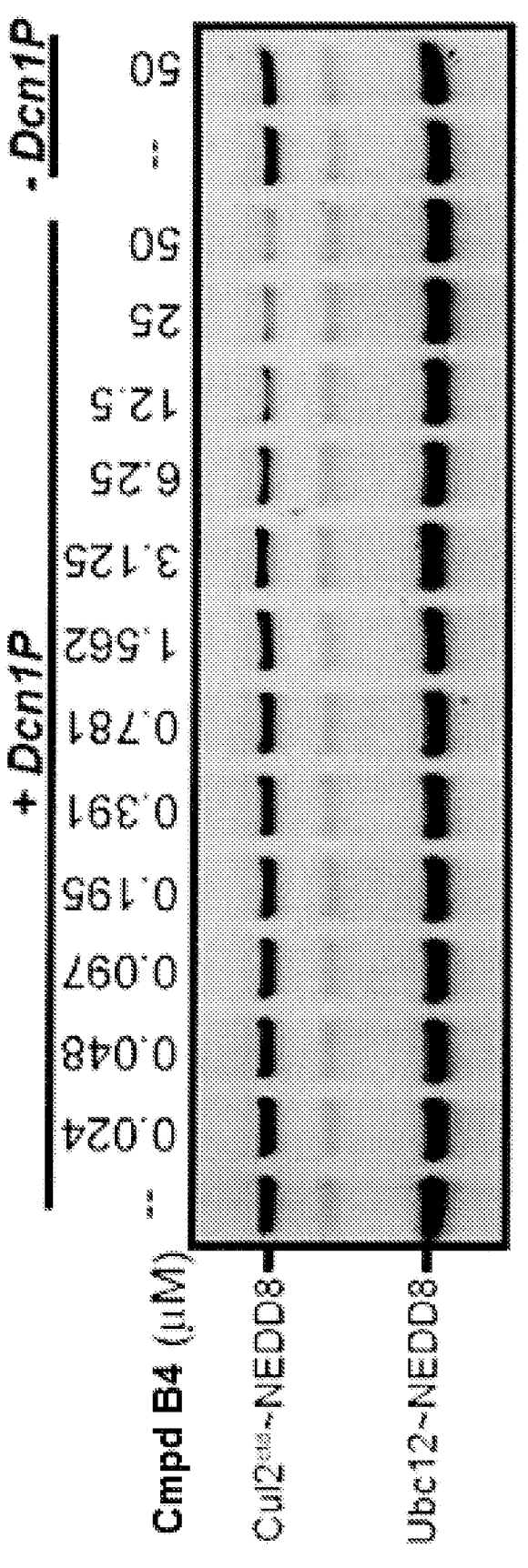
Figure 4C:
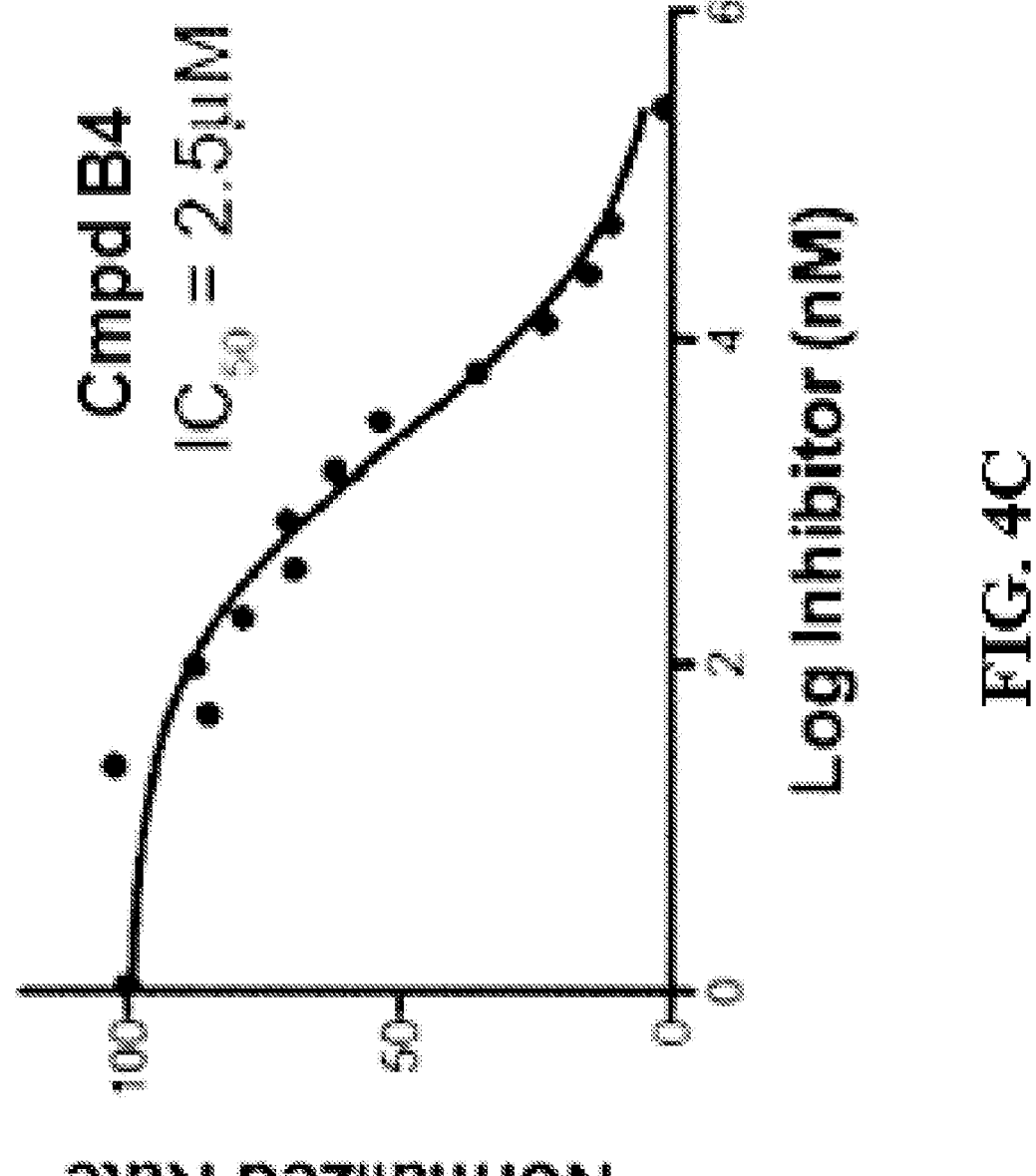
FIG. 4C shows a representative dose-response curve for the pulse-chase assay.

The Pulse-Chase assay and related data are illustrated in FIG. 4A-C. Compound inhibition of Dcn1$^P$-mediated co-E3 activity was monitored using pulse-chase assays to exclusively monitor effects of Nedd8 transfer to Cul2 without sensing earlier steps in the reaction. For the "pulse", 10 μM of Ubc12 was loaded for 15 minutes at room temperature with 0.2 μM APPBP1/UBA3, 15 μM [$^{FAM}$]-Nedd8, in 50 mM Hepes, 100 mM NaCl, 1.25 mM ATP, 2.5 mM MgCl$_2$, pH 7.5. Load reactions were quenched by the addition of EDTA to 50 mM and incubated on ice for 5 minutes. Chase reactions involved dilution of the UBC12~[$^{FAM}$]-Nedd8 thioester conjugate to 40 nM in 50 mM Tris, 50 mM NaCl, 50 mM EDTA, 0.5 mg/mL BSA, pH 6.8. Chase reactions were initiated at 0° C. by the addition of pre-mixed CUL2$^{CTD}$:DCN1$^P$ complexes, with or without the indicated concentrations of small molecule inhibitor, at a final concentration of 125 nM. Aliquots were removed at the indicated times and quenched with 2×SDS-PAGE sample buffer. Reaction products were heated at 70° C. for 1.5 minutes and separated on 4-12% NuPAGE gels (Invitrogen). Fluorescent gels were visualized by scanning on a Typhoon imager (GE).

c. Cell Lysis and Western Blot

Cell pellets harvested from a 6 well dish were resuspended in 30-40 μL of lysis buffer (50 mM Tris, 150 mM NaCl, 0.5% NP-40, 0.1% SDS, 6.5 M Urea, 2 mM 1,10-orthophenanthroline, 1× Halt Protease and Phosphatase inhibitor cocktail (ThermoFisher), 0.25 kU Universal Nuclease (ThermoFisher), pH 7.5). Cell pellet suspensions were incubated on ice for 25 minutes with occasional mixing by pipetting up and down. Lysates were cleared by centrifugation at 13 K rpm for 20 minutes and the supernatant was removed as total cell lysate sample. Protein concentration of the cell lysate was determined by BCA assay (Pierce) using BSA as a control. Cell lysates were diluted into 2×SDS-PAGE sample buffer such that 25 μg of total protein was loaded per well. Samples were heated at 95° C. for 2 minutes, briefly cleared by pulse centrifugation, and separated on 4-12% NuPAGE gels (Invitrogen). Gels were transferred to PVDF membranes (BIO-RAD) at 100V for 90 minutes at 4° C. Membranes were blocked for 1 hour in blocking buffer consisting of 1×TBS, 0.1% Tween-20, and 5% Blotting grade non-fat dry milk (BIO-RAD). Primary antibodies were prepared in blocking buffer and incubated with membranes overnight at 4° C. with rocking. Membranes were extensively washed in 1×TBS, 0.1% Tween-20. Secondary antibodies were prepared in blocking buffer according to the manufactures recommendations and incubated with membranes for 1 hour at room temperature. After extensive washing the membranes were developed with SuperSignal West Pico Chemiluminescent substrate (ThermoFisher) and developed by film exposure (HyBlot CL, Denville scientific).

4. Solubility

Solubility assays were carried out on a Biomek FX lab automation workstation (Beckman Coulter, Inc., Fullerton, CA) using pSOL Evolution software (pION Inc., Woburn, MA). The detailed method is described as following. Compound stock (10 mM in DMSO, 10 μL) was added to 1-propanol (190 μL) to make a reference stock plate. Reference stock solution (5 μL) was mixed with 1-propanol (70 μL) and citrate phosphate buffered saline (75 μL) to make the reference plate which was then measured with UV detection. Test compound stock (10 mM, 6 μL) was added to buffer (594 μL) in a 96-well storage plate and mixed. The storage plate was sealed and incubated at room temperature for 18 hours. The suspension was then filtered through a 96-well filter plate (pION Inc., Woburn, MA). Filtrate (75 μL) was mixed with 1 propanol (75 μL) to make the sample plate, and the UV spectrum (250 nm-500 nm) of the sample plate was read. Calculation was carried out by μSOL Evolution software based on the AUC (area under curve) of UV spectrum of the sample plate and the reference plate. All compounds were tested in triplicate.

5. Permeability

Parallel Artificial Membrane Permeability Assay (PAMPA) was conducted on a Biomek FX lab automation workstation (Beckman Coulter, Inc., Fullerton, CA) using PAMPA evolution 96 command software (pION Inc., Woburn, MA). Test compound stock (10 mM in DMSO, 3 μL) was mixed with citrate phosphate buffered saline (597 μL) to make diluted test compound. Diluted test compound (150 μL) was transferred to a UV plate (pION Inc., Woburn, MA) and the UV spectrum (250 nm-500 nm) was read as the reference plate. Each well of the donor plate in a PAMPA sandwich plate (pION Inc., Woburn, MA) contained a filter that was painted on one side with 4 μL GIT lipid (pION Inc., Woburn, MA) to form a membrane. Each well in the acceptor plate in a PAMPA sandwich, preloaded with magnetic stir bars, was filled with acceptor solution buffer (200 μL, pION Inc., Woburn, MA). The donor plate was filled with diluted test compound (180 μL). The PAMPA sandwich was assembled by placing the donor plate over the acceptor plate. The combined PAMPA plate was placed on a pIon Gut-Box™, a stirring apparatus that allows equilibrium to be reached quicker. Aqueous Boundary Layer of the pIon Gut-Box™ was set to 40 μm and the compounds stirred for 30 minutes. The UV spectrum (250 nm-500 nm) of the donor and the acceptor were read. The permeability coefficient was calculated using PAMPA evolution 96 command software (pION Inc., Woburn, MA) based on the whole spectrum measured from the reference plate, the donor plate, and the acceptor plate. All compounds were tested in triplicates.

6. In Vivo Pharmacokinetic (PK) Methods

The first in vivo experiment was an IV dose ranging in adult female C57BL/6 mice that establishes acute tolerability and rough plasma PK parameters (using a single animal per dose/time point). Clinical signs and symptoms were monitored daily (weight loss, disruption of locomotor coordination, hunching, lack of grooming, lethargy, etc.) and organ function (kidney, liver, blood) and tissue histopathology (major organs) checked after 2 days. Dosage levels were estimated based on in vitro cytotoxicity and efficacy studies previously performed for the new chemical entity (NCE) and comparison to toxicity of structurally and/or pharmacologically similar compounds. Three dosages were selected (i.e., low, mid, and high) from a range of dosages (this generally ranges between 1 and 200 mg/kg). Six mice/dosage group were administered a single IV dosage of compound on day 1. Administration of compound began with the lowest dosage group, and were only escalated if there were no obvious immediate negative consequences (e.g., death, convulsion, ataxia, aberrant behavior, or evident pain observed within 15 minutes of observation). Dosage escalation was continued until serious adverse events were observed or the high dosage was reached (usually a maximum of 200 mg/kg). Once dosing was complete, animals were observed for 2 days. During this period, a single retro-orbital blood sample (100 L) was collected from each mouse in the study (at 5 min, 15 min, 30 min, 1 h, 4 h, 24 h, and 48 h, respectively). Only one sample was collected from each mouse. These samples allow monitoring of clinical chemistries (e.g., renal, liver, and hematopoietic function) and rough drug levels. At 48 hours, all mice were euthanized and a terminal blood sample collected by cardiac puncture. After euthanasia, selected animals were necropsied. Tissue samples from liver, lung, brain, and kidney were collected from selected animals after sacrifice. Endpoints initially assessed included daily clinical observations for the 2 day period, body weights, clinical chemistry, complete blood counts, and gross observations of tissues at necropsy. In select cases detailed pathology, with particular focus on liver and kidney function, were carried out. These studies were used to establish IVIC correlations and a MTD.

7. High-Throughput Screen (HTS)

Figure 5A:
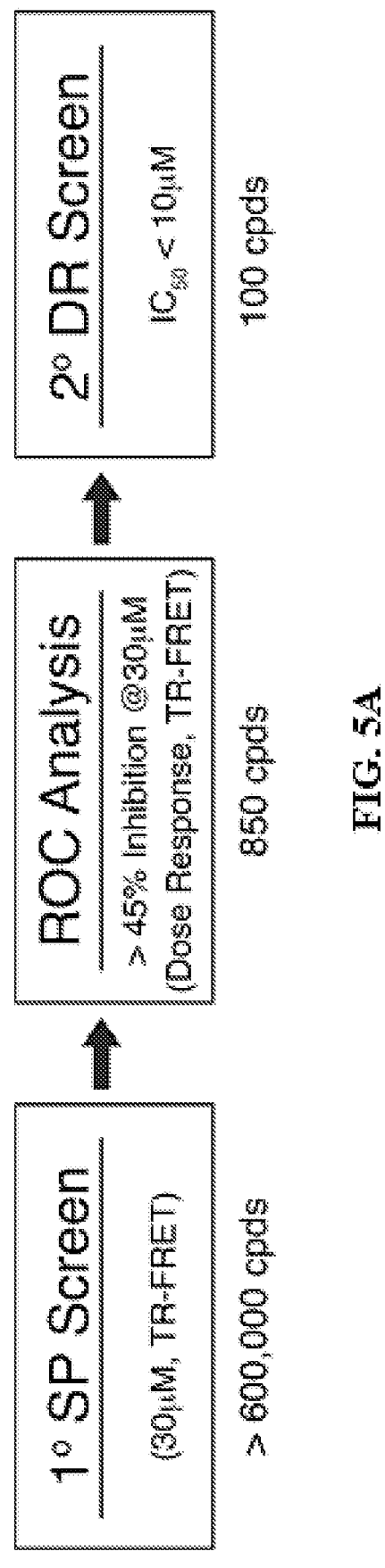
FIG. 5A and FIG. 5B show representative images pertaining to the high-throughput screen. Specifically, a high-throughput screening flowchart (5A) and the raw data of compounds screened (5B) are shown.
Figure 5B:
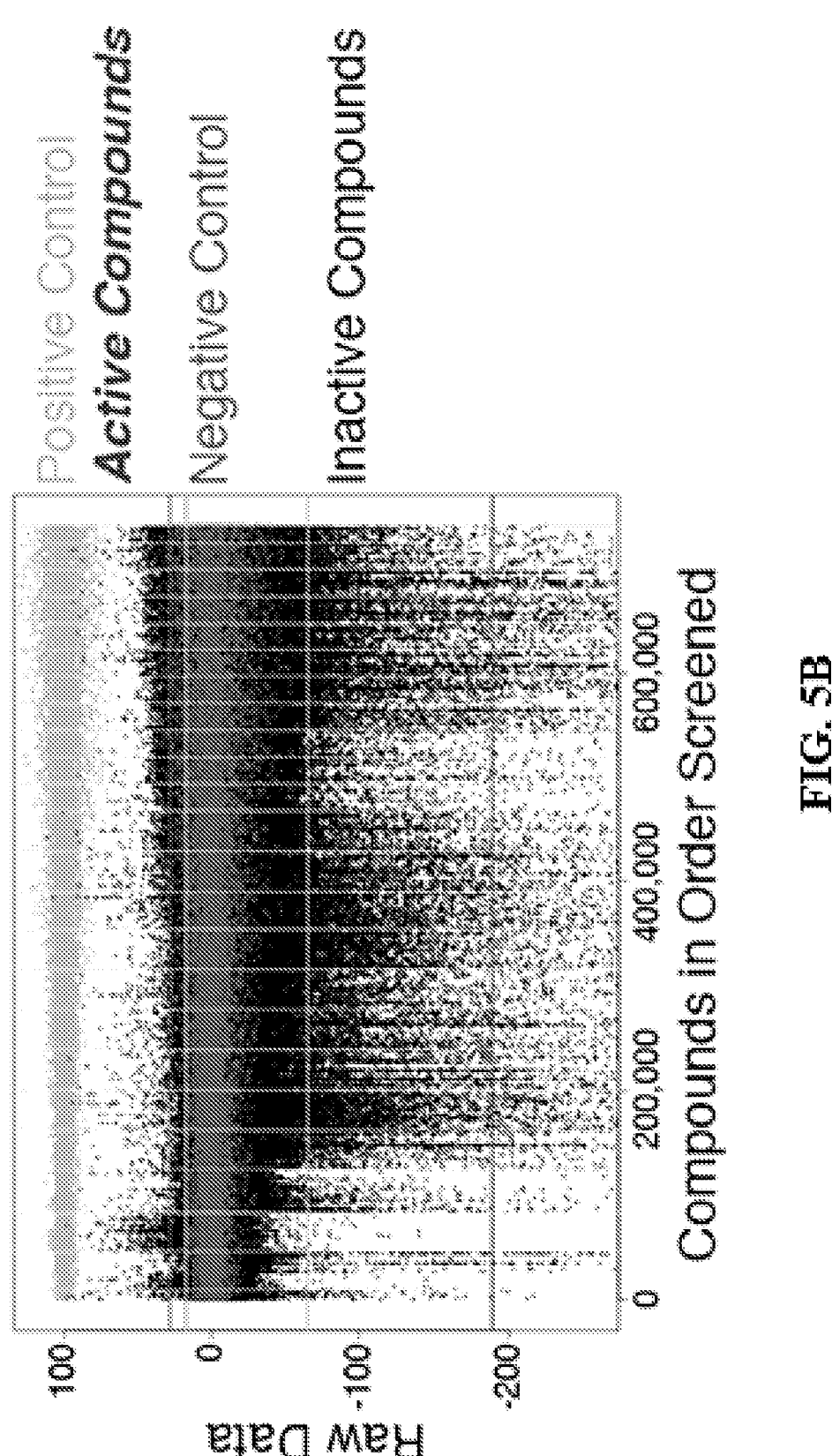

A primary screen followed by receiver operating characteristic (ROC) analysis resulted in the identification of 850 compounds (see FIG. 5A). This was narrowed to 100 compounds having an $IC_{50}$ of less than 10 μM using a second screen. A graphical representation of the screen is shown in FIG. 5B.

Figure 6A:
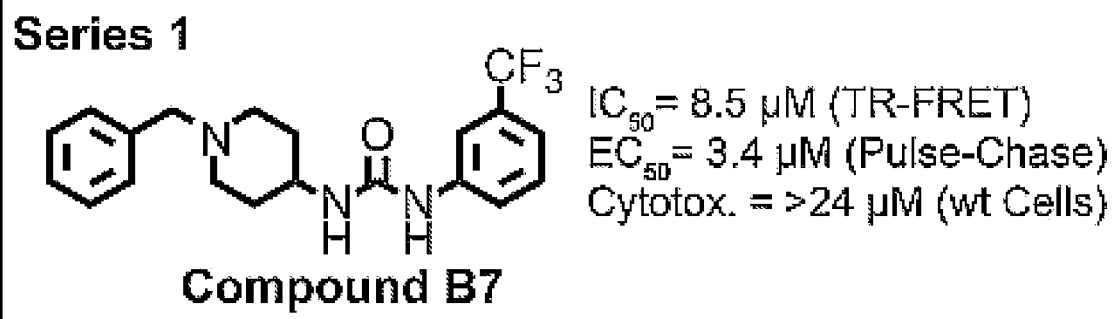
FIG. 6A-D show representative data for the dose-dependent inhibition of the DCN1-UBC12$^{NAc}$ interaction of compounds B7, E1, and F1 using the TR-FRET assay method described herein. Specifically, representative structures (6A), inhibition of DCN1-UBC12 binding (6B), dose-dependent inhibition of labeled NEDD8 transfer from UBC12 to CUL2$^{CTD}$-RBX2 using the pulse-chase neddylation assay method described herein (6C), and superimposition of X-ray crystal structures (1.7-2.0 Å res) of DCN1 bound to UBC12$^{NAc}$ or representative members of the compounds (6D) are shown. The figure shows that each of these three compounds is able to occupy the targeted binding pocket.
Figure 6A:
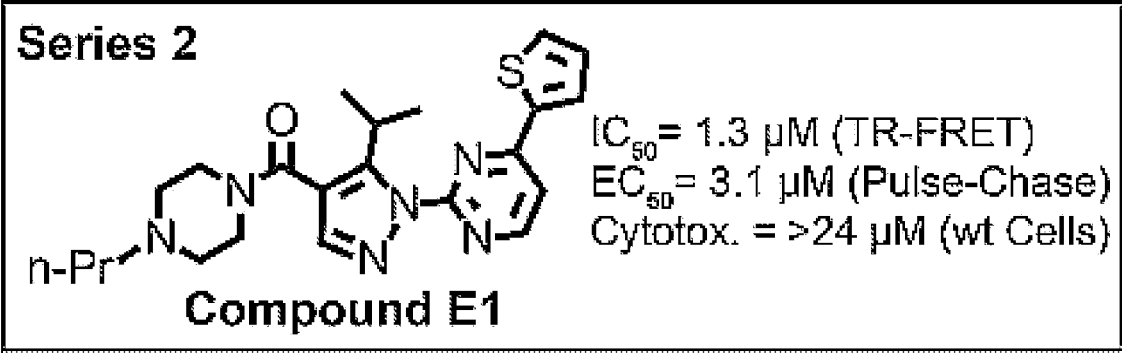
Figure 6A:
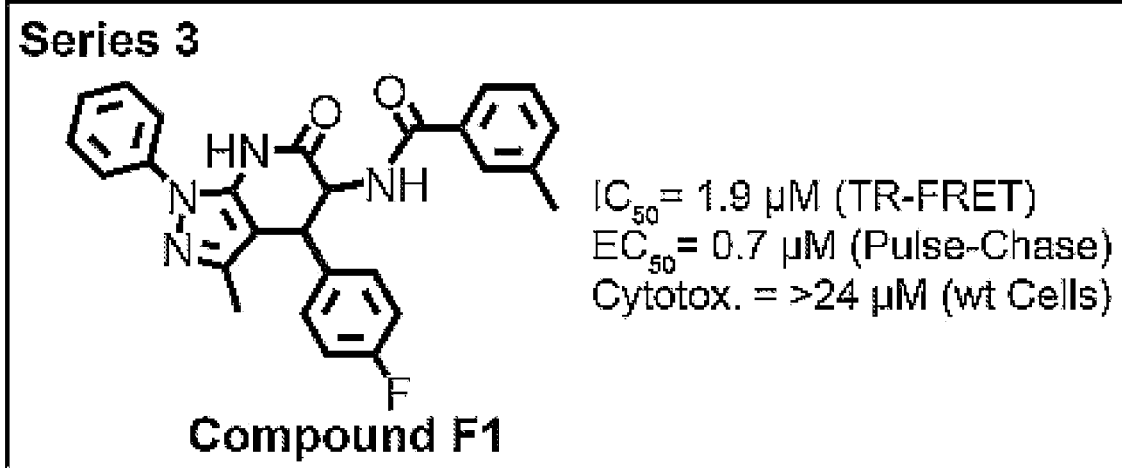
Figure 6B:
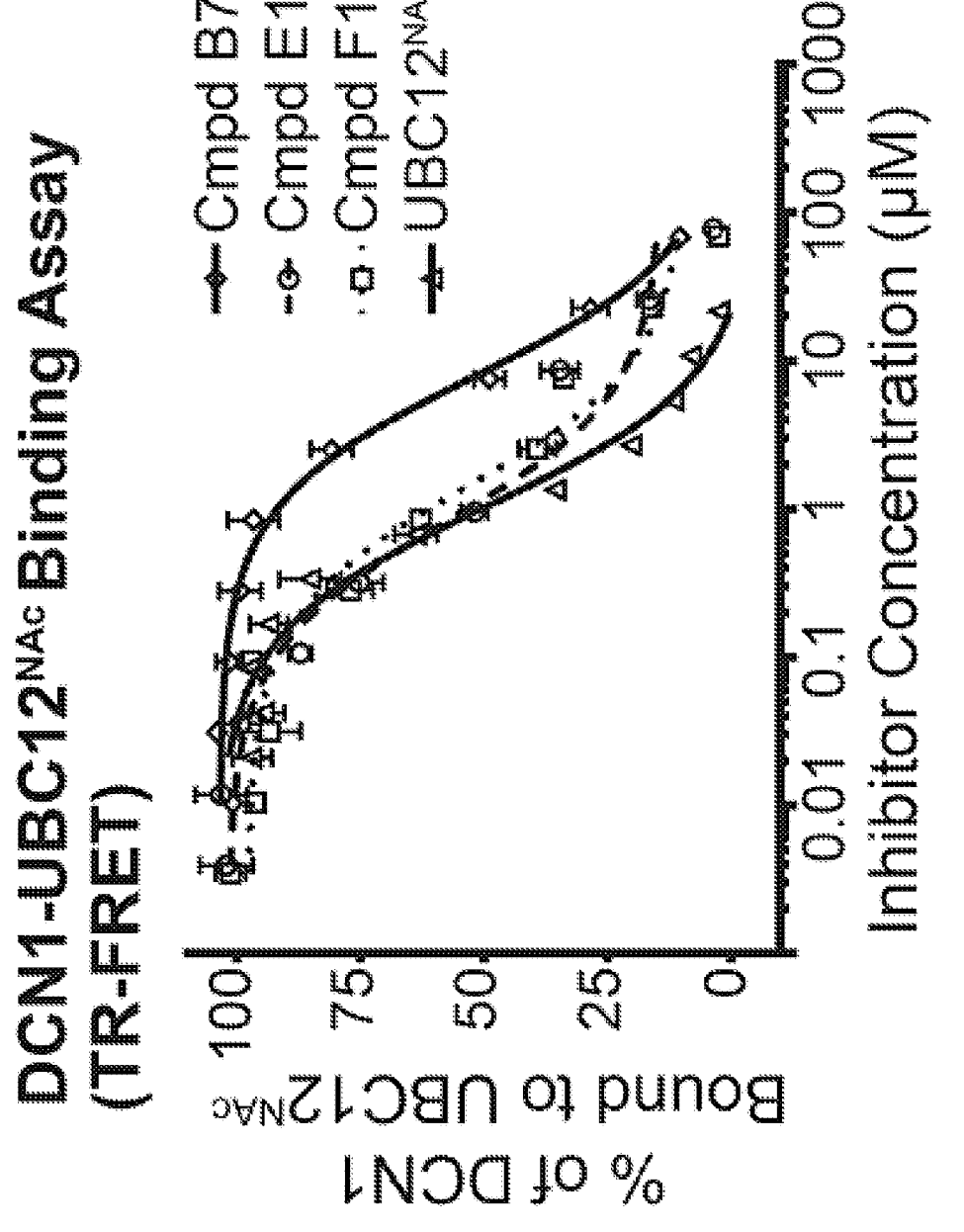
Figure 6C:
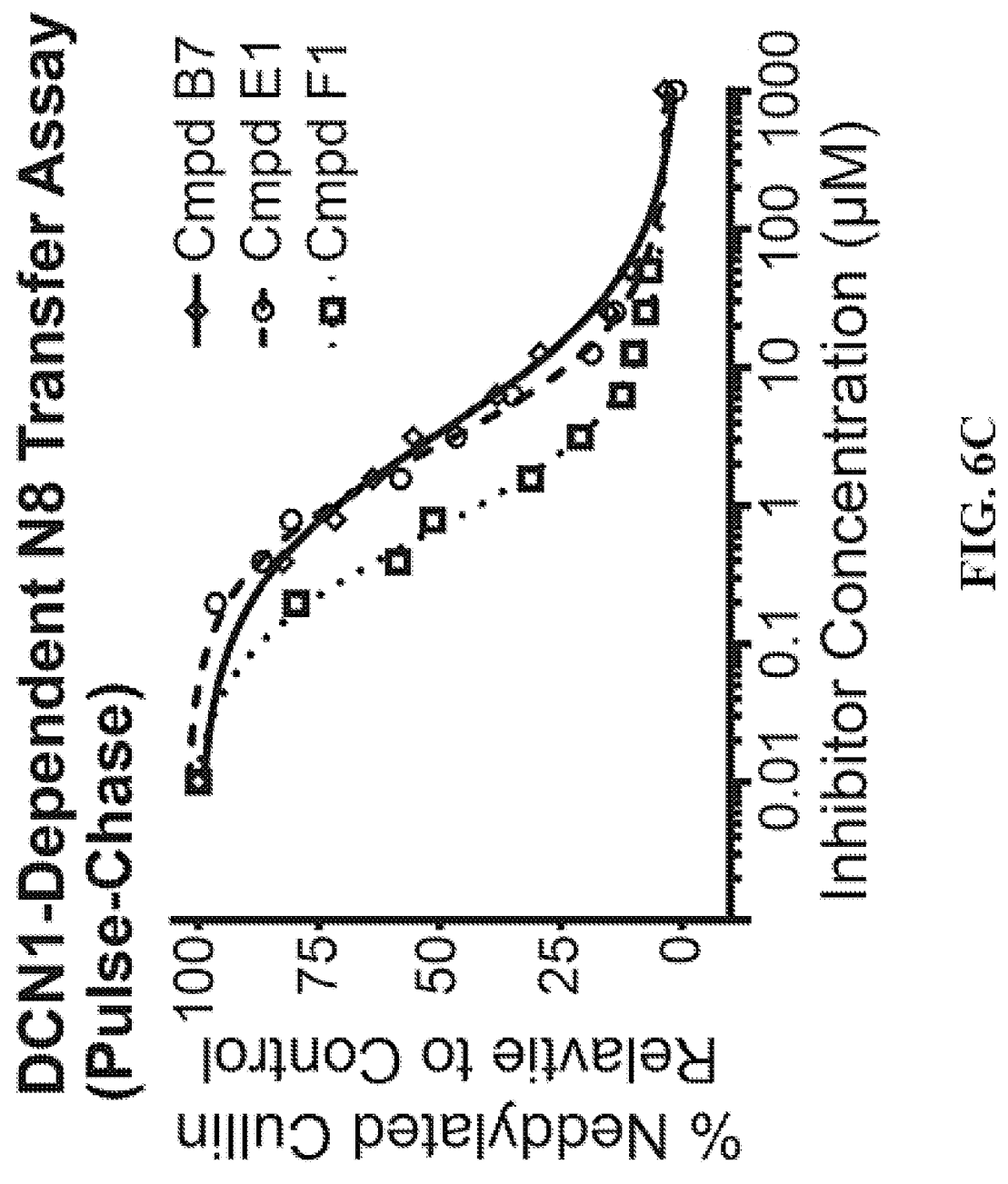
Figure 6D:
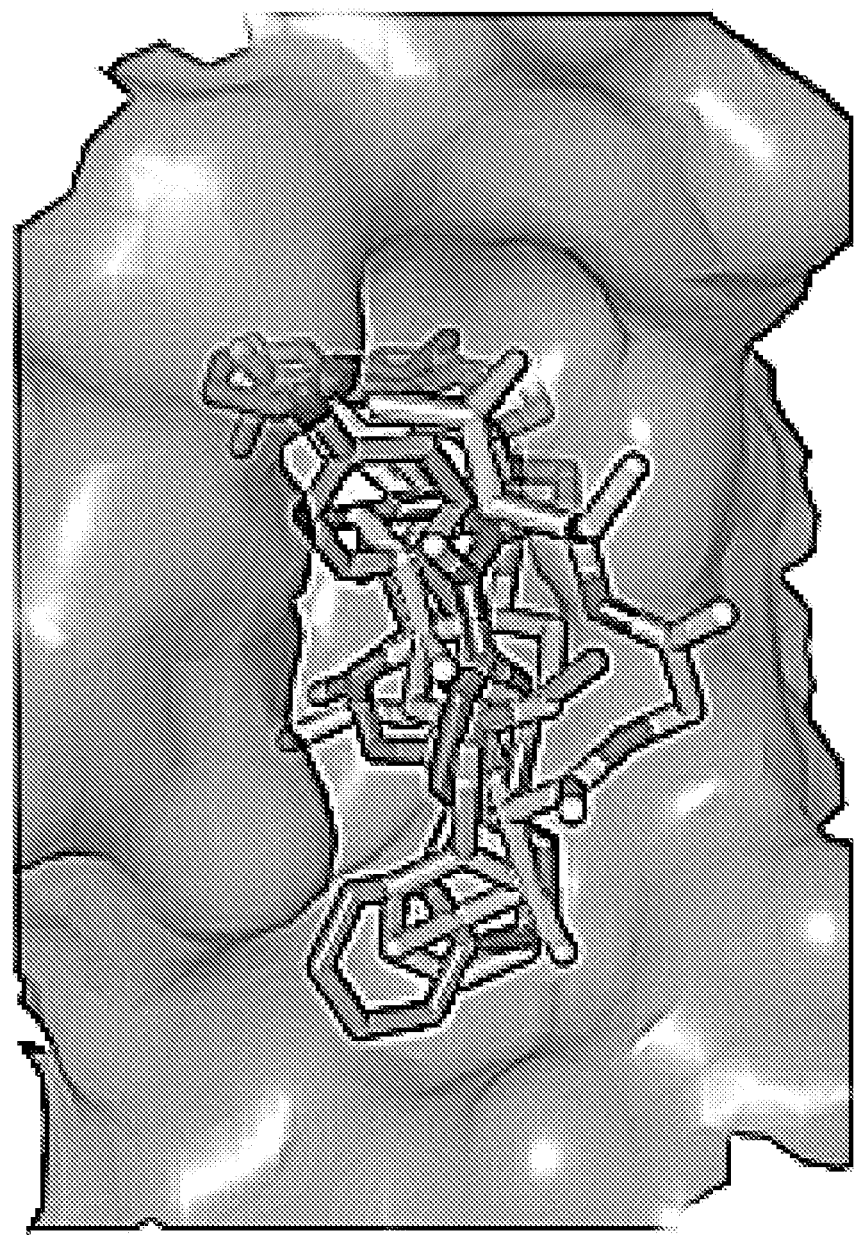

Out of these 100 compounds, three chemical scaffolds were selected for validation. Representative structures of these scaffolds are illustrated in FIG. 6A. Each of these compounds demonstrated the ability to block DCN1-UBC12 binding (FIG. 6B) and inhibit neddylation (6C). Additionally, these analogs were non-toxic to wild type cells and offered synthetic tractability. An overlay these compounds co-crystalized with DCN1 is illustrated in FIG. 6D.

8. Biochemical Validation and Characterization of B7

As shown in FIG. 8, B7 specifically inhibits DCN1 dependent nedylation.

9. Development of a Structure Activity Relationship

A 1.8A co-crystal structure of B7 and DCN1 illustrated five subpockets for optimization (FIG. 9A). A SAR based on B7 is shown in FIG. 9B.

A summary of the potency gains for the 329 series is shown in FIG. 10.

10. Compound Activity Determined in the TR-FRET Assay

Compounds in Table 2 (compound nos. A1-A308) were prepared by the methods described herein. The compounds in Tables 3 (compound nos. B1-B124), 4 (compound nos. C1-C71), 5 (compound nos. D1-D33), 6 (compound nos. E1-E62), and 7 (compound nos. F1-F33) were obtained from commercial sources. The $IC_{50}$ values (provided in μM) were determined using the TR-FRET assay described herein above. The 95% confidence interval (indicated as "CI" in the tables) for the $IC_{50}$ was calculated by as described herein.

TABLE 2

| No. | Structure | TR-FRET $IC_{50}$ (μM) | TR-FRET 95% CI $IC_{50}$ (μM) |
|---|---|---|---|
| A1 | | 0.0043 | 0.0031-0.0059 |

TABLE 2-continued

| No. | Structure | TR-FRET IC$_{50}$ ($\mu$M) | TR-FRET 95% CI IC$_{50}$ ($\mu$M) |
|-----|-----------|------------------------------|-------------------------------------|
| A2 | | 0.0068 | 0.0027-0.0168 |
| A3 | | 0.018 | 0.0106-0.0305 |
| A4 | | 0.035 | 0.0303-0.0406 |

TABLE 2-continued

| No. | Structure | TR-FRET IC$_{50}$ ($\mu$M) | TR-FRET 95% CI IC$_{50}$ ($\mu$M) |
|-----|-----------|------------------|-------------------------|
| A5 | | 0.0559 | 0.0421-0.0744 |
| A6 | | 0.058 | 0.0449-0.0748 |
| A7 | | 0.0765 | 0.0440-0.1331 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A8 | | 0.0767 | 0.0444-0.1327 |
| A9 | | 0.0788 | 0.0540-0.1149 |
| A10 | | 0.0789 | 0.0699-0.0929 |

TABLE 2-continued

| No. | Structure | TR-FRET IC$_{50}$ (µM) | TR-FRET 95% CI IC$_{50}$ (µM) |
|---|---|---|---|
| A11 | | 0.0818 | 0.0596-0.1123 |
| A12 | | 0.0827 | 0.0676-0.1013 |
| A13 | | 0.083 | 0.0612-0.1125 |

TABLE 2-continued

| No. | Structure | TR-FRET IC$_{50}$ (µM) | TR-FRET 95% CI IC$_{50}$ (µM) |
|---|---|---|---|
| A14 | | 0.0853 | 0.0651-0.1117 |
| A15 | | 0.0885 | 0.0634-0.1234 |
| A16 | | 0.0905 | 0.0776-0.1055 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A17 | | 0.0951 | 0.0839-0.1077 |
| A18 | | 0.1108 | 0.0878-0.1398 |
| A19 | | 0.1165 | 0.1006-0.1350 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A20 | | 0.1165 | 0.0992-0.1367 |
| A21 | | 0.119 | 0.0896-0.1580 |
| A22 | | 0.1312 | 0.1004-0.1714 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A23 | | 0.1405 | 0.1325-0.1489 |
| A24 | | 0.1541 | 0.0667-0.3561 |
| A25 | | 0.1547 | 0.0827-0.2891 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A26 | | 0.163 | 0.0861-0.3085 |
| A27 | | 0.1648 | 0.1425-0.1907 |
| A28 | | 0.1663 | 0.1165-0.2376 |

TABLE 2-continued

| No. | Structure | TR-FRET IC$_{50}$ (µM) | TR-FRET 95% CI IC$_{50}$ (µM) |
|---|---|---|---|
| A29 | | 0.1721 | 0.1269-0.2335 |
| A30 | | 0.1776 | 0.1407-0.2242 |
| A31 | | 0.1838 | 0.1454-0.2323 |

TABLE 2-continued

| No. | Structure | TR-FRET IC$_{50}$ (μM) | TR-FRET 95% CI IC$_{50}$ (μM) |
|---|---|---|---|
| A32 | | 0.1905 | 0.0942-0.3853 |
| A33 | | 0.1996 | 0.1331-0.2994 |
| A34 | | 0.2006 | 0.1270-0.3170 |

TABLE 2-continued

| No. | Structure | TR-FRET IC$_{50}$ (μM) | TR-FRET 95% CI IC$_{50}$ (μM) |
|---|---|---|---|
| A35 | | 0.2025 | 0.1305-0.3145 |
| A36 | | 0.2058 | 0.1626-0.2605 |
| A37 | | 0.2069 | 0.1770-0.2419 |

TABLE 2-continued

| No. | Structure | TR-FRET IC$_{50}$ ($\mu$M) | TR-FRET 95% CI IC$_{50}$ ($\mu$M) |
|-----|-----------|-----|-----|
| A38 | | 0.208 | 0.1216-0.3560 |
| A39 | | 0.2128 | 0.1438-0.3148 |
| A40 | | 0.2274 | 0.1871-0.2765 |

TABLE 2-continued

| No. | Structure | TR-FRET IC$_{50}$ ($\mu$M) | TR-FRET 95% CI IC$_{50}$ ($\mu$M) |
|-----|-----------|------------------|-------------------------|
| A41 | | 0.2373 | 0.1977-0.2849 |
| A42 | | 0.2405 | 0.2118-0.2731 |
| A43 | | 0.2459 | 0.1937-0.3121 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A44 | | 0.2542 | 0.1980-0.3265 |
| A45 | | 0.2556 | 0.0954-0.6847 |
| A46 | | 0.257 | 0.1754-0.3765 |

TABLE 2-continued

| No. | Structure | TR-FRET IC$_{50}$ ($\mu$M) | TR-FRET 95% CI IC$_{50}$ ($\mu$M) |
|-----|-----------|---------------------------|-----------------------------------|
| A47 | | 0.2591 | 0.2017-0.3329 |
| A48 | | 0.2604 | 0.2379-0.2851 |
| A49 | | 0.265 | 0.1965-0.3573 |

TABLE 2-continued

| No. | Structure | TR-FRET IC$_{50}$ (µM) | TR-FRET 95% CI IC$_{50}$ (µM) |
|---|---|---|---|
| A50 | | 0.2677 | 0.1897-0.3778 |
| A51 | | 0.2733 | 0.2106-0.3547 |
| A52 | | 0.2815 | 0.1994-0.3973 |

TABLE 2-continued

| No. | Structure | TR-FRET IC$_{50}$ (µM) | TR-FRET 95% CI IC$_{50}$ (µM) |
|---|---|---|---|
| A53 | | 0.287 | 0.2146-0.3840 |
| A54 | | 0.2951 | 0.2205-0.3948 |
| A55 | | 0.3033 | 0.1742-0.5283 |

TABLE 2-continued

| No. | Structure | TR-FRET IC$_{50}$ (μM) | TR-FRET 95% CI IC$_{50}$ (μM) |
| --- | --- | --- | --- |
| A56 | | 0.3148 | 0.2213-0.4478 |
| A57 | | 0.3151 | 0.2707-0.3667 |
| A58 | | 0.3457 | 0.2813-0.4248 |

TABLE 2-continued

| No. | Structure | TR-FRET IC$_{50}$ (μM) | TR-FRET 95% CI IC$_{50}$ (μM) |
|---|---|---|---|
| A59 | | 0.3553 | 0.1772-0.7123 |
| A60 | | 0.3575 | 0.2479-0.5154 |
| A61 | | 0.3707 | 0.2523-0.5444 |

TABLE 2-continued

| No. | Structure | TR-FRET IC$_{50}$ (μM) | TR-FRET 95% CI IC$_{50}$ (μM) |
|---|---|---|---|
| A62 | | 0.385 | 0.2858-0.5186 |
| A63 | | 0.4133 | 0.3034-0.5630 |
| A64 | | 0.4137 | 0.2505-0.6833 |

TABLE 2-continued

| No. | Structure | TR-FRET IC$_{50}$ (µM) | TR-FRET 95% CI IC$_{50}$ (µM) |
|---|---|---|---|
| A65 | | 0.4455 | 0.3754-0.5287 |
| A66 | | 0.4696 | 0.3972-0.5551 |
| A67 | | 0.4817 | 0.3905-0.5942 |

TABLE 2-continued

| No. | Structure | TR-FRET IC$_{50}$ ($\mu$M) | TR-FRET 95% CI IC$_{50}$ ($\mu$M) |
|-----|-----------|------------------|---------------------|
| A68 | | 0.488 | 0.2600-0.9160 |
| A69 | | 0.5667 | 0.3521-0.9120 |
| A70 | | 0.5826 | 0.4368-0.7771 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A71 | | 0.5888 | 0.3242-1.0693 |
| A72 | | 0.6211 | 0.2865-1.3466 |
| A73 | | 0.6257 | 0.3383-1.1573 |

TABLE 2-continued

| No. | Structure | TR-FRET IC$_{50}$ ($\mu$M) | TR-FRET 95% CI IC$_{50}$ ($\mu$M) |
|---|---|---|---|
| A74 | | 0.6538 | 0.4449-0.9607 |
| A75 | | 0.7308 | 0.5252-1.0169 |
| A76 | | 0.7572 | 0.5478-1.0467 |

TABLE 2-continued

| No. | Structure | TR-FRET IC$_{50}$ (μM) | TR-FRET 95% CI IC$_{50}$ (μM) |
|---|---|---|---|
| A77 | | 0.798 | 0.6379-0.9983 |
| A78 | | 0.8008 | 0.5270-1.2169 |
| A79 | | 0.81 | 0.6382-1.0280 |

TABLE 2-continued

| No. | Structure | TR-FRET IC$_{50}$ (µM) | TR-FRET 95% CI IC$_{50}$ (µM) |
|---|---|---|---|
| A80 | | 0.8167 | 0.6656-1.0022 |
| A81 | | 0.8804 | 0.4915-1.5769 |
| A82 | | 0.883 | 0.7172-1.0872 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A83 | | 0.9015 | 0.2750-2.9554 |
| A84 | | 0.9175 | 0.6102-1.3797 |
| A85 | | 0.9798 | 0.7895-1.2158 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A86 | | 0.9905 | 0.7176-1.3671 |
| A87 | | 1.0124 | 0.7461-1.3738 |
| A88 | | 1.0279 | 0.4158-2.5409 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A89 | | 1.0886 | 0.9252-1.2807 |
| A90 | | 1.1274 | 1.0372-1.2255 |
| A91 | | 1.1851 | 0.8353-1.6814 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A92 | | 1.2279 | 0.7823-1.9275 |
| A93 | | 1.2609 | 0.9820-1.6190 |
| A94 | | 1.2933 | 1.0083-1.6589 |

TABLE 2-continued

| No. | Structure | TR-FRET IC$_{50}$ ($\mu$M) | TR-FRET 95% CI IC$_{50}$ ($\mu$M) |
|---|---|---|---|
| A95 | | 1.3205 | 0.9198-1.8959 |
| A96 | | 1.3323 | 0.9603-1.8483 |
| A97 | | 1.3466 | 1.0624-1.7069 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A98 | | 1.3848 | 0.9447-2.0300 |
| A99 | | 1.4106 | 1.1377-1.7490 |
| A100 | | 1.4107 | 1.0196-1.9519 |

TABLE 2-continued

| No. | Structure | TR-FRET IC$_{50}$ (μM) | TR-FRET 95% CI IC$_{50}$ (μM) |
|---|---|---|---|
| A101 | | 1.5969 | 1.0120-2.5199 |
| A102 | | 1.6241 | 1.1455-2.3026 |
| A103 | | 1.7351 | 0.5046-5.9664 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A104 | | 1.8517 | 1.4829-2.3124 |
| A105 | | 1.8708 | 1.0731-3.2616 |
| A106 | | 1.889 | 1.3251-2.6930 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A107 | | 2.0493 | 1.6329-2.5717 |
| A108 | | 2.112 | 1.2823-3.4785 |
| A109 | | 2.1965 | 1.0475-4.6058 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A110 | | 2.2068 | 1.4093-3.4554 |
| A111 | | 2.236 | 0.9370-5.3362 |
| A112 | | 2.3008 | 1.3973-3.7886 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A113 | | 2.3487 | 0.9737-5.6653 |
| A114 | | 2.3532 | 1.4898-3.7169 |
| A115 | | 2.3643 | 1.6985-3.2911 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A116 | | 2.369 | 1.5344-3.6575 |
| A117 | | 2.3797 | 0.6016-9.4128 |
| A118 | | 0.1432 | 0.1260-0.1627 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A119 | | 0.3528 | 0.2980-0.4176 |
| A120 | | 0.616 | 0.4754-0.7982 |
| A121 | | 1.0027 | 0.7864-1.2786 |

TABLE 2-continued

| No. | Structure | TR-FRET IC$_{50}$ (μM) | TR-FRET 95% CI IC$_{50}$ (μM) |
|---|---|---|---|
| A122 | | 1.1249 | 0.8162-1.5504 |
| A123 | | 1.1317 | 0.9404-1.3619 |
| A124 | | 1.592 | 1.2691-1.9971 |

TABLE 2-continued

| No. | Structure | TR-FRET IC$_{50}$ ($\mu$M) | TR-FRET 95% CI IC$_{50}$ ($\mu$M) |
|-----|-----------|---------|-----------|
| A125 | | 1.7707 | 0.6774-4.6286 |
| A126 | | 1.7923 | 1.3622-2.3582 |
| A127 | | 2.2285 | 1.7106-2.9031 |

TABLE 2-continued

| No. | Structure | TR-FRET IC$_{50}$ (µM) | TR-FRET 95% CI IC$_{50}$ (µM) |
|---|---|---|---|
| A128 | | 2.3876 | 1.9984-2.8525 |
| A129 | | 2.672 | 1.2426-5.7459 |
| A130 | | 2.955 | 2.5077-3.4821 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A131 | | 3.1458 | 2.6158-3.7831 |
| A132 | | 3.1697 | 2.3408-4.2921 |
| A133 | | 3.2081 | 2.1223-4.8494 |

TABLE 2-continued

| No. | Structure | TR-FRET IC$_{50}$ (µM) | TR-FRET 95% CI IC$_{50}$ (µM) |
|---|---|---|---|
| A134 | | 3.339 | 1.1837-9.4182 |
| A135 | | 3.3458 | 2.0551-5.4470 |
| A136 | | 3.5652 | 2.8723-4.4254 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A137 | | 3.7969 | 2.6007-5.5432 |
| A138 | | 4.0483 | 2.1871-7.4935 |
| A139 | | 4.13 | 2.0612-8.2751 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A140 | | 4.2032 | 2.5997-6.7959 |
| A141 | | 4.2245 | 1.9996-8.9251 |
| A142 | | 4.265 | 2.9539-6.1581 |

TABLE 2-continued

| No. | Structure | TR-FRET IC$_{50}$ ($\mu$M) | TR-FRET 95% CI IC$_{50}$ ($\mu$M) |
|---|---|---|---|
| A143 | | 4.2727 | 2.2716-8.0369 |
| A144 | | 4.4871 | 3.8607-5.2153 |
| A145 | | 4.5711 | 3.6351-5.7480 |

TABLE 2-continued

| No. | Structure | TR-FRET IC$_{50}$ ($\mu$M) | TR-FRET 95% CI IC$_{50}$ ($\mu$M) |
|---|---|---|---|
| A146 | | 4.8053 | 3.4588-6.6760 |
| A147 | | 4.8509 | 3.0208-7.7899 |
| A148 | | 4.9807 | 3.3849-7.3289 |

TABLE 2-continued

| No. | Structure | TR-FRET IC$_{50}$ (μM) | TR-FRET 95% CI IC$_{50}$ (μM) |
|---|---|---|---|
| A149 | | 5.2455 | 3.2586-8.4440 |
| A150 | | 5.3976 | 3.2695-8.9111 |
| A151 | | 5.6637 | 0.8927-35.9312 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A152 | | 6.2695 | 4.6269-8.4953 |
| A153 | | 6.4673 | 5.4851-7.6254 |
| A154 | | 6.5146 | 4.6465-9.1336 |

TABLE 2-continued

| No. | Structure | TR-FRET IC$_{50}$ (μM) | TR-FRET 95% CI IC$_{50}$ (μM) |
|---|---|---|---|
| A155 | | 6.7664 | 1.1192-40.9071 |
| A156 | | 7.1127 | 5.5349-9.1402 |
| A157 | | 7.1133 | 3.2143-15.7417 |

TABLE 2-continued

| No. | Structure | TR-FRET IC$_{50}$ (µM) | TR-FRET 95% CI IC$_{50}$ (µM) |
|---|---|---|---|
| A158 | | 7.6702 | 1.2273-47.9364 |
| A159 | | 7.7201 | 4.7565-12.5303 |
| A160 | | 7.894 | 5.9381-10.4940 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A161 | | 7.9438 | 5.0536-12.4868 |
| A162 | | 8.2158 | 6.4070-10.5351 |
| A163 | | 8.4154 | 4.6173-15.3379 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A164 | | 8.9036 | 7.5237-10.5366 |
| A165 | | 9.4336 | 6.1569-14.4540 |
| A166 | | 10.078 | 5.0680-20.0407 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A167 | | 10.5055 | 7.5372-14.6427 |
| A168 | | 10.5755 | 6.5024-17.2000 |
| A169 | | 10.9975 | 6.9277-17.4582 |

TABLE 2-continued

| No. | Structure | TR-FRET IC$_{50}$ (μM) | TR-FRET 95% CI IC$_{50}$ (μM) |
|---|---|---|---|
| A170 | | 11.6082 | 7.4777-18.0203 |
| A171 | | 12.6803 | 9.5798-16.7843 |
| A172 | | 12.9244 | 10.8392-15.4109 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A173 | | 13.1183 | 7.8583-21.8992 |
| A174 | | 13.2315 | 2.2390-78.1921 |
| A175 | | 13.5721 | 9.1187-20.2006 |

TABLE 2-continued

| No. | Structure | TR-FRET IC$_{50}$ (μM) | TR-FRET 95% CI IC$_{50}$ (μM) |
|---|---|---|---|
| A176 | | 13.6771 | 6.4981-28.7876 |
| A177 | | 14.4818 | 8.4235-24.8974 |
| A178 | | 15.8165 | 10.0696-24.8433 |

TABLE 2-continued

| No. | Structure | TR-FRET IC$_{50}$ ($\mu$M) | TR-FRET 95% CI IC$_{50}$ ($\mu$M) |
|---|---|---|---|
| A179 | | 16.5673 | 9.1091-30.1319 |
| A180 | | 19.7764 | 4.7838-81.7566 |
| A181 | | 19.8496 | 10.6132-37.1240 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A182 | | 21.1432 | 14.2570-31.3556 |
| A183 | | 21.8667 | 13.9880-34.1830 |
| A184 | | 28.9836 | 6.3966-131.3276 |

621

622

TABLE 2-continued

| No. | Structure | TR-FRET IC$_{50}$ (μM) | TR-FRET 95% CI IC$_{50}$ (μM) |
|-----|-----------|------------------------|-------------------------------|
| A185 | | 29.9878 | 22.5036-39.9612 |
| A186 | | 33.3747 | 13.0389-85.4264 |
| A187 | | 33.8271 | 25.5578-44.7718 |

TABLE 2-continued

| No. | Structure | TR-FRET IC$_{50}$ (μM) | TR-FRET 95% CI IC$_{50}$ (μM) |
|---|---|---|---|
| A188 | | 34.3414 | 22.8755-51.5544 |
| A189 | | 37.7602 | 26.9517-52.9033 |
| A190 | | 37.7943 | 27.2713-52.3779 |

TABLE 2-continued

| No. | Structure | TR-FRET IC$_{50}$ (µM) | TR-FRET 95% CI IC$_{50}$ (µM) |
|---|---|---|---|
| A191 | | 44.8867 | 30.3335-66.4222 |
| A192 | | 55.3039 | 47.8987-63.8540 |
| A193 | | <0.0029 | 0.0000-0.0000 |

TABLE 2-continued

| No. | Structure | TR-FRET IC$_{50}$ ($\mu$M) | TR-FRET 95% CI IC$_{50}$ ($\mu$M) |
|---|---|---|---|
| A194 | | >10.3500 | 1035.0000-1035.0000 |
| A195 | | >100.4082 | UNDEFINED |
| A196 | | >11.8232 | UNDEFINED |

TABLE 2-continued

| No. | Structure | TR-FRET IC$_{50}$ (μM) | TR-FRET 95% CI IC$_{50}$ (μM) |
|---|---|---|---|
| A197 | | >110.6188 | UNDEFINED |
| A198 | | >12.8652 | 5.7531-13.7676 |
| A199 | | >14.5145 | UNDEFINED |

TABLE 2-continued

| No. | Structure | TR-FRET IC$_{50}$ ($\mu$M) | TR-FRET 95% CI IC$_{50}$ ($\mu$M) |
|---|---|---|---|
| A200 | | >15.0348 | 7.1679-12.4868 |
| A201 | | >19.0501 | 0.8747-1905.0147 |
| A202 | | >19.3776 | 17.1210-364.3399 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A203 | | >20.2035 | 22.2072-125.9922 |
| A204 | | >20.2212 | 0.9658-37.1188 |
| A205 | | >20.7611 | 13.0808-158.9975 |

TABLE 2-continued

| No. | Structure | TR-FRET IC$_{50}$ (μM) | TR-FRET 95% CI IC$_{50}$ (μM) |
|---|---|---|---|
| A206 | | >20.8584 | 0.0854-884.4852 |
| A207 | | >20.9812 | UNDEFINED |
| A208 | | >21.0855 | UNDEFINED |

TABLE 2-continued

| No. | Structure | TR-FRET IC$_{50}$ (µM) | TR-FRET 95% CI IC$_{50}$ (µM) |
|-----|-----------|------------------------|-------------------------------|
| A209 | | >21.5221 | 0.0448-2152.2124 |
| A210 | | >21.6637 | 0.0036-2166.3717 |
| A211 | | >21.8201 | UNDEFINED |

TABLE 2-continued

| No. | Structure | TR-FRET IC$_{50}$ (μM) | TR-FRET 95% CI IC$_{50}$ (μM) |
|---|---|---|---|
| A212 | | >22.5280 | 0.2550-660.3627 |
| A213 | | >22.5339 | 14.1419-24.9048 |
| A214 | | >22.8614 | 19.7100-757.5998 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A215 | | >23.3953 | 0.3100-2339.5280 |
| A216 | | >23.7581 | UNDEFINED |
| A217 | | >23.9027 | UNDEFINED |

TABLE 2-continued

| No. | Structure | TR-FRET IC$_{50}$ ($\mu$M) | TR-FRET 95% CI IC$_{50}$ ($\mu$M) |
|-----|-----------|------------------|----------------------|
| A218 | | >23.9853 | 26.4436-99.7144 |
| A219 | | >24.2330 | UNDEFINED |
| A220 | | >24.500 | UNDEFINED |

TABLE 2-continued

| No. | Structure | TR-FRET IC$_{50}$ (μM) | TR-FRET 95% CI IC$_{50}$ (μM) |
|-----|-----------|------------------------|-------------------------------|
| A221 | | >24.7994 | 20.0832-62.0985 |
| A222 | | >25.2389 | UNDEFINED |
| A223 | | >25.3417 | UNDEFINED |

TABLE 2-continued

| No. | Structure | TR-FRET IC$_{50}$ (μM) | TR-FRET 95% CI IC$_{50}$ (μM) |
|---|---|---|---|
| A224 | | >25.3422 | 6.4541-14.6457 |
| A225 | | >26.0944 | UNDEFINED |
| A226 | | >26.6490 | 25.4146-45.1599 |

TABLE 2-continued

| No. | Structure | TR-FRET IC$_{50}$ ($\mu$M) | TR-FRET 95% CI IC$_{50}$ ($\mu$M) |
|---|---|---|---|
| A227 | | >26.9676 | 0.1624-2696.7552 |
| A228 | | >28.2537 | UNDEFINED |
| A229 | | >28.6372 | 0.5602-210.1291 |

TABLE 2-continued

| No. | Structure | TR-FRET IC$_{50}$ (μM) | TR-FRET 95% CI IC$_{50}$ (μM) |
|---|---|---|---|
| A230 | | >28.6637 | 27.1187-57.5044 |
| A231 | | >28.9115 | 25.8812-50.0814 |
| A232 | | >38.6812 | UNDEFINED |

TABLE 2-continued

| No. | Structure | TR-FRET IC$_{50}$ (µM) | TR-FRET 95% CI IC$_{50}$ (µM) |
|-----|-----------|------------------------|-------------------------------|
| A233 | | >39.4188 | UNDEFINED |
| A234 | | >40.6250 | 42.0317-1017.2422 |
| A235 | | >41.1250 | UNDEFINED |

TABLE 2-continued

| No. | Structure | TR-FRET IC$_{50}$ (μM) | TR-FRET 95% CI IC$_{50}$ (μM) |
|---|---|---|---|
| A236 | | >45.4312 | 0.0204-4543.1250 |
| A237 | | >48.4312 | UNDEFINED |
| A238 | | >49.3878 | UNDEFINED |

TABLE 2-continued

| No. | Structure | TR-FRET IC$_{50}$ (μM) | TR-FRET 95% CI IC$_{50}$ (μM) |
|-----|-----------|------------------------|-------------------------------|
| A239 | | >51.2500 | UNDEFINED |
| A240 | | >51.7250 | UNDEFINED |
| A241 | | >52.3813 | UNDEFINED |

TABLE 2-continued

| No. | Structure | TR-FRET IC$_{50}$ ($\mu$M) | TR-FRET 95% CI IC$_{50}$ ($\mu$M) |
|---|---|---|---|
| A242 | | >52.4844 | UNDEFINED |
| A243 | | >52.7625 | UNDEFINED |
| A244 | | >53.6000 | 52.6506-1123.8142 |

TABLE 2-continued

| No. | Structure | TR-FRET IC$_{50}$ ($\mu$M) | TR-FRET 95% CI IC$_{50}$ ($\mu$M) |
|-----|-----------|------------------------------|-------------------------------------|
| A245 | | >53.8750 | UNDEFINED |
| A246 | | >55.6375 | 55.9756-230.8414 |
| A247 | | >58.5250 | 8.1205-5852.5000 |

TABLE 2-continued

| No. | Structure | TR-FRET IC$_{50}$ ($\mu$M) | TR-FRET 95% CI IC$_{50}$ ($\mu$M) |
|---|---|---|---|
| A248 | | >58.9103 | UNDEFINED |
| A249 | | >59.6296 | UNDEFINED |
| A250 | | >59.8250 | 36.2264-247.4433 |

TABLE 2-continued

| No. | Structure | TR-FRET IC$_{50}$ (µM) | TR-FRET 95% CI IC$_{50}$ (µM) |
|-----|-----------|------------------------|-------------------------------|
| A251 | | >59.8750 | UNDEFINED |
| A252 | | >6.4580 | 0.3975-143.0230 |
| A253 | | >6.8855 | 3.2819-5.6694 |

TABLE 2-continued

| No. | Structure | TR-FRET IC$_{50}$ (μM) | TR-FRET 95% CI IC$_{50}$ (μM) |
|-----|-----------|------------------------|-------------------------------|
| A254 | | >60.1250 | UNDEFINED |
| A255 | | >60.1667 | 26.2871-153.8493 |
| A256 | | >60.3750 | UNDEFINED |

TABLE 2-continued

| No. | Structure | TR-FRET IC$_{50}$ ($\mu$M) | TR-FRET 95% CI IC$_{50}$ ($\mu$M) |
|-----|-----------|-----------------------------|-----------------------------------|
| A257 | | >61.8250 | UNDEFINED |
| A258 | | >62.1688 | UNDEFINED |
| A259 | | >62.3813 | UNDEFINED |

TABLE 2-continued

| No. | Structure | TR-FRET IC$_{50}$ ($\mu$M) | TR-FRET 95% CI IC$_{50}$ ($\mu$M) |
|---|---|---|---|
| A260 | | >62.5000 | 0.0000-6250.0000 |
| A261 | | >63.2692 | UNDEFINED |
| A262 | | >63.3781 | UNDEFINED |

TABLE 2-continued

| No. | Structure | TR-FRET IC$_{50}$ ($\mu$M) | TR-FRET 95% CI IC$_{50}$ ($\mu$M) |
|---|---|---|---|
| A263 | | >64.6259 | UNDEFINED |
| A264 | | >65.4487 | UNDEFINED |
| A265 | | >65.6813 | UNDEFINED |

TABLE 2-continued

| No. | Structure | TR-FRET IC$_{50}$ (μM) | TR-FRET 95% CI IC$_{50}$ (μM) |
|---|---|---|---|
| A266 | | >66.1875 | 2.2497-1017.2420 |
| A267 | | >66.8688 | UNDEFINED |
| A268 | | >67.0750 | UNDEFINED |

TABLE 2-continued

| No. | Structure | TR-FRET IC$_{50}$ (µM) | TR-FRET 95% CI IC$_{50}$ (µM) |
|-----|-----------|------------------------|-------------------------------|
| A269 | | >67.1875 | UNDEFINED |
| A270 | | >67.3063 | UNDEFINED |
| A271 | | >67.4562 | UNDEFINED |

TABLE 2-continued

| No. | Structure | TR-FRET IC$_{50}$ (μM) | TR-FRET 95% CI IC$_{50}$ (μM) |
|---|---|---|---|
| A272 | | >67.5250 | UNDEFINED |
| A273 | | >67.9750 | UNDEFINED |
| A274 | | >68.1625 | 9.0475-937.4115 |

TABLE 2-continued

| No. | Structure | TR-FRET IC$_{50}$ (µM) | TR-FRET 95% CI IC$_{50}$ (µM) |
|---|---|---|---|
| A275 | | >68.6188 | UNDEFINED |
| A276 | | >68.7075 | UNDEFINED |
| A277 | | >68.8250 | UNDEFINED |

TABLE 2-continued

| No. | Structure | TR-FRET IC$_{50}$ (μM) | TR-FRET 95% CI IC$_{50}$ (μM) |
|-----|-----------|------------------------|-------------------------------|
| A278 | | >69.1500 | UNDEFINED |
| A279 | | >7.7817 | 0.5892-1.1781 |
| A280 | | >70.0812 | UNDEFINED |

TABLE 2-continued

| No. | Structure | TR-FRET IC$_{50}$ (μM) | TR-FRET 95% CI IC$_{50}$ (μM) |
|-----|-----------|------------------------|-------------------------------|
| A281 | | >70.6500 | UNDEFINED |
| A282 | | >71.2925 | 326.9563-1104.5488 |
| A283 | | >72.0938 | 2.2723-3.0983 |

TABLE 2-continued

| No. | Structure | TR-FRET IC$_{50}$ ($\mu$M) | TR-FRET 95% CI IC$_{50}$ ($\mu$M) |
|-----|-----------|---------------------------|-----------------------------------|
| A284 | | >72.2938 | UNDEFINED |
| A285 | | >72.4000 | UNDEFINED |
| A286 | | >72.4188 | UNDEFINED |

TABLE 2-continued

| No. | Structure | TR-FRET IC$_{50}$ (µM) | TR-FRET 95% CI IC$_{50}$ (µM) |
|-----|-----------|-----------------------|-------------------------------|
| A287 | | >72.4917 | UNDEFINED |
| A288 | | >72.9062 | 86.3190-250.5144 |
| A289 | | >73.2479 | 2.8041-1279.1997 |

TABLE 2-continued

| No. | Structure | TR-FRET IC$_{50}$ ($\mu$M) | TR-FRET 95% CI IC$_{50}$ ($\mu$M) |
|-----|-----------|------------------------------|-------------------------------------|
| A290 | | >74.0000 | UNDEFINED |
| A291 | | >77.0938 | 14.9315-7709.3750 |
| A292 | | >77.2789 | UNDEFINED |

TABLE 2-continued

| No. | Structure | TR-FRET IC$_{50}$ ($\mu$M) | TR-FRET 95% CI IC$_{50}$ ($\mu$M) |
|---|---|---|---|
| A293 | | >78.2051 | UNDEFINED |
| A294 | | >81.0256 | UNDEFINED |
| A295 | | >81.1250 | UNDEFINED |

TABLE 2-continued

| No. | Structure | TR-FRET IC$_{50}$ ($\mu$M) | TR-FRET 95% CI IC$_{50}$ ($\mu$M) |
|---|---|---|---|
| A296 | | >83.4000 | UNDEFINED |
| A297 | | >83.6125 | UNDEFINED |
| A298 | | >85.0000 | UNDEFINED |

TABLE 2-continued

| No. | Structure | TR-FRET IC$_{50}$ (µM) | TR-FRET 95% CI IC$_{50}$ (µM) |
|-----|-----------|------------------------|-------------------------------|
| A299 | | >85.6688 | UNDEFINED |
| A300 | | >85.8438 | UNDEFINED |
| A301 | | >86.1437 | UNDEFINED |

TABLE 2-continued

| No. | Structure | TR-FRET IC$_{50}$ (µM) | TR-FRET 95% CI IC$_{50}$ (µM) |
|-----|-----------|-----------|-----------|
| A302 | | >86.8812 | UNDEFINED |
| A303 | | >89.9188 | UNDEFINED |
| A304 | | >9.7362 | UNDEFINED |
| A305 | | >92.6531 | UNDEFINED |

TABLE 2-continued

| No. | Structure | TR-FRET IC$_{50}$ (µM) | TR-FRET 95% CI IC$_{50}$ (µM) |
|-----|-----------|------------------------|-------------------------------|
| A306 | | >98.0952 | UNDEFINED |
| A307 | | >98.0952 | UNDEFINED |
| A308 | | >98.6000 | UNDEFINED |
| | | 3.33 | — |

TABLE 2-continued

| No. | Structure | TR-FRET IC$_{50}$ ($\mu$M) | TR-FRET 95% CI IC$_{50}$ ($\mu$M) |
|-----|-----------|----------------------------|-----------------------------------|
| | | 33.8 | — |
| | | >53 | — |
| | | >60 | — |

TABLE 2-continued

| No. | Structure | TR-FRET IC$_{50}$ (μM) | TR-FRET 95% CI IC$_{50}$ (μM) |
|---|---|---|---|
| | | >24 | — |
| | | >41 | — |
| | | 0.110 | — |

TABLE 2-continued

| No. | Structure | TR-FRET IC$_{50}$ (μM) | TR-FRET 95% CI IC$_{50}$ (μM) |
|-----|-----------|------------------------|-------------------------------|
| | | 0.172 | — |
| | | 0.095 | — |
| | | 0.208 | — |

TABLE 2-continued

| No. | Structure | TR-FRET IC$_{50}$ (μM) | TR-FRET 95% CI IC$_{50}$ (μM) |
|-----|-----------|------------------------|-------------------------------|
| | | 0.165 | — |
| | | 0.018 | — |
| | | <0.01 | — |

TABLE 2-continued

| No. | Structure | TR-FRET IC$_{50}$ (μM) | TR-FRET 95% CI IC$_{50}$ (μM) |
|---|---|---|---|
| | | <0.01 | — |
| | | 0.154 | — |
| | | <0.01 | — |
| | | <0.01 | — |

TABLE 3

| No. | Structure | TR-FRET IC$_{50}$ (μM) | TR-FRET 95% CI IC$_{50}$ (μM) |
|---|---|---|---|
| B1 | | 2.7294 | 1.8431-4.0421 |
| B2 | | 2.9997 | 1.8937-4.7517 |
| B3 | | 3.8459 | 1.5393-9.6091 |

TABLE 3-continued

| No. | Structure | TR-FRET IC$_{50}$ (μM) | TR-FRET 95% CI IC$_{50}$ (μM) |
|-----|-----------|------------------------|-------------------------------|
| B4 | | 4.0588 | 1.9327-8.5240 |
| B5 | | 5.6383 | 3.8210-8.3198 |
| B6 | | 6.8481 | 5.4183-8.6551 |

TABLE 3-continued

| No. | Structure | TR-FRET IC$_{50}$ (µM) | TR-FRET 95% CI IC$_{50}$ (µM) |
|---|---|---|---|
| B7 | | 8.7522 | 2.6325-29.0985 |
| B8 | | 16.5926 | 7.9981-34.4225 |
| B9 | | 18.5517 | 14.9466-23.0263 |

TABLE 3-continued

| No. | Structure | TR-FRET IC$_{50}$ ($\mu$M) | TR-FRET 95% CI IC$_{50}$ ($\mu$M) |
|-----|-----------|-----------|-----------|
| B10 | | 20.1623 | 14.0762-28.8799 |
| B11 | | 23.8095 | 13.7905-41.1074 |
| B12 | | 29.3208 | 23.9140-35.9501 |

TABLE 3-continued

| No. | Structure | TR-FRET IC$_{50}$ ($\mu$M) | TR-FRET 95% CI IC$_{50}$ ($\mu$M) |
|---|---|---|---|
| B13 | | 37.531 | 33.6724-41.8319 |
| B14 | | 43.0092 | 23.2458-79.5754 |
| B15 | | 49.6896 | 43.4200-56.8644 |
| B16 | | 50.7397 | 42.8230-60.1199 |

TABLE 3-continued

| No. | Structure | TR-FRET IC$_{50}$ (μM) | TR-FRET 95% CI IC$_{50}$ (μM) |
|---|---|---|---|
| B17 | | 55.593 | 5.9696-517.7179 |
| B18 | | 64.1332 | 56.2556-73.1140 |
| B19 | | <0.0040 | 0.0000-0.0000 |

TABLE 3-continued

| No. | Structure | TR-FRET IC$_{50}$ ($\mu$M) | TR-FRET 95% CI IC$_{50}$ ($\mu$M) |
|---|---|---|---|
| B20 | | <0.0041 | 0.0000-0.0000 |
| B21 | | <0.0041 | 0.0000-8148.1481 |
| B22 | | >102.7407 | UNDEFINED |

TABLE 3-continued

| No. | Structure | TR-FRET IC$_{50}$ (μM) | TR-FRET 95% CI IC$_{50}$ (μM) |
|-----|-----------|------------------------|--------------------------------|
| B23 | | >112.5926 | UNDEFINED |
| B24 | | >15.1852 | UNDEFINED |
| B25 | | >16.2963 | UNDEFINED |

TABLE 3-continued

| No. | Structure | TR-FRET IC$_{50}$ (µM) | TR-FRET 95% CI IC$_{50}$ (µM) |
|-----|-----------|------------------------|-------------------------------|
| B26 | | >164.9383 | UNDEFINED |
| B27 | | >28.1481 | UNDEFINED |
| B28 | | >46.2963 | UNDEFINED |

TABLE 3-continued

| No. | Structure | TR-FRET IC$_{50}$ ($\mu$M) | TR-FRET 95% CI IC$_{50}$ ($\mu$M) |
|-----|-----------|------------------------------|--------------------------------------|
| B29 | | >50.3311 | UNDEFINED |
| B30 | | >53.3333 | UNDEFINED |
| B31 | | >54.2993 | UNDEFINED |

TABLE 3-continued

| No. | Structure | TR-FRET IC$_{50}$ (µM) | TR-FRET 95% CI IC$_{50}$ (µM) |
|---|---|---|---|
| B32 | | >55.2925 | 0.0000-5529.2517 |
| B33 | | >55.4074 | UNDEFINED |
| B34 | | >55.4730 | 43.5296-148.4678 |

TABLE 3-continued

| No. | Structure | TR-FRET IC$_{50}$ (μM) | TR-FRET 95% CI IC$_{50}$ (μM) |
|---|---|---|---|
| B35 | | >55.9259 | UNDEFINED |
| B36 | | >57.7778 | UNDEFINED |
| B37 | | >60.5850 | UNDEFINED |

TABLE 3-continued

| No. | Structure | TR-FRET IC$_{50}$ (μM) | TR-FRET 95% CI IC$_{50}$ (μM) |
|-----|-----------|------------------------|-------------------------------|
| B38 | | >61.2517 | UNDEFINED |
| B39 | | >61.8458 | UNDEFINED |
| B40 | | >62.7710 | UNDEFINED |

TABLE 3-continued

| No. | Structure | TR-FRET IC$_{50}$ (μM) | TR-FRET 95% CI IC$_{50}$ (μM) |
|-----|-----------|------------------------|-------------------------------|
| B41 | | >63.8639 | 12.2427-973.8752 |
| B42 | | >64.4444 | UNDEFINED |
| B43 | | >64.4595 | 90.6607-4612.3936 |

TABLE 3-continued

| No. | Structure | TR-FRET IC$_{50}$ (μM) | TR-FRET 95% CI IC$_{50}$ (μM) |
|-----|-----------|------------------------|-------------------------------|
| B44 | | >64.4626 | UNDEFINED |
| B45 | | >65.5193 | UNDEFINED |
| B46 | | >66.3084 | UNDEFINED |

TABLE 3-continued

| No. | Structure | TR-FRET IC$_{50}$ (μM) | TR-FRET 95% CI IC$_{50}$ (μM) |
|---|---|---|---|
| B47 | | >66.9630 | UNDEFINED |
| B48 | | >67.0272 | UNDEFINED |
| B49 | | >67.5676 | 100.6651-5323.0922 |

TABLE 3-continued

| No. | Structure | TR-FRET IC$_{50}$ (µM) | TR-FRET 95% CI IC$_{50}$ (µM) |
|---|---|---|---|
| B50 | | >67.5676 | UNDEFINED |
| B51 | | >67.5676 | UNDEFINED |
| B52 | | >67.5676 | UNDEFINED |
| B53 | | >67.5676 | UNDEFINED |

TABLE 3-continued

| No. | Structure | TR-FRET IC$_{50}$ (μM) | TR-FRET 95% CI IC$_{50}$ (μM) |
|---|---|---|---|
| B54 | | >67.5676 | 9.5044-19.4626 |
| B55 | | >67.5676 | 9.8205-106.2847 |
| B56 | | >67.5676 | 6.6102-8.5553 |
| B57 | | >67.5676 | 15.4797-297.7283 |
| B58 | | >67.5676 | 98.2711-228.5870 |

TABLE 3-continued

| No. | Structure | TR-FRET IC$_{50}$ (µM) | TR-FRET 95% CI IC$_{50}$ (µM) |
|---|---|---|---|
| B59 | | >67.5676 | 1.8072-9.5271 |
| B60 | | >67.5676 | UNDEFINED |
| B61 | | >67.5676 | 1.7087-676.0557 |
| B62 | | >67.5676 | 27.9190-4832.9951 |

TABLE 3-continued

| No. | Structure | TR-FRET IC$_{50}$ (μM) | TR-FRET 95% CI IC$_{50}$ (μM) |
|---|---|---|---|
| B63 | | >67.5676 | 58.1999-631.5172 |
| B64 | | >67.5676 | 55.1041-458.2514 |
| B65 | | >67.5676 | 64.8346-315.2559 |
| B66 | | >67.5676 | UNDEFINED |

TABLE 3-continued

| No. | Structure | TR-FRET IC$_{50}$ (μM) | TR-FRET 95% CI IC$_{50}$ (μM) |
|-----|-----------|----------------------|-------------------------------|
| B67 | | >67.5676 | UNDEFINED |
| B68 | | >67.5676 | UNDEFINED |
| B69 | | >67.5676 | 7.3333-220.8075 |
| B70 | | >67.5676 | UNDEFINED |

TABLE 3-continued

| No. | Structure | TR-FRET IC$_{50}$ ($\mu$M) | TR-FRET 95% CI IC$_{50}$ ($\mu$M) |
|---|---|---|---|
| B71 | | >67.5676 | UNDEFINED |
| B72 | | >67.5676 | UNDEFINED |
| B73 | | >67.5676 | UNDEFINED |
| B74 | | >67.5676 | UNDEFINED |

TABLE 3-continued

| No. | Structure | TR-FRET IC$_{50}$ (µM) | TR-FRET 95% CI IC$_{50}$ (µM) |
|-----|-----------|------------------------|-------------------------------|
| B75 | | >67.5676 | UNDEFINED |
| B76 | | >67.5676 | UNDEFINED |
| B77 | | >67.5676 | UNDEFINED |
| B78 | | >67.5676 | UNDEFINED |

TABLE 3-continued

| No. | Structure | TR-FRET IC$_{50}$ (μM) | TR-FRET 95% CI IC$_{50}$ (μM) |
|---|---|---|---|
| B79 | | >67.5676 | UNDEFINED |
| B80 | | >67.5676 | 50.1543-4007.9051 |
| B81 | | >67.5676 | 0.0000-6756.7568 |

TABLE 3-continued

| No. | Structure | TR-FRET IC$_{50}$ ($\mu$M) | TR-FRET 95% CI IC$_{50}$ ($\mu$M) |
|-----|-----------|---------------------------|-----------------------------------|
| B82 | | >67.5676 | UNDEFINED |
| B83 | | >67.5676 | UNDEFINED |
| B84 | | >67.5676 | UNDEFINED |

TABLE 3-continued

| No. | Structure | TR-FRET IC$_{50}$ (μM) | TR-FRET 95% CI IC$_{50}$ (μM) |
|-----|-----------|------------------------|-------------------------------|
| B85 | | >67.5676 | UNDEFINED |
| B86 | | >67.5676 | UNDEFINED |
| B87 | | >67.5676 | UNDEFINED |

TABLE 3-continued

| No. | Structure | TR-FRET IC$_{50}$ (μM) | TR-FRET 95% CI IC$_{50}$ (μM) |
|---|---|---|---|
| B88 | | >67.5676 | 6756.7568-6756.7568 |
| B89 | | >67.5676 | UNDEFINED |
| B90 | | >67.5676 | 134.2168-1059.8908 |
| B91 | | >67.5676 | 82.2878-463.0489 |

TABLE 3-continued

| No. | Structure | TR-FRET IC$_{50}$ (μM) | TR-FRET 95% CI IC$_{50}$ (μM) |
|---|---|---|---|
| B92 | | >67.5676 | 0.0344-6756.7568 |
| B93 | | >67.5676 | UNDEFINED |
| B94 | | >67.5676 | UNDEFINED |
| B95 | | >67.5676 | UNDEFINED |

TABLE 3-continued

| No. | Structure | TR-FRET IC$_{50}$ (µM) | TR-FRET 95% CI IC$_{50}$ (µM) |
|---|---|---|---|
| B96 | | >67.5676 | UNDEFINED |
| B97 | | >67.5676 | UNDEFINED |
| B98 | | >67.5676 | UNDEFINED |

TABLE 3-continued

| No. | Structure | TR-FRET IC$_{50}$ (µM) | TR-FRET 95% CI IC$_{50}$ (µM) |
|-----|-----------|------------------------|-------------------------------|
| B99 | | >68.0272 | 1.2318-6802.7211 |
| B100 | | >68.0907 | UNDEFINED |
| B101 | | >69.8458 | 11.3551-58.9502 |
| B102 | | >70.5669 | 0.0000-7056.6893 |

TABLE 3-continued

| No. | Structure | TR-FRET IC$_{50}$ (μM) | TR-FRET 95% CI IC$_{50}$ (μM) |
|-----|-----------|------------------------|-------------------------------|
| B103 | | >70.6803 | UNDEFINED |
| B104 | | >70.9388 | UNDEFINED |
| B105 | | >71.2608 | UNDEFINED |
| B106 | | >71.4815 | UNDEFINED |

TABLE 3-continued

| No. | Structure | TR-FRET IC$_{50}$ (µM) | TR-FRET 95% CI IC$_{50}$ (µM) |
|-----|-----------|------------------------|-------------------------------|
| B107 | | >72.2948 | 5.5303-589.4732 |
| B108 | | >72.7937 | 11.3234-60.6478 |
| B109 | | >72.8395 | UNDEFINED |
| B110 | | >73.1156 | UNDEFINED |

TABLE 3-continued

| No. | Structure | TR-FRET IC$_{50}$ (µM) | TR-FRET 95% CI IC$_{50}$ (µM) |
|---|---|---|---|
| B111 | | >73.1973 | 1.0662-4378.8894 |
| B112 | | >73.4921 | UNDEFINED |
| B113 | | >74.0408 | UNDEFINED |
| B114 | | >74.0741 | UNDEFINED |

TABLE 3-continued

| No. | Structure | TR-FRET IC$_{50}$ (μM) | TR-FRET 95% CI IC$_{50}$ (μM) |
|-----|-----------|------------------------|-------------------------------|
| B115 | | >74.5926 | UNDEFINED |
| B116 | | >74.8265 | 68.0622-167.8832 |
| B117 | | >77.0612 | 61.7710-123.0128 |
| B118 | | >78.4830 | UNDEFINED |

TABLE 3-continued

| No. | Structure | TR-FRET IC$_{50}$ (μM) | TR-FRET 95% CI IC$_{50}$ (μM) |
|---|---|---|---|
| B119 | | >79.0123 | UNDEFINED |
| B120 | | >79.1111 | UNDEFINED |
| B121 | | >81.8519 | 121.8292-332.4057 |
| B122 | | >84.8148 | UNDEFINED |

TABLE 3-continued

| No. | Structure | TR-FRET IC$_{50}$ ($\mu$M) | TR-FRET 95% CI IC$_{50}$ ($\mu$M) |
|---|---|---|---|
| B123 | | >89.3129 | UNDEFINED |
| B124 | | >90.3704 | UNDEFINED |

TABLE 4

| No. | Structure | TR-FRET IC$_{50}$ ($\mu$M) | TR-FRET 95% CI IC$_{50}$ ($\mu$M) |
|---|---|---|---|
| C1 | | 8.0715 | 5.2447-12.4220 |
| C2 | | 8.8447 | 1.2114-64.5776 |

TABLE 4-continued

| No. | Structure | TR-FRET IC$_{50}$ ($\mu$M) | TR-FRET 95% CI IC$_{50}$ ($\mu$M) |
|---|---|---|---|
| C3 | | 22.4495 | 12.1694-41.4138 |
| C4 | | 26.2751 | 21.3924-32.2722 |
| C5 | | 30.0778 | 23.7388-38.1095 |
| C6 | | 38.1136 | 30.4330-47.7326 |
| C7 | | >46.0135 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C8 | | >67.5676 | 54.1895-101.0997 |
| C9 | | >76.6599 | UNDEFINED |
| C10 | | >42.9054 | UNDEFINED |
| C11 | | >48.7162 | UNDEFINED |
| C12 | | >65.8503 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C13 | | >66.2766 | UNDEFINED |
| C14 | | >67.5676 | 69.5329-155.4592 |
| C15 | | >67.5676 | 0.6644-1093.7411 |
| C16 | | >67.5676 | 51.6302-88.5578 |
| C17 | | >67.5676 | 1.8472-5440.4188 |
| C18 | | >67.5676 | UNDEFINED |

TABLE 4-continued

| No. | Structure | TR-FRET IC$_{50}$ (μM) | TR-FRET 95% CI IC$_{50}$ (μM) |
|-----|-----------|------------------------|-------------------------------|
| C19 | | >67.5676 | UNDEFINED |
| C20 | | >67.5676 | 0.4257-6756.7568 |
| C21 | | >67.5676 | UNDEFINED |
| C22 | | >67.5676 | 14.0272-32.8926 |
| C23 | | >67.5676 | 0.0000-6756.7568 |

TABLE 4-continued

| No. | Structure | TR-FRET IC$_{50}$ (μM) | TR-FRET 95% CI IC$_{50}$ (μM) |
|-----|-----------|------------------------|-------------------------------|
| C24 | | >67.5676 | 0.0080-6756.7568 |
| C25 | | >67.5676 | 9.7936-46.2566 |
| C26 | | >67.5676 | 74.2528-121.5992 |
| C27 | | >67.5676 | UNDEFINED |
| C28 | | >67.5676 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C29 | | >67.5676 | 74.7494-196.2412 |
| C30 | | >67.5676 | 0.4851-3788.9836 |
| C31 | | >67.5676 | UNDEFINED |
| C32 | | >67.5676 | 66.1810-704.1597 |
| C33 | | >67.5676 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C34 | | >67.5676 | UNDEFINED |
| C35 | | >67.5676 | UNDEFINED |
| C36 | | >67.5676 | UNDEFINED |
| C37 | | >67.5676 | UNDEFINED |
| C38 | | >67.5676 | UNDEFINED |

TABLE 4-continued

| No. | Structure | TR-FRET IC$_{50}$ (µM) | TR-FRET 95% CI IC$_{50}$ (µM) |
|---|---|---|---|
| C39 | | >67.5676 | UNDEFINED |
| C40 | | >67.5676 | 17.0228-30.6092 |
| C41 | | >67.5676 | UNDEFINED |
| C42 | | >67.5676 | 0.0000-6756.7568 |
| C43 | | >67.5676 | UNDEFINED |
| C44 | | >67.5676 | 2.5861-2510.5638 |

TABLE 4-continued

| No. | Structure | TR-FRET IC$_{50}$ ($\mu$M) | TR-FRET 95% CI IC$_{50}$ ($\mu$M) |
|---|---|---|---|
| C45 | | >67.5676 | UNDEFINED |
| C46 | | >67.5676 | UNDEFINED |
| C47 | | >67.5676 | UNDEFINED |
| C48 | | >67.5676 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C49 | | >67.5676 | 113.4793-611.2645 |
| C50 | | >67.5676 | UNDEFINED |
| C51 | | >67.5676 | UNDEFINED |
| C52 | | >67.5676 | UNDEFINED |
| C53 | | >67.5676 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C54 | | >67.5676 | 76.4138-1569.8824 |
| C55 | | >67.5676 | 61.1166-112.7074 |
| C56 | | >67.5676 | UNDEFINED |
| C57 | | >67.5676 | 59.9594-134.2790 |
| C58 | | >67.5676 | 9.8483-33.1861 |

TABLE 4-continued

| No. | Structure | TR-FRET IC$_{50}$ (µM) | TR-FRET 95% CI IC$_{50}$ (µM) |
|---|---|---|---|
| C59 | | >67.5676 | UNDEFINED |
| C60 | | >67.5676 | 34.2675-124.7857 |
| C61 | | >67.5676 | UNDEFINED |
| C62 | | >67.5676 | 6.8076-11.4162 |
| C63 | | >67.5676 | 79.8085-111.0447 |

TABLE 4-continued

| No. | Structure | TR-FRET IC$_{50}$ ($\mu$M) | TR-FRET 95% CI IC$_{50}$ ($\mu$M) |
|---|---|---|---|
| C64 | | >67.5676 | UNDEFINED |
| C65 | | >68.1088 | 6810.8844-6810.8844 |
| C66 | | >75.5714 | UNDEFINED |
| C67 | | >75.6463 | UNDEFINED |
| C68 | | >75.7075 | UNDEFINED |

TABLE 4-continued

| No. | Structure | TR-FRET IC$_{50}$ ($\mu$M) | TR-FRET 95% CI IC$_{50}$ ($\mu$M) |
|---|---|---|---|
| C69 | | >81.4252 | UNDEFINED |
| C70 | | >83.8163 | UNDEFINED |
| C71 | | >92.2449 | UNDEFINED |

TABLE 5

| No. | Structure | TR-FRET IC$_{50}$ ($\mu$M) | TR-FRET 95% CI IC$_{50}$ ($\mu$M) |
|---|---|---|---|
| D1 | | 2.3063 | 1.3986-3.8032 |

TABLE 5-continued

| No. | Structure | TR-FRET IC$_{50}$ (µM) | TR-FRET 95% CI IC$_{50}$ (µM) |
|-----|-----------|----------------|-------------------|
| D2 | | 8.5313 | 1.1836-61.4939 |
| D3 | | 14.7235 | 10.2741-21.0997 |
| D4 | | 17.9672 | 14.0825-22.9236 |

TABLE 5-continued

| No. | Structure | TR-FRET IC$_{50}$ (µM) | TR-FRET 95% CI IC$_{50}$ (µM) |
|-----|-----------|------------------------|-------------------------------|
| D5 | | 18.1837 | 15.6458-21.1334 |
| D6 | | 18.5332 | 13.7047-25.0628 |
| D7 | | 19.472 | 15.8174-23.9711 |

TABLE 5-continued

| No. | Structure | TR-FRET IC$_{50}$ (μM) | TR-FRET 95% CI IC$_{50}$ (μM) |
|---|---|---|---|
| D8 | | 19.7994 | 14.5061-27.0243 |
| D9 | | 21.8462 | 19.3209-24.7016 |
| D10 | | 25.3616 | 15.4650-41.5914 |

TABLE 5-continued

| No. | Structure | TR-FRET IC$_{50}$ ($\mu$M) | TR-FRET 95% CI IC$_{50}$ ($\mu$M) |
|---|---|---|---|
| D11 | | 30.6017 | 26.0947-35.8872 |
| D12 | | 31.3749 | 25.1248-39.1799 |
| D13 | | 45.3389 | 36.3075-56.6167 |

TABLE 5-continued

| No. | Structure | TR-FRET IC$_{50}$ ($\mu$M) | TR-FRET 95% CI IC$_{50}$ ($\mu$M) |
|-----|-----------|---------|---------|
| D14 | | 66.3995 | 53.0325-83.1357 |
| D15 | | >46.1824 | UNDEFINED |
| D16 | | >48.7162 | 30.9817-403.5800 |

TABLE 5-continued

| No. | Structure | TR-FRET IC$_{50}$ ($\mu$M) | TR-FRET 95% CI IC$_{50}$ ($\mu$M) |
|---|---|---|---|
| D17 | | >53.9116 | UNDEFINED |
| D18 | | >60.8299 | UNDEFINED |
| D19 | | >62.9048 | UNDEFINED |

TABLE 5-continued

| No. | Structure | TR-FRET IC$_{50}$ (μM) | TR-FRET 95% CI IC$_{50}$ (μM) |
|---|---|---|---|
| D20 | | >67.2789 | UNDEFINED |
| D21 | | >67.5676 | UNDEFINED |
| D22 | | >67.5676 | 56.4833-109.8071 |

TABLE 5-continued

| No. | Structure | TR-FRET IC$_{50}$ ($\mu$M) | TR-FRET 95% CI IC$_{50}$ ($\mu$M) |
|---|---|---|---|
| D23 | | >67.5676 | 33.6639-939.2716 |
| D24 | | >67.5676 | 91.2059-306.4395 |
| D25 | | >67.5676 | UNDEFINED |

TABLE 5-continued

| No. | Structure | TR-FRET IC$_{50}$ (μM) | TR-FRET 95% CI IC$_{50}$ (μM) |
|-----|-----------|------------------------|-------------------------------|
| D26 | | >67.5676 | UNDEFINED |
| D27 | | >67.5676 | UNDEFINED |
| D28 | | >67.5676 | UNDEFINED |

TABLE 5-continued

| No. | Structure | TR-FRET IC$_{50}$ (µM) | TR-FRET 95% CI IC$_{50}$ (µM) |
|-----|-----------|------------------------|-------------------------------|
| D29 | | >67.5676 | 61.2358-113.0293 |
| D30 | | >67.5676 | 0.0000-6756.7568 |
| D31 | | >67.5676 | 1.7843-6756.7568 |
| D32 | | >67.5676 | UNDEFINED |

TABLE 5-continued

| No. | Structure | TR-FRET IC$_{50}$ (µM) | TR-FRET 95% CI IC$_{50}$ (µM) |
|-----|-----------|------------------------|-------------------------------|
| D33 | | >67.5676 | UNDEFINED |

TABLE 6

| No. | Structure | TR-FRET IC$_{50}$ (µM) | TR-FRET 95% CI IC$_{50}$ (µM) |
|-----|-----------|------------------------|-------------------------------|
| E1 | | 1.0653 | 0.4774-2.3771 |
| E2 | | 4.5337 | 2.2375-9.1861 |
| E3 | | 7.7689 | 4.6765-12.9062 |

TABLE 6-continued

| No. | Structure | TR-FRET IC$_{50}$ (μM) | TR-FRET 95% CI IC$_{50}$ (μM) |
|---|---|---|---|
| E4 | | 13.1162 | 5.5361-31.0755 |
| E5 | | 17.4271 | 3.8318-79.2579 |
| E6 | | 18.8305 | 14.3288-24.7465 |
| E7 | | 21.273 | 4.6780-96.7381 |

TABLE 6-continued

| No. | Structure | TR-FRET IC$_{50}$ ($\mu$M) | TR-FRET 95% CI IC$_{50}$ ($\mu$M) |
| --- | --- | --- | --- |
| E8 | | 22.7768 | 17.6763-29.3491 |
| E9 | | 23.0707 | 19.4045-27.4296 |
| E10 | | 25.0224 | 9.0115-69.4804 |
| E11 | | 26.0468 | 8.1940-82.7967 |

TABLE 6-continued

| No. | Structure | TR-FRET IC$_{50}$ ($\mu$M) | TR-FRET 95% CI IC$_{50}$ ($\mu$M) |
|---|---|---|---|
| E12 | | 28.2862 | 21.0872-37.9429 |
| E13 | | 28.7927 | 24.2634-34.1674 |
| E14 | | 29.854 | 21.5289-41.3984 |
| E15 | | 32.1313 | 25.0716-41.1789 |

TABLE 6-continued

| No. | Structure | TR-FRET IC$_{50}$ ($\mu$M) | TR-FRET 95% CI IC$_{50}$ ($\mu$M) |
|---|---|---|---|
| E16 | | 33.3324 | 7.3784-150.5813 |
| E17 | | 34.4048 | 28.3248-41.7901 |
| E18 | | 38.0948 | 30.5464-47.5084 |
| E19 | | 42.0748 | 36.5451-48.4413 |
| E20 | | 48.1668 | 41.1592-56.3675 |

TABLE 6-continued

| No. | Structure | TR-FRET IC$_{50}$ (µM) | TR-FRET 95% CI IC$_{50}$ (µM) |
|---|---|---|---|
| E21 | | 49.1794 | 38.5317-62.7695 |
| E22 | | 54.8584 | 42.7705-70.3627 |
| E23 | | 57.8625 | 39.7999-84.1224 |
| E24 | | 61.6275 | 46.5043-81.6688 |
| E25 | | 63.0304 | 40.6818-97.6563 |

TABLE 6-continued

| No. | Structure | TR-FRET IC$_{50}$ (µM) | TR-FRET 95% CI IC$_{50}$ (µM) |
|-----|-----------|------------------------|-------------------------------|
| E26 | | 65.2492 | 58.0917-73.2885 |
| E27 | | >16.6667 | UNDEFINED |
| E28 | | >37.3649 | UNDEFINED |
| E29 | | >67.5676 | UNDEFINED |
| E30 | | >67.5676 | 0.2863-6756.7568 |

TABLE 6-continued

| No. | Structure | TR-FRET IC$_{50}$ (μM) | TR-FRET 95% CI IC$_{50}$ (μM) |
|-----|-----------|------------------------|-------------------------------|
| E31 | | >67.5676 | 3.1493-330.6271 |
| E32 | | >67.5676 | UNDEFINED |
| E33 | | >67.5676 | 57.9497-187.1727 |
| E34 | | >67.5676 | UNDEFINED |
| E35 | | >67.5676 | 61.9155-119.2880 |

TABLE 6-continued

| No. | Structure | TR-FRET IC$_{50}$ ($\mu$M) | TR-FRET 95% CI IC$_{50}$ ($\mu$M) |
|-----|-----------|---------------------------|-----------------------------------|
| E36 | | >67.5676 | UNDEFINED |
| E37 | | >67.5676 | 71.0726-164.5650 |
| E38 | | >67.5676 | 70.2336-197.2314 |
| E39 | | >67.5676 | 55.0041-118.2456 |
| E40 | | >67.5676 | UNDEFINED |
| E41 | | >67.5676 | 0.9635-3503.9712 |

TABLE 6-continued

| No. | Structure | TR-FRET IC$_{50}$ (μM) | TR-FRET 95% CI IC$_{50}$ (μM) |
|---|---|---|---|
| E42 | | >67.5676 | 17.6210-28.4331 |
| E43 | | >67.5676 | 81.5867-140.7985 |
| E44 | | >67.5676 | 61.8060-214.2171 |
| E45 | | >67.5676 | 74.0386-90.0536 |
| E46 | | >67.5676 | UNDEFINED |

TABLE 6-continued

| No. | Structure | TR-FRET IC$_{50}$ (μM) | TR-FRET 95% CI IC$_{50}$ (μM) |
|-----|-----------|------------------------|-------------------------------|
| E47 | | >67.5676 | 66.4215-213.9161 |
| E48 | | >67.5676 | UNDEFINED |
| E49 | | >67.5676 | 73.7759-202.1264 |
| E50 | | >67.5676 | UNDEFINED |
| E51 | | >67.5676 | UNDEFINED |
| E52 | | >67.5676 | UNDEFINED |

TABLE 6-continued

| No. | Structure | TR-FRET IC$_{50}$ ($\mu$M) | TR-FRET 95% CI IC$_{50}$ ($\mu$M) |
|-----|-----------|----------------------------|-----------------------------------|
| E53 | | >67.5676 | 0.4342-6756.7568 |
| E54 | | >67.5676 | 0.9527-3618.8827 |
| E55 | | >67.5676 | UNDEFINED |
| E56 | | >67.5676 | UNDEFINED |
| E57 | | >67.5676 | 62.1999-144.5630 |

TABLE 6-continued

| No. | Structure | TR-FRET IC$_{50}$ (µM) | TR-FRET 95% CI IC$_{50}$ (µM) |
|---|---|---|---|
| E58 | | >67.5676 | 0.6383-6756.7568 |
| E59 | | >67.5676 | UNDEFINED |
| E60 | | >68.0272 | UNDEFINED |
| E61 | | >71.5782 | UNDEFINED |

TABLE 6-continued

| No. | Structure | TR-FRET IC$_{50}$ (μM) | TR-FRET 95% CI IC$_{50}$ (μM) |
|-----|-----------|----------------------|-------------------------------|
| E62 | | >77.0177 | UNDEFINED |

TABLE 7

| No. | Structure | TR-FRET IC$_{50}$ (μM) | TR-FRET 95% CI IC$_{50}$ (μM) |
|-----|-----------|----------------------|-------------------------------|
| F1 | | 1.935 | 1.2224-3.0628 |
| F2 | | 3.7094 | 2.2125-6.2189 |
| F3 | | 21.9998 | 12.2172-39.6155 |

TABLE 7-continued

| No. | Structure | TR-FRET IC$_{50}$ (μM) | TR-FRET 95% CI IC$_{50}$ (μM) |
|-----|-----------|------------------------|-------------------------------|
| F4 | | 25.9143 | 22.7434-29.5273 |
| F5 | | 35.1027 | 29.1240-42.3088 |
| F6 | | 39.4957 | 34.6503-45.0188 |
| F7 | | 41.5262 | 28.5214-60.4608 |
| F8 | | >46.7347 | UNDEFINED |

TABLE 7-continued

| No. | Structure | TR-FRET IC$_{50}$ (μM) | TR-FRET 95% CI IC$_{50}$ (μM) |
|-----|-----------|-----------------------|-------------------------------|
| F9 | | >67.5676 | UNDEFINED |
| F10 | | >67.5676 | UNDEFINED |
| F11 | | >67.5676 | UNDEFINED |
| F12 | | >67.5676 | 60.1678-628.0859 |

TABLE 7-continued

| No. | Structure | TR-FRET IC$_{50}$ (µM) | TR-FRET 95% CI IC$_{50}$ (µM) |
|---|---|---|---|
| F13 | | >67.5676 | 131.4340-6756.7568 |
| F14 | | >67.5676 | 28.7806-6756.7568 |
| F15 | | >67.5676 | 14.3310-32.3865 |
| F16 | | >67.5676 | 0.8312-1857.2411 |

TABLE 7-continued

| No. | Structure | TR-FRET IC$_{50}$ ($\mu$M) | TR-FRET 95% CI IC$_{50}$ ($\mu$M) |
|---|---|---|---|
| F17 | | >67.5676 | 6.5651-17.7109 |
| F18 | | >67.5676 | UNDEFINED |
| F19 | | >67.5676 | 69.0184-607.5412 |
| F20 | | >67.5676 | UNDEFINED |

TABLE 7-continued

| No. | Structure | TR-FRET IC$_{50}$ (μM) | TR-FRET 95% CI IC$_{50}$ (μM) |
|-----|-----------|------------------------|-------------------------------|
| F21 | | >67.5676 | UNDEFINED |
| F22 | | >67.5676 | UNDEFINED |
| F23 | | >67.5676 | 102.6561-767.4137 |
| F24 | | >67.5676 | UNDEFINED |

TABLE 7-continued

| No. | Structure | TR-FRET IC$_{50}$ (μM) | TR-FRET 95% CI IC$_{50}$ (μM) |
|-----|-----------|------------------------|-------------------------------|
| F25 | | >67.5676 | UNDEFINED |
| F26 | | >67.5676 | UNDEFINED |
| F27 | | >67.5676 | UNDEFINED |
| F28 | | >67.5676 | UNDEFINED |

TABLE 7-continued

| No. | Structure | TR-FRET IC$_{50}$ (µM) | TR-FRET 95% CI IC$_{50}$ (µM) |
|---|---|---|---|
| F29 | | >67.5676 | UNDEFINED |
| F30 | | >67.5676 | 7.0436-6756.7568 |
| F31 | | >67.5676 | 128.9511-527.8405 |
| F32 | | >67.5676 | 57.0659-123.3180 |

TABLE 7-continued

| No. | Structure | TR-FRET IC$_{50}$ ($\mu$M) | TR-FRET 95% CI IC$_{50}$ ($\mu$M) |
|---|---|---|---|
| F33 | | >80.2721 | UNDEFINED |

11. Optimization of Binding to the Ile and Hinge Pockets of the Target Site

All non-commercially available analogs were prepared by the methods described herein. The IC$_{50}$ values (provided in $\mu$M) were determined using the TR-FRET assay described herein above. The 95% confidence interval (indicated as "CI" in the tables) for the IC$_{50}$ was calculated by as described herein. The average solubility (provided in $\mu$M) was determined as described herein. The membrane permeability (provided in $\times 10^{-6}$ cm/s) was determined using the parallel artificial membrane permeability assay ("Pampa") as described herein.

TABLE 8

| No | R$^{101}$ | IC$_{50}$ ($\mu$M) (TR-FRET) | 95% CI ($\mu$M) (TR-FRET) | Avg. Sol ($\mu$M) | Pampa ($\times 10^{-6}$ cm/s) |
|---|---|---|---|---|---|
| 1 | | 5.5 | 3.3-9.2 | 32 ± 1.6 | 670 ± 100 |
| 2 | | 3.3 | 2.1-5.4 | 44 ± 3.4 | 1200 ± 35 |
| 3 | | >77 | N/A | 0.3 ± 0.2 | 830 ± 1 |
| 4 | | >49 | N/A | 44 ± 1.4 | 1500 ± 1 |
| 5 | | 6.8 | 1.1-41 | 35 ± 8 | >2200 |

TABLE 8-continued

| No | R | EC50 (μM) (TR-FRET) | 95% CI (μM) (TR-FRET) | Avg. Sol (μM) | Pampa (×10⁻⁶ cm/s) |
|---|---|---|---|---|---|
| 6 | | 55 | 48-64 | 0.7 ± 0.6 | 1700 ± 1 |
| 7 | | 22 | 14-34 | 50 ± 2.7 | >2200 |
| 8 | | 17 | 9.1-30 | 14 ± 0.7 | >2200 |
| 9 | | 33 | 13-85 | 0.8 ± 0.4 | 1300 ± 43 |
| 10 | | 13 | 11-15 | 19 ± 1.2 | >2200 |
| 11 | | >98 | N/A | 2.8 ± 0.8 | 910 ± 290 |

| No | R102 | EC50 (μM) (TR-FRET) | 95% CI (μM) (TR-FRET) | Avg. Sol (μM) | Pampa (×10⁻⁶ cm/s) |
|---|---|---|---|---|---|
| 12 | | >67 | N/A | 68 ± 3.4 | 1400 ± 250 |
| 13 | | 16 | 8.0-34 | ND | ND |
| 22 | | 36 | 24-53 | 2.4 ± 0.1 | >2200 |
| 14 | | >67 | N/A | ND | ND |

TABLE 8-continued

| 15 | | >67 | N/A | ND | ND |
|----|----|----|----|----|----|
| 16 | | >67 | N/A | ND | ND |
| 17 | | >64 | N/A | ND | ND |
| 18 | | >100 | N/A | ND | ND |
| 19 | | >71 | N/A | 1.0 ± 0.6 | 930 ± 190 |
| 20 | | >64 | N/A | 78 ± 5.5 | >2200 |
| 21 | | >68 | N/A | 75 ± 0.6 | 220 ± 120 |

12. Optimization of the Urea Moiety

All non-commercially available analogs were prepared by the methods described herein. The $IC_{50}$ values (provided in μM) were determined using the TR-FRET assay described herein above. The 95% confidence interval (indicated as "CI" in the tables) for the $IC_{50}$ was calculated by as described herein. The average solubility (provided in μM) was determined as described herein. The membrane permeability (provided in $\times 10^{-6}$ cm/s) was determined using the parallel artificial membrane permeability assay ("Pampa") as described herein.

TABLE 9

CF<sub>3</sub>

| No | R$^{103}$ | IC$_{50}$ (μM) (TR-FRET) | 95% CI (μM) (TR-FRET) | Avg. Sol (μM) | Pampa (×10$^{-6}$ cm/s) |
|---|---|---|---|---|---|
| 1 | | 11 | 7.5-15 | 61 ± 3.1 | 1600 ± 170 |
| 2 | | 1.0 | 0.72-1.5 | 70 ± 2.3 | >2200 |
| 3 | | 4.8 | 3.4-6.6 | 96 ± 9.7 | 1900 ± 200 |
| 4 | | 1.7 | 1.3-2.2 | 61 ± 3.7 | 1500 ± 5.4 |
| 5 | | >59 | N/A | 64 ± 7.6 | 1600 ± 1 |
| 6 | | 0.88 | 0.51-1.5 | 90 ± 12 | >2200 |
| 7 | | 0.80 | 0.64-1.0 | 69 ± 1.4 | >2200 |
| 8 | | 0.98 | 0.79-1.2 | 39 ± 2.9 | 1800 ± 1 |
| 9 | | 0.80 | 0.47-1.4 | <0.1 | 1300 ± 79 |

TABLE 9-continued

| No | R$^{103}$ | IC$_{50}$ (μM) (TR-FRET) | 95% CI (μM) (TR-FRET) | Avg. Sol (μM) | Pampa (×10$^{-6}$ cm/s) |
|----|-----------|---------------------------|------------------------|---------------|--------------------------|
| 10 | | 3.2 | 2.2-4.7 | 85 ± 2.7 | 700 ± 73 |
| 11 | | 1.3 | 0.98-1.6 | 66 ± 4.2 | >2200 |
| 12 | | 0.48 | 0.2-0.83 | 37 ± 2.4 | >2200 |

13. Further Optimization of Binding to the Ile Pocket of the Target Site

All non-commercially available analogs were prepared by the methods described herein. The IC$_{50}$ values (provided in μM) were determined using the TR-FRET assay described herein. The 95% confidence interval (indicated as "CI" in the tables) for the IC$_{50}$ was calculated by as described herein. Average solubility (provided in μM) was determined as described herein. Membrane permeability (provided in ×10$^{-6}$ cm/s) was determined using the parallel artificial membrane permeability assay ("Pampa") as described herein.

TABLE 10

| No | R$^{101}$ | IC$_{50}$ (μM) (TR-FRET) | 95% CI (μM) (TR-FRET) | Avg. Sol (μM) | Pampa (×10$^{-6}$ cm/s) |
|----|-----------|---------------------------|------------------------|---------------|--------------------------|
| 1 | | >63 | N/A | 71 ± 0.9 | >2200 |
| 2 | | 0.053 | 0.041-0.068 | 57 ± 1.4 | 1400 ± 39 |

TABLE 10-continued

| No | R[101] | IC$_{50}$ (µM) (TR-FRET) | 95% CI (µM) (TR-FRET) | Avg. Sol (µM) | Pampa ($\times 10^{-6}$ cm/s) |
|---|---|---|---|---|---|
| 3 | | >65 | N/A | 2.3 ± 1.5 | 440 ± 1 |
| 5 | | 26 | 19-37 | <0.1 | >2200 |
| 6 | | 0.76 | 0.55-1.0 | 0.5 ± 0.6 | <1 |
| 7 | | 0.84 | 0.46-1.5 | 1.0 ± 0.1 | <1 |
| 8 | | 0.98 | 0.79-1.2 | 39 ± 2.9 | 1800 ± 1 |
| 9 | | 0.11 | 0.066-0.19 | 70 ± 1.4 | >2200 |
| 10 | | 0.81 | 0.64-1.0 | 58 ± 1.4 | 1400 ± 540 |
| 11 | | 1.3 | 1.1-1.7 | ND | ND |
| 12 | | 0.14 | 0.098-0.19 | 60 ± 0.7 | >2200 |
| 13 | | 0.13 | 0.10-0.16 | 75 ± 1.8 | >2200 |
| 14 | | >73 | N/A | ND | ND |

TABLE 10-continued

| No | R[101] | IC$_{50}$ (μM) (TR-FRET) | 95% CI (μM) (TR-FRET) | Avg. Sol (μM) | Pampa (×10$^{-6}$ cm/s) |
|----|--------|--------------------------|------------------------|----------------|--------------------------|
| 15 | | 1.1 | 1.0-1.2 | ND | ND |
| 16 | | 0.18 | 0.14-0.22 | 5.8 ± 0.6 | >2200 |
| 17 | | 0.45 | 0.38-0.53 | 48 ± 0.3 | 990 ± 110 |
| 18 | | 0.67 | 0.57-0.78 | 1.2 ± 0.1 | <1 |
| 19 | | >70 | N/A | 6.3 ± 1.4 | 310 ± 540 |
| 20 | | 4.0 | 2.7-5.8 | 110 ± 2.4 | 50 ± 1.2 |
| 21 | | 2.0 | 1.1-3.5 | 54 ± 3.2 | >2200 |
| 22 | | 1.9 | 1.3-2.7 | 11 ± 0.3 | 300 ± 460 |
| 23 | | 12 | 8.2-16 | 30 ± 1.1 | >2200 |
| 24 | | 9.2 | 7.3-12 | 0.9 ± 0.1 | >2200 |

TABLE 10-continued

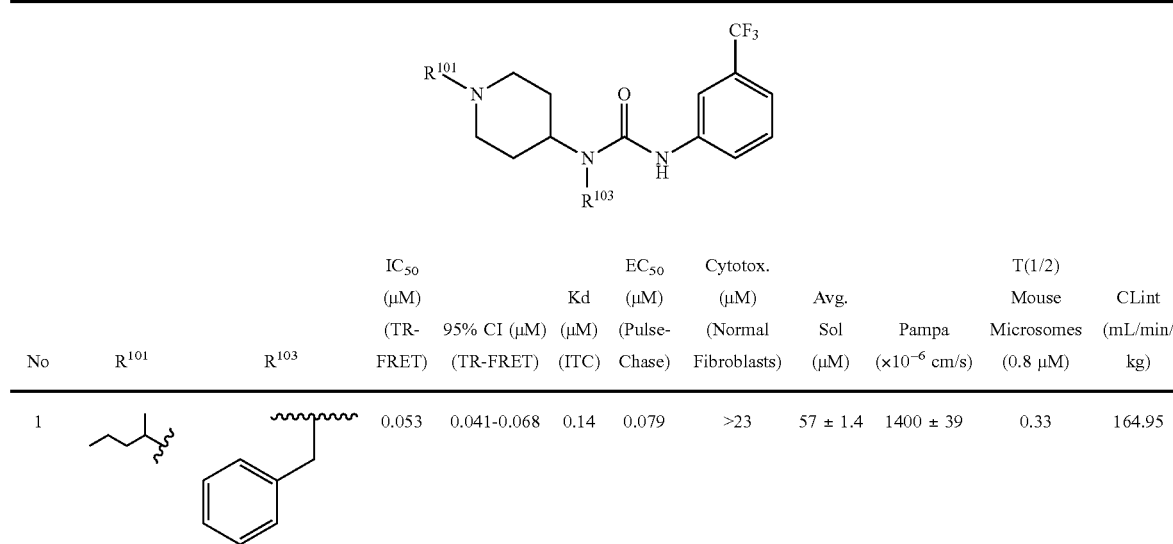

| No | R[101] | IC$_{50}$ ($\mu$M) (TR-FRET) | 95% CI ($\mu$M) (TR-FRET) | Avg. Sol ($\mu$M) | Pampa ($\times 10^{-6}$ cm/s) |
|---|---|---|---|---|---|
| 25 | | >67 | N/A | 0.4 ± 0.1 | 110 ± 190 |
| 26 | | 7.0 | 4.0-12 | <0.1 | >2200 |
| 27 | | 7.3 | 4.8-11 | 1.0 ± 1.3 | >2200 |

14. Optimization of Binding to the Target Site

All non-commercially available analogs were prepared by the methods described herein. The IC$_{50}$ values (provided in $\mu$M) were determined using the TR-FRET assay described herein above. The 95% confidence interval (indicated as "CI" in the tables) for the IC$_{50}$ was calculated by as described herein. The average solubility (provided in $\mu$M) was determined as described herein. The membrane permeability (provided in $\times 10^{-6}$ cm/s) was determined using the parallel artificial membrane permeability assay ("Pampa") as described herein.

TABLE 11

| No | R[101] | R[103] | IC$_{50}$ ($\mu$M) (TR-FRET) | 95% CI ($\mu$M) (TR-FRET) | Kd ($\mu$M) (ITC) | EC$_{50}$ ($\mu$M) (Pulse-Chase) | Cytotox. ($\mu$M) (Normal Fibroblasts) | Avg. Sol ($\mu$M) | Pampa ($\times 10^{-6}$ cm/s) | T(1/2) Mouse Microsomes (0.8 $\mu$M) | CLint (mL/min/kg) |
|---|---|---|---|---|---|---|---|---|---|---|---|
| 1 | | | 0.053 | 0.041-0.068 | 0.14 | 0.079 | >23 | 57 ± 1.4 | 1400 ± 39 | 0.33 | 164.95 |

TABLE 11-continued

| No | $R^{101}$ | $R^{103}$ | $IC_{50}$ (µM) (TR-FRET) | 95% CI (µM) (TR-FRET) | Kd (µM) (ITC) | $EC_{50}$ (µM) (Pulse-Chase) | Cytotox. (µM) (Normal Fibroblasts) | Avg. Sol (µM) | Pampa (×10⁻⁶ cm/s) | T(1/2) Mouse Microsomes (0.8 µM) | CLint (mL/min/ kg) |
|---|---|---|---|---|---|---|---|---|---|---|---|
| 2 | | | 0.11 | 0.066-0.19 | 0.70 | 0.140 | >28 | 70 ± 1.4 | >2200 | 0.10 | 591.20 |
| 3 | | | 0.19 | 0.14-0.26 | ND | 0.11 | >23 | 71 ± 4.4 | >2200 | 0.25 | 220.43 |
| 4 | | | 0.260 | 0.17-0.40 | ND | 0.37 | >23 | 75 ± 3.1 | >2200 | 0.19 | 277.46 |
| 5 | | | 0.48 | 0.28-0.83 | ND | 0.18 | >22 | 37 ± 2.4 | >2200 | 0.27 | 199.42 |
| 6 | | | 0.80 | 0.64-1.0 | 0.70 | 0.57 | >21 | 69 ± 1.4 | >2200 | 0.14 | 394.72 |
| 7 | | | 0.80 | 0.47-1.4 | ND | 1.7 | >39 | <0.1 | 1300 ± 79 | 0.38 | 143.21 |
| 8 | | | 0.98 | 0.79-1.2 | 0.86 | 0.40 | >18 | 39 ± 2.9 | 1800 ± 1 | 0.17 | 318.46 |
| 9 | | | 3.2 | 2.2-4.7 | ND | 0.49 | >23 | 66 ± 4.2 | >2200 | 0.09 | 629.68 |
| 10 | | | 5.5 | 3.3-9.2 | ND | 4.20 | >24 | 32 ± 1.6 | 670 ± 100 | 0.47 | 113.96 |

15. Selective Inhibition of Cullin Neddylation in Cancer Cells

As shown in FIG. 11A and FIG. 11B, compounds A7 and A18 selectively inhibit cullin neddylation in HCC95 cancer cells.

16. A7 Selectively Inhibits DCN1

As shown in FIG. 12A and FIG. 12B, A7 selectively inhibits DCN1 2-fold over DCN2, 250-fold over DCN3, and greater than 300-fold over each of DCN4 and DCN5.

17. A15 and A83 Affect Endosome Maturation

As shown in FIG. 13A-C, compounds A15 (10 μM on cells) and A83 (3 μM on cells) affect endosome maturation (13B) compared to DMSO (13A), and a negative control (13C).

18. Electron Microscopy

As shown in FIG. 14A-D, electron microscopy images of U-2 OS cells treated with DMSO (14A), compounds A15 (14B), A7 (14C), and A3 (14D) demonstrated the presence of large vacuolar structures.

19. Off-Target Selectivity

The off-target selectivity of A7 and A18 is illustrated in FIG. 15.

20. $DCN_1$'s Block Anchorage Independent Growth in HCC95 Cells

The ability of $DCN_1$'s to inhibit anchorage independent growth in HCC95 cells is illustrated in FIG. 16A and FIG. 16B.

21. In Vivo Plasma Pharmacokinetic Parameters of A7

The pharmacokinetic parameters of A7 are illustrated in FIG. 17A-D.

22. Testicular Accumulation of A7

A preliminary experiment was performed to evaluate the testicular accumulation of A7 (Table 12). Based on these data, the half-life of A7 was 4-5 hours and the maximum serum concentration was 1.5-3 μM.

TABLE 12

| | Single Dose (0 hr) | | Repeat Dose (0 and 7.5 hr) | |
|---|---|---|---|---|
| Time (hr) | Plasma Concentration (μM) | Testis Concentration (μM) | Plasma Concentration (μM) | Testis Concentration (μM) |
| 1.0 | 3.7 ± 0.95 | 2.1 ± 0.74 | — | — |
| 8.5 | — | — | 4.8 ± 1.3 | 16.7 ± 3.1 |
| 24.4 | 0.47 ± 0.32 | 4.4 ± 3.3 | 0.62 ± 0.16 | 6.2 ± 5.3 |

The results of an extended testis accumulation experiment are shown in Table 13.

TABLE 13

| | 50 mg/kg | | 100 mg/kg | |
|---|---|---|---|---|
| Time | Plasma Concentration (μM) | Testis Concentration (μM) | Plasma Concentration (μM) | Testis Concentration (μM) |
| 8.5 hr | 2.7 ± 0.72 | 11.7 ± 7.0 | 1.7 ± 0.7 | 16.1 ± 7.1 |
| Day 3 | 2.7 ± 2.4 | 11.6 ± 3.4 | 2.4 ± 1.2 | 25.9 ± 11.1 |
| Day 7 | 1.7 ± 1.2 | 8.25 ± 4.1 | 1.4 ± 0.6 | 31.2 ± 12.8 |

23. Spermatogenesis Study

A seven day spermatogenesis study was performed using A7 (oral gavage, B.I.D.). Three groups were evaluated (see FIG. 18 and Table 14). The results of the study are shown in Table 15.

TABLE 14

| Group | Weight (mg) |
|---|---|
| Vehicle | 184.1 ± 1.1 |
| 50 mpk | 146.3 ± 27.7 |
| 100 mpk | 150.1 ± 18.9 |

TABLE 15

| ID | Sperm Count | Motility | Viability (%) |
|---|---|---|---|
| Veh-1 | Normal | Good, forward | >50 |
| Veh-2 | Normal | Good, forward | >50 |
| Veh-3 | Normal | Good, forward | >50 |
| 50 mpk-1 | Low | Stationary | <20 |
| 50 mpk-2 | Low | Stationary | 0 |
| 50 mpk-3 | Normal | Good, erratic | >50 |
| 100 mpk-1 | Low | No movement | <10 |
| 100 mpk-2 | Low | Erratic | <5 |
| 100 mpk-3 | Low | Limited | <10 |

24. Prospective In Vivo Activity in a Mouse Xenograft Model

The following example of the anticipated in vivo effect of the disclosed compounds is prophetic. An example of an in vivo assay method for assessing the efficacy of the disclosed compounds in an animal model of tumor growth is given below.

Xenograft tumors are first established from an SK-MEL-2 cell culture at the St. Jude Children's Research Hospital Xenograft Core. After these tumors are established as a mouse xenograft model, they are routinely maintained in the CB-17 scid strain (Taconic Farms, Germantown, NY). Experimental animals are prepared by transplanting small pieces of dissected tumors from donor animals into recipient mice. All animal studies are performed in accordance with the St. Jude Children's Research Hospital Animal Care and Use Committee. SK-MEL-2 xenograft tumors were transplanted into male CB-17 scid mice on Day −21. On Days −7 to −5, a jugular vein catheter is surgically implanted into each mouse. Beginning on Day 1, the animals (8 for vehicle, 9 for drug-treatment) received daily infusions of vehicle (10% [(2-hydroxypropyl)-β-cyclodextrin]dissolved in 50 mM $Na_2HPO_4/NaH_2PO_4$, pH 7.4) or 100 mg/kg of a disclosed compound for 5 consecutive days. Infusions are carried out by placing the animals inside a continuous infusion system (Instech Laboratories, Plymouth Meeting, PA), and delivering the vehicle or drug solution via the jugular catheter at a rate of 4 µL/min with a SP230iw syringe pump (WPI, Sarasota, FL). Other suitable vehicles are known to one skilled in the art, e.g., 10% Tween 80 or 0.5% methylcellulose in a buffer suitable for infusion dosing. The total volume infused into the animals generally does not exceed 850 µL per day. Tumors are continuously measured during and after infusion periods, 5 times per week (weekdays). Tumor volumes are determined based on the following equation: $Tu_{vol}=(\delta_1/2+\delta_2/2)^{1.5708}$, where $\delta_1$ and $\delta_2$ are diameters measured with a caliper at right angles of each other. The size of the tumour typically range from 0.2 to 0.5 $cm^3$ at the times the infusions were initiated.

For example, compounds disclosed in Tables 1-6 or a pharmaceutically acceptable salt thereof, are expected to show at least partial activity in this mouse model.

For example, compounds having a structure represented by a formula:

each of $R^{1a}$, $R^{1b}$, and $R^{1c}$ is independently hydrogen, halogen, —$SF_5$, —$NO_2$, —$CH_3$, —$CH_2F$, —$CHF_2$, —$CF_3$, —$OCF_3$, —$NHCH_3$, —$N(CH_3)_2$, —$(CH_2)$-phenyl, —$(CH_2)$-pyridinyl, —$(CH_2)$-pyrimidinyl, —O-phenyl, —O-pyridinyl, or —O-pyrimidinyl, provided that at least one of $R^{1a}$, $R^{1b}$, and $R^{1c}$ is not hydrogen; or $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalkyl, or heterocycloalkenyl; and $R^{1c}$ is hydrogen, halogen, —OH, —$SCF_3$, —$SF_5$, —$NO_2$, —$CH_3$, —$CH_2F$, —$CHF_2$, —$CF_3$, —$OCF_3$, —$NHCH_3$, or —$N(CH_3)_2$; $R^2$ is C3-C6 alkyl, —(C1-C6)-$CF_3$, —(C1-C6)-C≡CH, —(C1-C3 alkyl)-cyclopropyl, —(C1-C3 alkyl)-cyclobutyl, —(C1-C3 alkyl)-cyclopentyl, —(C1-C3 alkyl)-cyclohexyl, —(C1-C3 alkyl)-(bicycloalkyl), —(C1-C3 alkyl)-(bicycloalkenyl), —(C1-C3)-aryl, —(C1-C3)-heteroaryl, —(C1-C3)-(bicyclic), or —$SO_2$—(C1-C6 alkyl); and $R^2$ is substituted with 0, 1, 2, or 3 groups independently selected from halogen, —OH, —$SCF_3$, —$SF_5$, —$NO_2$, —$CH_3$, —$CH_2F$, —$CHF_2$, —$CF_3$, —$OCF_3$, —$NHCH_3$, and —$N(CH_3)_2$; $R^3$ is C1-C8 alkyl; C1-C8 alkoxyalkyl; —(C1-C3 alkyl)-(C3-C8 cycloalkyl); or —(C1-C3 alkyl)-$Ar^1$; $Ar^1$ is aryl or heteroaryl substituted with 0, 1, 2, or 3 groups independently selected from halogen, —$SF_5$, —$NO_2$, —$CH_3$, —$CH_2F$, —$CHF_2$, —$CF_3$, —$OCF_3$, —$NHCH_3$, —$N(CH_3)_2$, —$NHC(O)CH_2Cl$, —$NHSO_2CH=CH_2$, —$NHC(O)CH=CH_2$, and —$(CH_2)NHC(O)CH=CH_2$; or a pharmaceutically acceptable salt thereof, are expected to show at least partial activity in this mouse model. Moreover, compounds prepared using the disclosed synthetic methods are also expected to show such effects.

25. Prospective Pharmaceutical Composition Examples

"Active ingredient" as used throughout these examples relates to one or more disclosed compounds or products of disclosed methods of making as described hereinbefore, or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

a. Pharmaceutical Composition for Oral Administration
A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a cancer, the method comprising administering to a subject in need thereof a therapeutically effective amount of a compound having a structure represented by formula:

or a pharmaceutically acceptable salt thereof, wherein
each of $R^{1a}$, $R^{1b}$, and $R^{1c}$ is independently hydrogen, halogen, $-SF_5$, $-NO_2$, $-CH_3$, $-CH_2F$, $-CHF_2$, $-CF_3$, $-OCF_3$, $-NHCH_3$, $-N(CH_3)_2$, $(CH_2)$-phenyl, $-(CH_2)$-pyridinyl, $-(CH_2)$-pyrimidinyl, $-O$-phenyl, $-O$-pyridinyl, or $-O$-pyrimidinyl, provided that at least one of $R^{1a}$, $R^{1b}$ and $R^{1c}$ is not hydrogen; or wherein $R^{1a}$ and $R^{1b}$ are optionally covalently bonded and, together with the intermediate atoms, comprise an optionally substituted 3- to 7-membered fused aryl, heteroaryl, cycloalkyl, cycloalkenyl, heterocycloalklyl, or heterocycloalkenyl; and wherein $R^{1c}$ is hydrogen, halogen, $-OH$, $-SCF_3$, $-SF_5$, $-NO_2$, $-CH_3$, $-CH_2F$, $-CHF_2$, $-CF_3$, $-OCF_3$, $-NHCH_3$, or $-N(CH_3)_2$;
$R^2$ is C3-C6 alkyl, $-(C1-C6\ alkyl)-CF_3$, $-(C1-C6\ alkyl)-C\equiv CH$, $-(C1-C3\ alkyl)$-cyclopropyl, $-(C1-C3\ alkyl)$-cyclobutyl, $-(C1-C3\ alkyl)$-cyclopentyl, $-(C1-C3\ alkyl)$-cyclohexyl, or $-SO_2-(C1-C6\ alkyl)$; and wherein $R^2$ is substituted with 0, 1, 2, or 3 groups independently selected from halogen, $-OH$, $-SCF_3$, $-SF_5$, $-NO_2$, $-CH_3$, $-CH_2F$, $-CHF_2$, $-CF_3$, $-OCF_3$, $-NHCH_3$, and $-N(CH_3)_2$; and
$R^3$ is $Ar^1$ or $-(C1-C3\ alkyl)-Ar^1$;
wherein $Ar^1$ is phenyl independently substituted with 0, 1, 2, or 3 groups selected from halogen, $-SF_5$, $-NO_2$, $-CH_3$, $-CH_2F$, $-CHF_2$, $-CF_3$, $-OCF_3$, $-NHCH_3$, and $-N(CH_3)_2$, or is pyridinyl having a structure represented by:

wherein each of $R^{20a}$, $R^{20b}$, $R^{20c}$, and $R^{20d}$ is independently selected from hydrogen, halogen, —SF$_5$, —NO$_2$, —CH$_3$, —CH$_2$F, —CHF$_2$, —CF$_3$, —OCF$_3$, —NHCH$_3$, —N(CH$_3$)$_2$, —NHC(O)CH=CH$_2$, and —(CH$_2$)NHC(O)CH=CH$_2$, provided that at least one of $R^{20a}$, $R^{20b}$, $R^{20c}$, and $R^{20d}$ is hydrogen; and wherein the cancer is a squamous cell carcinoma.

2. The method of claim 1, wherein each of $R^{1a}$, $R^{1b}$, and $R^{1c}$ is independently hydrogen, halogen, —SF$_5$, —CH$_3$, —CF$_3$, or —OCF$_3$, provided that at least one of $R^{1a}$, $R^{1b}$, and $R^{1c}$ is not hydrogen.

3. The method of claim 1, wherein $R^{1c}$ is hydrogen; and wherein each of $R^{1a}$ and $R^{1b}$ is independently halogen, —SF$_5$, —CH$_3$, —CF$_3$, or —OCF$_3$.

4. The method of claim 1, wherein $R^{1b}$ is hydrogen; and wherein each of $R^{1a}$ and $R^{1c}$ is independently halogen, —SF$_5$, —CH$_3$, —CF$_3$, or —OCF$_3$.

5. The method of claim 1, wherein each of $R^{1b}$ and $R^{1c}$ is hydrogen; and wherein $R^{1a}$ is independently halogen, —SF$_5$, —CH$_3$, —CF$_3$, or —OCF$_3$.

6. The method of claim 1, wherein R$^2$ is C3-C6 alkyl, —(CH$_2$)-cyclopropyl, —(CH$_2$)-cyclobutyl, —(CH$_2$)-cyclopentyl, or —(CH$_2$)-cyclohexyl.

7. The method of claim 1, wherein R$^2$ is C3-C6 alkyl or (CH$_2$)-cyclopropyl.

8. The method of claim 1, wherein R$^2$ is —(CH$_2$)-cyclopropyl.

9. The method of claim 1, wherein R$^2$ is C3-C6 alkyl.

10. The method of claim 1, wherein R$^2$ has a structure represented by a formula:

-continued

11. The method of claim 1, wherein Ar$^1$ is phenyl independently substituted with 0, 1, 2, or 3 groups selected from halogen, —SF$_5$, —NO$_2$, —CH$_3$, —CH$_2$F, —CHF$_2$, —CF$_3$, —OCF$_3$, —NHCH$_3$, and —N(CH$_3$)$_2$.

12. The method of claim 1, wherein Ar$^1$ is the pyridinyl group having the structure represented by:

13. The method of claim 1, wherein the compound has a structure represented by or a pharmaceutically acceptable salt thereof.

14. The method of claim 1, wherein the subject is human.

\* \* \* \* \*